(12) United States Patent
Pasteris

(10) Patent No.: US 8,618,137 B2
(45) Date of Patent: Dec. 31, 2013

(54) FUNGICIDAL HETEROCYCLIC COMPOUNDS

(75) Inventor: Robert James Pasteris, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 145 days.

(21) Appl. No.: 13/127,809

(22) PCT Filed: Dec. 2, 2009

(86) PCT No.: PCT/US2009/066318
§ 371 (c)(1),
(2), (4) Date: May 5, 2011

(87) PCT Pub. No.: WO2010/065579
PCT Pub. Date: Jun. 10, 2010

(65) Prior Publication Data
US 2011/0224258 A1    Sep. 15, 2011

Related U.S. Application Data

(60) Provisional application No. 61/119,137, filed on Dec. 2, 2008.

(51) Int. Cl.
*A01N 43/40* (2006.01)
*C07D 401/14* (2006.01)

(52) U.S. Cl.
USPC ......... 514/326; 514/340; 546/209; 546/269.7

(58) Field of Classification Search
USPC .................... 514/326, 340; 546/209, 269.7
See application file for complete search history.

(56) References Cited

U.S. PATENT DOCUMENTS 7,713,998 B2   5/2010   Nakai et al.

FOREIGN PATENT DOCUMENTS

| WO | 2004/058751 A1 | 7/2004 |
|---|---|---|
| WO | 2005/003128 A1 | 1/2005 |
| WO | 2005/087765 A1 | 9/2005 |
| WO | 2006/051826 A1 | 5/2006 |
| WO | 2007/014290 A2 | 2/2007 |
| WO | 2008/013622 A2 | 1/2008 |
| WO | 2008/013925 A2 | 1/2008 |
| WO | 2008/091580 A2 | 7/2008 |
| WO | 2008/091594 | * 7/2008 |
| WO | 2008/091594 A2 | 7/2008 |
| WO | 2009/055514 A2 | 4/2009 |
| WO | 2009/094407 A2 | 7/2009 |
| WO | 2009/094445 A2 | 7/2009 |
| WO | 2010/037479 A1 | 4/2010 |
| WO | WO2012082580 | * 6/2012 |

OTHER PUBLICATIONS

Barlaam et al. "Pyridine . . . " CA150:472757 (2009).*
Biftu et al. "Synthesis and use . . . " CA134:366803 (2001).*
Hanagan et al. "Azacyclic . . . " CA157:882830 (2012).*
Improper Markush p. 64-67 (20110.*
Dorwald "Side reactions . . . " p. ix, 1-16, 40-41 (2005).*
Exhibit 1 (2013).*
Mikaberidze et al. "Can high risk fungicides . . . " Inst. Integrat. Bio. p. 1-2 (2013).*
Johnson et al. "Acaridide, . . . " PLOS ONE v.8, p. 1-10 (2013).*
Classification of Fungi p. 1-9 from internet (2013).*
Fernandez0Ortuno et al. "The Qol fungicides . . . " Fungicides p. 203-220 (2010).*

\* cited by examiner

*Primary Examiner* — Celia Chang
(74) *Attorney, Agent, or Firm* — Jane O. Hamby; Renee M. Lett

(57) ABSTRACT

Disclosed are compounds of Formula 1, including all geometric and stereoisomers, tautomers, N-oxides, and salts thereof,

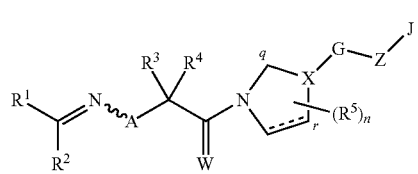

wherein
$R^1$, $R^2$, $R^3$, $R^4$, $R^5$, A, W, X, G, Z, J and n are as defined in the disclosure.

Also disclosed are compositions containing the compounds of Formula 1 and methods for controlling plant disease caused by a fungal pathogen comprising applying an effective amount of a compound or a composition of the invention.

6 Claims, No Drawings

FUNGICIDAL HETEROCYCLIC COMPOUNDS

FIELD OF THE INVENTION

This invention relates to certain heterocyclic compounds, their tautomers, N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT Patent Publication WO 2007/014290 discloses carboxamide derivatives of Formula i

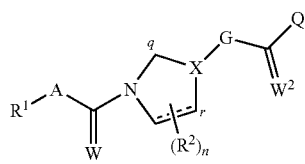

and their use as fungicides.

PCT Patent Publication WO 2008/013925 discloses azocyclic amides of Formula ii

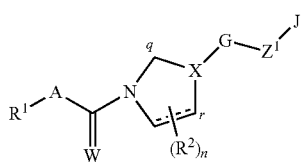

and their use as fungicides.

PCT Patent Publication WO 2008/091580 discloses amide derivatives of Formula iii

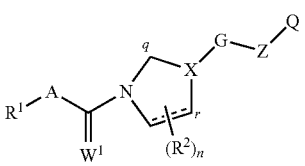

and their use as fungicides.

SUMMARY OF THE INVENTION

This invention is directed to compounds of Formula 1 (including all geometric and stereoisomers), tautomers, N-oxides, and salts thereof, agricultural compositions containing them and their use as fungicides:

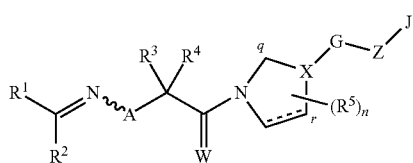

wherein

A is —O—, —S—, —N($R^7$)—, —C($R^8$)$_2$—, —OC($R^8$)$_2$—, —SC($R^8$)$_2$— or —N($R^7$)C($R^8$)$_2$—,
  wherein the bond projecting to the left is connected to the nitrogen atom of Formula 1, and the bond projecting to the right is connected to the carbon atom of Formula 1;

W is O or S;

G is an optionally substituted 5-membered heterocyclic ring;

Z is a direct bond, O, C(=O), S(=O)$_m$, CH($R^{12}$) or N($R^{13}$);

J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S(=O)$_s$(=N$R^{11}$)$_f$ and the silicon atom ring members are independently selected from SiR$^9$R$^{10}$, each ring or ring system optionally substituted with up to 5 substituents independently selected from R$^6$; or when Z is a direct bond then J is also C(=W$^2$)NT$^A$T$^B$;

W$^2$ is O or S;

T$^A$ is H or C$_1$-C$_3$ alkyl;

T$^B$ is CR$^{14}$R$^{15}$R$^{16}$;

X is a radical selected from

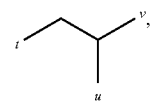

X$^1$

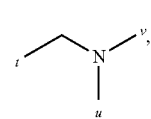

X$^2$

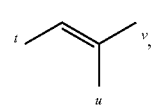

X$^3$

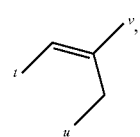

X$^4$

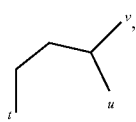

$X^5$

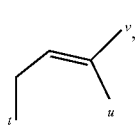

$X^6$

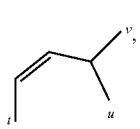

$X^7$

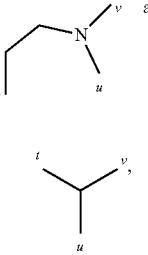

$X^8$ and $X^9$ wherein the bond of $X^1$, $X^2$, $X^3$, $X^4$, $X^5$, $X^6$, $X^7$, $X^8$ or $X^9$ which is identified with "t" is connected to the carbon atom identified with "q" of Formula 1, the bond which is identified with "u" is connected to the carbon atom identified with "r" of Formula 1, and the bond which is identified with "v" is connected to G of Formula 1;

$R^1$ is H, halogen, cyano, amino, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_4$-$C_6$ halocycloalkylalkyl, $C_3$-$C_6$ cycloalkenyl, $C_3$-$C_6$ halocycloalkenyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_2$-$C_6$ alkylcarbonyl, $C_2$-$C_6$ haloalkylcarbonyl, $C_4$-$C_6$ cycloalkylcarbonyl, $C_2$-$C_6$ alkoxycarbonyl, $C_4$-$C_6$ cycloalkoxycarbonyl, $C_5$-$C_6$ cycloalkylalkoxycarbonyl, $C_2$-$C_6$ alkylaminocarbonyl, $C_3$-$C_6$ dialkylaminocarbonyl, $C_1$-$C_6$ alkoxy, $C_1$-$C_6$ haloalkoxy, $C_3$-$C_6$ cycloalkoxy, $C_3$-$C_6$ halocycloalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_6$ cycloalkylthio, $C_1$-$C_6$ alkylamino, $C_2$-$C_6$ dialkylamino, $C_1$-$C_6$ haloalkylamino, $C_2$-$C_6$ halodialkylamino, $C_3$-$C_6$ cycloalkylamino, $C_2$-$C_6$ alkylcarbonylamino, $C_2$-$C_6$ haloalkylcarbonylamino, $C_1$-$C_6$ alkylsulfonylamino or $C_1$-$C_6$ haloalkylsulfonylamino;

$R^2$ is H, halogen, cyano, hydroxy, $C_1$-$C_3$ alkyl, $C_1$-$C_3$ haloalkyl, $C_1$-$C_3$ alkoxy, $C_1$-$C_3$ haloalkoxy or $C_1$-$C_3$ alkylthio; or $R^1$ and $R^2$ are taken together with the carbon atom to which they are attached to form a 3- to 7-membered ring containing ring members selected from carbon atoms and up to 4 heteroatoms independently selected from up to 2 O, up to 2 S, up to 2 N and up to 2 Si atoms, wherein up to 3 carbon atom ring members are independently selected from C(=O) and C(=S), the sulfur atom ring members are independently selected from $S(=O)_s(=NR^{11})_f$ and the silicon atom ring members are independently selected from $SiR^9R^{10}$, the ring optionally substituted with up to 4 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^3$ is an optionally substituted phenyl, an optionally substituted naphthalenyl or an optionally substituted 5- to 6-membered heteroaromatic ring; or H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyloxy, $C_2$-$C_4$ haloalkylcarbonyloxy, $C_2$-$C_5$ alkoxycarbonyloxy, $C_2$-$C_5$ alkylaminocarbonyloxy or $C_3$-$C_5$ dialkylaminocarbonyloxy;

$R^4$ is H, $C_1$-$C_3$ alkyl or $C_1$-$C_3$ haloalkyl; or $R^3$ and $R^4$ are taken together with the carbon atom to which they are attached to form a 3- to 6-membered saturated carbocyclic ring;

each $R^5$ is independently halogen, cyano, hydroxy, $C_1$-$C_4$ alkyl, $C_1$-$C_4$ alkenyl, $C_1$-$C_4$ haloalkyl or $C_1$-$C_4$ alkoxy; or two $R^5$ groups are taken together as $C_1$-$C_4$ alkylene or $C_2$-$C_4$ alkenylene to form a bridged bicyclic or fused bicyclic ring system; or two $R^5$ groups attached to adjacent ring carbon atoms joined by a double bond are taken together as —CH=CH—CH=CH— optionally substituted with up to 3 substituents independently selected from halogen, cyano, hydroxy, amino, nitro, $C_1$-$C_4$ alkyl, $C_1$-$C_4$ haloalkyl, $C_1$-$C_4$ alkoxy and $C_1$-$C_4$ haloalkoxy;

each $R^6$ is independently H, halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_2$-$C_6$ haloalkoxyalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, C$_2$-C$_6$ alkynyloxy, C$_2$-C$_6$ haloalkynyloxy, C$_2$-C$_6$ alkoxyalkoxy, C$_2$-C$_6$ alkylcarbonyloxy, C$_2$-C$_6$ haloalkylcarbonyloxy, C$_4$-C$_8$ cycloalkylcarbonyloxy, C$_3$-C$_6$ alkylcarbonylalkoxy, C$_1$-C$_6$ alkylthio, C$_1$-C$_6$ haloalkylthio, C$_3$-C$_8$ cycloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_3$-C$_8$ cycloalkylsulfonyl, C$_3$-C$_{10}$ trialkylsilyl, C$_1$-C$_6$ alkylsulfonylamino, C$_1$-C$_6$ haloalkylsulfonylamino, —NR$^{17}$R$^{18}$ or —Z$^2$Q;

each Z$^2$ is independently a direct bond, O, C(=O), S(=O)$_m$, CH(R$^{12}$) or N(R$^{13}$);

each Q is independently phenyl, benzyl, naphthalenyl, a 5- to 6-membered heteroaromatic ring or an 8- to 11-membered heteroaromatic bicyclic ring system, each optionally substituted with up to 2 substituents independently selected from R$^{6b}$ on carbon and nitrogen atom ring members, and each optionally substituted with up to 5 substituents independently selected from R$^{6a}$ on carbon atom ring members and selected from C$_1$-C$_3$ alkyl, C$_2$-C$_3$ alkylcarbonyl, C$_2$-C$_3$ alkoxycarbonyl or C$_1$-C$_3$ alkoxy on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S(=O)$_s$(=NR$^{11}$)$_p$, and the silicon atom ring members are independently selected from SiR$^9$R$^{10}$, each ring or ring system optionally substituted with up to 2 substituents independently selected from R$^{6b}$ on carbon and nitrogen atom ring members, up to 5 substituents independently selected from R$^{6a}$ on carbon atom ring members and selected from C$_1$-C$_3$ alkyl, C$_2$-C$_3$ alkylcarbonyl, C$_2$-C$_3$ alkoxycarbonyl and C$_1$-C$_3$ alkoxy on nitrogen atom ring members;

each R$^{6a}$ is independently halogen, hydroxy, amino, cyano, nitro, C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_6$-C$_{14}$ cycloalkylcycloalkyl, C$_1$-C$_6$ haloalkyl, C$_2$-C$_6$ haloalkenyl, C$_2$-C$_6$ haloalkynyl, C$_3$-C$_6$ halocycloalkyl, C$_1$-C$_4$ alkoxy, C$_1$-C$_4$ haloalkoxy, C$_1$-C$_4$ alkylthio, C$_1$-C$_4$ haloalkylthio, C$_1$-C$_4$ alkylsulfinyl, C$_1$-C$_4$ alkylsulfonyl, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl; or R$^6$ and R$^{6a}$ are taken together with the atoms to which they are attached to form a 5- to 7-membered ring containing ring members selected from carbon atoms and optionally up to 3 heteroatoms independently selected from up to 1 O, up to 1 S and up to 1 N atom, the ring optionally substituted with up to 3 substituents independently selected from halogen, cyano, nitro, C$_1$-C$_2$ alkyl and C$_1$-C$_2$ alkoxy on carbon atom ring members and cyano, C$_1$-C$_2$ alkyl and C$_1$-C$_2$ alkoxy on nitrogen atom ring members;

each R$^{6b}$ is independently phenyl optionally substituted with up to 3 substituents independently selected from halogen, cyano, C$_1$-C$_2$ alkyl, C$_1$-C$_2$ haloalkyl, C$_1$-C$_2$ alkoxy and C$_1$-C$_2$ haloalkoxy; or a 5- to 6-membered heteroaromatic ring containing ring members selected from carbon atoms and up to 4 heteroatoms independently selected from up to 2 O, up to 2 S and up to 4 N atoms, the ring optionally substituted with up to 3 substituents independently selected from halogen, cyano, C$_1$-C$_2$ alkyl, C$_1$-C$_2$ haloalkyl, C$_1$-C$_2$ alkoxy and C$_1$-C$_2$ haloalkoxy on carbon atom ring members and cyano, C$_1$-C$_2$ alkyl and C$_1$-C$_2$ alkoxy on nitrogen atom ring members; or a 3- to 7-membered nonaromatic ring containing ring members selected from carbon atoms and up to 4 heteroatoms independently selected from up to 2 O, up to 2 S and up to 4 N atoms, wherein up to 3 carbon atom ring members are independently selected from C(=O) and C(=S), the ring optionally substituted with up to 3 substituents independently selected from halogen, cyano, C$_1$-C$_2$ alkyl, C$_1$-C$_2$ haloalkyl, C$_1$-C$_2$ alkoxy and C$_1$-C$_2$ haloalkoxy on carbon atom ring members and cyano, C$_1$-C$_2$ alkyl and C$_1$-C$_2$ alkoxy on nitrogen atom ring members;

R$^7$ is H, cyano, C$_1$-C$_4$ alkyl, C$_1$-C$_4$ haloalkyl, C$_2$-C$_4$ alkoxyalkyl, C$_2$-C$_4$ alkylthioalkyl, C$_2$-C$_4$ alkylcarbonyl, C$_2$-C$_4$ haloalkylcarbonyl, C$_2$-C$_4$ alkoxycarbonyl, C$_2$-C$_4$ alkylaminocarbonyl, C$_3$-C$_5$ dialkylaminocarbonyl, C$_1$-C$_4$ alkylsulfonyl or C$_1$-C$_4$ haloalkylsulfonyl; or R$^2$ and R$^7$ are taken together with the linking atoms to which they are attached to form a 5- to 7-membered partially unsaturated ring containing ring members, in addition to the linking atoms, selected from carbon atoms and up to 3 heteroatoms independently selected from up to 1 O, up to 1 S and up to 1 N atom, the ring optionally substituted with up to 3 substituents independently selected from halogen, cyano, nitro, C$_1$-C$_2$ alkyl, C$_1$-C$_2$ haloalkyl, C$_1$-C$_2$ alkoxy and C$_1$-C$_2$ haloalkoxy on carbon atom ring members and cyano, C$_1$-C$_2$ alkyl and C$_1$-C$_2$ alkoxy on nitrogen atom ring members;

each R$^8$ is independently H, C$_1$-C$_3$ alkyl or C$_1$-C$_3$ haloalkyl;

each R$^9$ and R$^{10}$ is independently C$_1$-C$_5$ alkyl, C$_2$-C$_5$ alkenyl, C$_2$-C$_5$ alkynyl, C$_3$-C$_5$ cycloalkyl, C$_3$-C$_6$ halocycloalkyl, C$_4$-C$_{10}$ cycloalkylalkyl, C$_4$-C$_7$ alkylcycloalkyl, C$_5$-C$_7$ alkylcycloalkylalkyl, C$_1$-C$_5$ haloalkyl, C$_1$-C$_5$ alkoxy or C$_1$-C$_5$ haloalkoxy;

each R$^{11}$ is independently H, cyano, C$_1$-C$_6$ alkyl, C$_1$-C$_6$ haloalkyl, C$_3$-C$_8$ cycloalkyl, C$_3$-C$_8$ halocycloalkyl, C$_1$-C$_6$ alkoxy, C$_1$-C$_6$ haloalkoxy, C$_1$-C$_6$ alkylamino, C$_2$-C$_8$ dialkylamino, C$_1$-C$_6$ haloalkylamino or phenyl;

each R$^{12}$ is independently H, C$_1$-C$_4$ alkyl or C$_1$-C$_4$ haloalkyl;

each R$^{13}$ is independently H, C$_1$-C$_4$ alkyl, C$_1$-C$_4$ haloalkyl, C$_3$-C$_6$ cycloalkyl, C$_2$-C$_4$ alkylcarbonyl, C$_2$-C$_4$ haloalkylcarbonyl, C$_2$-C$_4$ alkoxycarbonyl or C$_2$-C$_4$ haloalkoxycarbonyl;

R$^{14}$ is H or C$_1$-C$_4$ alkyl;

R$^{15}$ is phenyl, benzyl, naphthalenyl or a 5- to 6-membered heteroaromatic ring, each optionally substituted on ring members with up to 3 substituents independently selected from R$^{19}$;

R$^{16}$ is H, cyano, nitro, C$_1$-C$_6$ alkyl, C$_2$-C$_6$ alkenyl or C$_2$-C$_6$ alkynyl;

each R$^{17}$ is independently H, C$_1$-C$_6$ alkyl, C$_1$-C$_6$ haloalkyl, C$_3$-C$_8$ cycloalkyl, C$_2$-C$_6$ alkylcarbonyl, C$_2$-C$_6$ haloalkylcarbonyl, C$_2$-C$_6$ alkoxycarbonyl or C$_2$-C$_6$ haloalkoxycarbonyl;

each $R^{18}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —$Z^3$Q;

each $R^{19}$ is independently halogen, cyano, hydroxy, $C_1$-$C_3$ alkyl, $C_1$-$C_3$ haloalkyl or $C_1$-$C_3$ alkoxy; or $R^{16}$ and $R^{19}$ are taken together with the atoms to which they are attached to form a 3- to 7-membered ring containing ring members selected from carbon atoms and up to 4 heteroatoms independently selected from up to 2 O, up to 2 S, up to 2 N and up to 2 Si atoms, wherein up to 2 carbon atom ring members are independently selected from C(=O) and C(=S), the sulfur atom ring members are independently selected from S(=O)$_s$(=NR$^{11}$)$_f$, and the silicon atom ring members are independently selected from SiR$^9$R$^{10}$, the ring optionally substituted with up to 4 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members;

each $Z^3$ is independently O, C(=O), S(=O)$_m$ or CH(R$^{12}$);

each m is independently 0, 1 or 2;

n is 0, 1 or 2; and s and f are independently 0, 1 or 2 in each instance of S(=O)$_s$(=NR$^{11}$)$_f$, provided that the sum of s and f is 0, 1 or 2.

More particularly, this invention pertains to a compound of Formula 1 (including all geometric and stereoisomers), tautomers, an N-oxide, or a salt thereof.

This invention also relates to a fungicidal composition comprising (a) a compound of Formula 1; and (b) at least one additional component selected from the group consisting of surfactants, solid diluents and liquid diluents.

This invention also relates to a fungicidal composition comprising (a) a compound of Formula 1; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed or bud of a vegetative propagation unit such as tuber, corm or rhizome.

In the above recitations, the term "alkyl", used either alone or in compound words such as "alkylthio" or "haloalkyl" includes straight-chain and branched alkyl, such as, methyl, ethyl, n-propyl, i-propyl, and the different butyl, pentyl and hexyl isomers. "Alkenyl" includes straight-chain and branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain and branched alkynes such as ethynyl, 1-propynyl, 2-propynyl, and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene isomers. "Alkenylene" denotes a straight-chain or branched alkenediyl containing one olefinic bond. Examples of "alkenylene" include CH=CH, $CH_2$CH=CH and CH=C($CH_3$).

"Alkoxy" includes, for example, methoxy, ethoxy, n-propyloxy, i-propyloxy, and the different butoxy, pentoxy and hexyloxy isomers. "Alkenyloxy" includes straight-chain and branched alkenyl attached to and linked through an oxygen atom. Examples of "alkenyloxy" include $H_2$C=CHCH$_2$O, $CH_3$CH=CHCH$_2$O and ($CH_3$)$_2$C=CHCH$_2$O. "Alkynyloxy" includes straight-chain and branched alkynyloxy moieties. Examples of "alkynyloxy" include HC≡CCH$_2$O, $CH_3$C≡CCH$_2$O and $CH_3$C≡CCH$_2$CH$_2$O. The term "alkylthio" includes straight-chain and branched alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$, and the different butylsulfinyl, pentylsulfinyl and hexylsulfinyl isomers. Examples of "alkylsulfonyl" include $CH_3S(=O)_2$, $CH_3CH_2S(=O)_2$, $CH_3CH_2CH_2S(=O)_2$, $(CH_3)_2CHS(=O)_2$, and the different butylsulfonyl, pentylsulfonyl and hexylsulfonyl isomers. "Alkylamino" includes an NH radical substituted with a straight-chain or branched alkyl group. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$.

"Alkylcarbonyl" denotes a straight-chain or branched alkyl group bonded to a $C(=O)$ moiety. Examples of "alkylcarbonyl" include $CH_3C(=O)$, $CH_3CH_2CH_2C(=O)$ and $(CH_3)_2CHC(=O)$. Examples of "alkoxycarbonyl" include $CH_3C(=O)$, $CH_3CH_2OC(=O)$, $CH_3CH_2CH_2C(=O)$, $(CH_3)_2CHOC(=O)$, and the different butoxy- and pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$, and the different butylamino- and pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CH(CH_3)NC(=O)$ and $CH_3CH_2CH_2(CH_3)NC(=O)$.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on another alkoxy moiety. "Alkoxyalkoxyalkyl" denotes alkoxyalkoxy substitution on alkyl. Examples of "alkoxyalkoxyalkyl" include $CH_3OCH_2OCH_2$ $CH_3OCH_2OCH_2CH_2$ and $CH_3CH_2OCH_2OCH_2$.

"Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonylalkyl" include the corresponding sulfoxides and sulfones, respectively. "Alkylcarbonylthio" denotes a straight-chain or branched alkylcarbonyl attached to and linked through a sulfur atom. Examples of "alkylcarbonylthio" include $CH_3C(=O)S$, $CH_3CH_2CH_2C(=O)S$ and $(CH_3)_2CHC(=O)S$.

"Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2CH_2NHCH_2$ and $CH_3CH_2NHCH_2CH_2$. Examples of "dialkylaminoalkyl" include $((CH_3)_2CH)_2NCH_2$, $(CH_3CH_2CH_2)_2NCH_2$ and $CH_3CH_2(CH_3)NCH_2CH_2$.

The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$. "Alkylsulfonylamino" denotes an NH radical substituted with alkylsulfonyl. Examples of "alkylsulfonylamino" include $CH_3CH_2S(=O)_2NH$ and $(CH_3)_2CHS(=O)_2NH$.

The term "alkylcarbonyloxy" denotes a straight-chain or branched alkyl bonded to a $C(=O)O$ moiety. Examples of "alkylcarbonyloxy" include $CH_3CH_2C(=O)O$ and $(CH_3)_2CHC(=O)O$. The term "alkylcarbonylalkoxy" denotes alkylcarbonyl bonded to an alkoxy moiety. Examples of "alkylcarbonylalkoxy" include $CH_3C(=O)CH_2CH_2O$ and $CH_3CH_2C(=O)CH_2O$. Examples of "alkoxycarbonyloxy" include $CH_3CH_2C(=O)O$ and $(CH_3)_2CHOC(=O)O$.

The term "alkylaminocarbonyloxy" denotes a straight-chain or branched alkylaminocarbonyl attached to and linked through an oxygen atom. Examples of "alkylaminocarbonyloxy" include $(CH_3)_2CHCH_2NHC(=O)O$ and $CH_3CH_2NHC(=O)O$. Examples of "dialkylaminocarbonyloxy" include $CH_3CH_2CH_2(CH_3)NC(=O)O$ and $(CH_3)_2NC(=O)O$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to a straight-chain or branched alkyl group. The term "alkylcycloalkyl" denotes alkyl substitution on a cycloalkyl moiety and includes, for example, ethylcyclopropyl, i-propylcyclobutyl, methylcyclopentyl and methylcyclohexyl. "Cycloalkenyl" includes groups such as cyclopentenyl and cyclohexenyl as well as groups with more than one double bond such as 1,3- or 1,4-cyclohexadienyl.

The term "cycloalkoxy" denotes cycloalkyl attached to and linked through an oxygen atom such as cyclopentyloxy and cyclohexyloxy. The term "cycloalkylthio" denotes cycloalkyl attached to and linked through a sulfur atom such as cyclopropylthio and cyclopentylthio; "cycloalkylsulfonyl" includes the corresponding sulfones. The term "cycloalkoxyalkyl" denotes cycloalkoxy substitution on an alkyl moiety. Examples of "cycloalkoxyalkyl" include cyclopropyloxymethyl, cyclopentyloxyethyl, and other cycloalkoxy groups bonded to a straight-chain or branched alkyl moiety. "Cycloalkylalkoxy" denotes cycloalkyl substitution on an alkoxy moiety. Examples of "cycloalkylalkoxy" include cyclopropylmethoxy, cyclopentylethoxy, and other cycloalkyl groups bonded to a straight-chain or branched alkoxy moiety.

"Alkylcycloalkylalkyl" denotes an alkyl group substituted with alkylcycloalkyl. Examples of "alkylcycloalkylalkyl" include methylcyclohexylmethyl and ethylcycloproylmethyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

"Cycloalkylamino" denotes an NH radical substituted with cycloalkyl. Examples of "cycloalkylamino" include cyclopropylamino and cyclohexylamino. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to a straight-chain or branched alkyl group.

"Cycloalkylcarbonyl" denotes cycloalkyl bonded to a $C(=O)$ group including, for example, cyclopropylcarbonyl and cyclopentylcarbonyl. The term "cycloalkoxycarbonyl" means cycloalkoxy bonded to a $C(=O)$ group, for example, cyclopropyloxycarbonyl and cyclopentyloxycarbonyl. "Cycloalkylaminocarbonyl" denotes cycloalkylamino bonded to a $C(=O)$ group, for example, cyclopentylaminocarbonyl and cyclohexylaminocarbonyl. "Cycloalkylalkoxycarbonyl" denotes cycloalkylalkoxy bonded to a $C(=O)$ group. Examples of "cycloalkylalkoxycarbonyl" include cyclopropylethoxycarbonyl and cyclopentylmethoxycarbonyl. "Cycloalkylcarbonyloxy" denotes cycloalkylcarbonyl attached to and linked through an oxygen atom. Examples of "cycloalkylcarbonyloxy" include cyclohexylcarbonyloxy and cyclopentylcarbonyloxy.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkenyl," "haloalkynyl" "haloalkoxy", "haloalkylthio", "haloalkylamino", "haloalkylsulfinyl", "haloalkylsulfonyl", "halocycloalkyl", and the like, are defined analogously to the term "haloalkyl". Examples of "haloalkenyl" include $Cl_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $F_2CHCH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylamino" include $CF_3(CH_3)CHNH$, $(CF_3)_2CHNH$ and $CH_2ClCH_2NH$. Examples of "haloalkylsulfinyl" include $CF_3S(=O)$, $CCl_3S(=O)$, $CF_3CH_2S(=O)$ and $CF_3CF_2S(=O)$. Examples of "haloalkylsulfonyl" include $CF_3S(=O)_2$, $CCl_3S(=O)_2$, $CF_3CH_2S(=O)_2$ and $CF_3CF_2S(=O)_2$. Examples of "halocycloalkyl" include 2-chlorocyclopropyl, 2-fluorocyclobutyl, 3-bromocyclopentyl and 4-chorocyclohexyl. The term "halodialkyl", either alone or in compound words such as "halodialkylamino", means at least one of the two alkyl groups is substituted with at least one halogen atom, and independently each halogenated alkyl group may be partially or fully substituted with halogen atoms which may be the same or different. Examples of "halodialkylamino" include $(BrCH_2CH_2)_2N$ and $BrCH_2CH_2(ClCH_2CH_2)N$.

"Hydroxyalkyl" denotes an alkyl group substituted with one hydroxy group. Examples of "hydroxyalkyl" include $HOCH_2CH_2$, $CH_3CH_2(OH)CH$ and $HOCH_2CH_2CH_2$.

"Trialkylsilyl" includes 3 branched and/or straight-chain alkyl radicals attached to and linked through a silicon atom, such as trimethylsilyl, triethylsilyl and tert-butyldimethylsilyl.

The total number of carbon atoms in a substituent group is indicated by the "$C_i$-$C_j$" prefix where i and j are numbers from 1 to 14. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "unsubstituted" in connection with a group such as a ring or ring system means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 4. As used herein, the term "optionally substituted" is used interchangeably with the phrase "substituted or unsubstituted" or with the term "(un)substituted." When a group (e.g., J) contains a substituent (e.g., $R^6$) which can be hydrogen, then when this substituent is taken as hydrogen, it is recognized that this is equivalent to said group being unsubstituted.

The number of optional substituents may be restricted by an expressed limitation. For example, the phrase "optionally substituted with up to 3 substituents independently selected from $R^6$" means that 0, 1, 2 or 3 substituents can be present (if the number of potential connection points allows). Similarly, the phrase "optionally substituted with up to 5 substituents independently selected from $R^6$" means that 0, 1, 2, 3, 4 or 5 substituents can be present if the number of available connection points allows. When a range specified for the number of substituents (e.g., x being an integer from 1 to 5 in Exhibit 3) exceeds the number of positions available for substituents on a ring (e.g., 2 positions available for $(R^6)_x$ on J-1 in Exhibit 3), the actual higher end of the range is recognized to be the number of available positions.

When a compound is substituted with a substituent bearing a subscript that indicates the number of said substituents can vary (e.g., $(R^6)_x$ in Exhibit 3 wherein x is 1 to 5), then said substituents are independently selected from the group of defined substituents, unless otherwise indicated. When a variable group is shown to be optionally attached to a position, for example $(R^{6a})_p$ in Exhibit 5 wherein p may be 0, then hydrogen may be at the position even if not recited in the definition of the variable group.

The term "optionally substituted" without recitation of number or identity of possible substituents (e.g., in definition of rings in G and $R^3$) refers to groups which are unsubstituted or have at least one non-hydrogen substituent that does not extinguish the biological activity possessed by the unsubstituted analog.

Naming of substituents in the present disclosure uses recognized terminology providing conciseness in precisely conveying to those skilled in the art the chemical structure. For sake of conciseness, locant descriptors may be omitted.

Unless otherwise indicated, a "ring" or "ring system" as a component of Formula 1 (e.g., substituent J and Q) is carbocyclic or heterocyclic. The term "ring system" denotes two or more connected rings. The term "spirocyclic ring system" denotes a ring system consisting of two rings connected at a single atom (so the rings have a single atom in common). Illustrative of a J moiety that is a spirocyclic ring system is J-29-27 shown in Exhibit A below. The term "bicyclic ring system" denotes a ring system consisting of two rings sharing two or more common atoms. In a "fused bicyclic ring system" the common atoms are adjacent, and therefore the rings share two adjacent atoms and a bond connecting them. In a "bridged bicyclic ring system" the common atoms are not adjacent (i.e. there is no bond between the bridgehead atoms). A "bridged bicyclic ring system" can be formed by bonding a segment of one or more atoms to nonadjacent ring members of a ring.

A ring, a bicyclic ring system or a spirocyclic ring system can be part of an extended ring system containing more than two rings wherein substituents on the ring, bicyclic ring system or spirocyclic ring system are taken together to form the additional rings, which may be in bicyclic and/or spirocyclic relationships with other rings in the extended ring system. For example, the J moiety J-29-30 shown in Exhibit A below consists of a dihydro isoxazoline ring substituted with one $R^6$ substituent which is —$Z^2Q$ wherein $Z^2$ is a —$CH_2$— group and Q is a phenyl ring substituted with an $R^{6a}$ substituent (—$CH_2$—) which is taken together with another $R^6$ substituent (—$CH_2$—) on the dihydro isoxazoline ring to form the additional six-membered ring in the ring system.

The term "ring member" refers to an atom (e.g., C, O, N or S) or other moiety (e.g., C(=O), C(=S), SiR$^9$R$^{10}$ or S(=O)$_s$(=NR$^{11}$)$_f$) forming the backbone of a ring or ring system. The term "aromatic" indicates that each of ring atom is essentially in the same plane and has a p-orbital perpendicular to the ring plane, and that (4n+2) π electrons, where n is a positive integer, are associated with the ring to comply with Hückel's rule The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

As used herein, the term "partially unsaturated ring" or "partially unsaturated heterocycle" refers to a ring which contains unsaturated ring atoms and one or more double bonds but which is not aromatic, for example a 4,5-dihydro-1H-pyrazol-1-yl ring.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or aromatic heterocyclic ring. "Saturated heterocyclic ring" refers to a heterocyclic ring containing only single bonds between ring members.

Unless otherwise indicated, heterocyclic rings and ring systems are attached to the remainder of Formula 1 through any available carbon or nitrogen atom by replacement of a hydrogen on said carbon or nitrogen atom.

The dotted line in Formula 1 and in other rings depicted in the present description indicates that the bond can be a single bond or double bond.

The wavy bond between the nitrogen atom and the atom represented by A in Formula 1, and in other rings depicted in the present description, indicates a single bond and the geometry about the adjacent double (i.e. the bond linking the nitrogen atom to the substituents R$^1$ and R$^2$) is either cis-(E), trans-(Z), or a mixture thereof.

As noted above, J is (inter alia) a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S(=O)$_s$(=NR$^{11}$)$_f$, and the silicon atom ring members are independently selected from SiR$^9$R$^{10}$, each ring or ring system optionally substituted with up to 5 substituents independently selected from R$^6$. In this definition the ring members selected from up to 2 O, up to 2 S, up to 4 N and up to 2 Si atoms are optional, because the number of heteroatom ring members may be zero. When no heteroatom ring members are present, the ring or ring system is carbocyclic. If at least one heteroatom ring member is present, the ring or ring system is heterocyclic. The definition of S(=O)$_s$(=NR$^{11}$)$_f$ allows up to 2 sulfur ring members, which can be oxidized sulfur moieties (e.g., S(=O) or S(=O)$_2$) or unoxidized sulfur atoms (i.e. when s and f are both zero). The nitrogen atom ring members may be oxidized as N-oxides, because compounds relating to Formula 1 also include N-oxide derivatives. The up to 3 carbon atom ring members selected from C(=O) and C(=S) are in addition to the up to 4 heteroatoms selected from up to 2 O, up to 2 S, up to 4 N and up to 2 Si atoms. As the R$^6$ substituents are optional, 0 to 5 substituents may be present, limited only by the number of available points of attachment on J. When the substituent R$^6$ is H, this is not counted as one of the 5 optional substituents. The substituents on silicon atom ring members are separately defined as R$^9$ and R$^{10}$.

As noted above, R$^1$ and R$^2$ may be taken together with the carbon atom to which they are attached to form a 3- to 7-membered ring. This 3- to 7-membered ring includes as a ring member the carbon atom to which the substituents R$^1$ and R$^2$ are attached. The other 2 to 6 ring members are selected from carbon atoms and up to 4 heteroatoms independently selected from up to 2 O, up to 2 S, up to 2 N and up to 2 Si atoms. In this definition the heteroatoms are optional, because the number of heteroatom ring members may be zero. When no heteroatom ring members are present, the ring is carbocyclic. If at least one heteroatom ring member is present, the ring is heterocyclic. The ring is optionally substituted with up to 4 substituents independently selected from halogen, cyano, C$_1$-C$_2$ alkyl, C$_1$-C$_2$ haloalkyl, C$_1$-C$_2$ alkoxy and C$_1$-C$_2$ haloalkoxy on carbon atom ring members and cyano, C$_1$-C$_2$ alkyl and C$_1$-C$_2$ alkoxy on nitrogen atom ring members. The nitrogen atom ring members may be oxidized as N-oxides, because compounds relating to Formula 1 also include N-oxide derivatives.

As noted above, Q is (inter alia) a 3- to 7-membered nonaromatic carbocyclic ring, a 5- to 7-membered nonaromatic heterocyclic ring or an 8- to 11-membered heteroaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S(=O)$_s$(=NR$^{11}$)$_f$, and the silicon atom ring members are independently selected from SiR$^9$R$^{10}$, each ring or ring system optionally substituted with up to 2 substituents independently selected from R$^{6b}$ on carbon and nitrogen atom ring members, up to 5 substituents independently selected from R$^{6a}$ on carbon atom ring members and selected from H, C$_1$-C$_3$ alkyl, C$_2$-C$_3$ alkylcarbonyl, C$_2$-C$_3$ alkoxycarbonyl and C$_1$-C$_3$ alkoxy on nitrogen atom ring members. In this definition the ring members selected from up to 2 O, up to 2 S, up to 4 N and up to 2 Si atoms are optional, because the number of heteroatom ring members may be zero. When no heteroatom ring members are present, the ring or ring system is carbocyclic. If at least one heteroatom ring member is present, the ring or ring system is heterocyclic. The definition of S(=O)$_s$(=NR$^{11}$)$_f$ allows up to 2 sulfur ring members, which can be oxidized sulfur moieties (e.g., S(=O) or S(=O)$_2$) or unoxidized sulfur atoms (i.e. when s and f are both zero). The nitrogen atom ring members may be oxidized as N-oxides, because compounds relating to Formula 1 also include N-oxide derivatives. The up to 3 carbon atom ring members selected from C(=O) and C(=S) are in addition to the up to 4 heteroatoms selected from up to 2 O, up to 2 S, up to 4 N and up to 2 Si atoms.

As noted above, R$^6$ and R$^{6a}$ may be taken together with the atoms to which they are attached to form a 5- to 7-membered ring including as ring members: (a) the two atoms to which the substituents R$^6$ and R$^{6a}$ are directly attached, (b) the intervening (i.e. other linking) atoms of J, Z$^2$ and Q, to which R$^6$ and R$^{6a}$ can be regarded as indirectly attached and (c) the R$^6$ and $R^{6a}$ substituents. The ring members of the ring are selected from carbon atoms and optionally up to 3 heteroatoms independently selected from up to 1 O, up to 1 S and up to 1 N atom. In this definition the ring members selected from up to 1 O, up to 1 S and up to 1 N atom are optional, because the number of heteroatom ring members may be zero. The ring is optionally substituted with up to 3 substituents independently selected from halogen, cyano, nitro, $C_1$-$C_2$ alkyl and $C_1$-$C_2$ alkoxy on carbon atom ring members and from cyano, $C_1$-$C_2$ alkyl and $C_1$-$C_2$ alkoxy on nitrogen atom ring members. These optional substituents (when present) are attached to available carbon and nitrogen atom ring members in the portion of the ring provided by $R^6$ and $R^{6a}$, and are in addition to substituents attached to J, $Z^2$ and Q.

As noted above, $R^2$ and $R^7$ may be taken together with the linking atoms to which they are attached to form a 5- to 7-membered partially unsaturated ring. The linking atoms are the carbon atom to which $R^2$ is directly attached, the nitrogen atom to which $R^7$ is directly attached (only present when A is —N($R^7$)—) and the intervening nitrogen atom depicted as "=N~" in Formula 1. Thus, the three linking atoms are "—C=N~N($R^7$)—". The linking atoms provide 3 ring members of the 5- to 7-membered ring. The other 2 to 4 ring members of the ring are provided by the $R^2$ and $R^7$ substituents. These other ring members are selected from carbon atoms and up to 3 heteroatoms independently selected from up to 1 O, up to 1 S and up to 1 N atom. In this definition the ring members selected from up to 1 O, up to 1 S and up to 1 N atom are optional, because the number of heteroatom ring members may be zero. The ring is optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members. These optional substituents (when present) are attached to available carbon and nitrogen atom ring members in the portion of the ring provided by $R^2$ and $R^7$, and are in addition to $R^1$ and the remainder of Formula 1 attached to the ring. The nitrogen atom ring members may be oxidized as N-oxides, because compounds relating to Formula 1 also include N-oxide derivatives.

As noted above, $R^{16}$ and $R^{19}$ may be taken together with the atoms to which they are attached to form a 3- to 7-membered ring, including as ring members: (a) the two atoms to which the substituents $R^{16}$ and $R^{19}$ are directly attached, (b) the intervening (i.e. other linking) atoms of $R^{15}$, to which $R^{16}$ and $R^{19}$ can be regarded as indirectly attached and (c) the $R^{16}$ and $R^{19}$ substituents. The ring members of the ring are selected from carbon atoms and up to 4 heteroatoms independently selected from up to 2 O, up to 2 S, up to 2 N and up to 2 Si atoms, wherein up to 2 carbon atom ring members are independently selected from C(=O) and C(=S), the sulfur atom ring members are independently selected from S(=O)$_s$(=N$R^{11}$)$_f$, and the silicon atom ring members are independently selected from Si$R^9R^{10}$, the ring optionally substituted with up to 4 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members. In this definition the ring members selected from up to 2 O, up to 2 S, up to 2 N and up to 2 Si atoms are optional, because the number of heteroatom ring members may be zero. The definition of S(=O)$_s$(=N$R^{11}$)$_f$ allows up to 2 sulfur ring members, which can be oxidized sulfur moieties (e.g., S(=O) or S(=O)$_2$) or unoxidized sulfur atoms (i.e. when s and f are both zero). The nitrogen atom ring members may be oxidized as N-oxides, because compounds relating to Formula 1 also include N-oxide derivatives. The up to 2 carbon atom ring members selected from C(=O) and C(=S) are in addition to the up to 4 heteroatoms selected from up to 2 O, up to 2 S, up to 2 N and up to 2 Si atoms. The optional substituents (when present) are attached to available carbon and nitrogen atom ring members in the portion of the ring provided by $R^{16}$ and $R^{19}$. The substituents on silicon atom ring members are separately defined as $R^9$ and $R^{10}$.

Compounds of Formula 1 can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Compounds of Formula 1 may be present as a mixture of stereoisomers, individual stereoisomers, or as an optically active form. For example, when J is J-29 (see Exhibit 3) bonded at the 3-position to the remainder of Formula 1 and has one $R^6$ substituent other than H at the 5-position, then Formula 1 possesses a chiral center at the carbon atom to which $R^6$ is bonded. The two enantiomers are depicted as Formula 1' and Formula 1" below and chiral center identified with an asterisk (*).

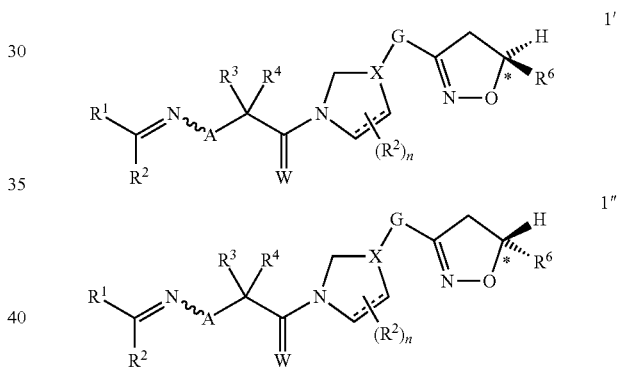

Compounds of Formula 1 comprise racemic mixtures, for example, equal amounts of the enantiomers of Formulae 1' and 1". In addition, compounds of Formula 1 include compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers).

Preferably the compositions of this invention of Formula 1 have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as A, $R^3$, $R^4$, $R^6$, $R^{6a}$, G, J, Q, $X^1$ through $X^9$, Z, $Z^2$ and $Z^3$ may themselves contain chiral centers. Compounds of Formula 1 comprise racemic mixtures as well as enriched and essentially pure stereoconfigurations at these additional chiral centers.

Compounds of Formula 1 can exist as one or more conformational isomers due to restricted rotation about the amide bond (e.g., C(=W)—N) in Formula 1. Compounds of Formula 1 comprise mixtures of conformational isomers. In addition, compounds of Formula 1 include compounds that are enriched in one conformer relative to others.

One skilled in the art recognizes that compounds of Formula 1 can exist in equilibrium with one or more of its respective tautomeric counterparts. Unless otherwise indicated, reference to a compound by one tautomer description is to be considered to include all tautomers. For example, when $R^2$ in Formula 1 is hydroxy, then reference to the tautomeric form depicted by Formula $1^1$ also includes the tautomic form depicted by Formula $1^2$.

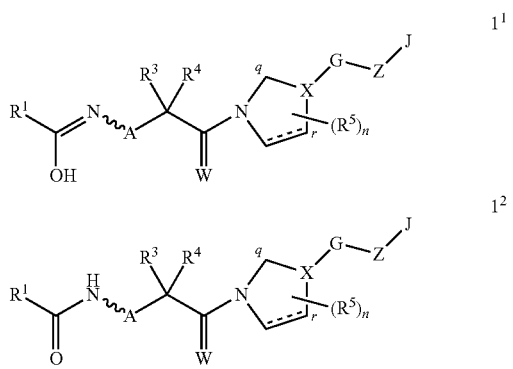

Additionally, some of the unsaturated rings and ring systems depicted in Exhibits 1, 2, 3 and 4 can have an arrangement of single and double bonds between ring members different from that depicted. Such differing arrangements of bonds for a particular arrangement of ring atoms correspond to different tautomers. For these unsaturated rings and ring systems, the particular tautomer depicted is to be considered representative of all the tautomers possible for the arrangement of ring atoms shown.

The compounds of the present invention include N-oxide derivatives of Formula 1. One skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in the literature, see for example: T. L. Gilchrist in Comprehensive Organic Synthesis, vol. 7, pp 748-750, S. V. Ley, Ed., Pergamon Press; M. Tisler and B. Stanovnik in Comprehensive Heterocyclic Chemistry, vol. 3, pp 18-20, A. J. Boulton and A. McKillop, Eds., Pergamon Press; M. R. Grimmett and B. R. T. Keene in Advances in Heterocyclic Chemistry, vol. 43, pp 149-161, A. R. Katritzky, Ed., Academic Press; M. Tisler and B. Stanovnik in Advances in Heterocyclic Chemistry, vol. 9, pp 285-291, A. R. Katritzky and A. J. Boulton, Eds., Academic Press; and G. W. H. Cheeseman and E. S. G. Werstiuk in Advances in Heterocyclic Chemistry, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. When the compounds forming the present mixtures and compositions contain acidic or basic moieties, a wide variety of salts can be formed, and these salts are useful in the present mixtures and compositions for controlling plant diseases caused by fungal plant pathogens (i.e. are agriculturally suitable). When a compound contains a basic moiety such as an amine function, salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound contains an acidic moiety such as a carboxylic acid or phenol, salts include those formed with organic or inorganic bases such as pyridine, triethylamine or ammonia, or amides, hydrides, hydroxides or carbonates of sodium, potassium, lithium, calcium, magnesium or barium.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include those described below. In the following Embodiments, Formula 1 includes geometric and stereoisomers, tautomers, N-oxides, and salts thereof, and reference to "a compound of Formula 1" includes the definitions of substituents specified in the Summary of the Invention unless further defined in the Embodiments.

Embodiment 1. A compound of Formula 1 wherein A is —O—, —S—, —N($R^7$)— or —OC($R^8$)$_2$—.

Embodiment 1a. A compound of Formula 1 or Embodiment 1 wherein each $R^8$ is H.

Embodiment 1b. A compound of Embodiment 1 wherein A is —O—, —S— or —N($R^7$)—.

Embodiment 2. A compound of Embodiment 1b wherein A is —O— or —N($R^7$)—.

Embodiment 3. A compound of Embodiment 2 wherein A is —N($R^7$)—.

Embodiment 3a. A compound of Embodiment 2 wherein A is —O—.

Embodiment 4. A compound of Formula 1 or any one of Embodiments 1 through 3 wherein $R^7$ when taken alone (i.e. not taken together with $R^2$) is H, $C_1$-$C_2$ alkyl, $C_1$-$C_2$ haloalkyl, $CH_3C(=O)$, $CF_3C(=O)$ or $CH_3C(=O)$.

Embodiment 5. A compound of Embodiment 4 wherein $R^7$ when taken alone is H or $C_1$-$C_2$ alkyl.

Embodiment 5a. A compound of Embodiment 5 wherein $R^7$ when taken alone is H or methyl.

Embodiment 5b. A compound of Formula 1 or any one of Embodiments 1 through 5a wherein $R^7$ is taken alone.

Embodiment 6. A compound of Formula 1 or any one of Embodiments 1 through 5b wherein W is O.

Embodiment 7. A compound of Formula 1 or any one of Embodiments 1 through 6 wherein X is $X^1$, $X^2$, $X^3$, $X^4$, $X^5$, $X^6$, $X^7$ or $X^8$.

Embodiment 8. A compound of Embodiment 7 wherein X is $X^1$, $X^2$ or $X^3$.

Embodiment 9. A compound of Embodiment 8 wherein X is $X^1$ or $X^2$.

Embodiment 10. A compound of Embodiment 9 wherein X is $X^1$.

Embodiment 11. A compound of Formula 1 or any one of Embodiments 1 through 10 wherein the ring comprising X is saturated.

Embodiment 12. A compound of Formula 1 or any one of Embodiments 1 through 11 wherein Z is a direct bond, CH($R^{12}$) or N($R^{13}$).

Embodiment 13. A compound of Embodiment 12 wherein Z is a direct bond.

Embodiment 14. A compound of Formula 1 or any one of Embodiments 1 through 12 wherein each $R^{13}$ is independently H, $C_1$-$C_3$ alkyl, $C_2$-$C_3$ alkylcarbonyl or $C_2$-$C_3$ alkoxycarbonyl.

Embodiment 15. A compound of Formula 1 or any one of Embodiments 1 through 14 wherein
each $R^5$ is independently halogen, cyano, hydroxy, $C_1$-$C_4$ alkyl, $C_1$-$C_2$ haloalkyl or $C_1$-$C_2$ alkoxy; or
two $R^5$ groups are taken together as $C_1$-$C_3$ alkylene or $C_2$-$C_3$ alkenylene to form a bridged bicyclic ring system; or
two $R^5$ groups attached to adjacent ring carbon atoms joined by a double bond are taken together as —CH=CH—CH=CH— optionally substituted with up to 2 substituents independently selected from halogen, $C_1$-$C_4$ alkyl, $C_1$-$C_4$ haloalkyl and $C_1$-$C_4$ alkoxy.

Embodiment 16. A compound of Embodiment 15 wherein each $R^5$ is independently halogen, cyano, hydroxy, $C_1$-$C_4$ alkyl, $C_1$-$C_2$ haloalkyl or $C_1$-$C_2$ alkoxy.

Embodiment 17. A compound of Embodiment 16 wherein each $R^5$ is independently halogen, cyano, $C_1$-$C_2$ alkyl, $C_1$-$C_2$ haloalkyl or $C_1$-$C_2$ alkoxy.

Embodiment 18. A compound of Embodiment 17 wherein each $R^5$ is independently cyano, methyl or methoxy.

Embodiment 19. A compound of Embodiment 18 wherein each $R^5$ is methyl.

Embodiment 20. A compound of Formula 1 or any one of Embodiments 1 through 19 wherein n is 0 or 1.

Embodiment 21. A compound of Embodiment 20 wherein n is 0.

Embodiment 22. A compound of Formula 1 or any one of Embodiments 1 through 21 wherein $R^1$ when taken alone (i.e. not taken together with $R^2$) is H, cyano, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_1$-$C_4$ alkoxy, $C_1$-$C_4$ haloalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_1$-$C_4$ alkylthio, $C_1$-$C_4$ haloalkylthio, $C_1$-$C_4$ alkylamino, $C_2$-$C_4$ dialkylamino, $C_1$-$C_4$ haloalkylamino or $C_2$-$C_4$ halodialkylamino.

Embodiment 23. A compound of Embodiment 22 wherein $R^1$ when taken alone is H, cyano, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_1$-$C_3$ alkoxy or $C_1$-$C_3$ haloalkoxy.

Embodiment 24. A compound of Embodiment 23 wherein $R^1$ when taken alone is H, $C_1$-$C_3$ alkyl or $C_1$-$C_3$ haloalkyl.

Embodiment 25. A compound of Embodiment 24 wherein $R^1$ when taken alone is H, $C_1$-$C_3$ alkyl or $C_1$-$C_3$ fluoroalkyl.

Embodiment 26. A compound of Embodiment 25 wherein $R^1$ when taken alone is H, methyl, trifluoromethyl or $CF_3CH_2$.

Embodiment 26a. A compound of Embodiment 26 wherein $R^1$ when taken alone is methyl, trifluoromethyl or $CF_3CH_2$.

Embodiment 26a. A compound of Formula 1 or any one of Embodiments 1 through 26 wherein $R^1$ is taken alone.

Embodiment 27. A compound of Formula 1 or any one of Embodiments 1 through 26a wherein $R^2$ when taken alone (i.e. not taken together with $R^1$ or $R^7$) is H, $C_1$-$C_3$ alkyl, $C_1$-$C_3$ alkoxy or $C_1$-$C_3$ haloalkyl.

Embodiment 28. A compound of Embodiment 27 wherein $R^2$ when taken alone is H, $C_1$-$C_3$ alkyl or $C_1$-$C_3$ haloalkyl.

Embodiment 29. A compound of Embodiment 28 wherein $R^2$ when taken alone is H, $C_1$-$C_2$ alkyl or $C_1$-$C_3$ fluoroalkyl.

Embodiment 29a. A compound of Embodiment 29 wherein $R^2$ when taken alone is H, methyl or trifluoromethyl.

Embodiment 29b. A compound of Formula 1 or any one of Embodiments 1 through 29a wherein $R^2$ is taken alone.

Embodiment 30. A compound of Formula 1 or any one of Embodiments 1 through 29b wherein when $R^1$ and $R^2$ are taken together with the carbon atom to which they are attached to form a ring, said ring has 3- to 6-members selected from carbon atoms and up to 2 heteroatoms independently selected from up to 2 O, up to 2 S and up to 2 N, wherein up to 1 carbon atom ring member is C(=O) or C(=S) and the ring is optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

Embodiment 30a. A compound of Embodiment 30 wherein $R^1$ and $R^2$ are taken together with the carbon atom to which they are attached to form the ring defined in Embodiment 30.

Embodiment 31. A compound of Formula 1 or any one of Embodiments 1 through 30a wherein when $R^2$ and $R^7$ are taken together with the linking atoms to which they are attached to form a 5- to 7-membered partially unsaturated ring, said ring contains members, in addition to the linking atoms, selected from carbon atoms and up to 3 heteroatoms independently selected from up to 1 O, up to 1 S and up to 1 N atom, the ring is optionally substituted with up to 2 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

Embodiment 31a. A compound of Embodiment 31 wherein $R^2$ and $R^7$ are taken together with the linking atoms to which they are attached to form the ring defined in Embodiment 31.

Embodiment 32. A compound of Embodiment 31 wherein when $R^2$ and $R^7$ are taken together with the linking atoms to which they are attached to form a 5- to 7-membered partially unsaturated ring, said ring contains ring members, in addition to the linking atoms, selected from carbon atoms and up to 3 heteroatoms independently selected from up to 1 O, up to 1 S and up to 1 N atom, the ring is optionally substituted on carbon atom ring members with up to 2 substituents independently selected from halogen and $C_1$-$C_2$ alkyl.

Embodiment 32a. A compound of Embodiment 32 wherein $R^2$ and $R^7$ are taken together with the linking atoms to which they are attached to form the ring defined in Embodiment 32.

Embodiment 32b. A compound of Embodiment 32 wherein when $R^2$ and $R^7$ are taken together with the linking atoms to which they are attached to form a 5- to 7-membered partially unsaturated ring, said ring contains ring members, in addition to the linking atoms, selected from carbon atoms, the ring is optionally substituted with up to 2 substituents independently selected from $C_1$-$C_2$ alkyl.

Embodiment 32c. A compound of Embodiment 32b wherein $R^2$ and $R^7$ are taken together with the linking atoms to which they are attached to form the ring defined in Embodiment 32b.

Embodiment 33. A compound of Formula 1 or any one of Embodiments 1 through 32a wherein $R^3$ is optionally substituted phenyl, optionally substituted naphthalenyl or an optionally substituted 5- to 6-membered heteroaromatic ring; or H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 34. A compound of Embodiment 33 wherein $R^3$ is H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 35. A compound of Embodiment 34 wherein $R^3$ is H, cyano, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 36. A compound of Embodiment 35 wherein $R^3$ is H, cyano, methyl, methoxy or $CH_3C(\!\!=\!\!O)O\!\!-\!\!$.

Embodiment 37. A compound of Embodiment 36 wherein $R^3$ is H or methyl.

Embodiment 37a. A compound of Embodiment 37 wherein $R^3$ is H.

Embodiment 38. A compound of Formula 1 or any one of Embodiments 1 through 33 wherein when $R^3$ is optionally substituted phenyl, optionally substituted naphthalenyl or an optionally substituted 5- to 6-membered heteroaromatic ring, the optionally substituted phenyl, optionally substituted naphthalenyl or optionally substituted 5- to 6-membered heteroaromatic ring is substituted with up to 3 optional substituents.

Embodiment 38a. A compound of Embodiment 38 wherein when $R^3$ is optionally substituted phenyl, optionally substituted naphthalenyl or an optionally substituted 5- to 6-membered heteroaromatic ring, the optionally substituted phenyl, optionally substituted naphthalenyl or optionally substituted 5- to 6-membered heteroaromatic ring is substituted with up to 2 optional substituents.

Embodiment 38b. A compound of Formula 1 or any one of Embodiments 1 through 38a wherein when $R^3$ is optionally substituted phenyl, optionally substituted naphthalenyl or an optionally substituted 5- to 6-membered heteroaromatic ring, then the optional substituents on the phenyl, naphthalenyl or 5- to 6-membered heteroaromatic ring are independently selected from $R^{25a}$ on carbon atom ring members and $R^{25b}$ on nitrogen atom ring members;

each $R^{25a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and each $R^{25b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 39. A compound of Embodiment 38b wherein each $R^{25a}$ is independently halogen, $C_1$-$C_2$ alkyl, $C_1$-$C_2$ haloalkyl or $C_1$-$C_2$ alkoxy.

Embodiment 40. A compound of Embodiment 39 wherein each $R^{25a}$ is independently Cl, Br, I, $C_1$-$C_2$ alkyl, trifluoromethyl or methoxy.

Embodiment 41. A compound of Embodiment 40 wherein each $R^{25a}$ is independently Cl, Br, $C_1$-$C_2$ alkyl or trifluoromethyl.

Embodiment 41a. A compound of Embodiment 38b wherein each $R^{25b}$ is independently $C_1$-$C_2$ alkyl, cyclopropyl or $C_2$-$C_4$ alkoxyalkyl.

Embodiment 41b. A compound of Embodiment 41a wherein each $R^{25b}$ is methyl.

Embodiment 42. A compound of Formula 1 or any one of Embodiments 1 through 41 wherein when $R^3$ is optionally substituted phenyl, optionally substituted naphthalenyl or an optionally substituted 5- to 6-membered heteroaromatic ring, then $R^3$ is other than optionally substituted naphthalenyl.

Embodiment 43. A compound of Formula 1 or any one of Embodiments 1 through 42 wherein when $R^3$ is optionally substituted phenyl or an optionally substituted 5- to 6-membered heteroaromatic ring, then $R^3$ is selected from U-1 through U-11 in Exhibit 1

Exibit 1

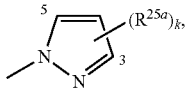 U-1

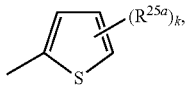 U-2

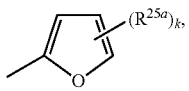 U-3

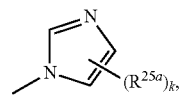 U-4

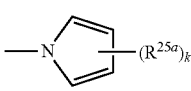 U-5

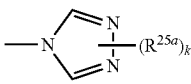 U-6

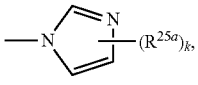 U-7

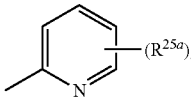 U-8

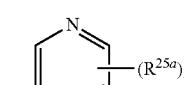 U-9

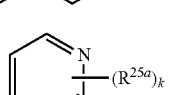 U-10

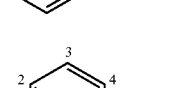 U-11 wherein the bond projecting to the left is connected to Formula 1; and k is 0, 1 or 2.

Embodiment 44. A compound of Embodiment 43 wherein $R^3$ is selected from U-1, U-4 and U-11.

Embodiment 45. A compound of Embodiment 44 wherein $R^3$ is U-1.

Embodiment 45a. A compound of any one of Embodiments 33 through 45 wherein when $R^3$ is optionally substituted phenyl or an optionally substituted 5- to 6-membered heteroaromatic ring, then $R^3$ is selected from U-1 through U-11; or when $R^3$ is H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy; then $R^3$ is selected H, cyano, hydroxy, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 46. A compound of Formula 1 or any one of Embodiments 1 through 45a wherein $R^4$ is H or $C_1$-$C_2$ alkyl.

Embodiment 47. A compound of Embodiment 46 wherein $R^4$ is H.

Embodiment 48. A compound of Formula 1 or any one of Embodiments 1 through 47 wherein G is a 5-membered heterocyclic ring, optionally substituted with up to 2 substituents independently selected from $R^{26}$ on carbon atom ring members and $R^{27}$ on nitrogen atom ring members;

each $R^{26}$ is independently halogen, $C_1$-$C_3$ alkyl or $C_1$-$C_3$ haloalkyl; and each $R^{27}$ is independently $C_1$-$C_3$ alkyl.

Embodiment 49. A compound of Embodiment 48 wherein G is a 5-membered heterocyclic ring selected from the group consisting of G-1 through G-59 in Exhibit 2

Exhibit 2

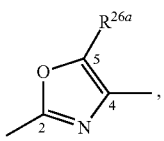 G-1

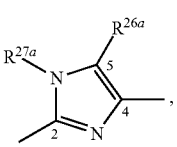 G-2

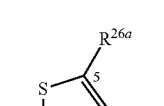 G-3

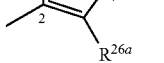 G-4

-continued
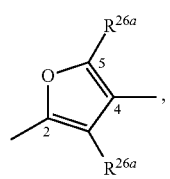  G-5
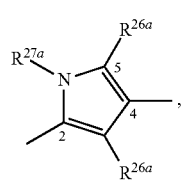  G-6
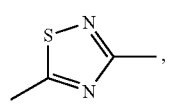  G-7
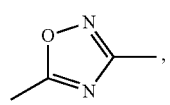  G-8
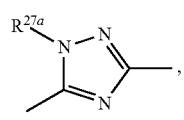  G-9
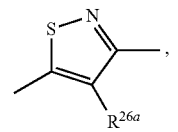  G-10
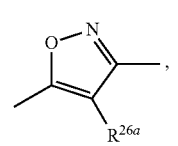  G-11
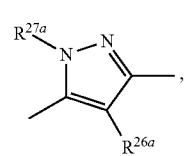  G-12
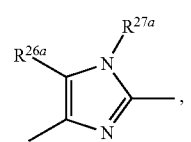  G-13
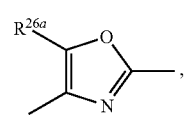  G-14
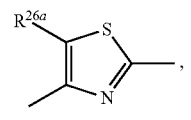  G-15
-continued
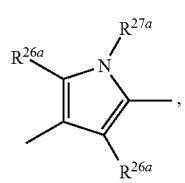  G-16
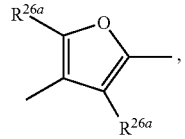  G-17
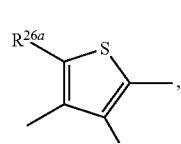  G-18
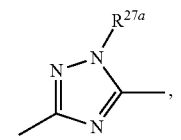  G-19
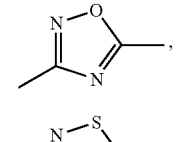  G-20
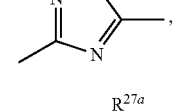  G-21
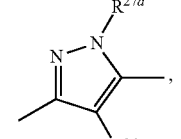  G-22
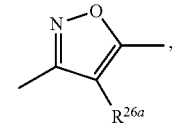  G-23
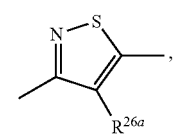  G-24
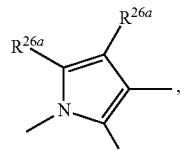  G-25
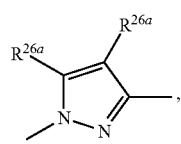  G-26

-continued
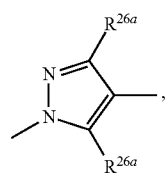 G-27
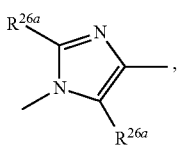 G-28
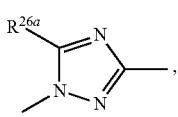 G-29
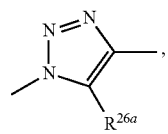 G-30
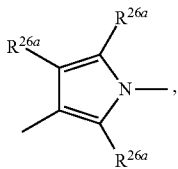 G-31
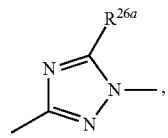 G-32
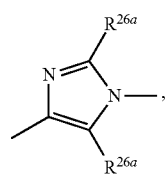 G-33
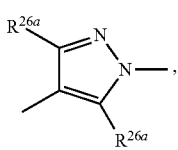 G-34
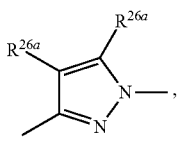 G-35
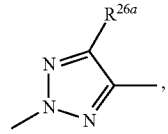 G-36
-continued
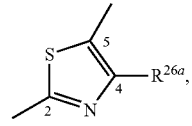 G-37
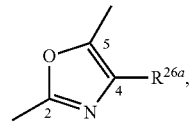 G-38
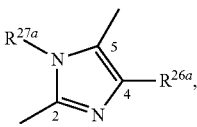 G-39
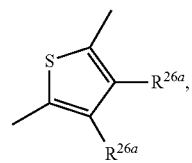 G-40
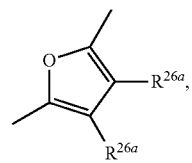 G-41
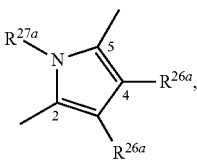 G-42
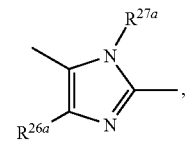 G-43
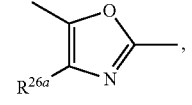 G-44
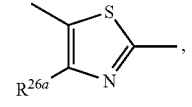 G-45
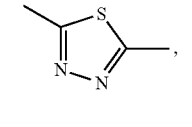 G-46
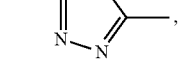 G-47

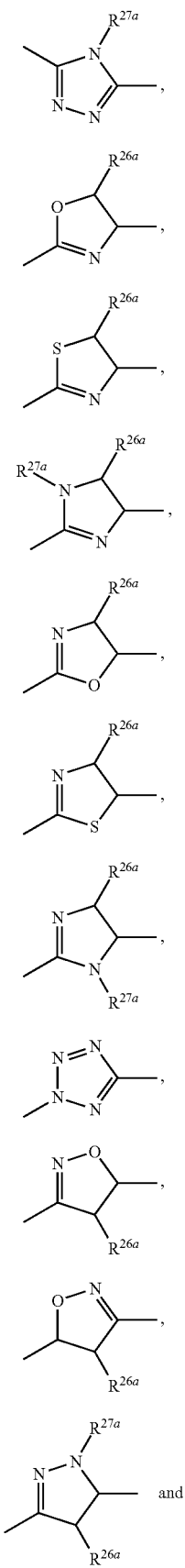

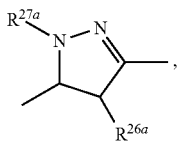

wherein the bond projecting to the left is connected to X, and the bond projecting to the right is connected to Z in Formula 1; each $R^{26a}$ is independently selected from H and $R^{26}$; and $R^{27a}$ is selected from H and $R^{27}$.

Embodiment 50. A compound of Embodiment 49 wherein G is selected from G-1 through G-3, G-7, G-8, G-10, G-11, G-14, G-15, G-23, G-24, G-26 through G-28, G-30, G-36 through G-38 and G-49 through G-55.

Embodiment 51. A compound of Embodiment 50 wherein G is selected from G-1, G-2, G-7, G-8, G-14, G-15, G-23, G-24, G-26, G-27, G-36, G-37, G-38, G-49, G-50 and G-55.

Embodiment 52. A compound of Embodiment 51 wherein G is selected from G-1, G-2, G-15, G-26, G-27, G-36, G-37 and G-38.

Embodiment 53. A compound of Embodiment 52 wherein G is selected from G-1, G-2, G-15, G-26 and G-36.

Embodiment 54. A compound of Embodiment 53 wherein G is G-1.

Embodiment 55. A compound of Embodiment 53 wherein G is G-2.

Embodiment 56. A compound of Embodiment 53 wherein G is G-15.

Embodiment 57. A compound of Embodiment 53 wherein G is G-26.

Embodiment 58. A compound of Embodiment 53 wherein G is G-36.

Embodiment 59. A compound of any one of Embodiments 49 through 58 wherein each $R^{26a}$ is independently H, halogen or $C_1$-$C_3$ alkyl.

Embodiment 60. A compound of Embodiment 59 wherein each $R^{26a}$ is independently H or methyl.

Embodiment 61. A compound of Embodiment 60 wherein each $R^{26a}$ is H.

Embodiment 62. A compound of any one of Embodiments 49 through 61 wherein each $R^{27}$ is independently H or methyl.

Embodiment 62a. A compound of Embodiment 62 wherein each $R^{27a}$ is H.

Embodiment 62b. A compound of Formula 1 or any one of Embodiments 48 through 62b wherein G is a heterocyclic ring unsubstituted except for its attachments to X and Z.

Embodiment 63. A compound of Formula 1 or any one of Embodiments 1 through 62b wherein J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from S(=O)$_s$, (=NR$^{11}$)$_p$, each ring or ring system is optionally substituted with up to 5 substituents independently selected from R$^6$; or when Z is a direct bond then J is also C(=W$^2$)NT$^A$T$^B$.

Embodiment 63a. A compound of Embodiment 63 wherein J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from S(=O)$_s$(=NR$^{11}$)$_f$, each ring or ring system substituted with 1 substituent which is —Z$^2$Q and optionally substituted with up to 3 substituents independently selected from R$^6$ other than —Z$^2$Q or when Z is a direct bond then J is also C(=W$^2$)NT$^A$T$^B$.

Embodiment 63b. A compound of Embodiment 63a wherein J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from S(=O)$_s$(=NR$^{11}$)$_f$, each ring or ring system substituted with 1 substituent which is —Z$^2$Q and optionally substituted with up to 1 substituent selected from R$^6$ other than —Z$^2$Q; or when Z is a direct bond then J is also C(=W$^2$)NT$^A$T$^B$.

Embodiment 63c. A compound of Embodiment 63 wherein J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from S(=O)$_s$(=NR$^{11}$)$_f$, each ring or ring system substituted with 1 or 2 substituents independently selected from R$^6$ other than —Z$^2$Q; or when Z is a direct bond then J is also C(=W$^2$)NT$^A$T$^B$.

Embodiment 64. A compound of Embodiment 63 wherein when J is other than C(=W$^2$)NT$^A$T$^B$, then J is a ring selected from J-1 through J-82 in Exhibit 3

Exhibit 3

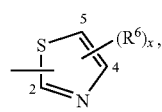
J-1

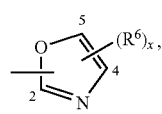
J-2

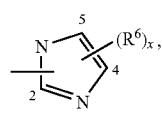
J-3

-continued

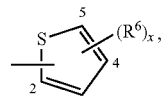
J-4

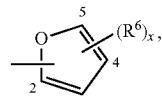
J-5

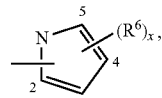
J-6

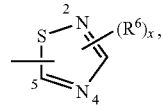
J-7

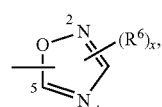
J-8

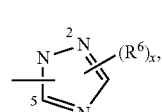
J-9

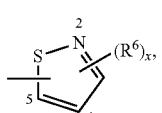
J-10

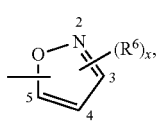
J-11

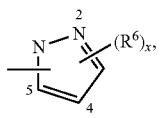
J-12

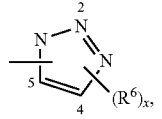
J-13

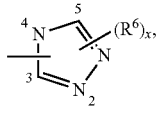
J-14

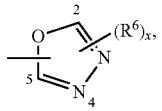
J-15

-continued
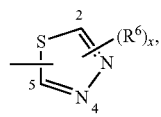　J-16
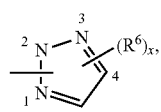　J-17
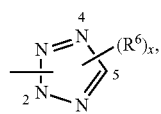　J-18
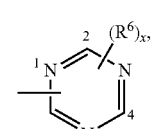　J-19
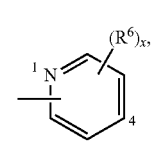　J-20
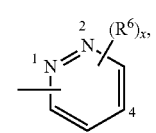　J-21
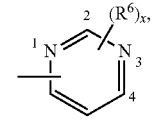　J-22
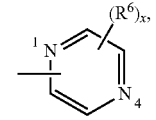　J-23
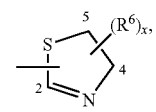　J-24
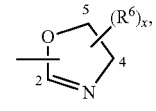　J-25
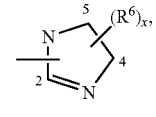　J-26
-continued
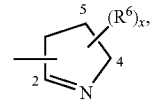　J-27
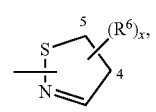　J-28
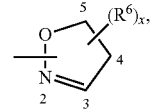　J-29
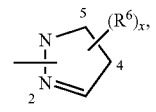　J-30
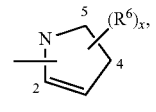　J-31
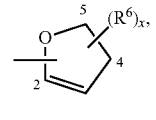　J-32
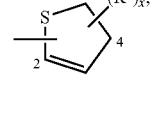　J-33
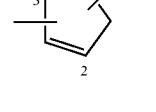　J-34
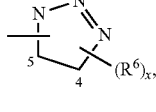　J-35
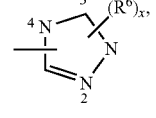　J-36
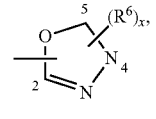　J-37
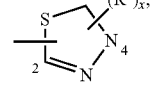　J-38

J-39 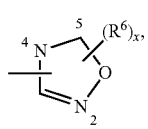
J-40 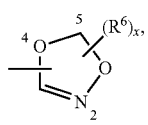
J-41 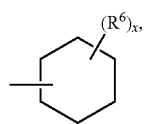
J-42 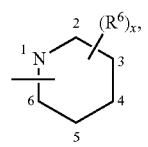
J-43 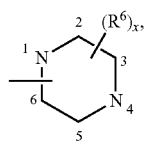
J-44 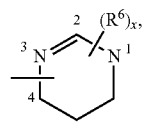
J-45 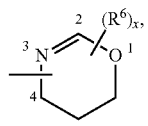
J-46 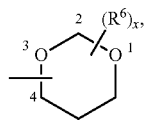
J-47 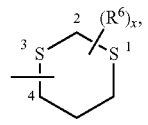
J-48 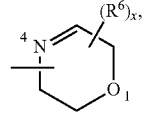
J-49 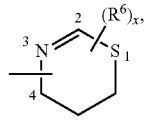
J-50 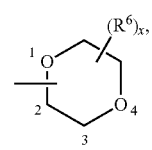
J-51 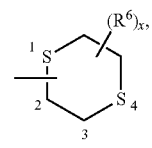
J-52 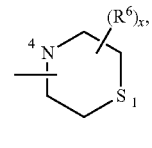
J-53 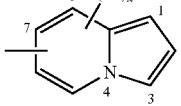
J-54 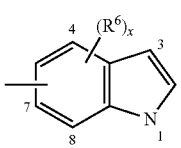
J-55 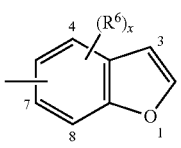
J-56 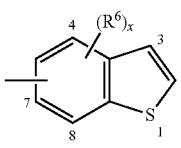
J-57 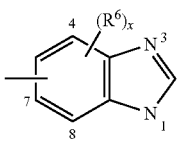
J-58 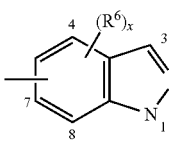
J-59 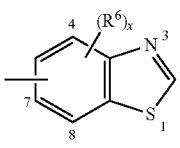

-continued
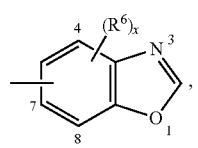 J-60
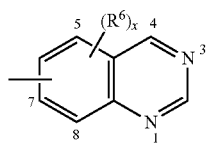 J-61
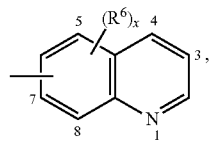 J-62
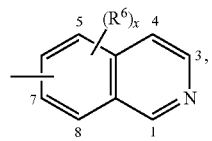 J-63
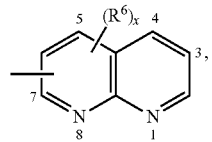 J-64
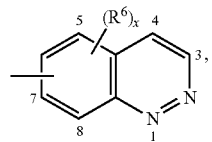 J-65
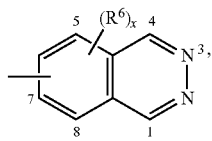 J-66
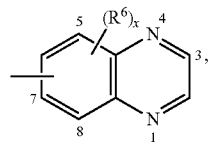 J-67
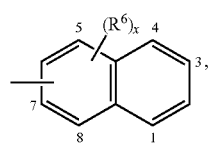 J-68
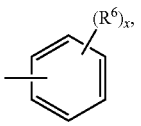 J-69
-continued
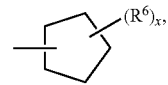 J-70
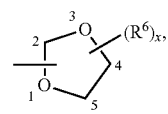 J-71
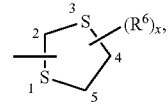 J-72
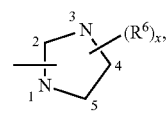 J-73
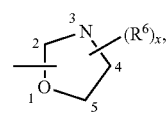 J-74
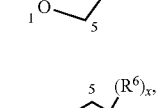 J-75
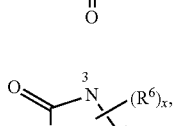 J-76
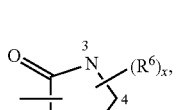 J-77
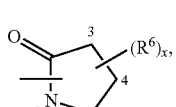 J-78
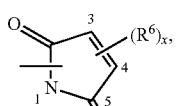 J-79
J-80

-continued

J-81

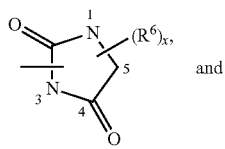

and

J-82

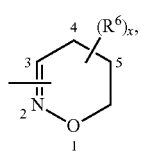

wherein the floating bond is connected to Z in Formula 1 through any available carbon or nitrogen atom of the depicted ring or ring system; and x is an integer from 0 to 5.

Embodiment 64a. A compound of Embodiment 64 wherein J is a ring selected from the group consisting of J-1 through J-82, x is an integer from 1 to 5, and when x is 2, 3, 4 or 5, then at most one instance of $R^6$ is —$Z^2Q$.

Embodiment 65. A compound of Embodiment 64 or 64a wherein J is a ring selected from the group consisting of J-29-1 through J-29-60 in Exhibit A.

Exhibit A

J-29-1

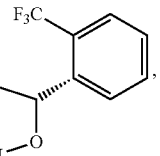

J-29-2

J-29-3

J-29-4

J-29-5

-continued

J-29-6

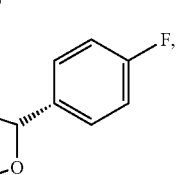

J-29-7

J-29-8

J-29-9

J-29-10

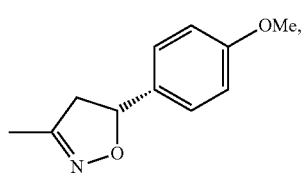

J-29-11

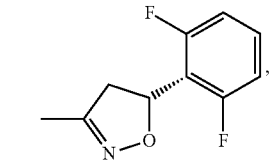

J-29-12

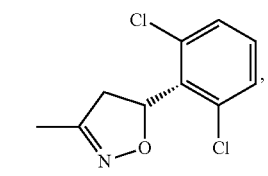

J-29-13

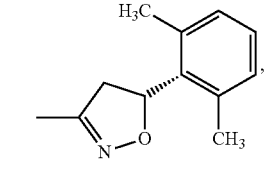

J-29-14

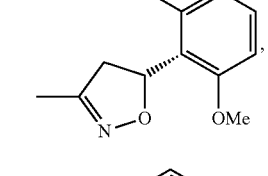

J-29-15 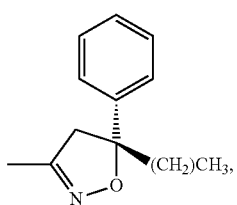
J-29-16 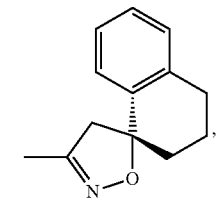
J-29-17 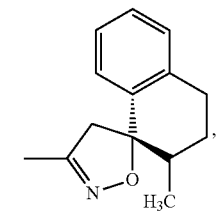
J-29-18 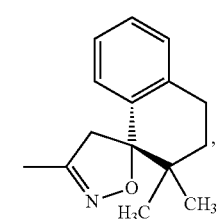
J-29-19 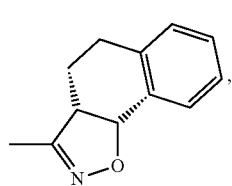
J-29-20 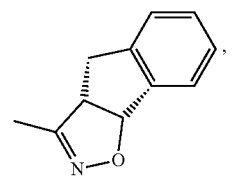
J-29-21 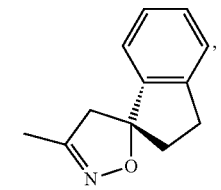
J-29-22 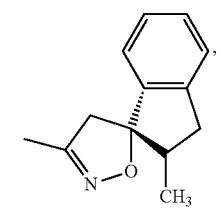
J-29-23 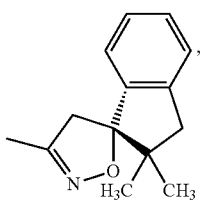
J-29-24 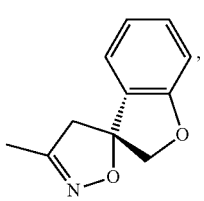
J-29-25 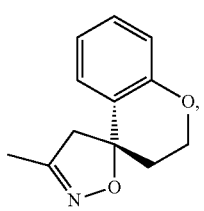
J-29-26 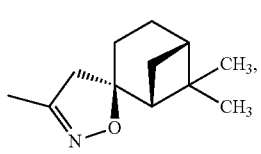
J-29-27 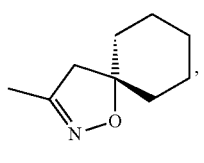
J-29-28 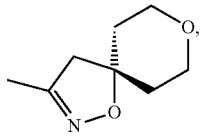
J-29-29 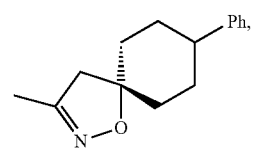
J-29-30 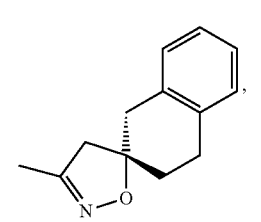
J-29-31 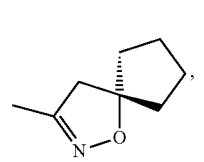

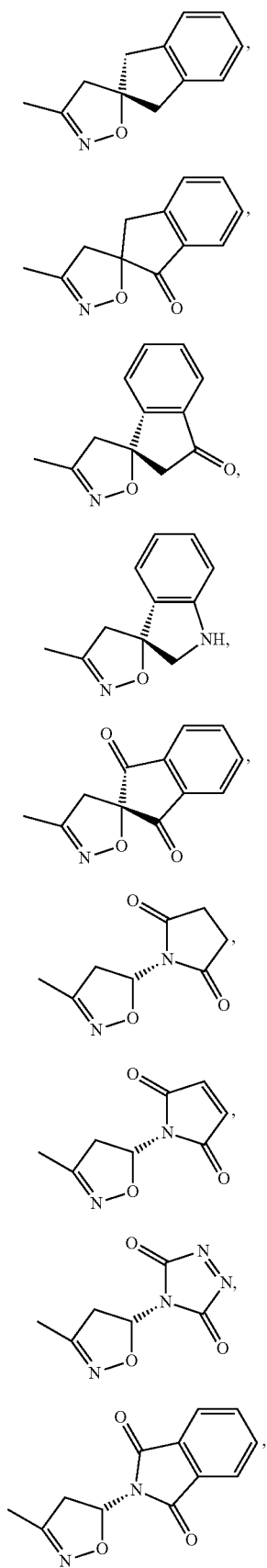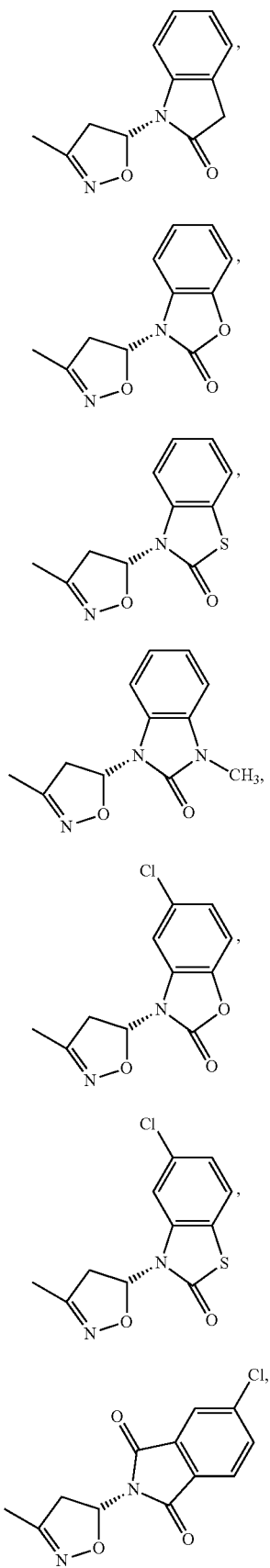

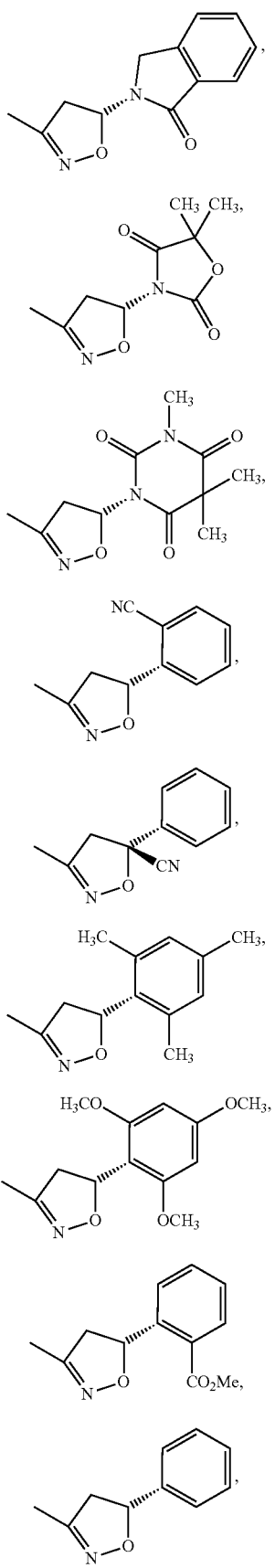

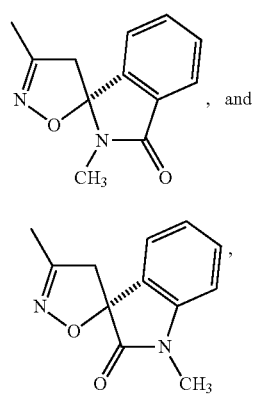

wherein the bond projecting to the left is connected to Z in Formula 1.

Embodiment 66. A compound of Embodiment 64 or 64a wherein J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69.

Embodiment 67. A compound of Embodiment 66 wherein J is selected from J-4, J-5, J-8, J-11, J-15, J-16, J-20, J-29, J-30, J-37, J-38 and J-69.

Embodiment 68. A compound of Embodiment 67 wherein J is selected from J-4, J-5, J-11, J-20, J-29, J-37, J-38 and J-69.

Embodiment 69. A compound of Embodiment 68 wherein J is J-11.

Embodiment 70. A compound of Embodiment 68 wherein J is J-29.

Embodiment 71. A compound of Embodiment 68 wherein J is J-69.

Embodiment 72. A compound of any one of Embodiments 64 through 71 wherein x is 1, 2 or 3

Embodiment 72a. A compound of Embodiment 72 wherein x is 1 or 2.

Embodiment 73. A compound of Embodiment 72a wherein x is 1.

Embodiment 74. A compound of Embodiment 69 wherein the 3-position of J-11 is connected to Z of Formula 1, and J-11 is substituted at the 5-position with a substituent selected from $R^6$ other than H.

Embodiment 75. A compound of Embodiment 74 wherein the 3-position of J-11 is connected to Z of Formula 1, and J-11 is substituted at the 5-position with $-Z^2Q$.

Embodiment 76. A compound of Embodiment 70 wherein the 3-position of J-29 is connected to Z of Formula 1, and J-29 is substituted at the 5-position with a substituent selected from $R^6$ other than H.

Embodiment 77. A compound of Embodiment 76 wherein the 3-position of J-29 is connected to Z of Formula 1, and J-29 is substituted at the 5-position with $-Z^2Q$.

Embodiment 78. A compound of Formula 1 or any one of Embodiments 1 through 77 wherein each $R^6$ when taken alone (i.e. not taken together with $R^{6a}$) is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —$NR^{17}R^{18}$ or —$Z^2Q$.

Embodiment 79. A compound of Embodiment 78 wherein each $R^6$ when taken alone is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{17}R^{18}$ or —$Z^2Q$.

Embodiment 80. A compound of Embodiment 78 wherein each $R^6$ when taken alone is independently H, halogen, cyano, $C_1$-$C_6$ alkyl, $C_1$-$C_6$ haloalkyl, $C_1$-$C_6$ alkoxy, $C_1$-$C_6$ haloalkoxy, —$NR^{17}R^{18}$ or —$Z^2Q$.

Embodiment 80a. A compound of Embodiment 80 wherein each $R^6$ when taken alone is independently H, cyano, $C_1$-$C_6$ alkyl, $C_1$-$C_6$ haloalkyl, $C_1$-$C_6$ alkoxy, $C_1$-$C_6$ haloalkoxy, —$NR^{17}R^{18}$ or —$Z^2Q$.

Embodiment 80b. A compound of Embodiment 80a wherein each $R^6$ when taken alone is independently H, cyano, $C_1$-$C_3$ alkyl, $C_1$-$C_3$ haloalkyl, $C_1$-$C_3$ alkoxy, $C_1$-$C_3$ haloalkoxy, —$NR^{17}R^{18}$ or —$Z^2Q$.

Embodiment 81. A compound of Embodiment 78 wherein each $R^6$ when taken alone is independently H, halogen, $C_1$-$C_3$ alkyl, $C_1$-$C_3$ haloalkyl or —$Z^2Q$.

Embodiment 81a. A compound of Embodiment 81 wherein each $R^6$ when taken alone is independently H, $C_1$-$C_3$ alkyl, $C_1$-$C_3$ haloalkyl or —$Z^2Q$.

Embodiment 82. A compound of Embodiment 81 wherein each $R^6$ when taken alone is —$Z^2Q$.

Embodiment 79a. A compound of Formula 1 or any one of Embodiments 1 through 82 wherein each $R^6$ is taken alone.

Embodiment 83. A compound of Formula 1 or any one of Embodiments 1 through 82 wherein each $Z^2$ is independently a direct bond, O, C(=O), S(=O)$_2$ or CH($R^{12}$).

Embodiment 84. A compound of Embodiment 83 wherein each $Z^2$ is direct bond.

Embodiment 85. A compound of Formula 1 or any one of Embodiments 1 through 84 wherein each $R^{18}$ is independently $C_1$-$C_3$ alkyl or —$Z^3Q$.

Embodiment 86. A compound of Embodiment 85 wherein each $R^{18}$ is independently $C_1$-$C_3$ alkyl.

Embodiment 87. A compound of Formula 1 or any one of Embodiments 1 through 85 wherein each $Z^3$ is independently C(=O) or S(=O)$_2$.

Embodiment 88. A compound of Embodiment 87 wherein each $Z^3$ is C(=O).

Embodiment 89. A compound of Formula 1 or any one of Embodiments 1 through 88 wherein only one instance of $R^6$ is —$Z^2Q$ Embodiment 90. A compound of Embodiment 63 wherein when Z is a direct bond, then J is C(=$W^2$)N$T^AT^B$.

Embodiment 91. A compound of Formula 1 or any one of Embodiments 1 through 90 wherein when J is C($W^2$)N$T^AT^B$, then J is selected from J-83 through J-93 in Exhibit 4

Exhibit 4

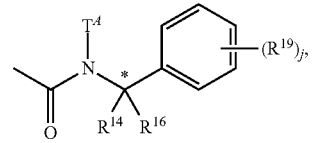
J-83

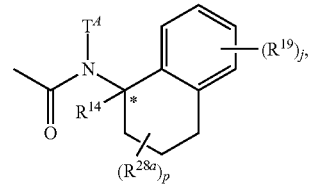
J-84

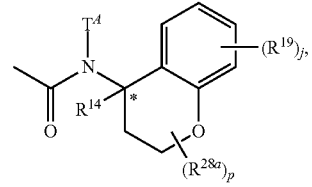
J-85

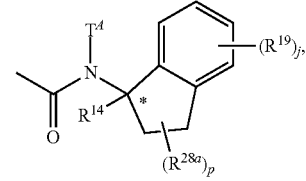
J-86

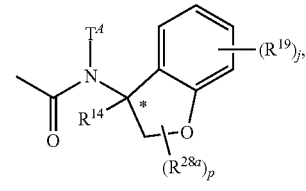
J-87

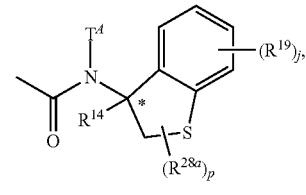
J-88

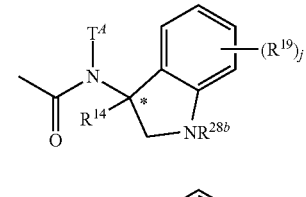
J-89

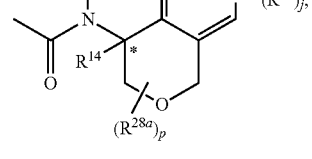
J-90

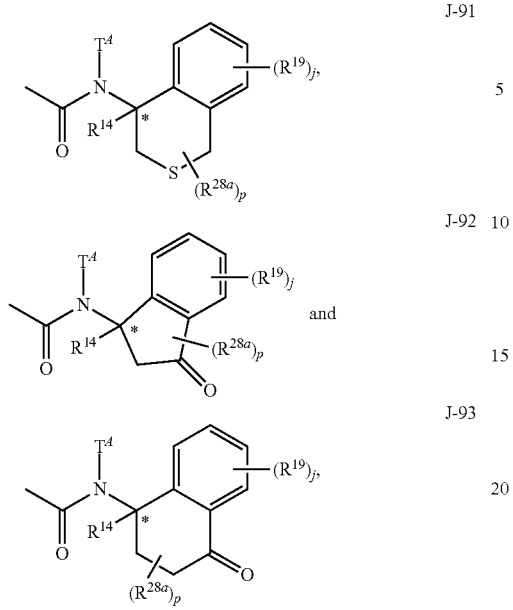

wherein the bond projecting to the left is connected to G in Formula 1, and the carbon atom identified with an asterisk (*) contains a stereocenter; each $R^{28a}$ is independently selected from halogen, hydroxy, $C_1$-$C_2$ alkyl and $C_1$-$C_2$ alkoxy and attached to carbon ring members; $R^{28b}$ is selected from halogen, $C_1$-$C_2$ alkyl and $C_1$-$C_2$ alkoxy; and each j and p is independently 0, 1 or 2.

Embodiment 92. A compound of Formula 1 or any one of Embodiments 1 through 91 wherein $W^2$ is O.

Embodiment 93. A compound of Formula 1 or any one of Embodiments 1 through 92 wherein $T^4$ is H or methyl.

Embodiment 94. A compound of Formula 1 or any one of Embodiments 1 through 93 wherein $R^{14}$ is H or methyl.

Embodiment 95. A compound of Formula 1 or any one of Embodiments 1 through 90 and 92 through 94 wherein $R^{15}$ is phenyl, benzyl or pyridinyl, each optionally substituted on ring members with up to 3 substituents independently selected from $R^{19}$.

Embodiment 96. A compound of Formula 1 or any one of Embodiments 1 through 95 wherein each $R^{19}$ when taken alone (i.e. not taken together with $R^{16}$) is independently halogen or $C_1$-$C_3$ alkyl.

Embodiment 97. A compound of Formula 1 or any one of Embodiments 1 through 97 wherein $R^{16}$ when taken alone (i.e. not taken together with $R^{19}$) is H or $C_1$-$C_3$ alkyl.

Embodiment 98. A compound of Embodiment 97 wherein $R^{16}$ when taken alone is H or methyl.

Embodiment 99. A compound of Formula 1 or any one of Embodiments 1 through 98 wherein when $R^{16}$ and $R^{19}$ are taken together with the atoms to which they are attached to form a 3- to 7-membered ring, said ring contains ring members selected from carbon atoms and up to 2 heteroatoms independently selected from up to 2 O, up to 2 S, up to 2 N, wherein up to 2 carbon atom ring members are independently selected from C(=O) and C(=S), and the sulfur atom ring members are independently selected from $S(=O)_s(=NR^{11})_f$, and the ring is optionally substituted with up to 3 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members.

Embodiment 100. A compound of Formula 1 or any one of Embodiments 1 through 99 wherein each Q is independently phenyl, benzyl, naphthalenyl, a 5- to 6-membered heteroaromatic ring or an 8- to 11-membered heteroaromatic bicyclic ring system, each optionally substituted with up to 1 substituent selected from $R^{6b}$ on carbon and nitrogen atom ring members, up to 5 substituents independently selected from $R^{6a}$ on carbon atom ring members and selected from $C_1$-$C_3$ alkyl, $C_2$-$C_3$ alkylcarbonyl, $C_2$-$C_3$ alkoxycarbonyl or $C_1$-$C_3$ alkoxy on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{11})_f$, and the silicon atom ring members are independently selected from $SiR^9R^{10}$, each ring or ring system optionally substituted with up to 1 substituent selected from $R^{6b}$ on carbon and nitrogen atom ring members, up to 5 substituents independently selected from $R^{6a}$ on carbon atom ring members and selected from $C_1$-$C_3$ alkyl, $C_2$-$C_3$ alkylcarbonyl, $C_2$-$C_3$ alkoxycarbonyl and $C_1$-$C_3$ alkoxy on nitrogen atom ring members.

Embodiment 101. A compound of Embodiment 100 wherein Q is a ring selected from Q-1 through Q-102, shown below in Exhibit 5.

Exhibit 5

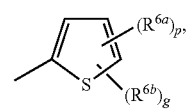

Q-1

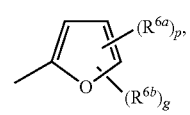

Q-2

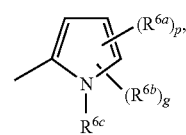

Q-3

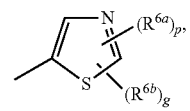

Q-4

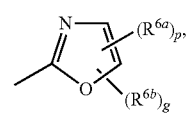

Q-5

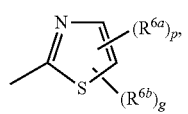 Q-6
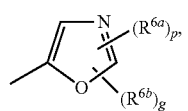 Q-7
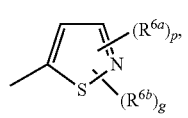 Q-8
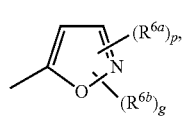 Q-9
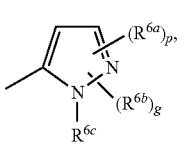 Q-10
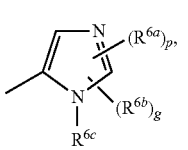 Q-11
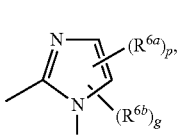 Q-12
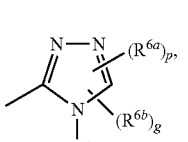 Q-13
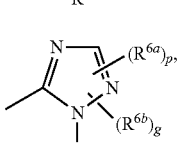 Q-14
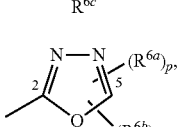 Q-15
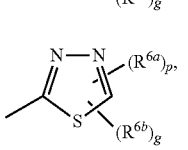 Q-16
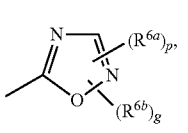 Q-17
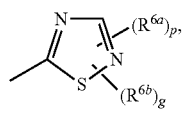 Q-18
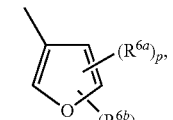 Q-19
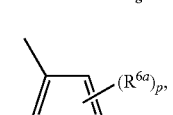 Q-20
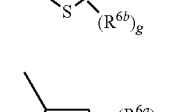 Q-21
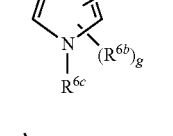 Q-22
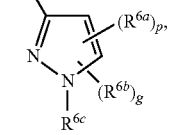 Q-23
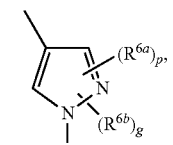 Q-24
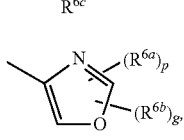 Q-25
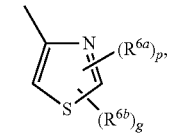 Q-26
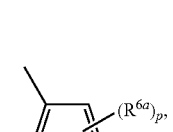 Q-27

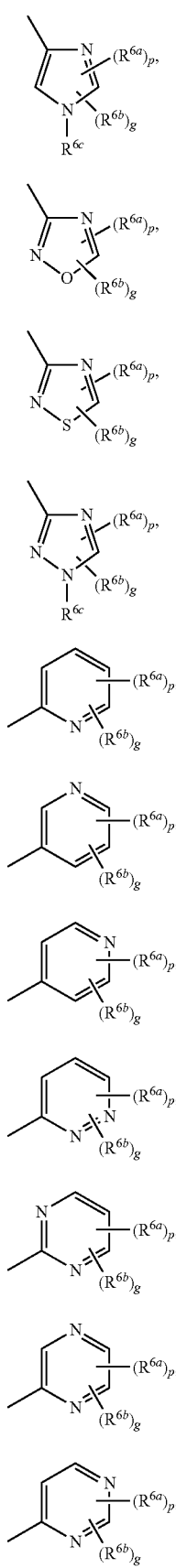
Q-28
Q-29
Q-30
Q-31
Q-32
Q-33
Q-34
Q-35
Q-36
Q-37
Q-38
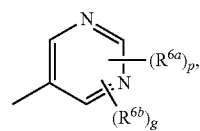 Q-39
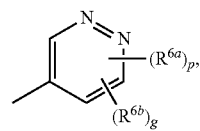 Q-40
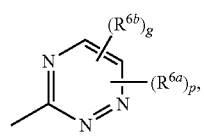 Q-41
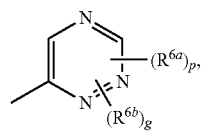 Q-42
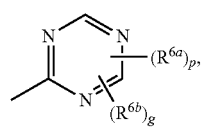 Q-43
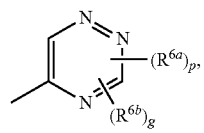 Q-44
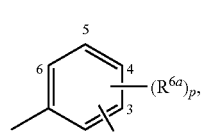 Q-45
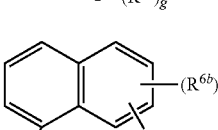 Q-46
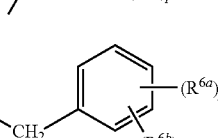 Q-47
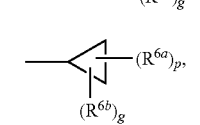 Q-48
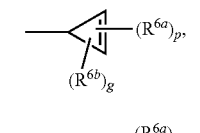 Q-49
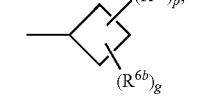 Q-50

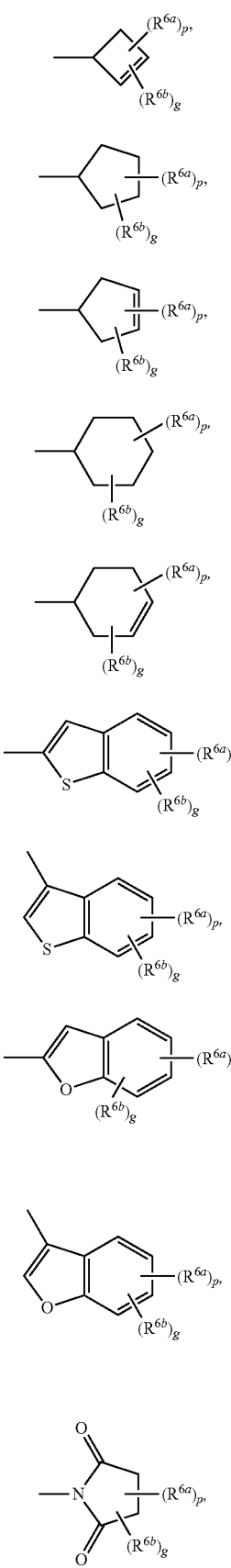
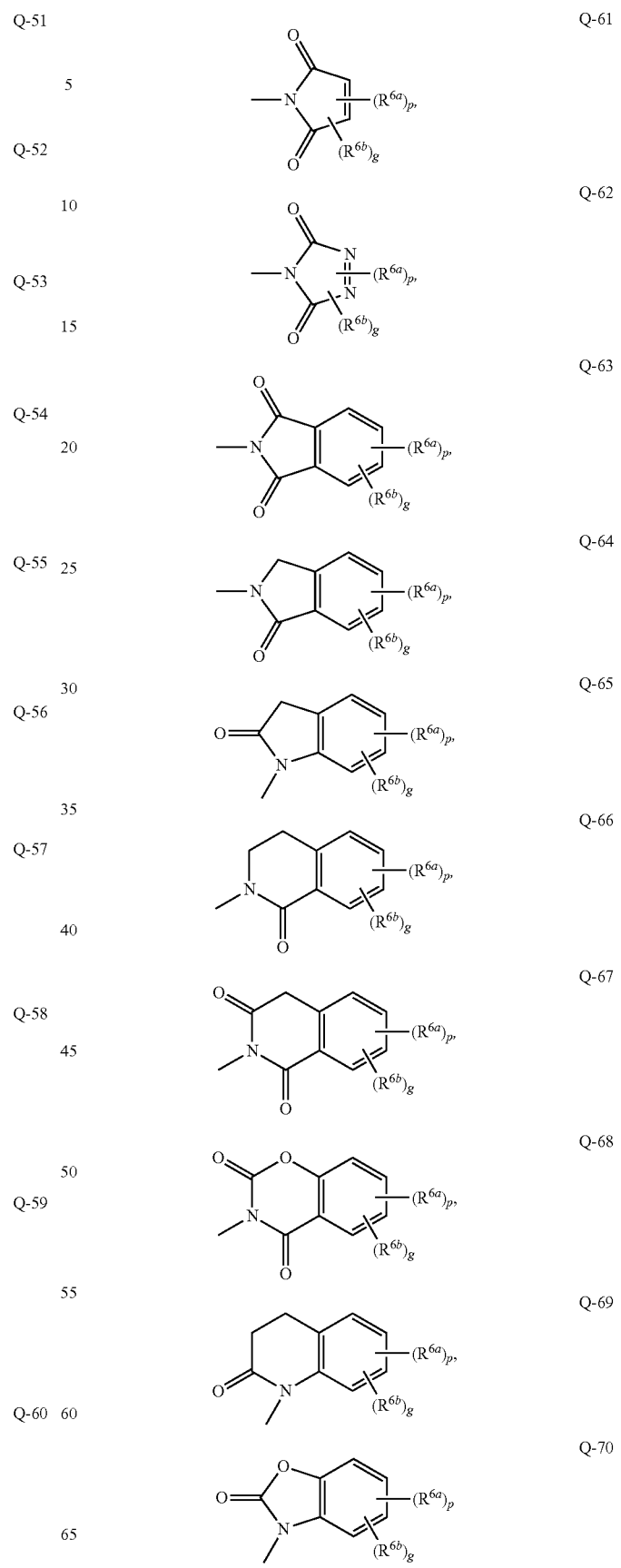

-continued
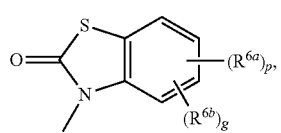 Q-71
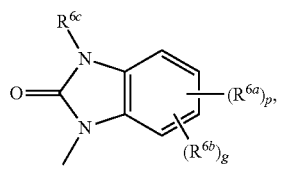 Q-72
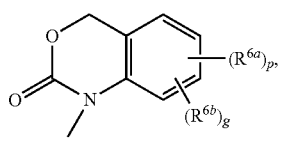 Q-73
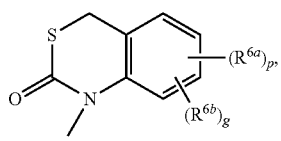 Q-74
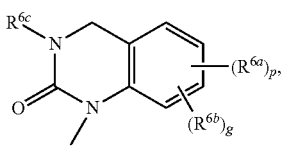 Q-75
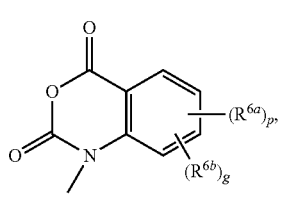 Q-76
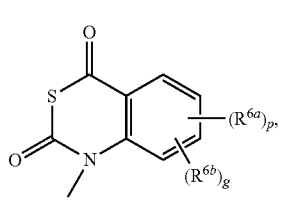 Q-77
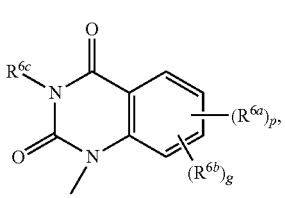 Q-78
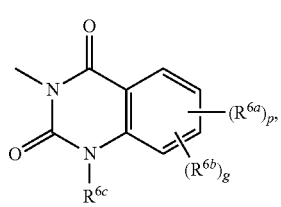 Q-79
-continued
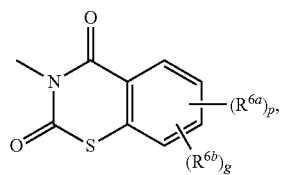 Q-80
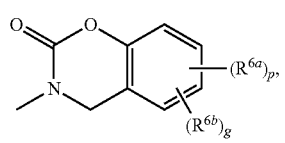 Q-81
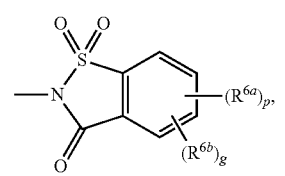 Q-82
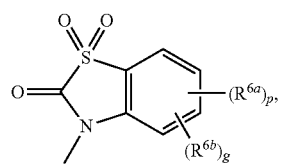 Q-83
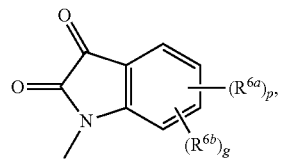 Q-84
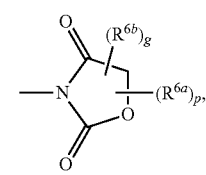 Q-85
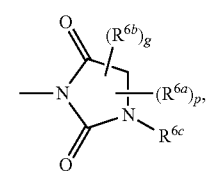 Q-86
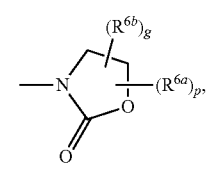 Q-87
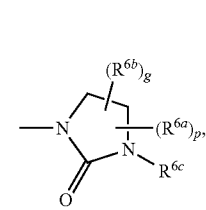 Q-88

| Q-89 | 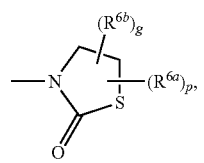 |
| Q-90 | 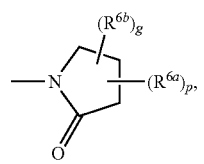 |
| Q-91 | 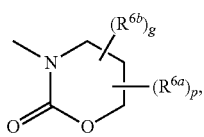 |
| Q-92 | 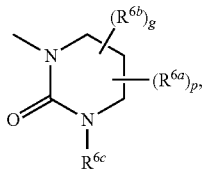 |
| Q-93 | 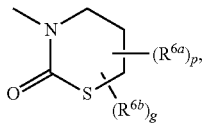 |
| Q-94 | 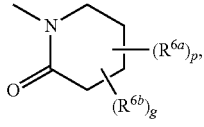 |
| Q-95 | 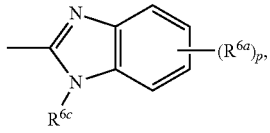 |
| Q-96 | 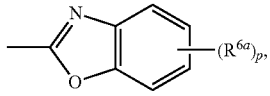 |
| Q-97 | 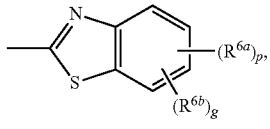 |
| Q-98 | 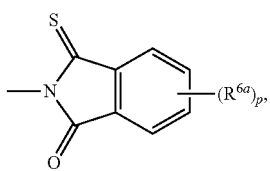 |

| Q-99 | 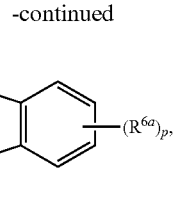 |
| Q-100 | 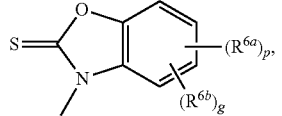 |
| Q-101 | 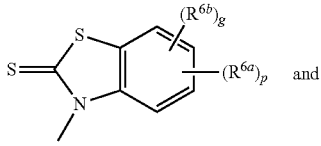 and |
| Q-102 | 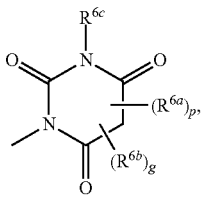 | wherein the bond projecting to the left is connected to $Z^2$ in Formula 1; each $R^{6c}$ is independently selected from H, $C_1$-$C_3$ alkyl, $C_2$-$C_3$ alkylcarbonyl, $C_2$-$C_3$ alkoxycarbonyl and $C_1$-$C_3$ alkoxy; p is an integer from 0 to 5; and g is an integer from 0 to 1.

Embodiment 102. A compound of Embodiment 101 wherein p is 0, 1, 2 or 3.

Embodiment 102a. A compound of Embodiment 101 wherein p is 0, 1 or 2.

Embodiment 102b. A compound of Embodiment 101a wherein p is 1 or 2.

Embodiment 103. A compound of any one of Embodiments 101-102b wherein Q is selected from Q-1, Q-20, Q-32 through Q-34, Q-45 through Q-47, Q-60 through Q-73, Q-76 through Q-79, Q-84 through Q-94 and Q-98 through Q-102.

Embodiment 104. A compound of Embodiment 103 wherein Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102.

Embodiment 105. A compound of Embodiment 104 wherein Q is selected from Q-45, Q-63, Q-64, Q-65, Q-68, Q-69, Q-70, Q-71, Q-72, Q-84 and Q-85.

Embodiment 106. A compound of Embodiment 105 wherein Q is selected from Q-45, Q-63, Q-65, Q-70, Q-71, Q-72, Q-84 and Q-85.

Embodiment 107. A compound of Embodiment 106 wherein Q is selected from Q-45, Q-63, Q-65, Q-70, Q-71, Q-72 and Q-84.

Embodiment 107a. A compound of Embodiment 107 wherein Q is selected from Q-45, Q-63, Q-70, Q-71, Q-72 and Q-84.

Embodiment 108. A compound of Formula 1 or any one of Embodiments 1 through 107 wherein each $R^{6a}$ when taken alone (i.e. not taken together with $R^6$) is independently halogen, hydroxy, amino, cyano, nitro, $C_1$-$C_3$ alkyl, $C_1$-$C_3$ haloalkyl, $C_1$-$C_3$ alkoxy or $C_1$-$C_3$ haloalkoxy.

Embodiment 108a. A compound of Embodiment 108 wherein each $R^{6a}$ when taken alone is independently halogen, hydroxy, amino, cyano, nitro, $C_1$-$C_2$ alkyl, $C_1$-$C_2$ haloalkyl, $C_1$-$C_2$ alkoxy or $C_1$-$C_2$ haloalkoxy.

Embodiment 108b. A compound of Embodiment 108a wherein each $R^{6a}$ when taken alone is independently halogen, hydroxy, cyano, $C_1$-$C_2$ alkyl, $C_1$-$C_2$ haloalkyl or $C_1$-$C_2$ alkoxy.

Embodiment 108c. A compound of Embodiment 108b wherein each $R^{6a}$ when taken alone is independently halogen, hydroxy, cyano, $C_1$-$C_2$ alkyl or $C_1$-$C_2$ alkoxy.

Embodiment 108d. A compound of Embodiment 108c wherein each $R^{6a}$ when taken alone is independently F, Cl, Br, hydroxy, cyano, methyl or methoxy.

Embodiment 108e. A compound of Embodiment 108c wherein each $R^{6a}$ when taken alone is F.

Embodiment 108f. A compound of Embodiment 108c wherein each $R^{6a}$ when taken alone is cyano or methyl.

Embodiment 109. A compound of Formula 1 or any one of Embodiments 1 through 108f wherein each $R^{6a}$ is taken alone.

Embodiment 111. A compound of any one of Formula 1 or any one of Embodiments 1 through 109 wherein when $R^6$ and $R^{6a}$ are taken together with the atoms to which they are attached to form a ring, said ring is 5- to 6-membered ring and contains ring members selected from carbon atoms and up to 3 heteroatoms selected from up to 1 O, up to 1 S and up to 1 N atom, and the ring is optionally substituted with up to 2 substituents independently selected from halogen, $C_1$-$C_2$ alkyl and $C_1$-$C_2$ alkoxy on carbon atom ring members and $C_1$-$C_2$ alkyl on nitrogen atom ring members.

Embodiment 112. A compound of Embodiment 111 wherein when $R^6$ and $R^{6a}$ are taken together with the atoms to which they are attached to form a ring, the ring contains ring members selected from carbon atoms and up to 1 heteroatom selected from up to 1 O, up to 1 S and up to 1 N atom, and the ring is optionally substituted on carbon atom ring members with up to 1 substituent independently selected from halogen, $C_1$-$C_2$ alkyl and $C_1$-$C_2$ alkoxy.

Embodiments of this invention, including Embodiments 1-112 above as well as any other embodiments described herein, can be combined in any manner, and the descriptions of variables in the embodiments pertain not only to the compositions comprising the compounds of Formula 1 but also to the compounds of Formula 1, the starting compounds and intermediate compounds useful for preparing the compounds of Formula 1 unless further defined in the Embodiments. In addition, embodiments of this invention, including Embodiments 1-112 above as well as any other embodiments described herein, and any combination thereof, pertain to the compositions and methods of the present invention. Combinations of Embodiments 1-112 are illustrated by:

Embodiment A1. A compound of Formula 1 wherein
A is —O—, —S— or —N($R^7$)—;
G is a 5-membered heterocyclic ring, optionally substituted with up to 2 substituents independently selected from $R^{26}$ on carbon atom ring members and $R^{27}$ on nitrogen atom ring members;
each $R^{26}$ is independently halogen, $C_1$-$C_3$ alkyl or $C_1$-$C_3$ haloalkyl;
each $R^{27}$ is independently $C_1$-$C_3$ alkyl;
Z is a direct bond, CH($R^{12}$) or N($R^{13}$);
J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from S(=O)$_s$(=NR$^{11}$)$_t$, each ring or ring system optionally substituted with up to 5 substituents independently selected from $R^6$; or when Z is a direct bond then J is also C(=W$^2$)NT$^A$T$^B$;
X is X$^1$, X$^2$, X$^3$, X$^4$, X$^5$, X$^6$, X$^7$ or X$^8$;
$R^1$ is H, cyano, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_1$-$C_4$ alkoxy, $C_1$-$C_4$ haloalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_1$-$C_4$ alkylthio, $C_1$-$C_4$ haloalkylthio, $C_1$-$C_4$ alkylamino, $C_2$-$C_4$ dialkylamino, $C_1$-$C_4$ haloalkylamino or $C_2$-$C_4$ halodialkylamino;
$R^2$ is H, $C_1$-$C_3$ alkyl, $C_1$-$C_3$ alkoxy or $C_1$-$C_3$ haloalkyl; or
$R^1$ and $R^2$ are taken together with the carbon atom to which they are attached to form a 3- to 6-membered ring containing ring members selected from carbon atoms and up to 2 heteroatoms independently selected from up to 2 O, up to 2 S and up to 2 N, wherein up to 1 carbon atom ring member is C(=O) or C(=S) and the ring is optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;
$R^3$ is optionally substituted phenyl, optionally substituted naphthalenyl or an optionally substituted 5- to 6-membered heteroaromatic ring; or H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy;
$R^4$ is H or $C_1$-$C_2$ alkyl;
each $R^5$ is independently halogen, cyano, hydroxy, $C_1$-$C_4$ alkyl, $C_1$-$C_2$ haloalkyl or $C_1$-$C_2$ alkoxy;
$R^6$ is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{17}$R$^{18}$ or —Z$^2$Q;
each $Z^2$ is independently a direct bond, O, C(=O), S(=O)$_2$ or CH($R^{12}$);
each Q is independently phenyl, benzyl, naphthalenyl, a 5- to 6-membered heteroaromatic ring or an 8- to 11-membered heteroaromatic bicyclic ring system, each optionally substituted with up to 1 substituent selected from $R^{6b}$ on carbon and nitrogen atom ring members, up to 5 substituents independently selected from $R^{6a}$ on carbon atom ring members and selected from $C_1$-$C_3$ alkyl, $C_2$-$C_3$ alkylcarbonyl, $C_2$-$C_3$ alkoxycarbonyl or $C_1$-$C_3$ alkoxy on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{11})_f$, and the silicon atom ring members are independently selected from $SiR^9R^{10}$, each ring or ring system optionally substituted with up to 1 substituent selected from $R^{6b}$ on carbon and nitrogen atom ring members, up to 5 substituents independently selected from $R^{6a}$ on carbon atom ring members and selected from $C_1$-$C_3$ alkyl, $C_2$-$C_3$ alkylcarbonyl, $C_2$-$C_3$ alkoxycarbonyl and $C_1$-$C_3$ alkoxy on nitrogen atom ring members;

each $R^{6a}$ is independently halogen, hydroxy, amino, cyano, nitro, $C_1$-$C_3$ alkyl, $C_1$-$C_3$ haloalkyl, $C_1$-$C_3$ alkoxy or $C_1$-$C_3$ haloalkoxy; or $R^6$ and $R^{6a}$ are taken together with the atoms to which they are attached to form a 5- to 6-membered ring containing ring members selected from carbon atoms and up to 3 heteroatoms selected from up to 1 O, up to 1 S and up to 1 N atom, the ring optionally substituted with up to 2 substituents independently selected from halogen, $C_1$-$C_2$ alkyl and $C_1$-$C_2$ alkoxy on carbon atom ring members and $C_1$-$C_2$ alkyl on nitrogen atom ring members;

$R^7$ is H, $C_1$-$C_2$ alkyl, $C_1$-$C_2$ haloalkyl, $CH_3C(=O)$, $CF_3C(=O)$ or $CH_3C(=O)$; or $R^2$ and $R^7$ are taken together with the linking atoms to which they are attached to form a 5- to 7-membered partially unsaturated ring containing ring members, in addition to the linking atoms, selected from carbon atoms and up to 3 heteroatoms independently selected from up to 1 O, up to 1 S and up to 1 N atom, the ring optionally substituted with up to 2 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

each $R^{13}$ is independently H, $C_1$-$C_3$ alkyl, $C_2$-$C_3$ alkylcarbonyl or $C_2$-$C_3$ alkoxycarbonyl;

each $R^{18}$ is independently $C_1$-$C_3$ alkyl or —$Z^3Q$; and each $Z^3$ is independently C(=O) or $S(=O)_2$.

Embodiment A2. A compound of Embodiment A1 wherein
A is —O— or —N($R^7$)—;
G is one of G-1 through G-59 shown in Exhibit 2 wherein the bond projecting to the left is connected to X, and bond projecting to the right is connected to Z in Formula 1;
each $R^{26a}$ is independently selected from H and $R^{26}$;
$R^{27a}$ is selected from H and $R^{27}$;
Z is a direct bond;
J is one of J-1 through J-82 shown in Exhibit 3 wherein the floating bond is connected to Z in Formula 1 through any available carbon or nitrogen atom of the depicted ring or ring system;
x is an integer from 1 to 5;
when x is 2, 3, 4 or 5, then at most one instance of $R^6$ is —$Z^2Q$; or J is $C(=W^2)NT^AT^B$;
$W^2$ is O;
X is $X^1$, $X^2$ or $X^3$;
$R^1$ is H, cyano, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_1$-$C_3$ alkoxy or $C_1$-$C_3$ haloalkoxy;
$R^2$ H, $C_1$-$C_3$ alkyl or $C_1$-$C_3$ haloalkyl;
$R^3$ is phenyl, naphthalenyl or a 5- or 6-membered heteroaromatic ring, each ring or ring system optionally substituted with up to 3 substituents independently selected from $R^{25a}$ on carbon atom ring members and $R^{25b}$ on nitrogen atom ring members; or H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy;

each $R^{25a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $R^{25b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

each $R^5$ is independently cyano, methyl or methoxy;

each $R^6$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{17}R^{18}$ or —$Z^2Q$;

each $Z^2$ is a direct bond;

Q is one of Q-1 through Q-102 shown in Exhibit 5 wherein the bond projecting to the left is connected to $Z^2$ in Formula 1;

each $R^{6c}$ is independently selected from H, $C_1$-$C_3$ alkyl, $C_2$-$C_3$ alkylcarbonyl, $C_2$-$C_3$ alkoxycarbonyl and $C_1$-$C_3$ alkoxy;

p is an integer from 0 to 5;

g is an integer from 0 to 1;

each $R^{6a}$ is independently halogen, hydroxy, amino, cyano, nitro, $C_1$-$C_2$ alkyl, $C_1$-$C_2$ haloalkyl, $C_1$-$C_2$ alkoxy or $C_1$-$C_2$ haloalkoxy; or $R^6$ and $R^{6a}$ are taken together with the atoms to which they are attached to form an optionally substituted 5- to 6-membered ring containing ring members selected from carbon atoms and up to 1 heteroatom selected from up to 1 O, up to 1 S and up to 1 N atom, the ring optionally substituted on carbon atom ring members with up to 1 substituent independently selected from halogen, $C_1$-$C_2$ alkyl and $C_1$-$C_2$ alkoxy;

$R^7$ is H or $C_1$-$C_2$ alkyl; or

R² and R⁷ are taken together with the linking atoms to which they are attached to form a 5- to 7-membered partially unsaturated ring containing ring members, in addition to the linking atoms, selected from carbon, the ring optionally substituted with up to 2 substituents independently selected from independently selected from $C_1$-$C_2$ alkyl.

each $R^{18}$ is independently $C_1$-$C_3$ alkyl; and n is 0 or 1.

Embodiment A3. A compound of Embodiment A2 wherein

W is O;

G is selected from G-1, G-2, G-7, G-8, G-14, G-15, G-23, G-24, G-26, G-27, G-36, G-37, G-38, G-49, G-50 and G-55;

x is 1, 2 or 3;

J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69; or J is one of J-83 through J-91 shown in Exhibit 4 wherein the bond projecting to the left is connected to X, and the bond projecting to the right is connected to G in Formula 1, the carbon atom identified with an asterisk (*) contains a stereocenter;

each $R^6$ is independently H, cyano, $C_1$-$C_6$ alkyl, $C_1$-$C_6$ haloalkyl, $C_1$-$C_6$ alkoxy, $C_1$-$C_6$ haloalkoxy, —$NR^{17}R^{18}$ or —$Z^2Q$;

each $R^{28a}$ is independently selected from halogen, hydroxy, $C_1$-$C_2$ alkyl and $C_1$-$C_2$ alkoxy and attached to carbon ring members;

$R^{28b}$ is selected from halogen, $C_1$-$C_2$ alkyl and $C_1$-$C_2$ alkoxy;

each j and p is independently 0, 1 or 2;

X is $X^1$ or $X^2$;

$R^1$ is H, $C_1$-$C_3$ alkyl or $C_1$-$C_3$ fluoroalkyl;

$R^2$ is H, $C_1$-$C_2$ alkyl or $C_1$-$C_3$ fluoroalkyl;

$R^3$ is one of U-1 through U-11 shown in Exhibit 1 wherein the bond projecting to the left is connected to Formula 1;

k is 0, 1 or 2; or $R^3$ is H, cyano, hydroxy, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy;

Q is selected from Q-1, Q-20, Q-32 through Q-34, Q-45 through Q-47, Q-60 through Q-73, Q-76 through Q-79, Q-84 through Q-94 and Q-98 through Q-102;

each $R^{6a}$ is independently halogen, hydroxy, cyano, $C_1$-$C_2$ alkyl, $C_1$-$C_2$ haloalkyl or $C_1$-$C_2$ alkoxy; and $R^7$ is H or methyl.

Embodiment A4. A compound of Embodiment A3 wherein

A is —O—;

G is selected from G-1, G-2, G-15, G-26, G-27, G-36, G-37 and G-38;

J is selected from J-4, J-5, J-8, J-11, J-15, J-16, J-20, J-29, J-30, J-37, J-38 and J-69;

X is $X^1$;

$R^1$ is H, methyl, trifluoromethyl or $CF_3CH_2$;

$R^2$ is H, methyl, or trifluoromethyl;

$R^3$ is H, cyano, methyl, methoxy or $CH_3C(=O)O$—;

$R^4$ is H;

each $R^6$ is independently H, cyano, $C_1$-$C_3$ alkyl, $C_1$-$C_3$ haloalkyl, $C_1$-$C_3$ alkoxy, $C_1$-$C_3$ haloalkoxy, —$NR^{17}R^{18}$ or —$Z^2Q$;

Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102;

each $R^{6a}$ is independently halogen, hydroxy, cyano, $C_1$-$C_2$ alkyl or $C_1$-$C_2$ alkoxy; and n is 0.

Embodiment A5. A compound of Embodiment A4 wherein

G is selected from G-1, G-2, G-15, G-26 and G-36;

x is 1 or 2;

J is selected from J-4, J-5, J-11, J-20, J-29, J-37, J-38 and J-69;

$R^1$ is methyl, trifluoromethyl or $CF_3CH_2$;

$R^3$ is H;

each $R^6$ is independently H, $C_1$-$C_3$ alkyl, $C_1$-$C_3$ haloalkyl or —$Z^2Q$;

Q is selected from Q-45, Q-63, Q-64, Q-65, Q-68, Q-69, Q-70, Q-71, Q-72, Q-84 and Q-85; and each $R^{6a}$ is independently F, Cl, Br, hydroxy, cyano, methyl or methoxy.

Embodiment A6. A compound of Embodiment A5 wherein

G is G-1;

x is 1;

J is J-29;

$R^6$ is —$Z^2Q$; and

Q is selected from Q-45, Q-63, Q-70, Q-71, Q-72 and Q-84.

Embodiment A7. A compound of Embodiment A6 wherein

Q is Q-45;

p is 1 or 2; and each $R^{6a}$ is F.

Embodiment A8. A compound of Embodiment A6 wherein

Q is Q-45;

p is 1; and $R^{6a}$ is cyano or methyl.

Q is selected from Q-45, Q-63, Q-70, Q-71, Q-72 and Q-84.

Specific embodiments include compounds of Formula 1 selected from the group consisting of:

2,2,2-trifluoroacetaldehyde 2-[2-[4-[4-[5-(2,6-difluorophenyl)-4,5-dihydro-3-isoxazolyl]-2-thiazolyl]-1-piperidinyl]-2-oxoethyl]-2-methylhydrazone;

2-[4,5-dihydro-3-[2-[1-[2-[[(2,2,2-trifluoroethylidene)amino]oxy]acetyl]-4-piperidinyl]-4-thiazolyl]-5-isoxazolyl]benzonitrile;

2,2,2-trifluoroacetaldehyde, O-[2-[4-[4-[5-(2,6-difluorophenyl)-4,5-dihydro-3-isoxazolyl]-2-thiazolyl]-1-piperidinyl]-2-oxoethyl]oxime;

1-[4-[4-[5-(2,6-difluorophenyl)-4,5-dihydro-3-isoxazolyl]-2-thiazolyl]-1-piperidinyl]-2-[4,5-dihydro-3-(trifluoromethyl)-1H-pyrazolyl-1-yl]ethanone;

1-[4-[4-[5-(2,6-difluorophenyl)-4,5-dihydro-3-isoxazolyl]-2-thiazolyl]-1-piperidinyl]-2-[4,5-dihydro-5-methyl-3-(trifluoromethyl)-1H-pyrazol-1-yl]ethanone;

1-[4-[4-[5-(2,6-difluorophenyl)-4,5-dihydro-3-isoxazolyl]-2-thiazolyl]-1-piperidinyl]-2-[4,5-dihydro-5,5-dimethyl-3-(trifluoromethyl)-1H-pyrazol-1-yl]ethanone;

2,2,2-trifluoroacetaldehyde, O-[2-[4-[4-(2,3-dihydrospiro[1H-indene-1,5'(4'H)-isoxazol]-3'-yl)-2-thiazolyl]-1-piperidinyl]-2-oxoethyl]oxime;

2,2,2-trifluoroacetaldehyde, O-[2-[4-[4-[4,5-dihydro-5-(2-oxo-3(2H)-benzoxazolyl)-3-isoxazolyl]-2-thiazolyl]-1-piperidinyl]-2-oxoethyl]oxime;

1,1,1-trifluoro-2-propanone, O-[2-[4-[4-[5-(2,6-difluorophenyl)-4,5-dihydro-3-isoxazolyl]-2-thiazolyl]-1-piperidinyl]-2-oxoethyl]oxime;

2-propanone, O-[2-[4-[4-[5-(2,6-difluorophenyl)-4,5-dihydro-3-isoxazolyl]-2-thiazolyl]-1-piperidinyl]-2-oxoethyl]oxime;

2-[4,5-dihydro-3-[2-[1-[2-[[(2,2,2,-trifluoro-1-methylethylidene)amino]oxy]acetyl]-4-piperidinyl]-4-thiazolyl]-5-isoxazolyl]benzonitrile;

1,1,1-trifluoro-2-propanone, O-[2-[4-[4-[4,5-dihydro-5-(2-oxo-3-(2H)-benzoxazolylidene)-3-isoxazolyl]-2-thiazolyl]-1-piperidinyl]-2-oxoethyl]oxime; and
2-propanone, O-[2-[4-[4-[5-(1,3-dihydro-1,3-dioxo-2H-isoindol-2-yl)-4,5-dihydro-3-isoxazolyl]-2-thiazolyl]-1-piperidinyl]-2-oxoethyl]oxime.

Of note are compounds of Formula 1 including geometric and stereoisomers, tautomers, N-oxides, and salts thereof (including but not limited to Embodiments 1-112 and A1-A6 above) wherein $R^2$ is H, halogen, cyano, hydroxy, $C_1$-$C_3$ alkyl, $C_1$-$C_3$ haloalkyl, $C_1$-$C_3$ alkoxy or $C_1$-$C_3$ haloalkoxy.

Also of note are compounds of Formula 1 including geometric and stereoisomers, tautomers, N-oxides, and salts thereof (including but not limited to Embodiments 1-112 and A1-A6 above) wherein each $R^3$ and $R^4$ attached to the same carbon atom are taken alone (i.e. not taken together to form a saturated carbocyclic ring).

Of further note are compounds of Formula 1 including geometric and stereoisomers, tautomers, N-oxides, and salts thereof (including but not limited to Embodiments 1-112 and A1-A6 above) wherein $R^{15}$ is phenyl, benzyl, naphthalenyl or a 5- to 6-membered heteroaromatic ring, each optionally substituted with up to 3 substituents independently selected from $R^{19}$ Of particular note are compounds of Formula 1 including geometric and stereoisomers, tautomers, N-oxides, and salts thereof (including but not limited to Embodiments 1-112 and A1-A6 above) wherein $R^2$ and $R^7$ are taken together with the linking atoms to which they are attached to form a 5- to 7-membered ring containing ring members, in addition to the linking atoms, selected from carbon atoms and up to 3 heteroatoms independently selected from up to 1 O, up to 1 S and up to 1 N atom, the ring optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

This invention provides a fungicidal composition comprising a compound selected from Formula 1 (including all geometric and stereoisomers, tautomers, N-oxides, and salts thereof) and at least one other fungicide. Of note as embodiments of such compositions are compositions comprising a compound corresponding to any of the compound embodiments described above.

This invention provides a fungicidal composition comprising a fungicidally effective amount of a compound selected from Formula 1 (including all geometric and stereoisomers, tautomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound selected from Formula 1 (including all geometric and stereoisomers, tautomers, N-oxides, and salts thereof). Of note as embodiments of such methods are methods comprising applying a fungicidally effective amount of a compound corresponding to any of the compound embodiments describeg above. Of particular note are embodiments where the compounds are applied as compositions of this invention.

One or more of the following methods and variations as described in Schemes 1-20 can be used to prepare the compounds of Formula 1. The definitions of $R^1$, $R^2$, $R^3$, $R^4$, $R^5$, $R^6$, $R^8$, A, G, J, W, $T^A$, $T^B$, W, $W^2$, X, Z and n in the compounds of Formulae 1-40 below are as defined above in the Summary of the Invention unless otherwise noted. Compounds of Formulae 1a and 1b are various subsets of Formula 1, and all substituents for Formulae 1a and 1b are as defined above for Formula 1 unless otherwise noted.

As shown in Scheme 1, compounds of Formula 1 wherein W is O can be prepared by coupling an acid chloride of Formula 2 with an amine of Formula 3 (or its acid salt) in the presence of an acid scavenger. Typical acid scavengers include amine bases such as triethylamine, N,N-diisopropylethylamine and pyridine. Other acid scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound N,N-dimethyl-4-pyridinamine. Acid salts of amines of Formula 3 can also be used in this method, provided that at least 2 equivalents of the acid scavenger is present. Typical acids used to form salts with amines include hydrochloric acid, oxalic acid and trifluoroacetic acid.

Scheme 1

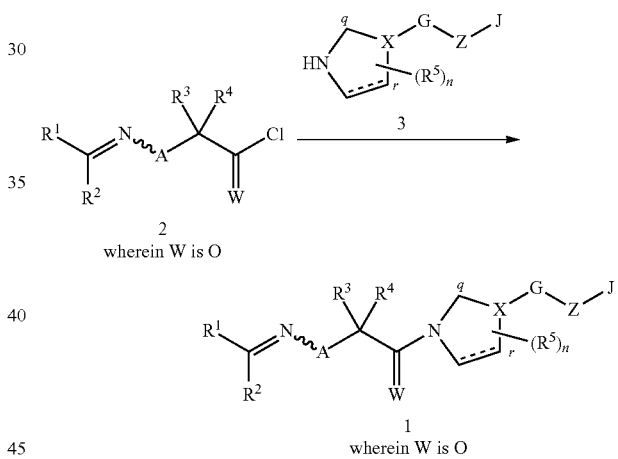

In a subsequent step, compounds of Formula 1 wherein W is O can be converted to the corresponding thioamides wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

As shown in Scheme 2, in an alternate procedure compounds of Formula 1 wherein W is O can be prepared by coupling of an acid of Formula 4 with an amine of Formula 3 (or its acid salt) in the presence of a dehydrative coupling reagent such as dicyclohexylcarbodiimide (DCC), 1-(3-dimethylaminopropyl)-3-ethylcarbodiimide hydrochloride (EDC) or O-benzotriazol-1-yl-N,N,N',N'-tetramethyluronium hexafluorophosphate (HBTU). In certain cases the presence of a polymer-supported reagent, such as polymer-bound cyclohexylcarbodiimide can be useful. Typically the method of Scheme 2 is conducted at a temperature between about 0-40° C., in a solvent such as dichloromethane or acetonitrile and in the presence of a base such as triethylamine or N,N-diisopropylethylamine.

The starting acids of Formula 4 are known and can be prepared by methods known to one skilled in the art. For leading references see, for example, Schumann et al., *Journal of Medicinal & Pharmaceutical Chemistry* 1962, 5, 464-77; Van Dijk et al., *Journal of Medicinal Chemistry* 1977, 20(9), 1199-206; Balsamo et al., *Journal of Medicinal Chemistry* 1989, 32, 1398-1401; and U.S. Pat. No. 4,584,014. Acids of Formula 4 are useful intermediates for preparing the acid chlorides of Formula 2 used in the method of Scheme 1. There are a variety of well-known conditions published in the chemistry literature for converting acids to acid chlorides which can be used.

Scheme 2

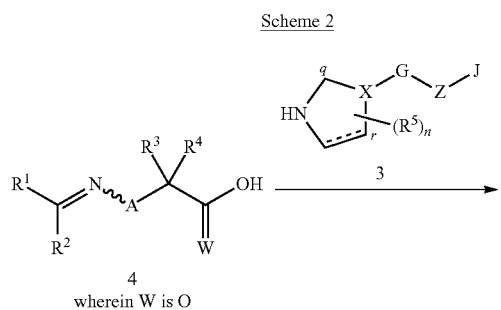

As the synthetic literature includes many methods for forming an amide-bond, the methods of Schemes 1 and 2 are simple representative examples of a wide variety of useful methods for preparing of compounds Formula 1.

In an alternative method, compounds of Formula 1 wherein A is —O—, —S— and —N(R$^7$)— and W is O can be prepared by reaction of a compound of Formula 5 and a haloacetamide of Formula 6 as shown in Scheme 3. The reaction is carried out in the presence of a base such as sodium hydride or potassium carbonate and a solvent such as tetrahydrofuran, N,N-dimethylformamide or acetonitrile typically at a temperature between about 0 to 80° C.

Scheme 3

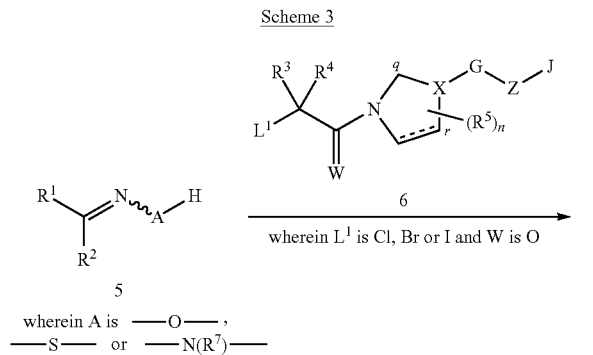

Imines, oximes and hydrazones of Formula 5 are known and can be prepared by methods known in the art; see, for example, S. Dayagi et al., in *The Chemistry of the Carbon-Nitrogen Double Bond*, ed. Patei, Interscience, New York 1970; Sandler et al., *Organic Functional Group Preparations*, Academic Press, New York 1972, 3, 372 and Hilgetag et al., *Preparative Organic Chemistry*, John Wiley & Sons, New York 1972, 504-515. Haloacetamides of Formula 6 can be prepared by reacting an amine of Formula 3 with an α-halo carboxylic acid halide or an α-halo carboxylic acid (or its anhydride), using conditions analogous to those described for the amide-forming reactions in Schemes 1 or 2.

Compounds of Formula 1 wherein A is —OC(R$^8$)$_2$—, —SC(R$^8$)$_2$— or —N(R$^7$)C(R$^8$)$_2$— and R$^4$ is H can be prepared by a base-catalyzed condensation reaction of a compound of Formula 5 with an α,β-unsaturated amide of Formula 7 as depicted in Scheme 4 wherein A in Formula 5 and C(R$^8$)$_2$ in Formula 7 form A in Formula 1. The reaction is carried out in the presence of a base such as sodium or potassium hydroxide, sodium hydride or potassium carbonate in a solvent such as tetrahydrofuran, N,N-dimethylformamide, ethanol or acetonitrile typically at a temperature between about 0 to 80° C. The α,β-unsaturated amides of Formula 7 can be prepared by coupling the corresponding α,β-unsaturated acids or acid chlorides with amines of Formula 3 using conditions analogous to those described for Schemes 1 and 2.

Scheme 4

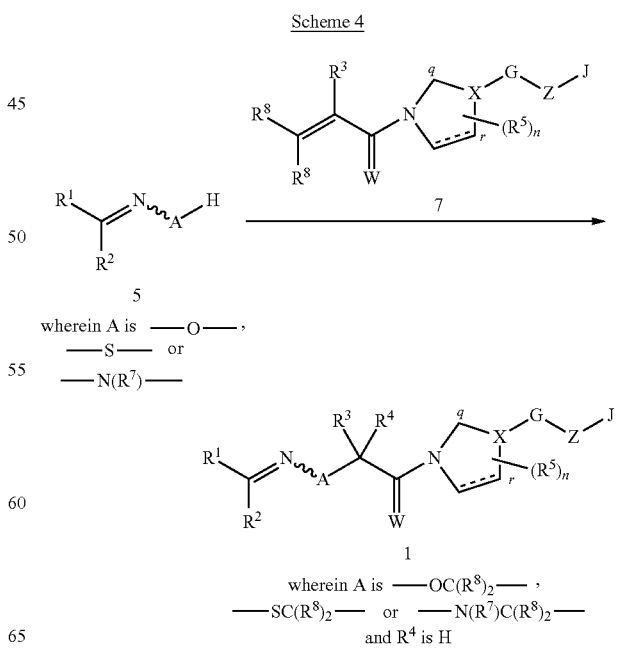

Compounds of Formula 1 can also be prepared by reacting a compound of Formula 8 with a compound of Formula 9 as illustrated in Scheme 5. The reaction is carried out in a solvent such as ethanol, tetrahydrofuran or water and optionally in the presence of an acid catalyst such as acetic acid, hydrochloric acid or sulfuric acid. Also, acid salts of Formula 9 can be used in the method of Scheme 5, preferably in the presence of at least one molar equivalent of an acid scavenger such as pyridine or triethylamine. The acids salts can be prepared by treating amines of Formula 9 with hydrochloric acid, oxalic acid or trifluoroacetic acid. The reaction of amines with carbonyl compounds is well known; see, for example, Dayagi et al., in *The Chemistry of the Carbon-Nitrogen Double Bond*, ed. Patei, Interscience, New York 1970; Sandler et al., *Organic Functional Group Preparations*, Academic Press, New York 1972, 3, 372 and Hilgetag et al., *Preparative Organic Chemistry*, John Wiley & Sons, New York 1972, 504-515. Compounds of Formula 8 are known or can be prepared by methods known to one skilled in the art. Compounds of Formula 9 can be prepared directly or by deprotection of corresponding N-protected compounds of Formula 9. The N-protected compounds of Formula 9 can be prepared by methods analogous to those already described for Schemes 1, 2, 3, and 4. The choice of a suitable nitrogen-protecting group will be apparent to one skilled in the art; methods for protecting nitrogen atoms with these protecting groups are described in Greene, T. W.; Wuts, P. G. M. *Protective Groups in Organic Synthesis*, 2nd ed.; Wiley: New York, 1991.

Scheme 5

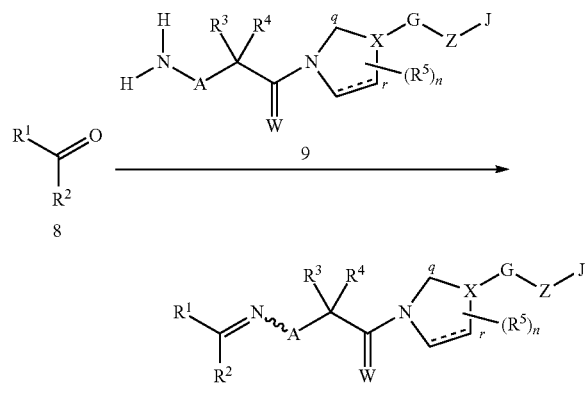

Compounds of Formula 1a (Formula 1 wherein the ring containing X is saturated) wherein X is $X^1$, $X^2$, $X^5$, $X^8$ or $X^9$ can be prepared from the corresponding unsaturated compounds of Formula 1b by catalytic hydrogenation as shown in Scheme 6. Typical conditions involve contacting a compound of Formula 1b with hydrogen gas at a pressure from about 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at ambient temperature (e.g., about 15-20° C.). This type of reduction is well-known; see, for example, *Catalytic Hydrogenation*, L. Cerveny, Ed., Elsevier Science, Amsterdam, 1986. One skilled in the art will recognize that certain other functionalities that may be present in compounds of Formula 1a can also be reduced under catalytic hydrogenation conditions, thus requiring a suitable choice of catalyst and conditions.

Scheme 6

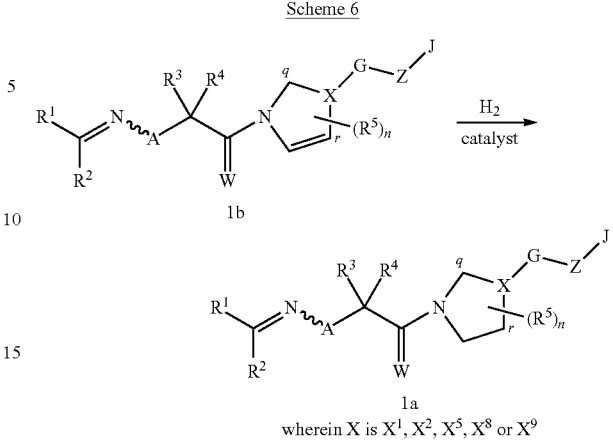

wherein X is $X^1$, $X^2$, $X^5$, $X^8$ or $X^9$

As depicted in Scheme 7, compounds of Formula 1 wherein X is $X^1$, $X^5$, $X^7$ or $X^9$ and G is linked to the ring containing X via a nitrogen atom can be prepared by displacement of an appropriate leaving group $L^2$ (e.g., Br, I, or a sulfonate, such as $CH_3S(O)_2O$ or $CF_3S(O)_2O$) in compounds of Formula 10 with a nitrogen-containing heterocycle of Formula 11 in the presence of a base. The reaction is typically carried out in a solvent such as N,N-dimethylformamide or acetonitrile at about 0 to 80° C. and in the presence of a base such as sodium hydride or potassium carbonate.

Compounds of Formula 10 can be prepared from the corresponding compounds of Formula 10 wherein $L^2$ is OH using general methods known in the art.

Scheme 7

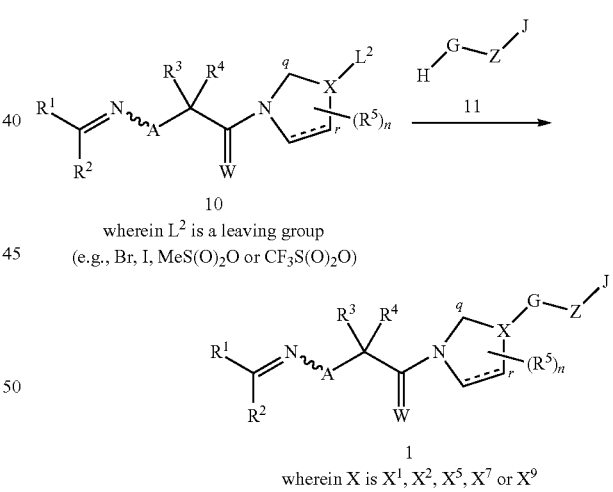

wherein X is $X^1$, $X^2$, $X^5$, $X^7$ or $X^9$

Compounds of Formula 1 wherein X is $X^2$ or $X^8$ can be prepared by reaction of a compound of Formula 12 with a heterocyclic compound of Formula 13 wherein $L^2$ is a leaving group (e.g., Br, I, or a sulfonate, such as $CH_3S(O)_2O$ or $CF_3S(O)_2O$) as shown in Scheme 8. The reaction is carried out in the presence of a base such as potassium carbonate and in a solvent such as dimethylsulfoxide, N,N-dimethylformamide or acetonitrile at a temperature between about 0 to 80° C.

Compounds of Formula 13 can be prepared from corresponding compounds of Formula 13 wherein $L^2$ is OH by methods known to one skilled in the art.

Scheme 8

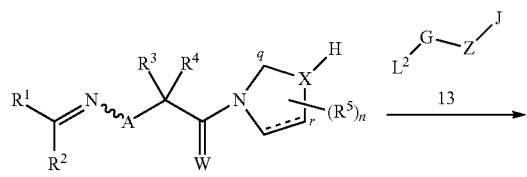

12
wherein L² is a leaving group
(e.g., Br, I, MeS(O)₂O or CF₃S(O)₂O)

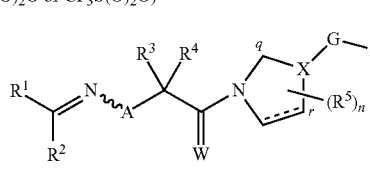

1
wherein X is X² or X⁸

Amines of Formula 3 can be prepared from compounds of Formula 14 wherein $Y^1$ is an amine protecting group via a deprotection reaction as shown in Scheme 9 (for amine deprotection methods see, for example, Greene, T. W.; Wuts, P. G. M. *Protective Groups in Organic Synthesis,* 2nd ed.; Wiley: New York, 1991). A wide array of amine protecting groups are suitable for the method of Scheme 9 and the choice of the appropriate protecting group will be apparent to one skilled in chemical synthesis. After deprotection, the amine of Formula 3 can be isolated as an acid salt or free amine by general methods known in the art.

Scheme 9

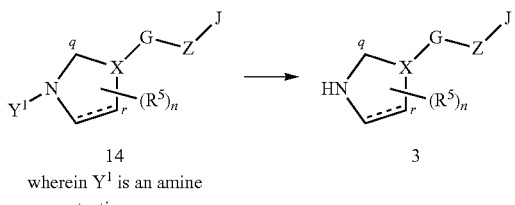

14
wherein Y¹ is an amine
protecting group

3

Amines of Formula 14 can be prepared using a method analogous to those described in Schemes 6, 7 or 8 above wherein the moiety $(R^1)(R^2)=N\sim AC(R^3)(R^4)C(=W)-$ in the compounds of Formulae 1b, 10 and 12 is replaced by $Y^1$.

Amines of Formula 14 can also be prepared by reaction of a suitably functionalized compound of Formula 15 with a suitably functionalized compound of Formula 16 as shown in Scheme 10. The functional groups $Y^2$ and $Y^3$ are selected from, but not limited to, moieties such as aldehydes, ketones, esters, acids, amides, thioamides, nitriles, amines, alcohols, thiols, hydrazines, oximes, amidines, amideoximes, olefins, acetylenes, halides, alkyl halides, methanesulfonates, trifluoromethanesulfonates, boronic acids, boronates, and the like, which under the appropriate reaction conditions, will allow for the construction of the various heterocyclic G rings. As an example, reaction of a compound of Formula 15 wherein $Y^2$ is a thioamide group with a compound of Formula 16 wherein $Y^3$ is a bromoacetyl group will give a compound of Formula 14 wherein G is a thiazole ring. The synthetic literature describes many general methods for forming 5-membered heteroaromatic rings and 5-membered partially saturated heterocyclic rings (e.g., G-1 through G-59); see, for example, *Comprehensive Heterocyclic Chemistry*, Volumes 4-6, A. R. Katritzky and C. W. Rees ditors-in-chief, Pergamon Press, Oxford, 1984; *Comprehensive Heterocyclic Chemistry II*, Volumes 2-4, A. R. Katritzky, C. W. Rees and E. F. V. Scriven editors-in-chief, Pergamon Press, Oxford, 1996; and the series, *The Chemistry of Heterocyclic Compounds*, E. C. Taylor, editor, Wiley, New York. Also, the use of intermediates of Formula 15 wherein X is $X^1$ and $Y^2$ is Br, I, methanesulfonate or trifluoromethanesulfonate to prepare organozinc reagents for use in cross-coupling reactions with aromatic rings has been described; see, for example, Bellotte, *Synlett* 1998, 379-380, and Nakamura et al., *Synlett* 2005, 1794-1798. One skilled in the art can easily determine the appropriate functional group needed for $Y^2$ and $Y^3$ to construct the desired heterocyclic G ring. Compounds of Formula 16 and 17 are known and can be prepared by methods known in the art.

Scheme 10

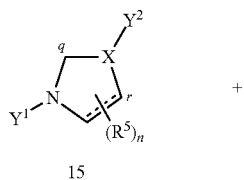

15
wherein Y¹ is an amine protecting
group and Y² is a suitable functional
group for construction of the desired
G ring

+

16
wherein Y³ is a suitable
functional group for construction
of the desired G ring

14
wherein Y¹ is an amine
protecting group

Compounds of Formula 14 wherein Z is O, S, or $N(R^{13})$ can be prepared by displacement of an appropriate leaving group $L^2$ (e.g., Br, I, or a sulfonate, such as $CH_3S(O)_2O$ or $CF_3S(O)_2O$) attached to Formula 17 with a compound of Formula 18 in the presence of a base as depicted in Scheme 11. Suitable bases include sodium hydride or potassium carbonate. The reaction is typically carried out in a solvent such as N,N-dimethylformamide or acetonitrile at a temperature between about 0 to 80° C.

Compounds of Formula 17 can be prepared from corresponding compounds of Formula 17 wherein $L^2$ is OH by general methods known in the art. The compounds of Formula 18 are known and can be prepared by general methods known in the art.

Scheme 11

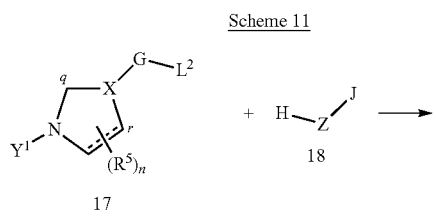

17
wherein L² is a leaving group
(e.g., Br, I, MeS(O)₂O or
CF₃S(O)₂O) and Y¹ is an amine
protecting group

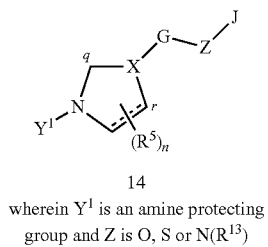

14
wherein Y¹ is an amine protecting
group and Z is O, S or N(R¹³)

Compounds of Formula 14 wherein Z is O, S, or N(R¹³) can also be prepared by displacement of an appropriate leaving group L² (e.g., Br, I, or a sulfonate, such as CH₃S(O)₂O or CF₃S(O)₂O) attached to Formula 19 with a compound of Formula 20 in the presence of a base as depicted in Scheme 12. Suitable bases include sodium hydride or potassium carbonate. The reaction is typically carried out in a solvent such as N,N-dimethylformamide or acetonitrile at a temperature between about 0 to 80° C.

Compounds of Formula 19 can be prepared from corresponding compounds of Formula 19 wherein L² is OH by general methods known in the art. Many of the compounds of Formula 19 are known and can be prepared by general methods known in the art.

Scheme 12

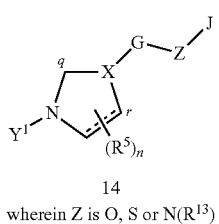

20 wherein L² is a leaving group (e.g., Br,
I, MeS(O)₂O or CF₃S(O)₂O) and
Y¹ is an amine protecting group 14
wherein Z is O, S or N(R¹³)

As shown in Scheme 13, compounds of Formula 14 wherein J is other than C(=W²)NT^A T^B can also be prepared by reaction of a compound of Formula 21 with a compound of Formula 22 wherein Y² and Y³ are selected from, but not limited to, aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates, boronic acids, boronates, and the like, which under the appropriate reaction conditions will allow the construction of the various heterocyclic J rings. As an example, reaction of a compound of Formula 21 wherein Y² is chloro oxime with a compound of Formula 22 wherein Y³ is an olefin or acetylene in the presence of base will provide a compound of Formula 14 wherein J is an isoxazoline or isoxazole, respectively. The synthetic literature includes many general methods for the formation of carbocyclic and heterocyclic rings and ring systems (e.g., J-1 through J-82); see, for example, *Comprehensive Heterocyclic Chemistry*, Volumes 4-6, A. R. Katritzky and C. W. Rees editors, Pergamon Press, New York, 1984; *Comprehensive Heterocyclic Chemistry II*, Volumes 2-4, A. R. Katritzky, C. W. Rees, and E. F. Scriven editors, Pergamon Press, New York, 1996; the series, *The Chemistry of Heterocyclic Compounds*, E. C. Taylor, editor, Wiley, New York, and *Rodd's Chemistry of Carbon Compounds*, Vol. 2-4, Elsevier, N.Y. General procedures for cycloaddition of nitrile oxides with olefins are well documented in the chemical literature. For relevant references see Lee, *Synthesis* 1982, 6, 508-509 and Kanemasa et al., *Tetrahedron* 2000, 56, 1057-1064 as well as references cited within. One skilled in the art can easily determine how to select an appropriate compound of Formula 21 and Formula 22 for construction of a particular desired heterocyclic J ring. Compounds of Formula 22 are known and can be prepared by general methods known in the art.

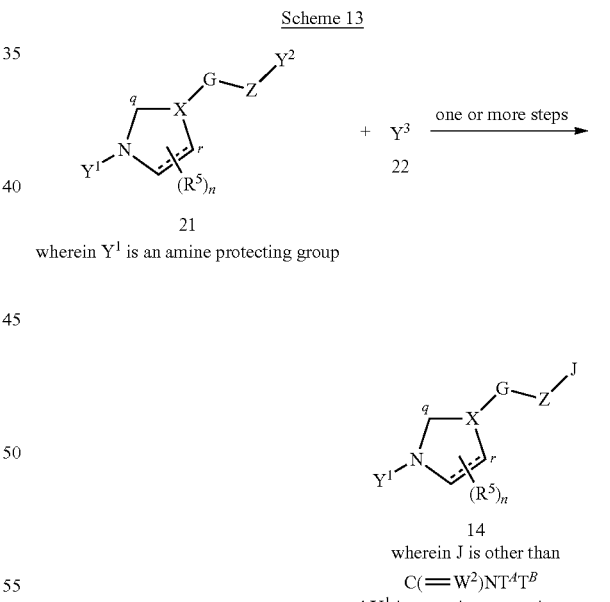

Scheme 13

21
wherein Y¹ is an amine protecting group 14
wherein J is other than
C(=W²)NT^A T^B
and Y¹ is an amine protecting group wherein Y² and Y³ are selected from aldehydes, ketones, esters, acids, amides,
thioamides, nitriles, amines, alcohols, thiols, hydrazines, oximes, amidines, amide
oximes, olefins, acetylenes, halides, alkyl halides, methanesulfonates,
trifluoromethanesulfonates, boronic acids, boronates, and the like As shown in Scheme 14, compounds of Formula 14a (Formula 14 wherein Z is a direct bond and J is C(=W²)NT^A T^B) wherein W² is O can be prepared by an amide-bond forming reaction using conditions analogous to those described for Scheme 1 or 2.

Scheme 14

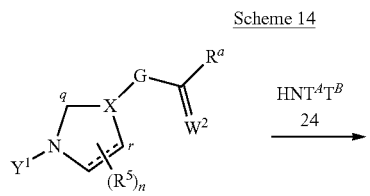

23
wherein $Y^1$ is an amine protecting group, $R^a$ is Cl or OH and $W^2$ is O

HNT$^A$T$^B$
24

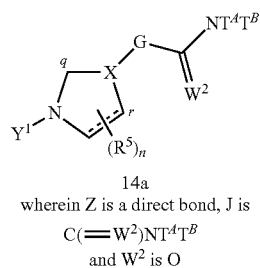

14a
wherein Z is a direct bond, J is
$C(=W^2)NT^AT^B$
and $W^2$ is O

Alternate approaches to preparing compounds of Formula 14a are disclosed in PCT Patent Publication WO 2007/014290.

In a subsequent step, amides of Formula 14a wherein $W^2$ is O can be converted to corresponding thioamides of Formula 14a wherein $W^2$ is S using a variety of standard thiating reagents such as pentasulfide or 2,4-bis(4-methoxyphenyl)-1,3-dithia-2,4-diphosphetane-2,4-disulfide (Lawesson's reagent).

In alternative method, as shown in Scheme 15, compounds of Formula 14 wherein Z is a direct bond can be prepared by coupling a halide (Br or Cl) of Formula 25 or 28 with a boronic acid of Formula 26 or 27 using well-known Suzuki palladium-catalyzed cross coupling reaction conditions. Many catalysts are useful for the Suzuki reaction; particularly useful catalysts include tetrakis(triphenylphosphine)palladium(0) and [1,1'-bis(diphenyl-phosphino)ferrocene]dichloropalladium(II). Solvents such as tetrahydrofuran, acetonitrile, diethyl ether and dioxane are suitable. The Suzuki reaction and related coupling procedures offer many alternatives for formation of the G-J bond. For leading references; see, for example, Zificsak et al., *Tetrahedron* 2004, 60, 8991-9016. For a thorough review of palladium-catalyzed cross coupling reactions applicable to the synthesis of G-J bonds, see *Palladium in Heterocyclic Chemistry: A Guide for the Synthetic Chemist*, J. J. Li and G. W. Gribble, editors, Elsevier, Oxford, UK, 2000.

Scheme 15

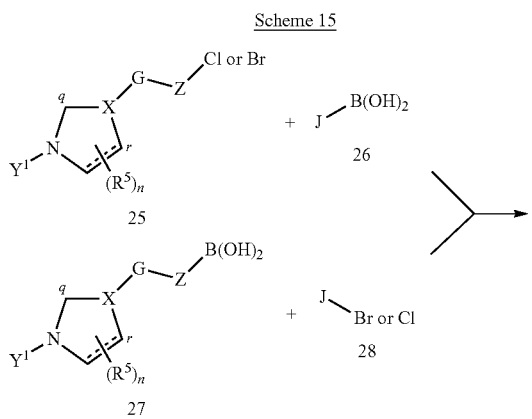

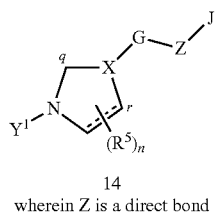

14
wherein Z is a direct bond wherein $Y^1$ is an amine protecting group and Z is a direct bond One skilled in the art will recognize that many compounds of Formula 1 can be prepared directly using methods analogous to those described in Schemes 10 through 15 above wherein the group $Y^1$ is replaced with the moiety $(R^1)(R^2)$=N~AC($R^3$)($R^4$)C(=W)—. Thus, compounds corresponding to Formulae 15, 17, 20, 21, 23, 25 and 27 wherein $Y^1$ is replaced with $(R^1)(R^2)$=N~AC($R^3$)($R^4$)C(=W)— are useful intermediates for the preparation of compounds of Formula 1.

Particularly useful intermediates for preparing compounds of Formula 1 wherein X is $X^1$ are thioamides of Formula 29, which can be prepared from the corresponding nitriles of Formula 30 by treatment with hydrogen sulfide as shown in Scheme 16. The reaction carried out by contacting a compound of Formula 30 with hydrogen sulfide in the presence of an amine such as pyridine, diethylamine or diethanolamine. Alternatively, hydrogen sulfide can be used in the form of its bisulfide salt in combination with an alkali metal or ammonia. This type of reaction is well documented in the literature; see, for example, European Patent EP 696581.

Scheme 16

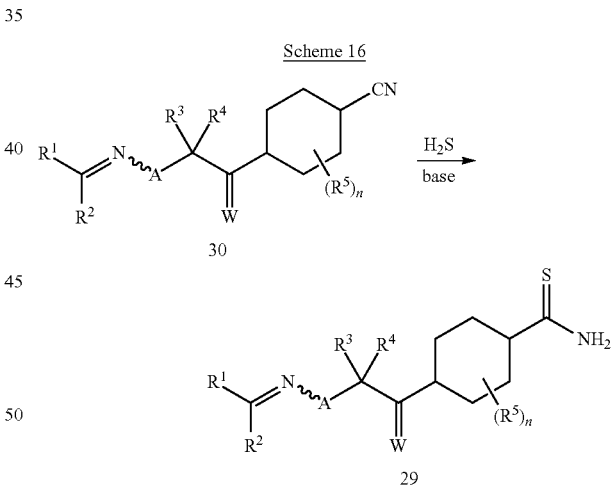

Compounds of Formula 30 can be prepared using a method analogous to one described in Scheme 1, 2, 3, 4 or 5 wherein X is $X^1$, and G-Z-J in the compounds of Formulae 3, 6, 7 and 9 is replaced by cyano. Particularly useful is a method analogous to Scheme 3 wherein Formula 6 is replaced with a compound of Formula 6a (Formula 6 wherein X is $X^1$ and G-Z-J is replaced by cyano). Compounds of Formula 6a can be prepared by contacting a cyanopiperidine of Formula 31 with an appropriate acid chloride of Formula 32 typically in the presence of a base as shown for Method A in Scheme 17. Preferred conditions involve the use of an aqueous solution of an inorganic base such as an alkali metal or alkaline-earth carbonate, bicarbonate, or phosphate, and a non-water miscible organic solvent such as toluene, ethyl acetate or 1,2-dichloroethane. Compounds of Formula 6a can also be prepared by contacting a compound of Formula 33 wherein $R^b$ is a tertiary alkyl group (e.g., $Me_3C$—) with an amide dehydrating agent such as thionyl chloride or phosphorus oxychloride in a suitable solvent as shown for Method B in Scheme 17. A particularly preferred solvent for this transformation is an N,N-dialkylamide such as N,N-dimethylformamide. The reaction is typically carried out by adding 0.9 to 2 equivalents, preferably 1.1 equivalents, of phosphorus oxychloride or thionyl chloride to a mixture of a compound of Formula 33 and 0.5 to 10 parts by weight of solvent, at a temperature in which the reaction rapidly proceeds during the addition (typically a temperature between about 35 to 55° C.).

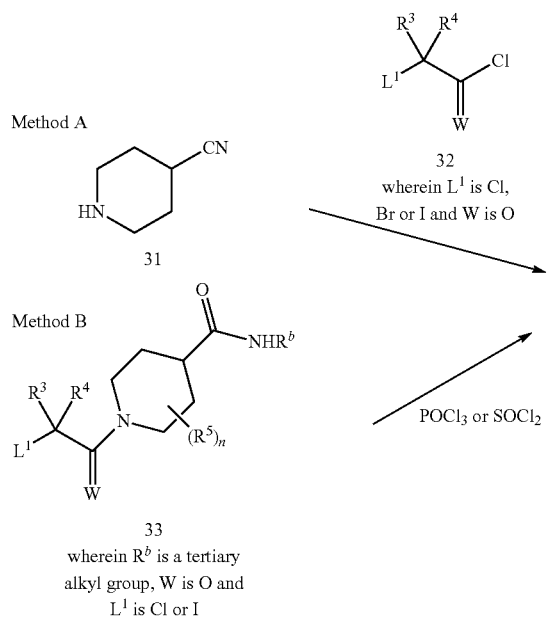

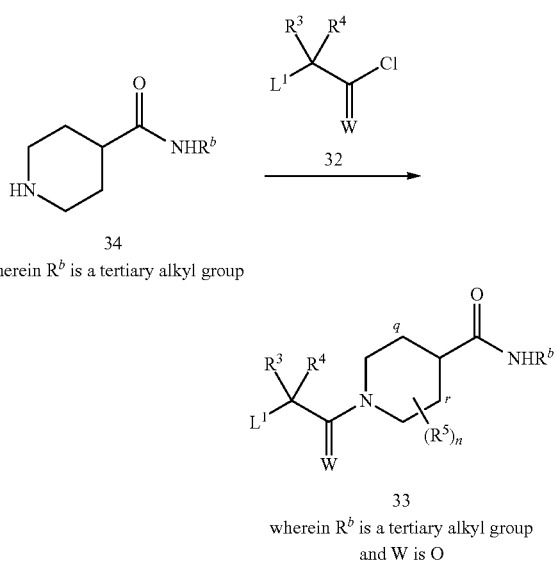

Methods for preparing compounds of Formula 34 from 4-cyanopyridine or isonicotinic acid are known in the art; see, for example, German patent application DE 3537762, which discloses a preparation of N-t-butyl pyridinecarboxamides from cyanopyridines and t-butanol and Nelsen et al., *J. Org. Chem.*, 1990, 55, 3825 for hydrogenation of N-methylisonicotinamide with a platinum catalyst.

Haloketones of Formula 38 are particularly useful intermediates for preparing certain chiral compounds of Formula 1 wherein J is, for example, selected from J-29-1 through J-29-12 as shown in Exhibit A. Of note are (R)-configured haloketone intermediates of Formula 38, which afford the more fungicidally active final products of Formula 1 after coupling with thioamides of Formula 29 (further steps maybe needed after coupling with thioamides to obtain a compound of Formula 1). Haloketones of Formula 38 can be prepared by the multi-step reaction sequences shown in Scheme 19.

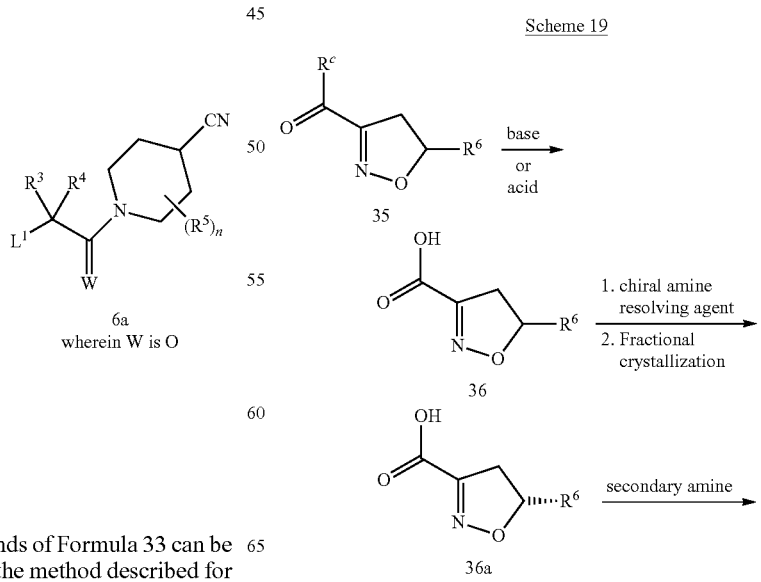

As shown in Scheme 18, compounds of Formula 33 can be prepared by a method analogous to the method described for Method A in Scheme 17.

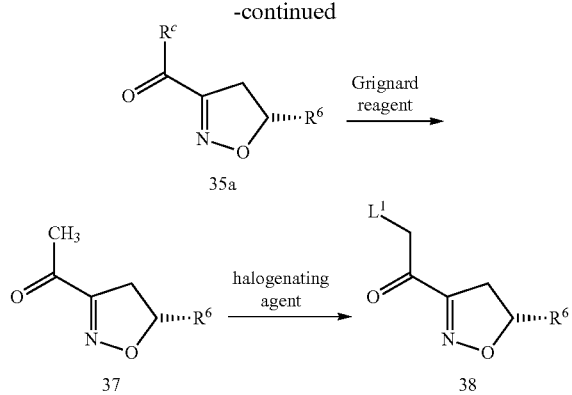

wherein $R^c$ is $C_2$-$C_3$ dialkylamino, $C_2$-$C_6$ haloalkylamine, 1-piperdinyl, 1-pyrrolidinyl or 4-morpholinyl and $L^1$ is Cl, Br or I In Scheme 19, compounds of Formula 35 are hydrolyzed under acidic or basic conditions according to well-known methods to provide compounds of Formula 36. For example, treating compounds of Formula 35 with sodium hydroxide (preferably a slight molar excess of sodium hydroxide relative to the compound of Formula 35) in an appropriate solvent such as tetrahydrofuran or methanol at a temperature between about 25 to 45° C. provides salts of compounds of Formula 36. The carboxylic acid products of Formula 36 can be isolated by adjusting the pH of the reaction mixture to about 1 to 3, and then filtering the reaction mixture or extracting the reaction mixture with an organic solvent (optionally after concentration of the reaction mixture). Racemic compounds of Formula 36 can be reacted with a suitable chiral amine resolving agent to form diastereomeric salts, and then resolved by classical fractional crystallization to provide compounds of Formula 36a (pure enantiomers or enantiomerically enriched). Suitable chiral amine resolving agents include, for example, cinchonine, dihydrocinchonine or a mixture thereof. In particular, a mixture of cinchonine-dihydrocinchonine in about a 85:15 ratio is useful for providing the (R)-configured carboxylic acids of Formula 36a wherein $R^6$ is a substituted phenyl group as the less soluble salt. The chiral amine bases are readily available from commercial sources. Compounds of Formula 36a are converted to chiral amides of Formula 35a using an amide-bond forming reaction analogous to those described for Scheme 1 or 2. Ketones of Formula 37 can be prepared by reacting amides of Formula 35a (either pure enantiomers or enantiomerically enriched mixtures) with one molar equivalent of a Grignard reagent such as methylmagnesium chloride or bromide in a suitable solvent or solvent mixture such as tetrahydrofuran and toluene at a temperature between about 0 to 20° C. The ketones of Formula 37 can be isolated by quenching the reaction mixture with aqueous acid, extracting with an organic solvent and concentrating. The ketones of Formula 37 can be used without further purification or purified by standard techniques known in the art. Compounds of Formula 37 can be halogenated with a reagent such as sulfuryl chloride or bromine to provide haloketones of Formula 38. The haloketones of Formula 38 can be purified by crystallization from a solvent such as hexanes or methanol, or can be used without further purification in condensation reactions with thioamides.

One skilled in the art recognizes that Scheme 19 can also be practiced without the use of a resolving agent, thus a compound of Formula 36 can be converted directly to the racemic analog of Formula 35a, which can then be used to prepare racemic analogs of Formulae 37 and 38 and certain racemic compounds of Formula 1 (e.g., compounds containing racemic analogs of J-29-1 through J-29-12).

The isoxazoline carboxamides of Formula 35 can be prepared by cycloaddition of the corresponding hydroxamoyl chlorides of Formula 39 with olefin derivatives of Formula 40, as shown in Scheme 20.

Scheme 20

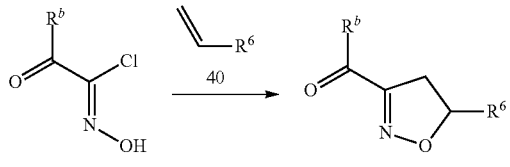

wherein $R^b$ is $C_2$-$C_3$ dialkylamino, $C_2$-$C_6$ haloalkylamine, 1-piperdinyl, 1-pyrrolidinyl or 4-morpholinyl In the method of Scheme 20, compounds of Formulae 39 and 40 are contacted in the presence of a base in a manner that minimize hydrolysis or dimerization of the hydroxamoyl chloride of Formula 39. In one typical procedure, the base, which can be a tertiary amine base such as triethylamine or an inorganic base such as an alkaline-earth metal carbonate, bicarbonate or phosphate, is mixed with a compound of Formula 40, and a compound of Formula 39 is added gradually at a temperature at which the cycloaddition proceeds at a relatively rapid rate, typically between 5 and 25° C. Alternatively, the base can be added gradually to the other two components (the compounds of Formulae 39 and 40). This alternative procedure is preferable when the hydroxamoyl chloride of Formula 39 is substantially insoluble in the reaction medium. The solvent in the reaction medium can be water or an inert organic solvent such as toluene, hexane or even the olefin derivative used in excess. The product can be separated from the salt co-product by filtration or washing with water, followed by evaporation of the solvent. The crude product can be purified by crystallization, or the crude product can be used directly in the methods of Scheme 19. Compounds of Formula 35 are useful precursors to the corresponding methyl ketones of Formula 37 and halomethyl ketones of Formula 38, and are also useful for preparing the resolved enantiomers of the compounds of Formulae 37 and 38 by hydrolysis, resolution, methyl ketone synthesis and halogenation, as shown in Scheme 19.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, Protective Groups in Organic Synthesis, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet, and "br m" means broad multiplet.

EXAMPLE 1

Preparation of 2,2,2-trifluoroacetaldehyde, O-[2-[4-[4-[5-(2,6-difluorophenyl)-4,5-dihydro-3-isoxazolyl]-2-thiazolyl]-1-piperidinyl]-2-oxoethyl]oxime (Compound 3)

Step A: Preparation of 5-(2,6-difluorophenyl)-4,5-dihydro-N,N-dimethyl-3-isoxazolecarboxamide A 1000-mL round bottom flask equipped with a mechanical stirrer, thermometer and addition funnel was charged with 2-(dimethylamino)-N-hydroxy-2-oxoethanimidoyl chloride (94.0 g, 0.62 mol) and a solution of 2,6-difluorostyrene (84.0 g, 0.60 mol) in chlorobenzene (275 g). The reaction mixture was cooled to 10° C., and a solution of potassium bicarbonate (70 g, 0.70 mol) in water (350 mL) was added dropwise over 1 h while maintaining the reaction temperature between 10 to 15° C. When gas chromatography analysis of the reaction mixture showed about 3% of 2-(dimethylamino)-N-hydroxy-2-oxo-ethanimidoyl chloride remaining, water (200 mL) was added to the reaction mixture. The layers were separated, and the organic layer was washed with water (300 mL) and concentrated under reduced pressure. Toluene was added to the resulting residu, and the mixture was again concentrated under reduced pressure to provide the title compound as an oil (144 g).

$^1$H NMR (CDCl$_3$): δ 3.1 (s, 3H), 3.3 (s, 3H), 3.4 (m, 1H), 3.57 (m, 1H), 6.0 (m, 1H), 6.95 (m, 2H), 7.35 (m, 1H).

Step B: Preparation of 1-(4,5-dihydro-5-(2,6-difluorophenyl)-3-isoxazolyl)ethanone A 1000-mL flask equipped with thermometer and addition funnel was charged with 5-(2,6-difluorophenyl)-4,5-dihydro-N,N-dimethyl-3-isoxazolecarboxamide (i.e. the product of Step A) (80.0 g, 0.31 mol) and toluene (320 mL). The reaction mixture was cooled to –5° C., and a solution of methyl magnesium bromide (3.0 M in tetrahydrofuran, 120 mL, 0.36 mmol) was added dropwise while maintaining the reaction temperature between –10 to –5° C. When gas chromatography analysis of the reaction mixture showed about 2% of 5-(2,6-difluorophenyl)-4,5-dihydro-N,N-dimethyl-3-isoxazolecarboxamide remaining, the reaction mixture was poured into a stirred solution of concentrated hydrochloric acid (80 mL) and water (320 mL) while maintaining the temperature of the mixture between 10 to 30° C. The organic layer was separated, washed with saturated aqueous sodium chloride solution (80 mL) and concentrated under reduced pressure. The resulting oil was crystallized from hexanes (100 mL) and collected by filtration washing with hexanes. The resulting solid was dried in a vacuum oven overnight at 23° C. to provide the title compound as a waxy, off-white solid (65 g), melting at 47-50° C.

$^1$H NMR (CDCl$_3$): δ 2.6 (s, 3H), 3.3 (m, 1H), 3.5 (m, 1H), 6.1 (m, 1H), 6.9 (m, 2H), 7.3 (m, 1H).

Step C: Preparation of 2-bromo-1-(4,5-dihydro-5-(2,6-difluorophenyl)-3-isoxazolyl)ethanone A 500-mL flask equipped with a mechanical stirrer, thermometer, addition funnel and scrubber was charged with 1-(4,5-dihydro-5-(2,6-difluorophenyl)-3-isoxazolyl)ethanone (i.e. the product of Step B) (60.0 g, 0.27 mmol) and dichloromethane (130 mL). The reaction mixture was heated at 33° C., and a solution of bromine (39.2 mL, 0.24 mol) in dichloromethane (100 mL) was added dropwise via the addition funnel. After about 5 mL of the bromine solution had been added, the addition was stopped and the reaction mixture was stirred at 33° C. for about 10 minutes, during which time the color of the reaction mixture changed from red to yellow. The reaction mixture was cooled to 5° C., and the remaining bromine solution was added dropwise over 90 minutes. After the addition was complete, the reaction mixture was washed with aqueous sodium bisulfite solution (3.5 g in 100 mL of water), the layers were separated and the organic layer was concentrated under reduced pressure. Hexanes were added to the resulting residue, and the mixture was filtered rinsing with hexanes to provide the title compound as a brown solid (73 g), which was used without further purification.

Step D: Preparation of 4-[4-[5-(2,6-difluorophenyl)-4,5-dihydro-3-isoxazolyl]-2-thiazolyl]piperidine A mixture of 1-tert-butoxycarbonylpiperidine-4-carbothioamide (7.33 g, 30 mmol) and 2-bromo-1-(4,5-dihydro-5-(2,6-difluorophenyl)-3-isoxazolyl)ethanone (i.e. the product of Step C) (9.12 g, 30 mmol) in acetone (100 mL) was heated at 45° C. for 3 h, and then stirred at room temperature overnight. The reaction mixture was concentrated, and the resulting residue was dissolved in dichloromethane (100 mL) and trifluoroacetic acid (40 mL), stirred at room temperature for 3 h and then concentrated under reduced pressure. The resulting oil was dissolved in aqueous hydrochloric acid solution (0.5 N, 200 mL) and extracted with ethyl acetate. The organic layer was basified by adding aqueous sodium hydroxide solution (10% in water), then washed with saturated aqueous sodium chloride solution, dried over magnesium sulfate, filtered and concentrated under reduced pressure to provide the title compound as a thick amber-colored oil (8.62 g, weight included residual ethyl acetate).

More aqueous sodium hydroxide solution (50% in water) was added to the hydrochloric acid solution, and the mixture was extracted with ethyl acetate. The organic layer was washed with saturated aqueous sodium chloride solution, dried over magnesium sulfate, filtered and concentrated under reduced pressure to provide more of the title product as an oil (1.33 g, weight included residual ethyl acetate).

¹H NMR (CDCl₃): δ 1.70-1.80 (m, 2H), 1.87 (br s, 1H), 2.22 (m, 2H), 2.77 (m, 2H), 3.18 (m, 3H), 3.62 (m, 1H), 3.80 (m, 1H), 6.05 (m, 1H), 6.92 (m, 2H), 7.30 (m, 1H), 7.64 (s, 1H).

Step E: Preparation of 2,2,2-trifluoroacetaldehyde, O-[2-[4-[4-[5-(2,6-difluorophenyl)-4,5-dihydro-3-isoxazolyl]-2-thiazolyl]-1-piperidinyl]-2-oxoethyl] oxime A mixture of O-(carboxymethyl)hydroxylamine hemihydrochloride (5.5 g, 25 mmol) and 2,2,2-trifluoro-1,1-ethanediol (10 g, 75 mmol, 75% solution in water) was allowed to stand. After 4 days the reaction mixture was diluted with dichloromethane, washed with water, dried over magnesium sulfate, filtered and concentrated under reduced pressure to provide 2-[(2,2,2-trifluoroethylidene)amino]oxy]acetic acid as a white powder (6.5 g).
¹H NMR (CDCl₃): δ 4.80 (s, 2H), 7.58 (m, 1H), 10.4 (br s, 1H).
A mixture of 2-[(2,2,2-trifluoroethylidene)amino]oxy] acetic acid (prepared as described in preceeding paragraph) (565 mg, 3.3 mmol), 4-[4-[5-(2,6-difluorophenyl)-4,5-dihydro-3-isoxazolyl]-2-thiazolyl]piperidine (i.e. the product of Step D) (1.50 g, 3.0 mmol), N3-(ethylcarbodimidoyl)-N1,N1-dimethyl-1,3-propanediamine hydrochloride (633 mg, 3.3 mmol), 1-hydroxybenzotriazole (40.5 mg, 0.30 mmol) and triethylamine (460 μL, 3.3 mmol) in dichloromethane (8 mL) was stirred at room temperature. After 3 h, the reaction mixture was diluted with dichloromethane, washed with water, aqueous hydrochloric acid solution (1 N), water, saturated aqueous sodium bicarbonate solution and saturated aqueous sodium chloride solution. The organic layer was dried over magnesium sulfate, filtered and concentrated under reduced pressure to provide a yellow oil (1.3 g). The oil was crystallized from methyl acetate (5 mL) to provide the title compound, a compound of the present invention, as a white solid (0.55 g) melting at 123-126° C.
Pentane (10 mL) was added to the methyl acetate filtrate and the mixture was filtered. The resulting solid was crystallized from methanol (3 mL) to provide more of the title compound as a white solid (455 mg) melting at 124-127° C.
¹H NMR (CDCl₃): δ 1.75-1.90 (m, 2H), 2.15-2.27 (m, 2H), 2.88 (m, 1H), 3.22 (m, 1H), 3.32 (m, 1H), 3.63 (m, 1H), 3.75-3.85 (m, 2H), 4.62 (m, 1H), 4.90 (m, 1H), 6.07 (m, 1H), 6.92 (m, 2H), 7.30 (m, 1H), 7.60 (m, 1H), 7.66 (s, 1H).

EXAMPLE 2

Preparation of cyclopentanone, O-[2-[4-[5-(2,6-difluorophenyl)-4,5-dihydro-3-isoxazolyl]-2-thiazolyl]-1-piperidinyl]-2-oxoethyl]oxime (Compound 5)

Step A: Preparation of 2-chloro-1-[4-[4-[5-(2,6-difluorophenyl)-4,5-dihydro-3-isoxazolyl]-2-thiazolyl]-1-piperidinyl]ethanone To a mixture of 4-[4-[5-(2,6-difluorophenyl)-4,5-dihydro-3-isoxazolyl]-2-thiazolyl]piperidine (i.e. the product of Example 1, Step D) (4.2 g, 12.0 mmol) and N,N-diisopropylethylamine (1.63 g, 12.6 mmol) in methylene chloride (25 mL) at 0° C. was added a solution of 2-chloroacetyl chloride (1.43 g, 1.26 mmol) in dichloromethane (3 mL), after which time the reaction mixture was allowed to warm to room temperature. After 4 h, the reaction mixture was poured into water and the layers were separated. The organic layer was washed with aqueous hydrochloric acid solution (1 N), saturated aqueous sodium bicarbonate solution and saturated aqueous sodium chloride solution, dried over magnesium sulfate, filtered and concentrated under reduced pressure. The resulting residue was purified by medium pressure liquid chromatography on silica gel (0 to 100% gradient of ethyl acetate in hexanes as eluant) to provide the title compound as a tan solid (2.8 g).
¹H NMR (CDCl₃): δ 1.78-1.97 (m, 2H), 2.18-2.31 (m, 2H), 2.86-2.95 (t, 1H), 3.26-3.39 (m, 2H), 3.60-3.86 (m, 2H), 3.95-4.02 (d, 1H), 4.04-4.16 (m, 2H), 4.57-4.62 (d, 1H), 6.07-6.12 (m, 1H), 6.09-6.12 (m, 2H), 7.26-7.36 (m, 1H), 7.66 (s, 1H).

Step B: Preparation of cyclopentanone, O-[2-[4-[5-(2,6-difluorophenyl)-4,5-dihydro-3-isoxazolyl]-2-thiazolyl]-1-piperidinyl]-2-oxoethyl]oxime To a mixture of sodium hydride (0.024 g, 0.60 mmol, 60% in mineral oil) in tetrahydrofuran (3 mL) at 0° C. was added a solution of cyclopentanone oxime (49.57 mg, 0.50 mmol) in tetrahydrofuran (2 mL). The reaction mixture was stirred for 30 minutes at 0° C., and then a solution of 2-chloro-1-[4-[4-[5-(2,6-difluorophenyl)-4,5-dihydro-3-isoxazolyl]-2-thiazolyl]-1-piperidinyl]ethanone (i.e. the product of Step A) (0.19 g, 0.45 mmol) in tetrahydrofuran (2 mL) was added. The reaction mixture was allowed to warm to room temperature. After 2 h, water (5 mL) was slowly added to the reaction mixture and the resulting aqueous mixture was extracted with ethyl acetate. The organic layer was dried over magnesium sulfate, filtered and concentrated under reduced pressure. The resulting residue was purified by medium pressure liquid chromatography on silica gel (0 to 100% gradient of ethyl acetate in hexanes as eluant) to provide the title compound, a compound of the present invention, as an amber-colored oil (0.162 g).
¹H NMR (CDCl₃): δ 1.60-1.70 (m, 2H), 1.70-1.84 (m, 4H), 2.12-2.24 (m, 2H), 2.32-2.41 (m, 2H), 2.42-2.52 (m, 2H), 2.79-2.89 (m, 1H), 3.18-3.26 (m 1H), 3.26-3.37 (m, 1H), 3.60-3.67 (m, 1H), 3.73-3.83 (m, 1H), 3.98-4.03 (m, 1H), 4.60-4.64 (m, 1H), 4.71 (s, 2H), 6.03-6.13 (m, 1H), 6.88-6.96 (m, 2H), 7.25-7.36 (m, 1H), 7.63 (s, 1H).

EXAMPLE 3

Preparation of N-methyl-N-[(1R)-1-phenylethyl]-2-[1-[2-[[(2,2,2-trifluoroethylidene)amino]oxy]acetyl]-4-piperidinyl]-4-thiazolecarboxamide (Compound 31)

To a mixture of 1,1-dimethylethyl 4-[4-[[methyl[(1R)-1-phenylethyl]amino]carbonyl]-2-thiazolyl]-1-piperidinecarboxylate (2.0 g, 4.65 mmol) (see PCT Patent Publication WO 2007/014290 for a method of preparation) in diethyl ether was added hydrochloric acid (2 N in diethyl ether, 23 mL). The reaction mixture was stirred at room temperature for 3 h, and then the solid was collected by filtration to give N-methyl-N-[(1R)-1-phenylethyl]-2-(4-piperidinyl)-4-thiazolecarboxamide hydrochloride (1.2 g). A mixture of N-methyl-N-[(1R)-1-phenylethyl]-2-(4-piperidinyl)-4-thiazolecarboxamide hydrochloride (0.11 g, 0.30 mmol), (2-[(2,2,2-trifluoroethylidene)amino]oxy]acetic acid (prepared by the method described Example 1, Step E) (62 mg, 0.36 mmol), N-(3-dimethylaminopropyl)-N-ethylcarbodiimide hydrochloride (81 mg, 0.42 mmol), N-hydroxybenzotriazole (5 mg) and triethylamine (0.10 mL, 0.72 mmol) in dry methylene chloride (8 mL) was stirred at room temperature for 3 h. The reaction mixture was diluted with methylene chloride and then washed with water, hydrochloric acid (0.1 N), water, saturated aqueous sodium bicarbonate solution and saturated aqueous sodium chloride solution, and dried over magnesium sulfate, filtered and concentrated under reduced pressure to give the title compound, a compound of the present invention, as a thick oil (130 mg).

$^1$H NMR (CDCl$_3$) δ 1.60-1.90 (br m, 5H), 2.10-2.25 (br m, 2H), 2.7-3.0 (br m, 4H), 3.15-3.30 (br m, 2H), 3.7-3.85 (br m, 1H), 4.4-4.6 (br m, 1H), 4.88 (br s, 2H), 5.7-6.2 (br m, 1H), 7.25-7.40 (m, 5H), 7.60 (m, 1H), 7.84 (s, 1H).

EXAMPLE 4

Preparation of 2,2,2-trifluoroacetaldehyde 2-[2-[4-[5-(2,6-difluorophenyl)-4,5-dihydro-3-isoxazolyl]-2-thiazolyl]-1-piperidinyl]-2-oxoethyl]-2-methylhydrazone (Compound 35)

Step A: Preparation of 1-[4-[4-[5-(2,6-difluorophenyl)-4,5-dihydro-3-isoxazolyl]-2-thiazolyl]-1-piperidinyl]-2-(1-methylhydrazinyl)ethanone To a mixture of methyl hydrazine (532 μL, 10.0 mmol) in tetrahydrofuran (1 mL) at 0° C. was added dropwise a solution of 2-chloro-1-[4-[4-[5-(2,6-difluorophenyl)-4,5-dihydro-3-isoxazolyl]-2-thiazolyl]-1-piperidinyl]ethanone (i.e. the product of Example 2, Step A) (425 mg, 1.0 mmol) in tetrahydrofuran (5 mL). The reaction mixture was stirred at room temperature overnight, and then concentrated under reduced pressure. The resulting residue was dissolved in dichloromethane, washed with water and saturated aqueous sodium chloride solution, dried over magnesium sulfate, filtered and concentrated under reduced pressure to provide the title compound as an oil (0.59 g weight including residual tetrahydrofuran), which was used without further purification.

Step B: Preparation of 2,2,2-trifluoroacetaldehyde 2-[2-[4-[5-(2,6-difluorophenyl)-4,5-dihydro-3-isoxazolyl]-2-thiazolyl]-1-piperidinyl]-2-oxoethyl]-2-methylhydrazone To a mixture of 1-[4-[4-[5-(2,6-difluorophenyl)-4,5-dihydro-3-isoxazolyl]-2-thiazolyl]-1-piperidinyl]-2-(1-methylhydrazinyl)ethanone (i.e. the product of Step A) (0.29 g weight including residual tetrahydrofuran) in methanol (3 mL) was added 2,2,2-trifluoro-1,1-ethanediol (209 mg, 1.35 mmol, 75% solution in water). The reaction mixture was stirred at room temperature overnight, and then diluted with dichloromethane. The organic layer was washed with water and saturated aqueous sodium chloride solution, dried over magnesium sulfate, filtered and concentrated under reduced pressure. The resulting residue was purified by medium pressure liquid chromatography on silica gel (0 to 100% gradient of ethyl acetate in hexanes as eluant) to provide the title compound, a compound of the present invention, as an oil (0.085 g).

$^1$H NMR (CDCl$_3$) δ 1.75-1.90 (m, 2H), 2.15-2.27 (m, 2H), 2.82 (m, 1H), 2.99 (s, 3H), 3.20 (m, 1H), 3.33 (m, 1H), 3.62 (m, 1H), 3.75-3.95 (m, 2H), 4.29 (m, 2H), 4.58 (m, 1H), 6.07 (m, 1H), 6.35 (m, 1H), 6.90 (m, 2H), 7.30 (m, 1H), 7.66 (s, 1H).

EXAMPLE 5

Preparation of 2,2,2-trifluoroacetic acid 2-[2-[4-[5-(2,6-difluorophenyl)-4,5-dihydro-3-isoxazolyl]-2-thiazolyl-1-piperidinyl]-2-oxoethyl]-2-methylhydrazide (Compound 36)

To a mixture of 1-[4-[4-[5-(2,6-difluorophenyl)-4,5-dihydro-3-isoxazolyl]-2-thiazolyl]-1-piperidinyl]-2-(1-methylhydrazinyl)ethanone (i.e. the product of Example 4, Step A) (0.29 g weight including residual tetrahydrofuran) and triethylamine (103 μL, 0.74 mmol) in dichloromethane (2 mL) at 0° C. was added trifluoroacetic anhydride (0.097 mL, 0.70 mmol). The reaction mixture was allowed to warm to room temperature, stirred overnight, and then diluted with dichloromethane. The organic layer was washed with water and saturated aqueous sodium chloride solution, dried over magnesium sulfate, filtered and concentrated under reduced pressure. The resulting residue was purified by medium pressure liquid chromatography on silica gel (0 to 100% gradient of ethyl acetate in hexanes as eluant) to provide the title compound, a compound of the present invention, as white, foamy solid (0.10 g).

$^1$H NMR (CDCl$_3$) δ 1.75-1.90 (m, 2H), 2.15-2.27 (m, 2H), 2.80-2.90 (m, 4H), 3.20 (m, 1H), 3.33 (m, 1H), 3.62 (m, 1H), 3.75-3.90 (m, 4H), 4.60 (m, 1H), 6.07 (m, 1H), 6.92 (m, 2H), 7.30 (m, 1H), 7.65 (m, 1H), 9.45 (s, 1H).

EXAMPLE 6

Preparation of N-[2-[4-[5-(2,6-difluorophenyl)-4,5-dihydro-3-isoxazolyl]-2-thiazolyl]-1-piperidinyl]-2-oxoethyloxy]-2,2,2-trifluoroacetamide (Compound 38)

Step A: Preparation of N-[2-[4-[5-(2,6-difluorophenyl)-4,5-dihydro-3-isoxazolyl]-2-thiazolyl]-1-piperidinyl]-2-oxoethoxy]-2,2-dimethylpropanamide To a mixture of sodium hydride (80 mg, 2.0 mmol, 60% in mineral oil) and N,N-dimethylformamide at 0° C. was added a solution of 1,1-dimethylethyl N-hydroxycarbamate (146 mg, 1.1 mmol) in N,N-dimethylformamide (1 mL). The reaction mixture was stirred at 0° C. for 30 minutes, and then a solution of 2-chloro-1-[4-[4-[5-(2,6-difluorophenyl)-4,5-dihydro-3-isoxazolyl]-2-thiazolyl]-1-piperidinyl]ethanone (i.e. the product of Example 2, Step A) (0.43 g, 1.0 mmol) in N,N-dimethylformamide (2 mL) was added. The reaction mixture was allowed to warm to room temperature and stirred for 2 h, and then water (5 mL) was slowly added. The mixture was extracted with ethyl acetate, and the organic layer was washed with citric acid solution (also known as 2-hydroxy-1,2,3-propanetricarboxylic acid) (20% in water) and saturated aqueous sodium bicarbonate solution, dried over magnesium sulfate, filtered and concentrated under reduced pressure. The resulting residue was purified by medium pressure liquid chromatography on silica gel (0 to 100% gradient of ethyl acetate in hexanes as eluant) to provide the title compound as an oil (0.37 g).

$^1$H NMR (CDCl$_3$): δ 1.47 (s, 9H), 1.8 (m, 2H), 2.2 (m, 2H), 2.85 (m, 1H), 3.20 (m 1H), 3.30 (m, 1H), 3.60-3.67 (m, 1H), 3.75-3.83 (m, 1H), 4.57 (s, 2H), 4.60 (m, 1H), 6.03-6.13 (m, 1H), 6.88-6.96 (m, 2H), 7.25-7.36 (m, 1H), 7.66 (s, 1H), 8.19 (s, 1H).

Step B: Preparation of 2-(aminooxy)-1-[4-[4-[5-(2,6-difluorophenyl)-4,5-dihydro-3-isoxazolyl]-2-thiazolyl]-1-piperidinyl]ethanone To a mixture of N-[2-[4-[5-(2,6-difluorophenyl)-4,5-dihydro-3-isoxazolyl]-2-thiazolyl]-1-piperidinyl]-2-oxoethoxy]-2,2-dimethylpropanamide (i.e. the product of Step A) (0.37 g, 0.71 mmol) in methanol (5 mL) was added a solution of hydrochloric acid (2 M in diethyl ether, 3.6 mL). After 3 h, the reaction mixture was concentrated under reduced pressure and partitioned between dichloromethane and saturated aqueous sodium bicarbonate solution. The organic layer was dried over magnesium sulfate, filtered and concentrated under reduced pressure to provide the title compound as a foamy, white solid (0.20 g).

$^1$H NMR (CDCl$_3$): δ 1.8 (m, 2H), 2.2 (m, 2H), 2.85 (m, 1H), 3.15 (m 1H), 3.30 (m, 1H), 3.60-3.67 (m, 1H), 3.70-3.83 (m, 2H), 4.40 (s, 2H), 4.63 (m, 1H), 5.93 (br s, 2H), 6.10 (m, 1H), 6.88-6.96 (m, 2H), 7.25-7.36 (m, 1H), 7.66 (s, 1H).

Step C: Preparation of N-[2-[4-[5-(2,6-difluorophenyl)-4,5-dihydro-3-isoxazolyl]-2-thiazolyl]-1-piperidinyl]-2-oxoethyloxy]-2,2,2-trifluoroacetamide To a mixture of 2-(aminooxy)-1-[4-[4-[5-(2,6-difluorophenyl)-4,5-dihydro-3-isoxazolyl]-2-thiazolyl]-1-piperidinyl]ethanone (i.e. the product of Step B) (0.20 g, 0.47 mmol) and triethylamine (0.073 mL, 0.52 mmol) in dichloromethane (2 mL) at 0° C. was added trifluoroacetic anhydride (0.065 mL, 0.47 mmol). The reaction mixture was allowed to warm to room temperature and stirred overnight. More triethylamine (0.095 mL, 0.68 mmol) and trifluoroacetic anhydride (0.044 mL, 0.32 mmol) were added to the reaction mixture. After 2 h, the reaction mixture was diluted with dichloromethane, the organic layer was washed with hydrochloric acid (1 N), saturated aqueous sodium bicarbonate solution and saturated aqueous sodium chloride solution, dried over magnesium sulfate, filtered and concentrated under reduced pressure to provide the title compound, a compound of the present invention, as an oil (0.14 g).

$^1$H NMR (CDCl$_3$) δ 1.8 (m, 2H), 2.2 (m, 2H), 2.95 (m, 1H), 3.15 (m 1H), 3.33 (m, 1H), 3.55-3.70 (m, 2H), 3.70-3.83 (m, 1H), 4.55 (m, 1H), 4.75 (s, 2H), 6.04 (m, 1H), 6.88-6.96 (m, 2H), 7.5 and 7.7 (m, 1H), 7.65 (s, 1H).

EXAMPLE 7

Preparation of 1-[4-[4-[5-(2,6-difluorophenyl)-4,5-dihydro-3-isoxazolyl]-2-thiazolyl]-1-piperidinyl]-2-(4,5-dihydro-3,5-dimethyl-1H-pyrazol-1-yl]ethanone (Compound 40)

Step A: Preparation of ethyl 4,5-dihydro-3,5-dimethyl-1H-pyrazole-1-acetate

A mixture of ethyl hydrazinoacetate hydrochloride (1.55 g, 10 mmol), 3-pentene-2-one (0.95 mL, 10 mmol) and sodium bicarbonate (1.00 g, 11.9 mmol) in ethanol (10 mL) was stirred at room temperature overnight. The reaction mixture was then filtered and concentrated under reduced pressure. The resulting oil was purified by medium pressure liquid chromatography on silica gel (0 to 100% gradient of ethyl acetate in hexanes as eluant) to provide the title compound as a yellow oil (0.26 g).

$^1$H NMR (CDCl$_3$): δ 1.27 (m, 6H), 1.94 (s, 3H), 2.35 (m, 1H), 2.75 (m, 1H), 3.42 (m, 1H), 3.60-3.85 (m 2H), 4.20 (m, 2H).

Step B: Preparation of 4,5-dihydro-3,5-dimethyl-1H-pyrazole-1-acetic acid

A mixture of ethyl 4,5-dihydro-3,5-dimethyl-1H-pyrazole-1-acetate (i.e. the product of Step A) (0.26 g, 0.0014 mol) and lithium hydroxide (0.072 g, 3 mmol) in a solution of methanol (2 mL), tetrahydrofuran (2 mL) and water (2 mL) was stirred overnight at room temperature. Saturated aqueous ammonium chloride solution was added to the reaction mixture, and the mixture was concentrated under reduced pressure. The resulting residue was dissolved in ethyl acetate, and the organic layer was concentrated under reduced pressure to provide the title compound as a colorless oil (0.10 g).

$^1$H NMR (CDCl$_3$) δ 1.29 (d, 3H), 1.97 (s, 3H), 2.37 (m, 1H), 2.77 (m, 1H), 3.3 (m, 1H), 3.5-3.8 (m 2H), 8.15 (m, 1H).

Step C: Preparation of 1-[4-[4-[5-(2,6-difluorophenyl)-4,5-dihydro-3-isoxazolyl]-2-thiazolyl]-1-piperidinyl]-2-(4,5-dihydro-3,5-dimethyl-1H-pyrazol-1-yl]ethanone A mixture of 4,5-dihydro-3,5-dimethyl-1H-pyrazole-1-acetic acid (i.e. the product of Step B) (0.10 g, 0.64 mmol), 4-[4-[5-(2,6-difluorophenyl)-4,5-dihydro-3-isoxazolyl]-2-thiazolyl]piperidine (i.e. the product of Example 1, Step D) (175 mg, 0.5 mmol), N3-(ethylcarbodimidoyl)-N1,N1-dimethyl-1,3-propanediamine hydrochloride (191 mg, 1.0 mmol), 1-hydroxybenzotriazole (5 mg, 0.037 mmol) and triethylamine (0.14 mL, 1.0 mmol) in dichloromethane (4 mL) was stirred at room temperature. After 6 h, more N3-(ethylcarbodimidoyl)-N1,N1-dimethyl-1,3-propanediamine hydrochloride (191 mg, 1.0 mmol) and triethylamine (0.14 mL, 1.0 mmol) were added to the reaction mixture. After 3 days, the reaction mixture was diluted with dichloromethane, washed with saturated aqueous ammonium chloride solution and concentrated under reduced pressure. The resulting residue was purified by medium pressure liquid chromatography on silica gel (0 to 100% gradient of ethyl acetate in hexanes, and then 20% methanol in ethyl acetate as eluant) to provide the title compound, a compound of the present invention, as a tan solid (124 mg).

$^1$H NMR (CDCl$_3$) δ 1.25 (m, 3H), 1.65-1.90 (m, 2H), 1.93 (s, 3H), 2.10-2.25 (m, 2H), 2.35 (m, 1H), 2.80 (m, 2H), 3.15-3.45 (m, 3H), 3.50-4.05 (m, 4H), 4.30 (m, 1H), 4.66 (m, 1H), 6.07 (m, 1H), 6.92 (m, 2H), 7.30 (m, 1H), 7.66 (s, 1H).

By the procedures described herein, together with methods known in the art, the following compounds of Tables 1 to 21 can be prepared. The following abbreviations are used in the Tables: t means tertiary, s means secondary, n means normal, i means iso, c means cyclo, Me means methyl, Et means ethyl, Pr means propyl, i-Pr means isopropyl, c-Pr means cyclopropyl, Bu means butyl, c-Bu means cyclobutyl, CN means cyano and Ph means phenyl.

TABLE 1

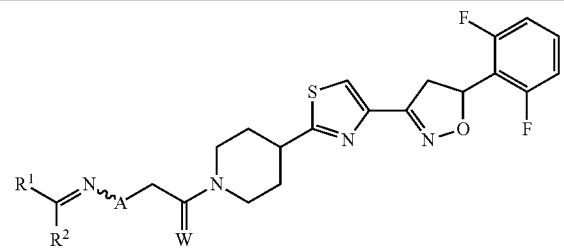

| R$^1$ | R$^2$ | A |
|---|---|---|
| W is O. | | |
| Me | Me | —O— |
| Me | Me | —S— |
| Me | Me | —NH— |
| Me | Me | —N(Me)— |
| Me | Me | —CH$_2$— |
| Me | Me | —C(Me)$_2$— |
| Me | Me | —OCH$_2$— |
| Me | Me | —SCH$_2$— |
| Me | Me | —NHCH$_2$— |

TABLE 1-continued

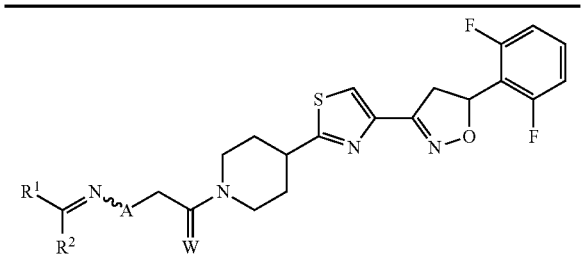

| R¹ | R² | A |
|---|---|---|
| Me | Me | —N(Me)CH₂— |
| Me | H | —O— |
| Et | H | —O— |
| n-Pr | H | —O— |
| i-Pr | H | —O— |
| n-Bu | H | —O— |
| i-Bu | H | —O— |
| t-Bu | H | —O— |
| hexyl | H | —O— |
| H | H | —O— |
| CN | H | —O— |
| NH₂ | H | —O— |
| HC(=O) | H | —O— |
| HOC(=O) | H | —O— |
| H₂NC(=O) | H | —O— |
| CH₂=CH | Me | —O— |
| CH₂=CHCH₂ | H | —O— |
| CH≡CCH₂ | H | —O— |
| CF₃ | H | —O— |
| CF₃ | Me | —O— |
| CF₃CH₂ | H | —O— |
| CF₃CH₂ | Me | —O— |
| ClCH₂CH₂ | H | —O— |
| c-Pr | H | —O— |
| c-pentyl | H | —O— |
| c-hexyl | H | —O— |
| 1-F-c-Pr | H | —O— |
| CF₂=CF | H | —O— |
| c-PrCH₂ | H | —O— |
| CH₃OCH₂ | H | —O— |
| CH₃SCH₂ | H | —O— |
| CH₃S(=O)CH₂ | H | —O— |
| CH₃S(=O)₂CH₂ | H | —O— |
| (CH₃)₂NCH₂ | H | —O— |
| CH₃C(=O) | H | —O— |
| CF₃C(=O) | H | —O— |
| c-PrC(=O) | H | —O— |
| CH₃OC(=O) | H | —O— |
| MeNHC(=O) | H | —O— |
| (Me)₂NC(=O) | H | —O— |
| MeO | H | —O— |
| EtO | H | —O— |
| i-PrO | H | —O— |
| CF₃O | H | —O— |
| c-BuO | H | —O— |
| CH₂=CHCH₂O | H | —O— |
| CH≡CCH₂O | H | —O— |
| MeOCH₂CH₂O | H | —O— |
| CH₃C(=O)O | H | —O— |
| CF₃C(=O)O | H | —O— |
| MeS | H | —O— |
| CF₃S | H | —O— |
| c-PrS | H | —O— |
| MeNH | H | —O— |
| (Me)₂N | H | —O— |
| ClCH₂CH₂NH | H | —O— |
| CH₃C(=O)NH | H | —O— |
| CF₃C(=O)NH | H | —O— |
| CH₃S(=O)₂NH | H | —O— |
| CF₃S(=O)₂NH | H | —O— |
| Cl | H | —O— |
| CF₃ | Et | —O— |
| CF₃ | n-Pr | —O— |
| CF₃ | i-Pr | —O— |
| CF₃ | CN | —O— |

TABLE 1-continued

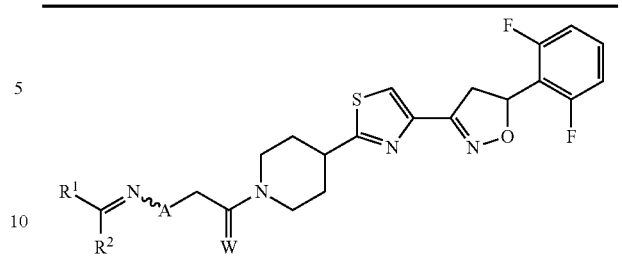

| R¹ | R² | A |
|---|---|---|
| CF₃ | CF₃ | —O— |
| CF₃ | CH₂Cl | —O— |
| CF₃ | Cl | —O— |
| CF₃ | Br | —O— |
| CF₃ | MeO | —O— |
| CF₃ | EtO | —O— |
| CF₃ | CF₃O | —O— |
| —CH₂CH₂— | | —O— |
| —CH₂CH₂CH₂— | | —O— |
| —CH₂(CH₂)₂CH₂— | | —O— |
| —CH₂(CH₂)₃CH₂— | | —O— |
| —(CH₂)₂O(CH₂)₂— | | —O— |
| CF₃CH₂ | H | —O— |
| CF₃CH₂ | Me | —O— |
| CF₃CH₂ | Et | —O— |
| CF₃CH₂ | CN | —O— |
| CF₃CH₂ | CF₃ | —O— |
| CF₃CH₂ | CH₂Cl | —O— |
| CF₃CH₂ | Cl | —O— |
| CF₃CH₂ | Br | —O— |
| CF₃CH₂ | MeO | —O— |
| CF₃CH₂ | EtO | —O— |
| CF₃CH₂ | CF₃O | —O— |
| Me | Et | —O— |
| Me | n-Pr | —O— |
| Me | i-Pr | —O— |
| Me | CN | —O— |
| Me | CF₃ | —O— |
| Me | CH₂Cl | —O— |
| Me | Cl | —O— |
| Me | Br | —O— |
| Me | MeO | —O— |
| Me | EtO | —O— |
| Me | CF₃O | —O— |
| CF₃ | H | —S— |
| CF₃ | H | —NH— |
| CF₃ | H | —N(Me)— |
| CF₃ | H | —CH₂— |
| CF₃ | H | —C(Me)₂— |
| CF₃ | H | —OCH₂— |
| CF₃ | H | —SCH₂— |
| CF₃ | H | —NHCH₂— |
| CF₃ | H | —N(Me)CH₂— |
| CF₃ | Me | —S— |
| CF₃ | Me | —NH— |
| CF₃ | Me | —N(Me)— |
| CF₃ | Me | —CH₂— |
| CF₃ | Me | —C(Me)₂— |
| CF₃ | Me | —OCH₂— |
| CF₃ | Me | —SCH₂— |
| CF₃ | Me | —NHCH₂— |
| CF₃ | Me | —N(Me)CH₂— |
| CCl₃ | H | —O— |
| CCl₃ | Me | —O— |
| CF₃CH₂ | H | —S— |
| CF₃CH₂ | H | —NH— |
| CF₃CH₂ | H | —N(Me)— |
| CF₃CH₂ | H | —CH₂— |
| CF₃CH₂ | H | —C(Me)₂— |
| CF₃CH₂ | H | —OCH₂— |
| CF₃CH₂ | H | —SCH₂— |
| CF₃CH₂ | H | —NHCH₂— |
| CF₃CH₂ | H | —N(Me)CH₂— |
| CF₃CH₂ | Me | —S— |
| CF₃CH₂ | Me | —NH— |

TABLE 1-continued

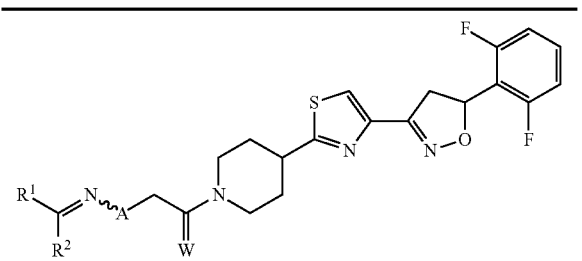

| R¹ | R² | A |
|---|---|---|
| CF₃CH₂ | Me | —N(Me)— |
| CF₃CH₂ | Me | —CH₂— |
| CF₃CH₂ | Me | —C(Me)₂— |
| CF₃CH₂ | Me | —OCH₂— |
| CF₃CH₂ | Me | —SCH₂— |
| CF₃CH₂ | Me | —NHCH₂— |
| CF₃CH₂ | Me | —N(Me)CH₂— |
| CF₃ | H | —OCH(Me)— |
| CF₃ | H | —CH(CF₃)— |
| | W is S. | |
| Me | Me | —O— |
| CF₃ | H | —O— |
| CF₃ | Me | —O— |
| CF₃ | H | —NH— |

TABLE 2

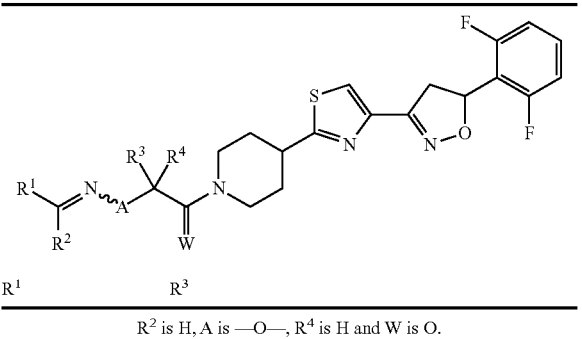

| R¹ | R³ |
|---|---|
| R² is H, A is —O—, R⁴ is H and W is O. | |
| CF₃ | Me |
| CF₃ | Et |
| CF₃ | n-Pr |
| CF₃ | i-Pr |
| CF₃ | i-Bu |
| CF₃ | CN |
| CF₃ | Cl |
| CF₃ | CH₂=CHCH₂ |
| CF₃ | CH≡CCH₂ |
| CF₃ | CF₃ |
| CF₃ | MeOCH₂ |
| CF₃ | CH₃SCH₂ |
| CF₃ | CH₃S(=O)CH₂ |
| CF₃ | CH₃S(=O)₂CH₂ |
| CF₃ | MeC(=O) |
| CF₃ | EtC(=O) |
| CF₃ | CF₃C(=O) |
| CF₃ | MeOC(=O) |
| CF₃ | EtOC(=O) |
| CF₃ | MeNHC(=O) |
| CF₃ | (Me)₂NC(=O) |
| CF₃ | MeO |
| CF₃ | EtO |
| CF₃ | CF₃O |
| CF₃ | MeS |
| CF₃ | CF₃S |
| CF₃ | CH₃S(=O) |
| CF₃ | CH₃S(=O)₂ |
| CF₃ | CH₃S(=O)₂ |

TABLE 2-continued

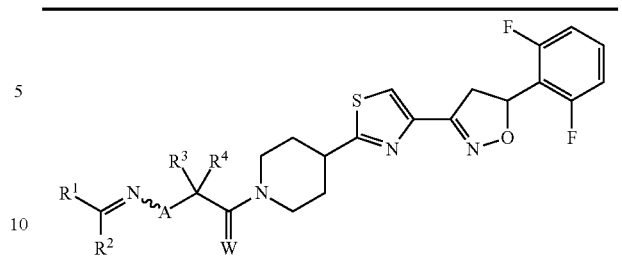

| R¹ | R³ |
|---|---|
| CF₃ | MeC(=O)O |
| CF₃ | CF₃C(=O)O |
| CF₃ | Ph |
| CF₃ | 2,5-di-Cl—Ph |
| CF₃ | 2-Cl-5-CF₃—Ph |
| CF₃ | 2,5-di-Me—Ph |
| CF₃ | 2-Me-5-CF₃—Ph |
| CF₃ | 3,5-di-Me-1H-pyrazol-1-yl |
| CF₃ | 5-Me-3-CF₃-1H-pyrazol-1-yl |
| CF₃ | 5-Cl-3-CF₃-1H-pyrazol-1-yl |
| CF₃ | 5-Br-3-CF₃-1H-pyrazol-1-yl |
| CF₃ | 5-Et-3-CF₃-1H-pyrazol-1-yl |
| CF₃ | 3,5-di-CF₃-1H-pyrazol-1-yl |
| CF₃ | 1-Me-3-CF₃-1H-pyrazol-5-yl |
| CF₃ | 1-Me-4-CF₃-1H-imidazol-2-yl |
| CF₃ | 3,5-di-Cl-1H-1,2,4-triazol-1-yl |
| CF₃ | 3,5-di-Br-1H-1,2,4-triazol-1-yl |
| CF₃CH₂ | Me |
| CF₃CH₂ | Et |
| CF₃CH₂ | MeO |
| CF₃CH₂ | EtO |
| CF₃CH₂ | MeC(=O) |
| CF₃CH₂ | MeOC(=O) |
| CF₃CH₂ | EtOC(=O) |
| CF₃CH₂ | MeNHC(=O) |
| CF₃CH₂ | (Me)₂NC(=O) |
| CF₃CH₂ | Cl |
| CF₃CH₂ | CN |
| CF₃CH₂ | CH₃S |
| CF₃CH₂ | Ph |
| CF₃CH₂ | 2,5-di-Cl—Ph |
| CF₃CH₂ | 2-Cl-5-CF₃—Ph |
| CF₃CH₂ | 2,5-di-Me—Ph |
| CF₃CH₂ | 2-Me-5-CF₃—Ph |
| CF₃CH₂ | 3,5-di-Me-1H-pyrazol-1-yl |
| CF₃CH₂ | 5-Me-3-CF₃-1H-pyrazol-1-yl |
| CF₃CH₂ | 5-Cl-3-CF₃-1H-pyrazol-1-yl |
| CF₃CH₂ | 5-Br-3-CF₃-1H-pyrazol-1-yl |
| CF₃CH₂ | 5-Et-3-CF₃-1H-pyrazol-1-yl |
| CF₃CH₂ | 3,5-di-CF₃-1H-pyrazol-1-yl |
| CF₃CH₂ | 1-Me-3-CF₃-1H-pyrazol-5-yl |
| CF₃CH₂ | 1-Me-4-CF₃-1H-imidazol-2-yl |
| CF₃CH₂ | 3,5-di-Cl-1H-1,2,4-triazol-1-yl |
| CF₃CH₂ | 3,5-di-Br-1H-1,2,4-triazol-1-yl |
| Me | Me |
| Me | Et |
| Me | MeO |
| Me | EtO |
| Me | MeC(=O) |
| Me | MeOC(=O) |
| Me | EtOC(=O) |
| Me | MeNHC(=O) |
| Me | (Me)₂NC(=O) |
| Me | Cl |
| Me | CN |
| Me | MeS |
| Me | Ph |
| Me | 2,5-di-Cl—Ph |
| Me | 2-Cl-5-CF₃—Ph |
| Me | 2,5-di-Me—Ph |
| Me | 2-Me-5-CF₃—Ph |
| Me | 3,5-di-Me-1H-pyrazol-1-yl |
| Me | 5-Me-3-CF₃-1H-pyrazol-1-yl |
| Me | 5-Cl-3-CF₃-1H-pyrazol-1-yl |
| Me | 5-Br-3-CF₃-1H-pyrazol-1-yl |

TABLE 2-continued

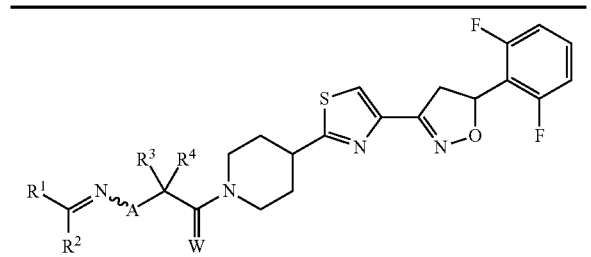

| R¹ | R³ |
|---|---|
| Me | 5-Et-3-CF₃-1H-pyrazol-1-yl |
| Me | 3,5-di-CF₃-1H-pyrazol-1-yl |
| Me | 1-Me-3-CF₃-1H-pyrazol-5-yl |
| Me | 1-Me-4-CF₃-1H-imidazol-2-yl |
| Me | 3,5-di-Cl-1H-1,2,4-triazol-1-yl |
| Me | 3,5-di-Br-1H-1,2,4-triazol-1-yl |

R² is Me, A is —O—, R⁴ is H and W is O.

| R¹ | R³ |
|---|---|
| CF₃ | Me |
| CF₃ | Et |
| CF₃ | MeO |
| CF₃ | EtO |
| CF₃ | MeC(=O) |
| CF₃ | MeOC(=O) |
| CF₃ | EtOC(=O) |
| CF₃ | MeNHC(=O) |
| CF₃ | (Me)₂NC(=O) |
| CF₃ | Cl |
| CF₃ | CN |
| CF₃ | MeS |
| CF₃ | Ph |
| CF₃ | 2,5-di-Cl—Ph |
| CF₃ | 2-Cl-5-CF₃—Ph |
| CF₃ | 2,5-di-Me—Ph |
| CF₃ | 2-Me-5-CF₃—Ph |
| CF₃ | 3,5-di-Me-1H-pyrazol-1-yl |
| CF₃ | 5-Me-3-CF₃-1H-pyrazol-1-yl |
| CF₃ | 5-Cl-3-CF₃-1H-pyrazol-1-yl |
| CF₃ | 5-Br-3-CF₃-1H-pyrazol-1-yl |
| CF₃ | 5-Et-3-CF₃-1H-pyrazol-1-yl |
| CF₃ | 3,5-di-CF₃-1H-pyrazol-1-yl |
| CF₃ | 1-Me-3-CF₃-1H-pyrazol-5-yl |
| CF₃ | 1-Me-4-CF₃-1H-imidazol-2-yl |
| CF₃ | 3,5-di-Cl-1H-1,2,4-triazol-1-yl |
| CF₃ | 3,5-di-Br-1H-1,2,4-triazol-1-yl |
| Me | Me |
| Me | Et |
| Me | MeO |
| Me | EtO |
| Me | MeC(=O) |
| Me | MeOC(=O) |
| Me | EtOC(=O) |
| Me | MeNHC(=O) |
| Me | (Me)₂NC(=O) |
| Me | Cl |
| Me | CN |
| Me | MeS |
| Me | Ph |
| Me | 2,5-di-Cl—Ph |
| Me | 2-Cl-5-CF₃—Ph |
| Me | 2,5-di-Me—Ph |
| Me | 2-Me-5-CF₃—Ph |
| Me | 3,5-di-Me-1H-pyrazol-1-yl |
| Me | 5-Me-3-CF₃-1H-pyrazol-1-yl |
| Me | 5-Cl-3-CF₃-1H-pyrazol-1-yl |
| Me | 5-Br-3-CF₃-1H-pyrazol-1-yl |
| Me | 5-Et-3-CF₃-1H-pyrazol-1-yl |
| Me | 3,5-di-CF₃-1H-pyrazol-1-yl |
| Me | 1-Me-3-CF₃-1H-pyrazol-5-yl |
| Me | 1-Me-4-CF₃-1H-imidazol-2-yl |
| Me | 3,5-di-Cl-1H-1,2,4-triazol-1-yl |
| Me | 3,5-di-Br-1H-1,2,4-triazol-1-yl |
| CF₃CH₂ | Me |
| CF₃CH₂ | Et |
| CF₃CH₂ | MeO |

TABLE 2-continued

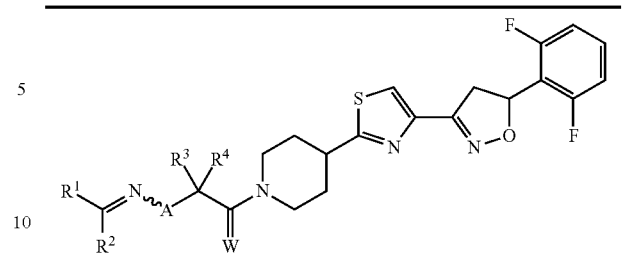

| R¹ | R³ |
|---|---|
| CF₃CH₂ | EtO |
| CF₃CH₂ | MeC(=O) |
| CF₃CH₂ | MeOC(=O) |
| CF₃CH₂ | EtOC(=O) |
| CF₃CH₂ | MeNHC(=O) |
| CF₃CH₂ | (Me)₂NC(=O) |
| CF₃CH₂ | Cl |
| CF₃CH₂ | CN |
| CF₃CH₂ | MeS |
| CF₃CH₂ | Ph |
| CF₃CH₂ | 2,5-di-Cl—Ph |
| CF₃CH₂ | 2-Cl-5-CF₃—Ph |
| CF₃CH₂ | 2,5-di-Me—Ph |
| CF₃CH₂ | 2-Me-5-CF₃—Ph |
| CF₃CH₂ | 3,5-di-Me-1H-pyrazol-1-yl |
| CF₃CH₂ | 5-Me-3-CF₃-1H-pyrazol-1-yl |
| CF₃CH₂ | 5-Cl-3-CF₃-1H-pyrazol-1-yl |
| CF₃CH₂ | 5-Br-3-CF₃-1H-pyrazol-1-yl |
| CF₃CH₂ | 5-Et-3-CF₃-1H-pyrazol-1-yl |
| CF₃CH₂ | 3,5-di-CF₃-1H-pyrazol-1-yl |
| CF₃CH₂ | 1-Me-3-CF₃-1H-pyrazol-5-yl |
| CF₃CH₂ | 1-Me-4-CF₃-1H-imidazol-2-yl |
| CF₃CH₂ | 3,5-di-Cl-1H-1,2,4-triazol-1-yl |
| CF₃CH₂ | 3,5-di-Br-1H-1,2,4-triazol-1-yl |

TABLE 2A

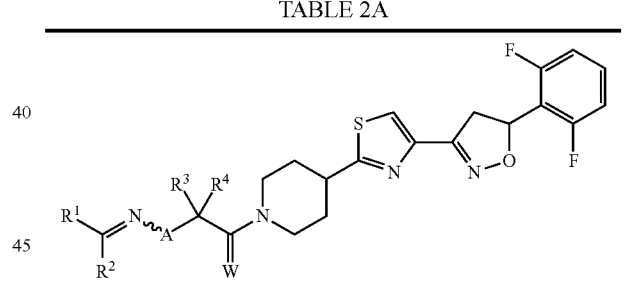

W is O.

| R¹ | R² | A | R³ | R⁴ |
|---|---|---|---|---|
| CF₃ | H | —OCH₂— | OH | H |
| CF₃ | H | —O— | Me | Me |
| CF₃ | H | —O— | Me | Et |
| CF₃ | H | —O— | H | CF₃ |
| CF₃ | H | —N(Et)— | H | H |
| CF₃ | H | —N(n-Pr)— | H | H |
| CF₃ | H | —N(i-Pr)— | H | H |
| CF₃ | H | —N(n-Bu)— | H | H |
| CF₃ | H | —N(CN)— | H | H |
| CF₃ | H | —N(CH₂CH₂Cl)— | H | H |
| CF₃ | H | —N(CH₂OCH₃)— | H | H |
| CF₃ | H | —N(SCH₂OCH₃)— | H | H |
| CF₃ | H | —N(C(=O)Me)— | H | H |
| CF₃ | H | —N(C(=O)CF₃)— | H | H |
| CF₃ | H | —N(C(=O)OMe)— | H | H |
| CF₃ | H | —N(C(=O)NHMe)— | H | H |
| CF₃ | H | —N(C(=O)NMe₂)— | H | H |
| CF₃ | H | —N(S(=O)₂Me)— | H | H |
| CF₃ | H | —N(S(=O)₂CF₃)— | H | H |
| CF₃ | Me | —N(Et)— | H | H |

TABLE 2A-continued

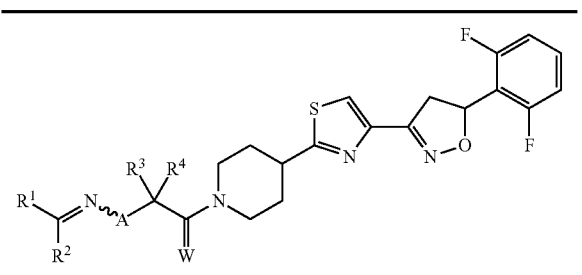

W is O.

| R¹ | R² | A | R³ | R⁴ |
|---|---|---|---|---|
| CF₃ | Me | —N(n-Pr)— | H | H |
| CF₃ | Me | —N(i-Pr)— | H | H |
| CF₃ | Me | —N(n-Bu)— | H | H |
| CF₃ | Me | —N(CN)— | H | H |
| Me | Me | —N(Et)— | H | H |
| Me | Me | —N(n-Pr)— | H | H |
| Me | Me | —N(i-Pr)— | H | H |
| Me | Me | —N(n-Bu)— | H | H |
| Me | Me | —N(CN)— | H | H |
| Me | H | —N(Et)— | H | H |
| Me | H | —N(n-Pr)— | H | H |
| Me | H | —N(i-Pr)— | H | H |
| Me | H | —N(n-Bu)— | H | H |
| Me | H | —N(CN)— | H | H |
| CF₃CH₂ | H | —N(Et)— | H | H |
| CF₃CH₂ | H | N(n-Pr)— | H | H |
| CF₃CH₂ | H | —N(i-Pr)— | H | H |
| CF₃CH₂ | H | —N(n-Bu)— | H | H |
| CF₃CH₂ | H | —N(CN)— | H | H |

TABLE 3

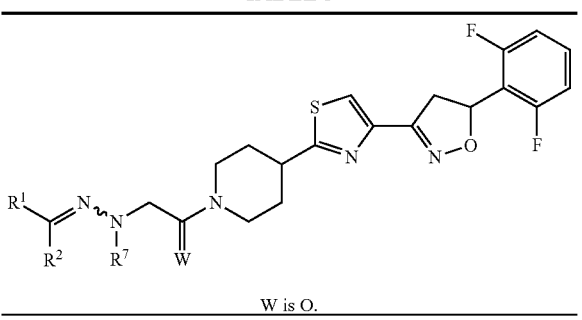

W is O.

| R¹ | R² | R⁷ |
|---|---|---|
| CF₃ | —CH₂CH₂— | |
| CF₃ | —CH₂CH(Me)— | |
| CF₃ | —CH₂C(Me)₂— | |
| CF₃ | —CH₂CH₂CH₂— | |
| Me | —CH₂CH₂— | |
| Me | —OC(Me)₂— | |
| CF₃ | —CH₂(CH₂)₂CH₂— | |
| CF₃ | —CH₂CH₂CH(Me)— | |
| CF₃ | —OCH₂— | |
| Me | —CH₂CH(Me)— | |
| Me | —CH₂C(Me)₂— | |
| Me | —CH₂CH₂CH₂— | |
| Me | —CH₂(CH₂)₂CH₂— | |
| Me | —CH(CHCF₃)— | |
| Me | —CH₂CH₂CH(Me)— | |
| Me | —CH₂CH₂CH(CF₃)— | |

TABLE 4

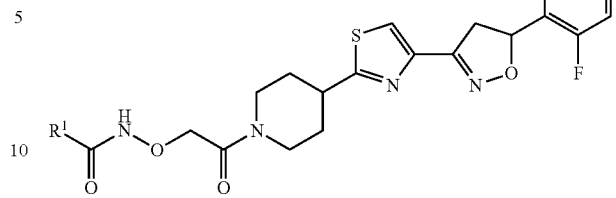

R¹

Me
Et
n-Pr
i-Pr
n-Bu
i-Bu
t-Bu
hexyl
H
CN
NH₂
HC(=O)
HOC(=O)
CH₂=CH
CH₂=CHCH₂
CH≡CCH₂
CF₃
CF₃CH₂
ClCH₂CH₂
c-Pr
c-hexyl
1-F-c-Pr
CF₂=CF
c-PrCH₂
MeOCH₂
MeSCH₂
CH₃S(=O)CH₂
CH₃S(=O)₂CH₂
(Me)₂NCH₂
MeC(=O)
CF₃C(=O)
c-PrC(=O)
MeOC(=O)
MeNHC(=O)
(Me)₂NC(=O)
MeO
EtO
i-PrO
CF₃O
c-BuO
CH₂=CHCH₂O
CH≡CCH₂O
MeOCH₂CH₂O
c-pentyl
CH₃C(=O)O
CF₃C(=O)O
MeS
CF₃S
c-PrS
MeNH
(Me)₂N
ClCH₂CH₂NH
CH₃C(=O)ONH
CF₃C(=O)ONH
MeS(=O)₂NH
CF₃S(=O)₂NH

TABLE 5

| R¹ | A |
|---|---|
| CF₃ | —S— |
| CF₃ | —NH— |
| CF₃ | N(Me)— |
| CF₃ | —CH₂— |
| CF₃ | —C(Me)₂— |
| CF₃ | —O— |
| CF₃ | —N(Et)— |
| CF₃ | —N(n-Pr)— |
| CF₃ | —N(i-Pr)— |
| CF₃ | —N(n-Bu)— |
| CF₃ | —N(CN)— |
| CF₃ | —OCH₂— |
| CF₃ | —SCH₂— |
| CF₃ | —NHCH₂— |
| CF₃ | —N(Me)CH₂— |
| Me | —S— |
| CF₃ | —N(CH₂CH₂Cl)— |
| CF₃ | —N(CH₂OMe)— |
| CF₃ | —N(SCH₂OMe)— |
| CF₃ | —N(C(=O)Me)— |
| CF₃ | —N(C(=O)OMe)— |
| CF₃ | —N(C(=O)NHMe)— |
| Me | —NH— |
| Me | —NMe— |
| Me | —CH₂— |
| Me | —C(Me)₂— |
| Me | —OCH₂— |
| CF₃ | —N(S(=O)₂Me)— |
| CF₃ | —N(S(=O)₂CF₃)— |
| Me | —N(Et)— |
| Me | —N(n-Pr)— |
| Me | —N(n-Bu)— |
| Me | —N(CN)— |
| Me | —SCH₂— |
| Me | —NHCH₂— |
| Me | —N(Me)CH₂— |
| CF₃ | —OCH(Me)— |
| CF₃ | —CH(CF₃)— |

TABLE 6

R⁴ is H.

| R¹ | R³ |
|---|---|
| CF₃ | Me |
| CF₃ | Et |
| CF₃ | n-Pr |
| CF₃ | i-Pr |
| CF₃ | i-Bu |

TABLE 6-continued

| R¹ | R³ |
|---|---|
| CF₃ | CN |
| CF₃ | Cl |
| CF₃ | CH₂=CHCH₂ |
| CF₃ | CH≡CCH₂ |
| CF₃ | CF₃ |
| CF₃ | MeOCH₂ |
| CF₃ | CH₃SCH₂ |
| CF₃ | MeS(=O)CH₂ |
| CF₃ | MeS(=O)₂CH₂ |
| CF₃ | MeC(=O) |
| CF₃ | EtC(=O) |
| CF₃ | CF₃C(=O) |
| CF₃ | MeOC(=O) |
| CF₃ | EtOC(=O) |
| CF₃ | MeNHC(=O) |
| CF₃ | Me₂NC(=O) |
| CF₃ | MeO |
| CF₃ | EtO |
| CF₃ | CF₃O |
| CF₃ | MeS |
| CF₃ | CF₃S |
| CF₃ | MeS(=O) |
| CF₃ | MeS(=O)₂ |
| CF₃ | CF₃S(=O)₂ |
| CF₃ | MeC(=O)O |
| CF₃ | Ph |
| CF₃ | 2,5-di-Cl—Ph |
| CF₃ | 2-Cl-5-CF₃—Ph |
| CF₃ | 2,5-di-Me—Ph |
| CF₃ | 2-Me-5-CF₃—Ph |
| CF₃ | 3,5-di-Me-1H-pyrazol-1-yl |
| CF₃ | 5-Me-3-CF₃-1H-pyrazol-1-yl |
| CF₃ | 5-Cl-3-CF₃-1H-pyrazol-1-yl |
| CF₃ | 5-Br-3-CF₃-1H-pyrazol-1-yl |
| CF₃ | 5-Et-3-CF₃-1H-pyrazol-1-yl |
| CF₃ | 3,5-di-CF₃-1H-pyrazol-1-yl |
| CF₃ | 1-Me-3-CF₃-1H-pyrazol-5-yl |
| CF₃ | 1-Me-4-CF₃-1H-imidazol-2-yl |
| CF₃ | 3,5-di-Cl-1H-1,2,4-triazol-1-yl |
| CF₃ | 3,5-di-Br-1H-1,2,4-triazol-1-yl |
| Me | Me |
| Me | Et |
| Me | MeO |
| Me | EtO |
| Me | MeC(=O) |
| Me | MeOC(=O) |
| Me | EtOC(=O) |
| Me | MeNHC(=O) |
| Me | Me₂NC(=O) |
| Me | Cl |
| Me | CN |
| Me | MeS |
| Me | Ph |
| Me | 2,5-di-Cl—Ph |
| Me | 2-Cl-5-CF₃—Ph |
| Me | 2,5-di-Me—Ph |
| Me | 2-Me-5-CF₃—Ph |
| Me | 3,5-di-Me-1H-pyrazol-1-yl |
| Me | 5-Me-3-CF₃-1H-pyrazol-1-yl |
| Me | 5-Cl-3-(CF₃)-1H-pyrazol-1-yl |
| Me | 5-Br-3-CF₃-1H-pyrazol-1-yl |
| Me | 5-Et-3-CF₃-1H-pyrazol-1-yl |
| Me | 3,5-di-CF₃-1H-pyrazol-1-yl |
| Me | 1-Me-3-CF₃-1H-pyrazol-5-yl |
| Me | 1-Me-4-CF₃-1H-imidazol-2-yl |

TABLE 6-continued

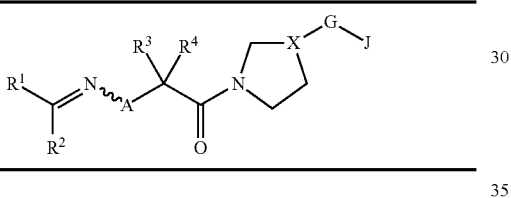

| R¹ | R³ |
|---|---|
| Me | 3,5-di-Cl-1H-1,2,4-triazol-1-yl |
| Me | 3,5-di-Br-1H-1,2,4-triazol-1-yl |
| | R⁴ is Me. |
| CF₃ | Me |
| | R⁴ is Et. |
| CF₃ | Me |
| | R⁴ is CF₃. |
| CF₃ | H |

TABLE 7

In Table 8 the structure of G-1 and G-2 is shown in Exhibit 2 in the above Embodiments. The substituent $R^{26a}$ attached to G shown in Exhibit 2 is H. The structure of J (e.g., J-29-1) is shown in Exhibit A in the above Embodiments, except when J is one of J-83-1 through J-93-1, then the structure of J is shown below. In the structures J-83-1 through J-93-1 the carbon atom identified with an asterisk (*) contains a stereocenter.

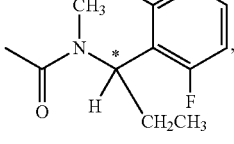
J-83-1

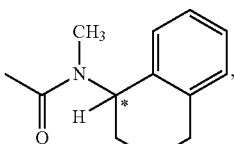
J-84-1

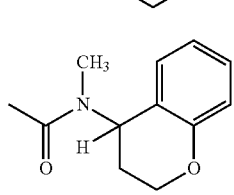
J-85-1

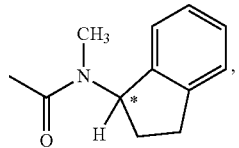
J-86-1

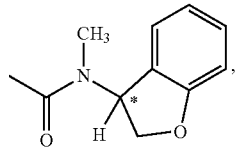
J-87-1

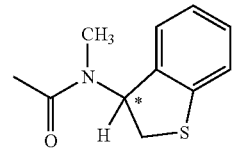
J-88-1

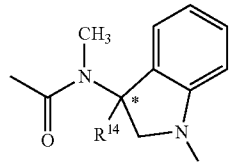
J-89-1

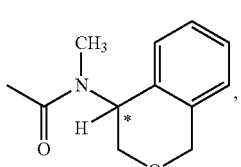
J-90-1

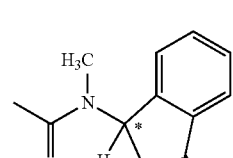
J-92-1

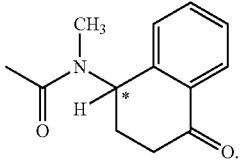
J-93-1

$R^1$ is Me, $R^2$ is H, A is —O—, $R^3$ is H, $R^4$ is H, X is $X^1$ and G is G-1.

| J | J | J | J | J | J | J |
|---|---|---|---|---|---|---|
| J-29-1 | J-29-11 | J-29-21 | J-29-31 | J-29-41 | J-29-51 | J-83-1 |
| J-29-2 | J-29-12 | J-29-22 | J-29-32 | J-29-42 | J-29-52 | J-84-1 |
| J-29-3 | J-29-13 | J-29-23 | J-29-33 | J-29-43 | J-29-53 | J-85-1 |
| J-29-4 | J-29-14 | J-29-24 | J-29-34 | J-29-44 | J-29-54 | J-88-1 |
| J-29-5 | J-29-15 | J-29-25 | J-29-35 | J-29-45 | J-29-55 | J-89-1 |
| J-29-6 | J-29-16 | J-29-26 | J-29-36 | J-29-46 | J-29-58 | J-90-1 |

-continued

| J | J | J | J | J | J | J |
|---|---|---|---|---|---|---|
| J-29-7 | J-29-17 | J-29-27 | J-29-37 | J-29-47 | J-29-59 | J-92-1 |
| J-29-8 | J-29-18 | J-29-28 | J-29-38 | J-29-48 | J-29-60 | J-93-1 |
| J-29-9 | J-29-19 | J-29-29 | J-29-39 | J-29-49 | J-86-1 | |
| J-29-10 | J-29-20 | J-29-30 | J-29-40 | J-29-50 | J-87-1 | |

The present disclosure also includes Tables 7A-1 through 7A-77, each of which is constructed the same as Table 7 above except that the row heading in Table 7 (i.e. "$R^1$ is Me, $R^2$ is H, A is —O—, $R^3$ is H, $R^4$ is H, X is $X^1$ and G is G-1") is replaced with the respective row headings shown below. For example, in Table 7A-1 the row heading is "$R^1$ is Me, $R^2$ is Me, A is —O—, $R^3$ is H, $R^4$ is H, X is $X^1$ and G is G-1", and J is as defined in Table 7 above.

| Table | Row Heading |
|---|---|
| 7A-1 | $R^1$ is Me, $R^2$ is Me, A is —O—, $R^3$ is H, $R^4$ is H, X is $X^1$ and G is G-1. |
| 7A-2 | $R^1$ is Me, $R^2$ is Me, A is —O—, $R^3$ is Me, $R^4$ is H, X is $X^1$ and G is G-1. |
| 7A-3 | $R^1$ is Et, $R^2$ is H, A is —O—, $R^3$ is H, $R^4$ is H, X is $X^1$ and G is G-1. |
| 7A-4 | $R^1$ is Et, $R^2$ is Me, A is —O—, $R^3$ is H, $R^4$ is H, X is $X^1$ and G is G-1. |
| 7A-5 | $R^1$ is Et, $R^2$ is Me, A is —O—, $R^3$ is Me, $R^4$ is H, X is $X^1$ and G is G-1. |
| 7A-6 | $R^1$ is $CF_3$, $R^2$ is H, A is —O—, $R^3$ is H, $R^4$ is H, X is $X^1$ and G is G-1. |
| 7A-7 | $R^1$ is $CF_3$, $R^2$ is Me, A is —O—, $R^3$ is H, $R^4$ is H, X is $X^1$ and G is G-1. |
| 7A-8 | $R^1$ is $CF_3$, $R^2$ is Me, A is —O—, $R^3$ is Me, $R^4$ is H, X is $X^1$ and G is G-1. |
| 7A-9 | $R^1$ is $CF_3CH_2$, $R^2$ is H, A is —O—, $R^3$ is H, $R^4$ is H, X is $X^1$ and G is G-1. |
| 7A-10 | $R^1$ is $CF_3CH_2$, $R^2$ is Me, A is —O—, $R^3$ is H, $R^4$ is H, X is $X^1$ and G is G-1. |
| 7A-11 | $R^1$ is $CF_3CH_2$, $R^2$ is Me, A is —O—, $R^3$ is Me, $R^4$ is H, X is $X^1$ and G is G-1. |
| 7A-12 | $R^1$ is Me, $R^2$ is H, A is —NH—, $R^3$ is H, $R^4$ is H, X is $X^1$ and G is G-1. |
| 7A-13 | $R^1$ is Me, $R^2$ is Me, A is —NH—, $R^3$ is H, $R^4$ is H, X is $X^1$ and G is G-1 |
| 7A-14 | $R^1$ is Me, $R^2$ is Me, A is —NH—, $R^3$ is Me, $R^4$ is H, X is $X^1$ and G is G-1. |
| 7A-15 | $R^1$ is Et, $R^2$ is H, A is —NH—, $R^3$ is H, $R^4$ is H, X is $X^1$ and G is G-1. |
| 7A-16 | $R^1$ is Et, $R^2$ is Me, A is —NH—, $R^3$ is H, $R^4$ is H, X is $X^1$ and G is G-1. |
| 7A-17 | $R^1$ is Et, $R^2$ is Me, A is —NH—, $R^3$ is Me, $R^4$ is H, X is $X^1$ and G is G-1. |
| 7A-18 | $R^1$ is $CF_3$, $R^2$ is H, A is —NH—, $R^3$ is H, $R^4$ is H, X is $X^1$ and G is G-1. |
| 7A-19 | $R^1$ is $CF_3$, $R^2$ is Me, A is —NH—, $R^3$ is H, $R^4$ is H, X is $X^1$ and G is G-1 |
| 7A-20 | $R^1$ is $CF_3$, $R^2$ is Me, A is —NH—, $R^3$ is Me, $R^4$ is H, X is $X^1$ and G is G-1. |
| 7A-21 | $R^1$ is $CF_3CH_2$, $R^2$ is H, A is —NH—, $R^3$ is H, $R^4$ is H, X is $X^1$ and G is G-1. |
| 7A-22 | $R^1$ is $CF_3CH_2$, $R^2$ is Me, A is —NH—, $R^3$ is H, $R^4$ is H, X is $X^1$ and G is G-1. |
| 7A-23 | $R^1$ is $CF_3CH_2$, $R^2$ is Me, A is —NH—, $R^3$ is Me, $R^4$ is H, X is $X^1$ and G is G-1. |
| 7A-24 | $R^1$ is Me, $R^2$ is H, A is —N(Me)—, $R^3$ is H, $R^4$ is H, X is $X^1$ and G is G-1. |
| 7A-25 | $R^1$ is Me, $R^2$ is Me, A is —N(Me)—, $R^3$ is H, $R^4$ is H, X is $X^1$ and G is G-1. |
| 7A-26 | $R^1$ is Me, $R^2$ is Me, A is —N(Me)—, $R^3$ is Me, $R^4$ is H, X is $X^1$ and G is G-1. |
| 7A-27 | $R^1$ is Et, $R^2$ is H, A is —N(Me)—, $R^3$ is H, $R^4$ is H, X is $X^1$ and G is G-1. |
| 7A-28 | $R^1$ is Et, $R^2$ is Me, A is —N(Me)—, $R^3$ is H, $R^4$ is H, X is $X^1$ and G is G-1. |
| 7A-29 | $R^1$ is Et, $R^2$ is Me, A is —N(Me)—, $R^3$ is Me, $R^4$ is H, X is $X^1$ and G is G-1. |
| 7A-30 | $R^1$ is $CF_3$, $R^2$ is H, A is —N(Me)—, $R^3$ is H, $R^4$ is H, X is $X^1$ and G is G-1. |
| 7A-31 | $R^1$ is $CF_3$, $R^2$ is Me, A is —N(Me)—, $R^3$ is H, $R^4$ is H, X is $X^1$ and G is G-1. |
| 7A-32 | $R^1$ is $CF_3$, $R^2$ is Me, A is —N(Me)—, $R^3$ is Me, $R^4$ is H, X is $X^1$ and G is G-1. |
| 7A-33 | $R^1$ is $CF_3CH_2$, $R^2$ is H, A is —N(Me)—, $R^3$ is H, $R^4$ is H, X is $X^1$ and G is G-1. |
| 7A-34 | $R^1$ is $CF_3CH_2$, $R^2$ is Me, A is —N(Me)—, $R^3$ is H, $R^4$ is H, X is $X^1$ and G is G-1. |
| 7A-35 | $R^1$ is $CF_3CH_2$, $R^2$ is Me, A is —N(Me)—, $R^3$ is Me, $R^4$ is H, X is $X^1$ and G is G-1. |
| 7A-36 | $R^1$ is Me, $R^2$ is H, A is —N(Et)—, $R^3$ is H, $R^4$ is H, X is $X^1$ and G is G-1. |
| 7A-37 | $R^1$ is Me, $R^2$ is Me, A is —N(Et)—, $R^3$ is H, $R^4$ is H, X is $X^1$ and G is G-1. |
| 7A-38 | $R^1$ is Me, $R^2$ is Me, A is —N(Et)—, $R^3$ is Me, $R^4$ is H, X is $X^1$ and G is G-1. |
| 7A-39 | $R^1$ is Et, $R^2$ is H, A is —N(Et)—, $R^3$ is H, $R^4$ is H, X is $X^1$ and G is G-1. |
| 7A-40 | $R^1$ is Et, $R^2$ is Me, A is —N(Et)—, $R^3$ is H, $R^4$ is H, X is $X^1$ and G is G-1. |
| 7A-41 | $R^1$ is Et, $R^2$ is Me, A is —N(Et)—, $R^3$ is Me, $R^4$ is H, X is $X^1$ and G is G-1. |
| 7A-42 | $R^1$ is $CF_3$, $R^2$ is H, A is —N(Et)—, $R^3$ is H, $R^4$ is H, X is $X^1$ and G is G-1. |
| 7A-43 | $R^1$ is $CF_3$, $R^2$ is Me, A is —N(Et)—, $R^3$ is H, $R^4$ is H, X is $X^1$ and G is G-1. |
| 7A-44 | $R^1$ is $CF_3$, $R^2$ is Me, A is —N(Et)—, $R^3$ is Me, $R^4$ is H, X is $X^1$ and G is G-1. |
| 7A-45 | $R^1$ is $CF_3CH_2$, $R^2$ is H, A is —N(Et)—, $R^3$ is H, $R^4$ is H, X is $X^1$ and G is G-1. |
| 7A-46 | $R^1$ is $CF_3CH_2$, $R^2$ is Me, A is —N(Et)—, $R^3$ is H, $R^4$ is H, X is $X^1$ and G is G-1. |
| 7A-47 | $R^1$ is $CF_3CH_2$, $R^2$ is Me, A is —N(Et)—, $R^3$ is Me, $R^4$ is H, X is $X^1$ and G is G-1. |
| 7A-48 | $R^1$ is $CF_3$, $R^2$ is H, A is —O—, $R^3$ is H, $R^4$ is H, X is $X^2$ and G is G-1. |
| 7A-49 | $R^1$ is $CF_3$, $R^2$ is Me, A is —O—, $R^3$ is H, $R^4$ is H, X is $X^2$ and G is G-1. |
| 7A-50 | $R^1$ is $CF_3$, $R^2$ is H, A is —NH—, $R^3$ is H, $R^4$ is H, X is $X^2$ and G is G-1. |
| 7A-51 | $R^1$ is $CF_3$, $R^2$ is Me, A is —NH—, $R^3$ is H, $R^4$ is H, X is $X^2$ and G is G-1. |
| 7A-52 | $R^1$ is $CF_3$, $R^2$ is H, A is —N(Me)—, $R^3$ is H, $R^4$ is H, X is $X^2$ and G is G-1. |
| 7A-53 | $R^1$ is $CF_3$, $R^2$ is Me, A is —N(Me)—, $R^3$ is H, $R^4$ is H, X is $X^2$ and G is G-1. |
| 7A-54 | $R^1$ is $CF_3$, $R^2$ is H, A is —N(Et)—, $R^3$ is H, $R^4$ is H, X is $X^2$ and G is G-1. |
| 7A-55 | $R^1$ is $CF_3$, $R^2$ is Me, A is —N(Et)—, $R^3$ is H, $R^4$ is H, X is $X^2$ and G is G-1. |
| 7A-56 | $R^1$ is $CF_3$, $R^2$ is H, A is —O—, $R^3$ is H, $R^4$ is H, X is $X^1$ and G is G-2. |
| 7A-57 | $R^1$ is $CF_3$, $R^2$ is Me, A is —O—, $R^3$ is H, $R^4$ is H, X is $X^1$ and G is G-2. |
| 7A-58 | $R^1$ is $CF_3$, $R^2$ is H, A is —NH—, $R^3$ is H, $R^4$ is H, X is $X^1$ and G is G-2. |
| 7A-59 | $R^1$ is $CF_3$, $R^2$ is Me, A is —NH—, $R^3$ is H, $R^4$ is H, X is $X^1$ and G is G-2. |
| 7A-60 | $R^1$ is $CF_3$, $R^2$ is H, A is —N(Me)—, $R^3$ is H, $R^4$ is H, X is $X^1$ and G is G-2. |
| 7A-61 | $R^1$ is $CF_3$, $R^2$ is Me, A is —N(Me)—, $R^3$ is H, $R^4$ is H, X is $X^1$ and G is G-2. |
| 7A-62 | $R^1$ is $CF_3$, $R^2$ is H, A is —N(Et)—, $R^3$ is H, $R^4$ is H, X is $X^1$ and G is G-2. |
| 7A-63 | $R^1$ is $CF_3$, $R^2$ is Me, A is —N(Et)—, $R^3$ is H, $R^4$ is H, X is $X^1$ and G is G-2. |
| 7A-64 | $R^1$ is $CF_3$, $R^2$ is H, A is —O—, $R^3$ is H, $R^4$ is H, X is $X^2$ and G is G-2. |
| 7A-65 | $R^1$ is $CF_3$, $R^2$ is Me, A is —O—, $R^3$ is H, $R^4$ is H, X is $X^2$ and G is G-2. |
| 7A-66 | $R^1$ is $CF_3$, $R^2$ is H, A is —NH—, $R^3$ is H, $R^4$ is H, X is $X^2$ and G is G-2. |

-continued

| Table | Row Heading |
|---|---|
| 7A-67 | $R^1$ is $CF_3$, $R^2$ is Me, A is —NH—, $R^3$ is H, $R^4$ is H, X is $X^2$ and G is G-2. |
| 7A-68 | $R^1$ is $CF_3$, $R^2$ is H, A is —N(Me)—, $R^3$ is H, $R^4$ is H, X is $X^2$ and G is G-2. |
| 7A-69 | $R^1$ is $CF_3$, $R^2$ is Me, A is —N(Me)—, $R^3$ is H, $R^4$ is H, X is $X^2$ and G is G-2. |
| 7A-70 | $R^1$ is $CF_3$, $R^2$ is H, A is —N(Et)—, $R^3$ is H, $R^4$ is H, X is $X^2$ and G is G-2. |
| 7A-71 | $R^1$ is $CF_3$, $R^2$ is Me, A is —N(Et)—, $R^3$ is H, $R^4$ is H, X is $X^2$ and G is G-2. |
| 7A-72 | $R^1$ is Me, $R^2$ is OH, A is —O—, $R^3$ is H, $R^4$ is H, X is $X^1$ and G is G-1. |
| 7A-73 | $R^1$ is $CF_3$, $R^2$ is OH, A is —O—, $R^3$ is H, $R^4$ is H, X is $X^1$ and G is G-1. |
| 7A-74 | $R^1$ is Me, $R^2$ is OH, A is —NH—, $R^3$ is H, $R^4$ is H, X is $X^1$ and G is G-1. |
| 7A-75 | $R^1$ is $CF_3$, $R^2$ is OH, A is —NH—, $R^3$ is H, $R^4$ is H, X is $X^1$ and G is G-1. |
| 7A-76 | $R^1$ is Me, $R^2$ is OH, A is —N(Me)—, $R^3$ is H, $R^4$ is H, X is $X^1$ and G is G-1. |
| 7A-77 | $R^1$ is $CF_3$, $R^2$ is OH, A is —N(Me)—, $R^3$ is H, $R^4$ is H, X is $X^1$ and G is G-1. |

TABLE 8

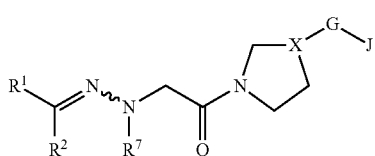

In Table 8 the structure of G-1 and G-2 is shown in Exhibit 2 in the above Embodiments. The substituent $R^{26a}$ attached to G shown in Exhibit 2 is H. The structure of J (e.g., J-29-1) is shown in Exhibit A in the above Embodiments, except when J is one of J-83-1 through J-93-1, then the structure of J is shown below. In the structures J-83-1 through J-93-1 the carbon atom identified with an asterisk (*) contains a stereocenter.

J-83-1

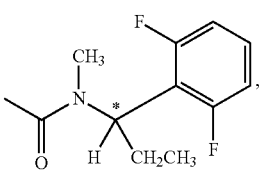

J-84-1

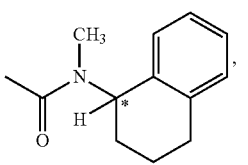

J-85-1

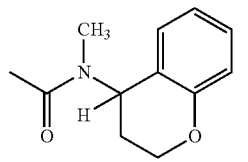

J-86-1

J-87-1

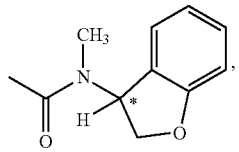

J-88-1

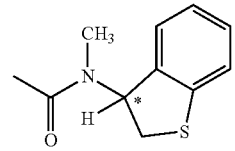

J-89-1

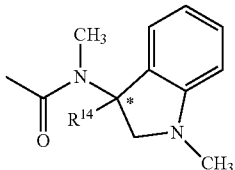

J-90-1

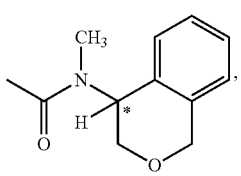

J-92-1

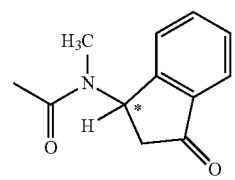

J-93-1

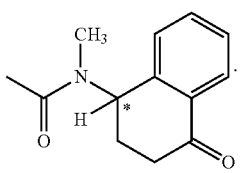

$R^1$ is Me, $R^2$ and $R^7$ are taken together as —$CH_2CH_2$—, X is $X^1$ and G is G-1.

| J | J | J | J | J | J | J |
|---|---|---|---|---|---|---|
| J-29-1 | J-29-11 | J-29-21 | J-29-31 | J-29-41 | J-29-51 | J-85-1 |
| J-29-2 | J-29-12 | J-29-22 | J-29-32 | J-29-42 | J-29-52 | J-86-1 |

-continued

| J | J | J | J | J | J | J |
|---|---|---|---|---|---|---|
| J-29-3 | J-29-13 | J-29-23 | J-29-33 | J-29-43 | J-29-53 | J-87-1 |
| J-29-4 | J-29-14 | J-29-24 | J-29-34 | J-29-44 | J-29-54 | J-88-1 |
| J-29-5 | J-29-15 | J-29-25 | J-29-35 | J-29-45 | J-29-55 | J-89-1 |
| J-29-6 | J-29-16 | J-29-26 | J-29-36 | J-29-46 | J-29-58 | J-90-1 |
| J-29-7 | J-29-17 | J-29-27 | J-29-37 | J-29-47 | J-29-59 | J-92-1 |
| J-29-8 | J-29-18 | J-29-28 | J-29-38 | J-29-48 | J-29-60 | J-93-1 |
| J-29-9 | J-29-19 | J-29-29 | J-29-39 | J-29-49 | J-83-1 | |
| J-29-10 | J-29-20 | J-29-30 | J-29-40 | J-29-50 | J-84-1 | |

The present disclosure also includes Tables 8A-1 through 8A-22, each of which is constructed the same as Table 8 above except that the row heading in Table 8 (i.e. "$R^1$ is Me, $R^2$ and $R^7$ are taken together as —$CH_2CH_2$—, X is $X^1$, and G is G-1") is replaced with the respective row heading shown below. For example, in Table 8A-1 the row heading is "$R^1$ is $CF_3$, $R^2$ and $R^7$ are taken together as —$CH_2CH_2$—, X is $X^1$ and G is G-1, and J is as defined in Table 8 above.

| Table | Row Heading |
|---|---|
| 8A-1 | $R^1$ is $CF_3$, $R^2$ and $R^7$ are taken together as —$CH_2CH_2$—, X is $X^1$ and G is G-1. |
| 8A-2 | $R^1$ is Me, $R^2$ and $R^7$ are taken together as —$CH_2CH(Me)$—, X is $X^1$ and G is G-1. |
| 8A-3 | $R^1$ is $CF_3$, $R^2$ and $R^7$ are taken together as —$CH_2CH(Me)$—, X is $X^1$ and G is G-1. |
| 8A-4 | $R^1$ is Me, $R^2$ and $R^7$ are taken together as —$CH_2CH_2CH_2$—, X is $X^1$ and G is G-1. |
| 8A-5 | $R^1$ is $CF_3$, $R^2$ and $R^7$ are taken together as —$CH_2CH_2CH_2$—, X is $X^1$ and G is G-1. |
| 8A-6 | $R^1$ is $CF_3$, $R^2$ and $R^7$ are taken together as —$CH_2CH_2$—, X is $X^2$ and G is G-1. |
| 8A-7 | $R^1$ is $CF_3$, $R^2$ and $R^7$ are taken together as —$CH_2CH(Me)$—, X is $X^2$ and G is G-1. |
| 8A-8 | $R^1$ is $CF_3$, $R^2$ and $R^7$ are taken together as —$CH_2CH_2CH_2$—, X is $X^2$ and G is G-1. |
| 8A-9 | $R^1$ is $CF_3$, $R^2$ and $R^7$ are taken together as —$CH_2CH_2$—, X is $X^1$ and G is G-2. |
| 8A-10 | $R^1$ is $CF_3$, $R^2$ and $R^7$ are taken together as —$CH_2CH(Me)$—, X is $X^1$ and G is G-2. |
| 8A-11 | $R^1$ is $CF_3$, $R^2$ and $R^7$ are taken together as —$CH_2CH_2CH_2$—, X is $X^1$ and G is G-2. |
| 8A-12 | $R^1$ is $CF_3$, $R^2$ and $R^7$ are taken together as —$CH_2CH_2$—, X is $X^2$ and G is G-2. |
| 8A-13 | $R^1$ is $CF_3$, $R^2$ and $R^7$ are taken together as —$CH_2CH(Me)$—, X is $X^2$ and G is G-2. |
| 8A-14 | $R^1$ is $CF_3$, $R^2$ and $R^7$ are taken together as —$CH_2CH_2CH_2$—, X is $X^2$ and G is G-2. |
| 8A-15 | $R^1$ is Me, $R^2$ and $R^7$ are taken together as —$CH_2CH(CF_3)$—, X is $X^1$ and G is G-1. |
| 8A-16 | $R^1$ is Me, $R^2$ and $R^7$ are taken together as —$CH_2CH(CF_3)$—, X is $X^1$ and G is G-2. |
| 8A-17 | $R^1$ is Me, $R^2$ and $R^7$ are taken together as —$CH_2CH(CF_3)$—, X is $X^2$ and G is G-1. |
| 8A-18 | $R^1$ is Me, $R^2$ and $R^7$ are taken together as —$CH_2CH(CF_3)$—, X is $X^2$ and G is G-2. |
| 8A-19 | $R^1$ is $CF_3$, $R^2$ and $R^7$ are taken together as —$CH_2CH(CF_3)$—, X is $X^1$ and G is G-1. |
| 8A-20 | $R^1$ is $CF_3$, $R^2$ and $R^7$ are taken together as —$CH_2CH(CF_3)$—, X is $X^1$ and G is G-2. |
| 8A-21 | $R^1$ is $CF_3$, $R^2$ and $R^7$ are taken together as —$CH_2CH(CF_3)$—, X is $X^2$ and G is G-1. |
| 8A-22 | $R^1$ is $CF_3$, $R^2$ and $R^7$ are taken together as —$CH_2CH(CF_3)$—, X is $X^2$ and G is G-2. |

TABLE 9

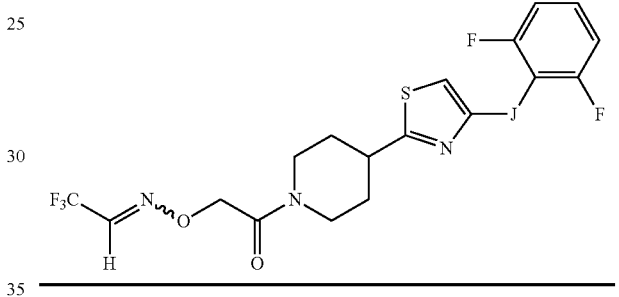

In Table 9 the structure of J (e.g., J-1) is shown in Exhibit 3 in the above Embodiments wherein x is 1 and $R^6$ is 2,6-difluorophenyl as depicted in the above structure. The numbers in parentheses following J refer to the attachment points of J to the thiazole ring and 2,6-difluorophenyl ring in the above structure. The first number is the ring position on J where the thiazole ring is attached and the second number is the ring position on J where the 2,6-difluorophenyl ring is attached.

| J | J | J | J | J | J | J |
|---|---|---|---|---|---|---|
| J-1 (2/4) | J-6 (3/1) | J-21 (3/6) | J-27 (5/3) | J-33 (4/2) | J-45 (2/4) | J-73 (4/2) |
| J-1 (2/5) | J-7 (5/3) | J-21 (5/3) | J-28 (3/5) | J-34 (1/3) | J-45 (2/5) | J-73 (1/3) |
| J-1 (4/2) | J-7 (3/5) | J-22 (2/4) | J-28 (5/3) | J-34 (1/4) | J-45 (2/6) | J-73 (1/4) |
| J-1 (5/2) | J-8 (5/3) | J-22 (2/5) | J-29 (3/5) | J-34 (3/5) | J-46 (2/4) | J-73 (4/1) |
| J-2 (2/4) | J-8 (3/5) | J-22 (4/6) | J-29 (5/3) | J-34 (3/1) | J-46 (2/5) | J-74 (3/5) |
| J-2 (2/5) | J-9 (4/1) | J-22 (4/2) | J-30 (3/5) | J-34 (4/1) | J-46 (4/2) | J-74 (5/3) |
| J-2 (4/2) | J-10 (3/5) | J-22 (5/2) | J-30 (5/3) | J-35 (4/1) | J-46 (5/2) | J-75 (3/5) |
| J-2 (5/2) | J-10 (5/3) | J-23 (2/5) | J-30 (3/1) | J-36 (1/3) | J-47 (2/4) | J-75 (5/3) |
| J-3 (4/1) | J-11 (3/5) | J-23 (2/6) | J-30 (4/1) | J-36 (3/1) | J-47 (2/5) | J-75 (2/4) |
| J-4 (2/4) | J-11 (5/3) | J-24 (2/4) | J-31 (2/4) | J-36 (3/5) | J-47 (4/2) | J-75 (2/5) |
| J-4 (2/5) | J-12 (3/1) | J-24 (2/5) | J-31 (2/5) | J-36 (5/3) | J-47 (5/2) | J-76 (3/6) |
| J-4 (4/2) | J-13 (1/4) | J-24 (4/2) | J-31 (3/5) | J-37 (2/5) | J-48 (3/5) | J-76 (6/3) |
| J-4 (5/2) | J-13 (4/1) | J-24 (5/2) | J-31 (3/1) | J-37 (5/2) | J-49 (2/4) | J-77 (3/5) |
| J-4 (3/5) | J-14 (5/3) | J-25 (2/4) | J-31 (4/1) | J-37 (2/4) | J-49 (2/5) | J-77 (5/3) |
| J-4 (5/3) | J-15 (2/5) | J-25 (2/5) | J-31 (4/2) | J-37 (4/2) | J-49 (4/2) | J-78 (1/3) |
| J-5 (2/5) | J-16 (2/5) | J-25 (4/2) | J-31 (5/2) | J-38 (2/5) | J-49 (5/2) | J-79 (1/3) |
| J-5 (4/2) | J-17 (4/2) | J-25 (5/2) | J-32 (2/4) | J-38 (5/2) | J-50 (2/6) | J-79 (3/1) |
| J-5 (5/2) | J-18 (5/2) | J-26 (2/4) | J-32 (2/5) | J-38 (2/4) | J-51 (2/6) | J-80 (1/3) |
| J-5 (3/5) | J-19 (2/4) | J-26 (2/5) | J-32 (3/5) | J-38 (4/2) | J-52 (2/6) | J-80 (3/1) |
| J-5 (5/3) | J-19 (4/2) | J-26 (4/2) | J-32 (5/3) | J-40 (3/5) | J-69 (1/3) | J-81 (3/5) |
| J-6 (2/4) | J-20 (2/4) | J-26 (5/2) | J-32 (5/2) | J-40 (5/3) | J-69 (1/4) | J-81 (5/3) |
| J-6 (3/5) | J-20 (2/5) | J-26 (4/1) | J-32 (4/2) | J-41 (1/3) | J-70 (1/3) | J-82 (3/5) |

-continued

| J | J | J | J | J | J | J |
|---|---|---|---|---|---|---|
| J-6 (2/5) | J-20 (2/6) | J-27 (2/4) | J-33 (2/4) | J-41 (1/4) | J-71 (2/4) | J-82 (3/6) |
| J-6 (4/2) | J-20 (3/5) | J-27 (2/5) | J-33 (2/5) | J-44 (1/3) | J-71 (4/2) | J-82 (5/3) |
| J-6 (5/2) | J-20 (4/2) | J-27 (3/5) | J-33 (3/5) | J-44 (2/4) | J-72 (2/4) | J-82 (6/3) |
| J-6 (4/2) | J20 (5/2) | J-27 (4/2) | J-33 (5/3) | J-44 (2/5) | J-72 (4/2) | |
| J-6 (5/3) | J-21 (3/5) | J-27 (5/2) | J-33 (5/2) | J-44 (2/6) | J-73 (2/4) | |

TABLE 10

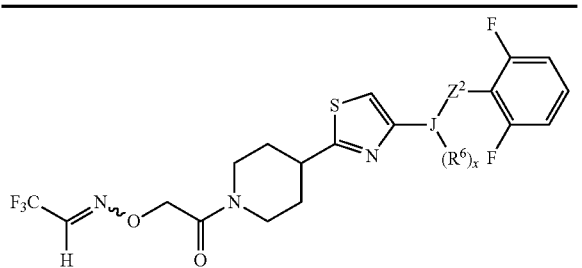

In Table 10 the structure of J (e.g., J-3) is shown in Exhibit 3 in the above Embodiments. The numbers in parentheses following J refer to the attachment points of J to the thiazole ring and $Z^2$ in the above structure. The first number is the ring position on J where the thiazole ring is attached and the second number is the ring position on J where $Z^2$ is attached. The $(R^6)_x$ column below identities $R^6$ substituents other than the —$Z^2$-2,6-difluorophenyl substituent depicted in the above structure.

A dash ("-") in the $Z^2$ column indicates a direct bond.

bers in parentheses following J refer to the attachment points of J to Z and the 2,6-difluorophenyl ring in the above structure. The first number is the ring position on J where Z is attached and the second number is the ring position on J where the 2,6-difluorophenyl ring is attached.

| Z | J |
|---|---|
| $CH_2$ | J-3 (1/4) |
| $CH_2$ | J-6 (1/3) |
| $CH_2$ | J-9 (1/4) |
| $CH_2$ | J-12 (1/3) |
| $CH_2$ | J-17 (2/4) |
| $CH_2$ | J-18 (2/5) |
| $CH_2$ | J-26 (1/4) |
| $CH_2$ | J-30 (1/3) |
| $CH_2$ | J-30 (1/4) |
| $CH_2$ | J-31 (1/3) |
| $CH_2$ | J-31 (1/4) |
| $CH_2$ | J-35 (1/4) |
| $CH_2$ | J-36 (1/3) |
| $CH_2$ | J-42 (1/3) |
| $CH_2$ | J-42 (1/4) |

| J | $(R^6)_x$ | $Z^2$ | J | $(R^6)_x$ | $Z^2$ | J | $(R^6)_x$ | $Z^2$ |
|---|---|---|---|---|---|---|---|---|
| J-3 (2/4) | 1-Me | — | J-74 (2/4) | 3-$CH_3$ | — | J-69 (1/3) | 4-$CF_3$O | — |
| J-3 (2/5) | 1-Me | — | J-74 (2/5) | 3-$CH_3$ | — | J-69 (1/3) | 4-MeS | — |
| J-3 (4/2) | 1-Me | — | J-74 (4/2) | 3-$CH_3$ | — | J-69 (1/3) | 4-MeS(=O) | — |
| J-3 (5/2) | 1-Me | — | J-74 (5/2) | 3-$CH_3$ | — | J-69 (1/3) | 4-MeS(=O)$_2$ | — |
| J-9 (5/3) | 1-Me | — | J-75 (3/5) | 2-$CH_3$ | — | J-69 (1/3) | 4-$CF_3$S | — |
| J-9 (3/5) | 1-Me | — | J-75 (5/3) | 2-$CH_3$ | — | J-69 (1/3) | 4-$CHF_2OCH_2$ | — |
| J-12 (3/5) | 1-Me | — | J-69 (1/3) | 4-F | — | J-69 (1/3) | 4-$CH_2OH$ | — |
| J-12 (5/3) | 1-Me | — | J-69 (1/3) | 4-Cl | — | J-74 (2/5) | 3-$CH_3C$(=O) | — |
| J-14 (3/5) | 1-Me | — | J-69 (1/3) | 4-OH | — | J-69 (1/3) | 4-$CH_3C$(=O)O | — |
| J-39 (3/5) | 4-Me | — | J-69 (1/3) | 4-$NH_2$ | — | J-69 (1/3) | 4-$CH_3C$(=O)S | — |
| J-39 (5/3) | 4-Me | — | J-69 (1/3) | 4-OEt | — | J-69 (1/3) | 4-MeNHC(=O) | — |
| J-69 (1/3) | 4-CN | O | J-69 (1/3) | 4-$NO_2$ | NH | J-69 (1/3) | 4-$CF_3$ | S |
| J-69 (1/3) | H | O | J-69 (1/3) | H | S | J-69 (1/3) | H | S(=O) |
| J-69 (1/3) | H | NH | J-69 (1/3) | H | NMe | J-69 (1/3) | H | S(=O)$_2$ |
| J-69 (1/3) | H | $CH_2$ | | | | | | |

A dash ("—") in the $Z^2$ column indicates a direct bond.

TABLE 11

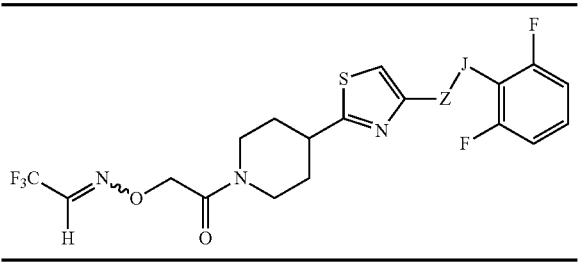

In Table 11 the structure of J (e.g., J-3) is shown in Exhibit 3 in the above Embodiments wherein x is 1 and $R^6$ is 2,6-difluorophenyl as depicted in the above structure. The num-

TABLE 12

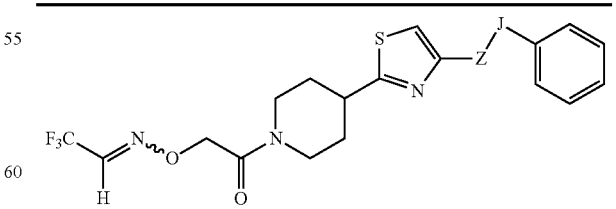

In Table 12 the structure of J (e.g., J-29) is shown in Exhibit 3 in the above Embodiments wherein x is 1 and $R^6$ is phenyl as depicted in the above structure. The numbers in parentheses following J refer to the attachment points of J to Z and the phenyl ring in the above structure. The first number is the ring position on J where Z is attached and the second number is the ring position on J where the phenyl ring is attached.

| Z | J |
|---|---|
| O | J-29 (3/5) |
| S | J-29 (3/5) |
| S(=O) | J-29 (3/5) |
| S(=O)₂ | J-29 (3/5) |
| NH | J-29 (3/5) |
| N(Me) | J-29 (3/5) |
| N(n-Pr) | J-29 (3/5) |
| CH₂ | J-29 (3/5) |
| CH(i-Bu) | J-29 (3/5) |

TABLE 13

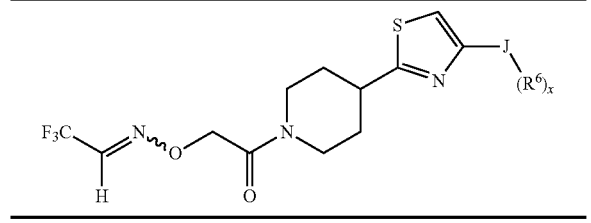

In Table 13 the structure of J (e.g., J-53) is shown in Exhibit 3 in the above Embodiments. The $(R^6)_x$ column below identifies $R^6$ substituents attached to the J ring. When $R^6$ is hydrogen, this is equivalent to J being unsubstituted (i.e. x is 0). The number in parentheses following J refers to the attachment point of J to the thiazole ring in the above structure.

TABLE 14

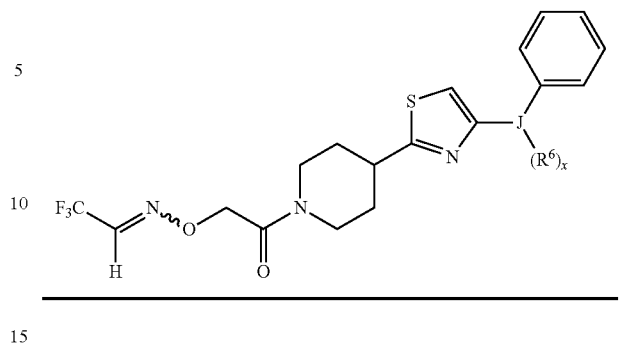

In Table 14 the structure of J (e.g., J-29) is shown in Exhibit 3 in the above Embodiments. The numbers in parentheses following J refer to the attachment points of J to the thiazole ring and 2,6-difluorophenyl ring in the above structure. The first number is the ring position on J where the thiazole ring is attached and the second number is the ring position on J where the 2,6-difluorophenyl ring is attached. The $(R^6)_x$ column below identifies $R^6$ substituents attached to the J ring other than the phenyl substituent depicted in the above structure.

| J | $(R^6)_x$ | J | $(R^6)_x$ | J | $(R^6)_x$ |
|---|---|---|---|---|---|
| J-53 (2) | H | J-29 (3) | 5-(4-Me-3-penyen-1-yl) | J-69 (1) | 3-c-Pr |
| J-54 (2) | H | J-29 (3) | 5-(3,3-di-Me-1-butyn-1yl) | J-69 (1) | 3-c-Bu |
| J-55 (2) | H | J-29 (3) | 5-(4-Me-c-hexyl) | J-69 (1) | 3-c-pentyl |
| J-56 (2) | H | J-29 (3) | 5-CF₂CF₃ | J-69 (1) | 3-c-hexyl |
| J-57 (2) | 1-Me | J-29 (3) | 5-(3,3-di-Cl-2-propen-1-yl) | J-69 (1) | 3-CF₃O |
| J-58 (3) | 1-Me | J-29 (3) | 5-Me₃Si | J-69 (1) | 3-i-PrO |
| J-59 (2) | H | J-69 (1) | 4-CF₃CH₂S(=O)₂ | J-69 (1) | 3-i-BuO |
| J-60 (2) | H | J-22 (2) | 4-i-BuNH | J-69 (1) | 3-Cl |
| J-61 (2) | H | J-22 (2) | 4-(Et)₂N | J-69 (1) | 3-Br |
| J-62 (2) | H | J-22 (2) | 4-c-hexyl-NH | J-69 (1) | 4-I |
| J-63 (3) | H | J-69 (1) | 4-i-PrOCH₂ | J-69 (1) | 4-Me |
| J-64 (2) | H | J-69 (1) | 4-i-PrC(=O)₂ | J-69 (1) | 4-Et |
| J-65 (3) | H | J-29 (3) | 5-CH₃C(=O)NH | J-69 (1) | 4-n-Pr |
| J-66 (6) | H | J-29 (3) | 5-(MeC(=O))₂N | J-69 (1) | 4-i-Pr |
| J-53 (2) | H | J-29 (3) | 5-PhC(=O)(Me)N | J-69 (1) | 4-n-Bu |
| J-53 (2) | H | J-29 (3) | 5-CH₃C(=O)(Et)N | J-69 (1) | 4-t-Bu |
| J-67 (2) | H | J-29 (3) | 5-PhC(=O)(Et)N | J-69 (1) | 4-CH₃(CH₂)₄ |
| J-68 (2) | H | J-29 (3) | 5-MeOC(=O)NH | J-69 (1) | 4-(Me)₂CH(CH₂)₂ |
| J-53 (2) | H | J-29 (3) | 5-EtOC(=O)NH | J-69 (1) | 4-(Me)₂C(Et) |
| J-53 (2) | H | J-29 (3) | 5-EtOC(=O)(Me)N | J-69 (1) | 4-c-Pr |
| J-53 (2) | H | J-69 (1) | 3-Cl | J-69 (1) | 4-c-Bu |
| J-53 (2) | H | J-69 (1) | 3-Br | J-69 (1) | 4-c-pentyl |
| J-68 (2) | H | J-69 (1) | 3-I | J-69 (1) | 4-c-hexyl |
| J-53 (2) | H | J-69 (1) | 3-Me | J-69 (1) | 4-CF₃O |
| J-53 (2) | H | J-69 (1) | 3-Et | J-69 (1) | 4-i-PrO |
| J-53 (2) | H | J-69 (1) | 3-n-Pr | J-69 (1) | 4-i-BuO |
| J-53 (2) | H | J-69 (1) | 3-i-Pr | J-69 (1) | 3,4-di-Cl |
| J-53 (2) | H | J-69 (1) | 3-Bu | J-69 (1) | 3,4-di-Br |
| J-53 (2) | H | J-69 (1) | 3-i-Bu | J-69 (1) | 3,4-di-Me |
| J-53 (2) | H | J-69 (1) | 3-s-Bu | J-69 (1) | 3,4-di-Et |
| J-53 (2) | H | J-69 (1) | 3-t-Bu | J-69 (1) | 3,4-di-MeO |
| J-53 (2) | H | J-69 (1) | 3-CH₃(CH₂)₄ | J-69 (1) | 3,4-di-EtO |
| J-69 (1) | 4-t-BuS(=O)₂ | J-69 (1) | 3-(Me)₂CH(CH₂)₂ | J-4 (2) | 5-i-Bu |
| J-69 (1) | 4-Et₂NC(=O) | J-69 (1) | 3-(Me)₂C(Et) | J-5 (2) | 5-i-Bu |

| J | $(R^6)_x$ |
|---|---|
| J-29 (3/5) | 4-Me |
| J-29 (3/5) | 5-Me |
| J-29 (3/5) | 4,5-di-Me |
| J-29 (3/5) | 4,4-di-Me |
| J-29 (3/5) | 5-Et |
| J-29 (3/5) | 5-c-Pr |
| J-29 (3/5) | 5-CF$_3$ |
| J-29 (3/5) | 5-MeO |
| J-26 (2/5) | 1-Me |

TABLE 15

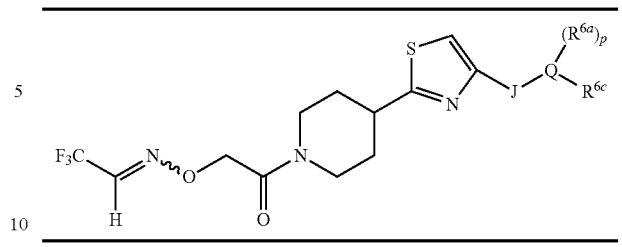

In Table 15 the structure of J (e.g., J-29) is shown in Exhibit 3 in the above Embodiments wherein x is 1, $R^6$ is —$Z^2Q$ and $Z^2$ is a direct bond. The number in parentheses following J refer to the attachment points of J to the thiazole ring and Q in the above structure. The first number is the ring position on J where the thiazole ring is attached and the second number is the ring position on J where Q is attached. The structure of Q (e.g., Q-3) is shown in Exhibit 5 in the above Embodiments wherein g is 0. The $(R^{6a})_p$ and $R^{6c}$ columns below indentify substituents attached to Q. A dash ("-") in the $(R^{6a})_p$ column below indicates no $R^{6a}$ substituent is present.

| J | Q | $(R^{6a})_p$ | $R^{6c}$ | J | Q | $(R^{6a})_p$ | $R^{6c}$ |
|---|---|---|---|---|---|---|---|
| J-29 (3/5) | Q-3 | — | Me | J-29 (3/5) | Q-88 | — | Me |
| J-29 (3/5) | Q-10 | — | Me | J-29 (3/5) | Q-92 | — | Me |
| J-29 (3/5) | Q-11 | — | Me | J-29 (3/5) | Q-95 | — | Me |
| J-29 (3/5) | Q-12 | — | Me | J-29 (3/5) | Q-102 | — | Me |
| J-29 (3/5) | Q-13 | — | Me | J-29 (3/5) | Q-72 | — | MeC(=O) |
| J-29 (3/5) | Q-14 | — | Me | J-29 (3/5) | Q-72 | — | MeOC(=O) |
| J-29 (3/5) | Q-21 | — | Me | J-29 (3/5) | Q-72 | — | MeO |
| J-29 (3/5) | Q-22 | — | Me | J-29 (3/5) | Q-72 | 5-Cl | Me |
| J-29 (3/5) | Q-23 | — | Me | J-29 (3/5) | Q-72 | 5-Me | Me |
| J-29 (3/5) | Q-28 | — | Me | J-29 (3/5) | Q-72 | 5-NO$_2$ | Me |
| J-29 (3/5) | Q-31 | — | Me | J-29 (3/5) | Q-72 | 5-NH$_2$ | Me |
| J-29 (3/5) | Q-72 | — | Me | J-29 (3/5) | Q-72 | 6-Cl | Me |
| J-29 (3/5) | Q-75 | — | Me | J-29 (3/5) | Q-72 | 6-Me | Me |
| J-29 (3/5) | Q-78 | — | Me | J-29 (3/5) | Q-72 | 6-NO$_2$ | Me |
| J-29 (3/5) | Q-79 | — | Me | J-29 (3/5) | Q-72 | 6-NH$_2$ | Me |
| J-29 (3/5) | Q-86 | — | Me | J-29 (3/5) | Q-72 | 5,6-di-Cl | Me |

TABLE 16

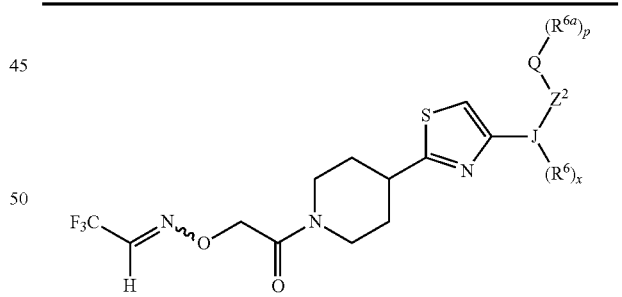

In Table 16 the structure of J (e.g., J-69) is shown in Exhibit 3 in the above Embodiments. The number in parentheses following J refer to the attachment points of J to the thiazole ring and $Z^2$ in the above structure. The first number is the ring position on J where the thiazole ring is attached and the second number is the ring position on J where $Z^2$ is attached. The $(R^6)_x$ column below identifies $R^6$ substituents attached to the J ring other than the —$Z^2Q$ substituent depicted in the above structure. A dash ("-") in the $Z^2$ column below indicates a direct bond. The structure of Q (e.g., Q-1) is shown in Exhibit 5 in the above Embodiments wherein g is 0 and the $R^{6c}$ substituent is hydrogen. The $(R^{6a})_p$ colunm below identifies substituents attached to the Q ring.

| J | $Z^2$ | $R^6$ | $(R^{6a})p$ | Q | J | $Z^2$ | $R^6$ | $(R^{6a})p$ | Q |
|---|---|---|---|---|---|---|---|---|---|
| J-69 (1/4) | O | H | H | Q-45 | J-29 (3/5) | — | H | 3-MeS(=O)$_2$ | Q-45 |
| J-29 (3/5) | — | H | H | Q-1 | J-29 (3/5) | — | H | 3-MeNH | Q-45 |
| J-29 (3/5) | — | H | H | Q-2 | J-29 (3/5) | — | H | 4-(Me)$_2$N | Q-45 |
| J-29 (3/5) | — | H | H | Q-4 | J-29 (3/5) | — | H | 2-MeOCH$_2$ | Q-45 |
| J-29 (3/5) | — | H | H | Q-5 | J-29 (3/5) | — | H | 3-MeC(O)$_2$ | Q-45 |
| J-29 (3/5) | — | H | H | Q-6 | J-29 (3/5) | — | H | 3-MeNHC(O) | Q-45 |
| J-29 (3/5) | — | H | H | Q-7 | J-29 (3/5) | — | H | 4-MeOC(O)O | Q-45 |
| J-29 (3/5) | — | H | H | Q-8 | J-29 (3/5) | — | H | 4-MeC(O)S | Q-45 |
| J-29 (3/5) | — | H | H | Q-9 | J-29 (3/5) | — | H | 3-(Me)$_2$NC(O) | Q-45 |
| J-29 (3/5) | — | H | H | Q-15 | J-29 (3/5) | — | H | 4-Me$_3$Si | Q-45 |
| J-29 (3/5) | — | H | H | Q-16 | J-29 (3/5) | — | H | 2,6-di-Et | Q-45 |
| J-29 (3/5) | — | H | H | Q-17 | J-29 (3/5) | — | H | 2,6-di-Cl | Q-45 |
| J-29 (3/5) | — | H | H | Q-18 | J-29 (3/5) | — | H | 2-OH | Q-45 |
| J-29 (3/5) | — | H | H | Q-19 | J-29 (3/5) | — | H | 4-CHF$_2$O | Q-45 |
| J-29 (3/5) | — | H | H | Q-20 | J-26 (2/5) | — | H | —CH$_2$CH$_2$— [Note 1] | Q-45 |
| J-29 (3/5) | — | H | H | Q-24 | J-26 (3/5) | — | H | 1-Me, —CH$_2$CH$_2$— [Note 1] | Q-45 |
| J-29 (3/5) | — | H | H | Q-25 | J-26 (2/5) | CH$_2$ | H | 4-OH | Q-45 |
| J-29 (3/5) | — | H | H | Q-26 | J-26 (2/5) | CH$_2$ | H | 4-MeO | Q-45 |
| J-29 (3/5) | — | H | H | Q-27 | J-26 (2/4) | CH$_2$ | H | 4-OH | Q-45 |
| J-29 (3/5) | — | H | H | Q-29 | J-26 (2/4) | CH$_2$ | H | 4-MeO | Q-45 |
| J-29 (3/5) | — | H | H | Q-30 | J-25 (2/4) | CH$_2$ | H | 4-OH | Q-45 |
| J-29 (3/5) | — | H | H | Q-32 | J-25 (2/4) | CH$_2$ | H | 4-MeO | Q-45 |
| J-29 (3/5) | — | H | H | Q-33 | J-1 (2/4) | — | 5-Me | 2,6-di-F | Q-45 |
| J-29 (3/5) | — | H | H | Q-34 | J-3 (2/5) | — | — | —CH$_2$CH$_2$— [Note 2] | Q-45 |
| J-29 (3/5) | — | H | H | Q-35 | J-29 (3/5) | NH$_2$ | H | 2,6-di-F | Q-45 |
| J-29 (3/5) | — | H | H | Q-36 | J-29 (3/5) | NMe | H | 2,6-di-F | Q-45 |
| J-29 (3/5) | — | H | H | Q-36 | J-29 (3/5) | NEt | H | 2,6-di-F | Q-45 |
| J-29 (3/5) | — | H | H | Q-37 | J-29 (3/5) | Nn-Pr | H | 2,6-di-F | Q-45 |
| J-29 (3/5) | — | H | H | Q-38 | J-29 (3/5) | — | H | H | Q-70 |
| J-29 (3/5) | — | H | H | Q-39 | J-29 (3/5) | — | H | H | Q-71 |
| J-29 (3/5) | — | H | H | Q-40 | J-29 (3/5) | — | H | H | Q-73 |
| J-29 (3/5) | — | H | H | Q-41 | J-29 (3/5) | — | H | H | Q-74 |
| J-29 (3/5) | — | H | H | Q-42 | J-29 (3/5) | — | H | H | Q-76 |
| J-29 (3/5) | — | H | H | Q-43 | J-29 (3/5) | — | H | H | Q-77 |
| J-29 (3/5) | — | H | H | Q-44 | J-29 (3/5) | — | H | H | Q-80 |
| J-29 (3/5) | — | H | H | Q-46 | J-29 (3/5) | — | H | H | Q-81 |
| J-29 (3/5) | CH$_2$ | H | H | Q-47 | J-29 (3/5) | — | H | H | Q-82 |
| J-29 (3/5) | — | H | H | Q-48 | J-29 (3/5) | — | H | H | Q-83 |
| J-29 (3/5) | — | H | H | Q-49 | J-29 (3/5) | — | H | H | Q-84 |
| J-29 (3/5) | — | H | H | Q-50 | J-29 (3/5) | — | H | H | Q-85 |
| J-29 (3/5) | — | H | H | Q-51 | J-29 (3/5) | — | H | H | Q-89 |
| J-29 (3/5) | — | H | H | Q-52 | J-29 (3/5) | — | H | H | Q-90 |
| J-29 (3/5) | — | H | H | Q-53 | J-29 (3/5) | — | H | H | Q-91 |
| J-29 (3/5) | — | H | H | Q-54 | J-29 (3/5) | — | H | H | Q-93 |
| J-29 (3/5) | — | H | H | Q-55 | J-29 (3/5) | — | H | H | Q-94 |
| J-29 (3/5) | — | H | H | Q-56 | J-29 (3/5) | — | H | H | Q-96 |
| J-29 (3/5) | — | H | H | Q-57 | J-29 (3/5) | — | H | H | Q-97 |
| J-29 (3/5) | — | H | H | Q-58 | J-29 (3/5) | — | H | H | Q-98 |
| J-29 (3/5) | — | H | H | Q-59 | J-29 (3/5) | — | H | H | Q-99 |
| J-29 (3/5) | — | H | H | Q-60 | J-29 (3/5) | — | H | H | Q-100 |
| J-29 (3/5) | — | H | H | Q-61 | J-29 (3/5) | — | H | H | Q-101 |
| J-29 (3/5) | — | H | H | Q-61 | J-29 (3/5) | — | H | 4-Cl | Q-71 |
| J-29 (3/5) | — | H | H | Q-61 | J-29 (3/5) | — | H | 5-Cl | Q-71 |
| J-29 (3/5) | — | H | H | Q-62 | J-29 (3/5) | — | H | 6-Cl | Q-71 |
| J-29 (3/5) | — | H | H | Q-63 | J-29 (3/5) | — | H | 7-Cl | Q-71 |
| J-29 (3/5) | — | H | H | Q-64 | J-29 (3/5) | — | H | 4-Me | Q-71 |
| J-29 (3/5) | — | H | H | Q-65 | J-29 (3/5) | — | H | 5-Me | Q-71 |
| J-29 (3/5) | — | H | H | Q-66 | J-29 (3/5) | — | H | 6-Me | Q-71 |
| J-29 (3/5) | — | H | H | Q-67 | J-29 (3/5) | — | H | 5-CF$_3$ | Q-71 |
| J-29 (3/5) | — | H | H | Q-68 | J-29 (3/5) | — | H | 5-NO$_2$ | Q-71 |
| J-29 (3/5) | — | H | H | Q-69 | J-29 (3/5) | — | H | 6-Br | Q-71 |
| J-29 (3/5) | — | H | 2-Me | Q-45 | J-29 (3/5) | — | H | 6-NO$_2$ | Q-71 |
| J-29 (3/5) | — | H | 3-Me | Q-45 | J-29 (3/5) | — | H | 6-NH$_2$ | Q-71 |
| J-29 (3/5) | — | H | 4-Me | Q-45 | J-29 (3/5) | — | H | 6-MeO | Q-71 |
| J-29 (3/5) | — | H | 2-Cl | Q-45 | J-29 (3/5) | — | H | 5,6-di-MeO | Q-71 |
| J-29 (3/5) | — | H | 3-Cl | Q-45 | J-29 (3/5) | — | H | 5,6-di-Cl | Q-71 |
| J-29 (3/5) | — | H | 4-Cl | Q-45 | J-29 (3/5) | — | H | 5-Cl | Q-70 |
| J-29 (3/5) | — | H | 2-MeO | Q-45 | J-29 (3/5) | — | H | 5-Me | Q-70 |
| J-29 (3/5) | — | H | 3-MeO | Q-45 | J-29 (3/5) | — | H | 5-NO$_2$ | Q-70 |
| J-29 (3/5) | — | H | 4-MeO | Q-45 | J-29 (3/5) | — | H | 5-NH$_2$ | Q-70 |
| J-29 (3/5) | — | H | 2-Et | Q-45 | J-29 (3/5) | — | H | 6-Cl | Q-70 |
| J-29 (3/5) | — | H | 3-i-Pr | Q-45 | J-29 (3/5) | — | H | 6-Me | Q-70 |
| J-29 (3/5) | — | H | 2,6-di-Me | Q-45 | J-29 (3/5) | — | H | 6-NO$_2$ | Q-70 |
| J-29 (3/5) | — | H | 4-CH$_2$=CH | Q-45 | J-29 (3/5) | — | H | 6-NH$_2$ | Q-70 |
| J-29 (3/5) | — | H | 4-CH≡C | Q-45 | J-29 (3/5) | — | H | 5,6-di-Cl | Q-70 |
| J-29 (3/5) | — | H | 4-c-Pr | Q-45 | J-29 (3/5) | — | H | 5-Cl,6-OH | Q-70 |

-continued

| J | $Z^2$ | $R^6$ | $(R^{6a})_p$ | Q | J | $Z^2$ | $R^6$ | $(R^{6a})_p$ | Q |
|---|---|---|---|---|---|---|---|---|---|
| J-29 (3/5) | — | H | 3-CF$_3$ | Q-45 | J-29 (3/5) | — | H | 4-Me | Q-63 |
| J-29 (3/5) | — | H | 3-CF$_3$O | Q-45 | J-29 (3/5) | — | H | 4-NO$_2$ | Q-63 |
| J-29 (3/5) | — | H | 4-Br | Q-45 | J-29 (3/5) | — | H | 4-NH$_2$ | Q-63 |
| J-29 (3/5) | — | H | 3-OH | Q-45 | J-29 (3/5) | — | H | 5-Cl | Q-63 |
| J-29 (3/5) | — | H | 3-NH$_2$ | Q-45 | J-29 (3/5) | — | H | 5-Me | Q-63 |
| J-29 (3/5) | — | H | 2-CN | Q-45 | J-29 (3/5) | — | H | 5-CN | Q-63 |
| J-29 (3/5) | — | H | 4-t-BuO | Q-45 | J-29 (3/5) | — | H | 5-NO$_2$ | Q-63 |
| J-29 (3/5) | — | H | 4-MeS | Q-45 | J-29 (3/5) | — | H | 5-NH$_2$ | Q-63 |
| J-29 (3/5) | — | H | 4-CF$_3$S | Q-45 | J-29 (3/5) | — | H | 5-MeCO$_2$ | Q-63 |
|  |  |  |  |  | J-29 (3/5) | — | H | 5,6-di-Cl | Q-63 |

[Note 1]:
$R^6$ at the 4-position of J-26 is taken together with $R^{6a}$ at the 2-position of Q-45.
[Note 2]:
$R^6$ at the 1-position of J-3 is taken together with $R^6$ at the 2-position of Q-45.

TABLE 17

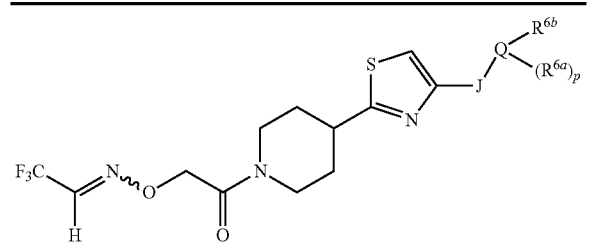

In Table 17 the structure of J (e.g., J-29) is shown in Exhibit 3 in the above Embodiments wherein x is 1 and $R^6$ is Q as depicted in the above structure. The number in parentheses following J refer to the attachment points of J to the thiazole ring and Q in the above structure. The first number is the ring position on J where the thiazole ring is attached and the second number is the ring position on J where Q is attached. The structure of Q (e.g., Q-87) is shown in Exhibit 5 in the above Embodiments wherein g is 1. The $(R^{6a})_p$ and $R^{6b}$ columns below identify substituents attached to the Q ring

| J | Q | $(R^{6a})_p$ | $R^{6b}$ |
|---|---|---|---|
| J-29 (3/5) | Q-87 | 6-F | 4-Ph |
| J-29 (3/5) | Q-45 |  | 2-Ph |

-continued

| J | Q | $(R^{6a})_p$ | $R^{6b}$ |
|---|---|---|---|
| J-29 (3/5) | Q-45 |  | 2-(1H-imidazol-2-yl) |
| J-29 (3/5) | Q-45 |  | 2-(1H-pyrazol-1-yl) |
| J-29 (3/5) | Q-45 |  | 2-(1H-1,2,4-triazol-1-yl) |
| J-29 (3/5) | Q-45 |  | 2-(1H-1,2,4-triazol-1-yl) |

TABLE 18

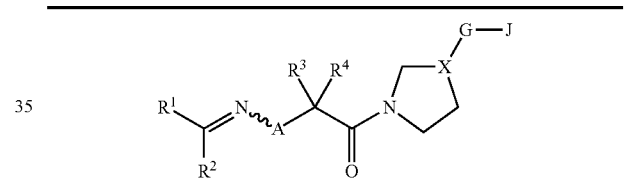

In Table 18 the structure of G-1 and G-2 is shown in Exhibit 2 in the above Embodiments wherein the bond projecting to the left is connected to X and the bond projecting to the right is connected to J in the above structure. The substituent $R^{26a}$ attached to G shown in Exhibit 2 is H.
J is $C(=W^2)NT^AT^B$ and $W^2$ is O.

| $R^1$ | $R^2$ | A | X | G | $NT^AT^B$ |
|---|---|---|---|---|---|
| CF$_3$ | H | —O— | $X^1$ | G-1 | (1R)-N-methyl-1-phenylethylamino |
| CF$_3$ | H | —O— | $X^1$ | G-1 | (1R)-N-methyl-1-phenylpropylamino |
| CF$_3$ | H | —O— | $X^1$ | G-1 | (1R)-N-methyl-1,2,3,4-tetrahydro-1-naphthalenylamino |
| CF$_3$ | H | —O— | $X^1$ | G-1 | N-methyl-4-hydroxy-1,2,3,4-tetrahydro-1-naphthalenylamino |
| CF$_3$ | H | —O— | $X^1$ | G-1 | N,2-dimethyl-1,2,3,4-tetrahydro-1-naphthalenylamino |
| CF$_3$ | H | —O— | $X^1$ | G-1 | N,2,2-trimethyl-1,2,3,4-tetrahydro-1-naphthalenylamino |
| CF$_3$ | H | —O— | $X^1$ | G-1 | (1R)-N-methyl-1-phenylethylamino |
| CF$_3$ | H | —O— | $X^1$ | G-1 | N-methyl-4-oxo-1,2,3,4-tetrahydro-1-naphthalenylamino |
| CF$_3$ | H | —O— | $X^1$ | G-1 | (1R)-N-methyl-1-indanylamino |
| CF$_3$ | H | —O— | $X^1$ | G-1 | N,2-dimethyl-1-indanylamino |
| CF$_3$ | H | —O— | $X^1$ | G-1 | N,2,2-trimethyl-1-indanylamino |
| CF$_3$ | H | —O— | $X^1$ | G-1 | N-methyl-3-hydroxy-1-indanylamino |
| CF$_3$ | H | —O— | $X^1$ | G-1 | N-methyl-3-oxo-1-indanylamino |
| CF$_3$ | H | —O— | $X^1$ | G-1 | (1R)-N-ethyl-1-phenylethylamino |
| CF$_3$ | H | —O— | $X^1$ | G-1 | (1R)-N-propyl-1-phenylethylamino |
| CF$_3$ | H | —O— | $X^1$ | G-1 | (1R)-NH-1-phenylethylamino |
| CF$_3$ | H | —O— | $X^1$ | G-1 | (1R)-N-methyl-1-(2-methylphenyl)ethylamino |
| CF$_3$ | H | —O— | $X^1$ | G-1 | (1R)-N-methyl-1-(2-fluorophenyl)ethylamino |
| CF$_3$ | H | —O— | $X^1$ | G-1 | (1R)-N-methyl-1-(2-chlorophenyl)ethylamino |
| CF$_3$ | H | —O— | $X^1$ | G-1 | (1R)-N-methyl-1-(2-bromophenyl)ethylamino |

-continued

| R¹ | R² | A | X | G | NT^A T^B |
|---|---|---|---|---|---|
| CF₃ | H | —O— | X¹ | G-1 | (1R)-N-methyl-1-(2-cyanophenyl)ethylamino |
| CF₃ | H | —O— | X¹ | G-1 | (1R)-N-methyl-1-(2-trifluoromethylphenyl)ethylamino |
| CF₃ | H | —O— | X¹ | G-1 | (1R)-N-methyl-1-(2-methoxyphenyl)ethylamino |
| CF₃ | H | —O— | X¹ | G-1 | (1R)-N-methyl-1-(2,6-dimethylphenyl)ethylamino |
| CF₃ | H | —O— | X¹ | G-1 | (1R)-N-methyl-1-(2,6-dimethoxyphenyl)ethylamino |
| CF₃ | H | —O— | X¹ | G-1 | (1R)-N-methyl-1-(2,6-difluorophenyl)ethylamino |
| CF₃ | H | —O— | X¹ | G-1 | (1R)-N-methyl-1-(2,6-dichlorophenyl)ethylamino |
| CF₃ | H | —O— | X¹ | G-1 | (1R)-N-methyl-1-(2,6-difluorophenyl)propylamino |
| CF₃ | H | —O— | X¹ | G-1 | (1R)-N-methyl-1-(2,6-difluorophenyl)butylamino |
| CF₃ | Me | —O— | X¹ | G-1 | (1R)-N-methyl-1-phenylethylamino |
| CF₃ | Me | —O— | X¹ | G-1 | (1R)-N-methyl-1-phenylpropylamino |
| CF₃ | Me | —O— | X¹ | G-1 | (1R)-N-methyl-1,2,3,4-tetrahydro-1-naphthalenylamino |
| CF₃ | Me | —O— | X¹ | G-1 | N-methyl-4-hydroxy-1,2,3,4-tetrahydro-1-naphthalenylamino |
| CF₃ | Me | —O— | X¹ | G-1 | N,2-dimethyl-1,2,3,4-tetrahydro-1-naphthalenylamino |
| CF₃ | Me | —O— | X¹ | G-1 | N,2,2-trimethyl-1,2,3,4-tetrahydro-1-naphthalenylamino |
| CF₃ | Me | —O— | X¹ | G-1 | N-methyl-4-oxo-1,2,3,4-tetrahydro-1-naphthalenylamino |
| CF₃ | Me | —O— | X¹ | G-1 | (1R)-N-methyl-1-indanylamino |
| CF₃ | Me | —O— | X¹ | G-1 | N,2-dimethyl-1-indanylamino |
| CF₃ | Me | —O— | X¹ | G-1 | N,2,2-trimethyl-1-indanylamino |
| CF₃ | Me | —O— | X¹ | G-1 | N-methyl-3-hydroxy-1-indanylamino |
| CF₃ | Me | —O— | X¹ | G-1 | N-methyl-3-oxo-1-indanylamino |
| CF₃ | Me | —O— | X¹ | G-1 | (1R)-N-ethyl-1-phenylethylamino |
| CF₃ | H | —O— | X¹ | G-1 | (1R)-N-methyl-1-phenylethylamino |
| CF₃ | Me | —O— | X¹ | G-1 | (1R)-N-propyl-1-phenylethylamino |
| CF₃ | Me | —O— | X¹ | G-1 | (1R)-NH-1-phenylethylamino |
| CF₃ | Me | —O— | X¹ | G-1 | (1R)-N-methyl-1-(2-methylphenyl)ethylamino |
| CF₃ | Me | —O— | X¹ | G-1 | (1R)-N-methyl-1-(2-fluorophenyl)ethylamino |
| CF₃ | Me | —O— | X¹ | G-1 | (1R)-N-methyl-1-(2-chlorophenyl)ethylamino |
| CF₃ | Me | —O— | X¹ | G-1 | (1R)-N-methyl-1-(2-bromophenyl)ethylamino |
| CF₃ | Me | —O— | X¹ | G-1 | (1R)-N-methyl-1-(2-cyanophenyl)ethylamino |
| CF₃ | Me | —O— | X¹ | G-1 | (1R)-N-methyl-1-(2-trifluoromethylphenyl)ethylamino |
| CF₃ | Me | —O— | X¹ | G-1 | (1R)-N-methyl-1-(2-methoxyphenyl)ethylamino |
| CF₃ | Me | —O— | X¹ | G-1 | (1R)-N-methyl-1-(2,6-dimethylphenyl)ethylamino |
| CF₃ | Me | —O— | X¹ | G-1 | (1R)-N-methyl-1-(2,6-dimethoxyphenyl)ethylamino |
| CF₃ | Me | —O— | X¹ | G-1 | (1R)-N-methyl-1-(2,6-difluorophenyl)ethylamino |
| CF₃ | Me | —O— | X¹ | G-1 | (1R)-N-methyl-1-(2,6-dichlorophenyl)ethylamino |
| CF₃ | Me | —O— | X¹ | G-1 | (1R)-N-methyl-1-(2,6-difluorophenyl)propylamino |
| CF₃ | Me | —O— | X¹ | G-1 | (1R)-N-methyl-1-(2,6-difluorophenyl)butylamino |
| CF₃ | H | —NH— | X¹ | G-1 | (1R)-N-methyl-1-phenylethylamino |
| CF₃ | H | —NH— | X¹ | G-1 | (1R)-N-methyl-1-phenylpropylamino |
| CF₃ | H | —NH— | X¹ | G-1 | (1R)-N-methyl-1,2,3,4-tetrahydro-1-naphthalenylamino |
| CF₃ | H | —NH— | X¹ | G-1 | N-methyl-4-hydroxy-1,2,3,4-tetrahydro-1-naphthalenylamino |
| CF₃ | H | —NH— | X¹ | G-1 | N,2-dimethyl-1,2,3,4-tetrahydro-1-naphthalenylamino |
| CF₃ | H | —NH— | X¹ | G-1 | N,2,2-trimethyl-1,2,3,4-tetrahydro-1-naphthalenylamino |
| CF₃ | H | —NH— | X¹ | G-1 | N-methyl-4-oxo-1,2,3,4-tetrahydro-1-naphthalenylamino |
| CF₃ | H | —NH— | X¹ | G-1 | (1R)-N-methyl-1-indanylamino |
| CF₃ | H | —NH— | X¹ | G-1 | N,2-dimethyl-1-indanylamino |
| CF₃ | H | —NH— | X¹ | G-1 | N,2,2-trimethyl-1-indanylamino |
| CF₃ | H | —NH— | X¹ | G-1 | N-methyl-3-hydroxy-1-indanylamino |
| CF₃ | H | —NH— | X¹ | G-1 | N-methyl-3-oxo-1-indanylamino |
| CF₃ | H | —NH— | X¹ | G-1 | (1R)-N-ethyl-1-phenylethylamino |
| CF₃ | H | —NH— | X¹ | G-1 | (1R)-N-propyl-1-phenylethylamino |
| CF₃ | H | —NH— | X¹ | G-1 | (1R)-NH-1-phenylethylamino |
| CF₃ | H | —NH— | X¹ | G-1 | (1R)-N-methyl-1-(2-methylphenyl)ethylamino |
| CF₃ | H | —NH— | X¹ | G-1 | (1R)-N-methyl-1-(2-fluorophenyl)ethylamino |
| CF₃ | H | —NH— | X¹ | G-1 | (1R)-N-methyl-1-(2-chlorophenyl)ethylamino |
| CF₃ | H | —NH— | X¹ | G-1 | (1R)-N-methyl-1-(2-bromophenyl)ethylamino |
| CF₃ | H | —NH— | X¹ | G-1 | (1R)-N-methyl-1-(2-cyanophenyl)ethylamino |
| CF₃ | H | —O— | X¹ | G-1 | (1R)-N-methyl-1-phenylethylamino |
| CF₃ | H | —NH— | X¹ | G-1 | (1R)-N-methyl-1-(2-trifluoromethylphenyl)ethylamino |
| CF₃ | H | —NH— | X¹ | G-1 | (1R)-N-methyl-1-(2-methoxyphenyl)ethylamino |
| CF₃ | H | —NH— | X¹ | G-1 | (1R)-N-methyl-1-(2,6-dimethylphenyl)ethylamino |
| CF₃ | H | —NH— | X¹ | G-1 | (1R)-N-methyl-1-(2,6-dimethoxyphenyl)ethylamino |
| CF₃ | H | —NH— | X¹ | G-1 | (1R)-N-methyl-1-(2,6-difluorophenyl)ethylamino |
| CF₃ | H | —NH— | X¹ | G-1 | (1R)-N-methyl-1-(2,6-dichlorophenyl)ethylamino |
| CF₃ | H | —NH— | X¹ | G-1 | (1R)-N-methyl-1-(2,6-difluorophenyl)propylamino |
| CF₃ | H | —NH— | X¹ | G-1 | (1R)-N-methyl-1-(2,6-difluorophenyl)butylamino |
| CF₃ | Me | —NH— | X¹ | G-1 | (1R)-N-methyl-1-phenylethylamino |
| CF₃ | Me | —NH— | X¹ | G-1 | (1R)-N-methyl-1-phenylpropylamino |
| CF₃ | Me | —NH— | X¹ | G-1 | (1R)-N-methyl-1,2,3,4-tetrahydro-1-naphthalenylamino |
| CF₃ | Me | —NH— | X¹ | G-1 | N-methyl-4-hydroxy-1,2,3,4-tetrahydro-1-naphthalenylamino |
| CF₃ | Me | —NH— | X¹ | G-1 | N,2-dimethyl-1,2,3,4-tetrahydro-1-naphthalenylamino |
| CF₃ | Me | —NH— | X¹ | G-1 | N,2,2-trimethyl-1,2,3,4-tetrahydro-1-naphthalenylamino |
| CF₃ | Me | —NH— | X¹ | G-1 | N-methyl-4-oxo-1,2,3,4-tetrahydro-1-naphthalenylamino |
| CF₃ | Me | —NH— | X¹ | G-1 | (1R)-N-methyl-1-indanylamino |
| CF₃ | Me | —NH— | X¹ | G-1 | N,2-dimethyl-1-indanylamino |
| CF₃ | Me | —NH— | X¹ | G-1 | N,2,2-trimethyl-1-indanylamino |
| CF₃ | Me | —NH— | X¹ | G-1 | N-methyl-3-hydroxy-1-indanylamino |

-continued

| R¹ | R² | A | X | G | NT^A T^B |
|---|---|---|---|---|---|
| CF₃ | Me | —NH— | X¹ | G-1 | N-methyl-3-oxo-1-indanylamino |
| CF₃ | Me | —NH— | X¹ | G-1 | (1R)-N-ethyl-1-phenylethylamino |
| CF₃ | Me | —NH— | X¹ | G-1 | (1R)-N-propyl-1-phenylethylamino |
| CF₃ | Me | —NH— | X¹ | G-1 | (1R)-NH-1-phenylethylamino |
| CF₃ | Me | —NH— | X¹ | G-1 | (1R)-N-methyl-1-(2-methylphenyl)ethylamino |
| CF₃ | Me | —NH— | X¹ | G-1 | (1R)-N-methyl-1-(2-fluorophenyl)ethylamino |
| CF₃ | Me | —NH— | X¹ | G-1 | (1R)-N-methyl-1-(2-chlorophenyl)ethylamino |
| CF₃ | Me | —NH— | X¹ | G-1 | (1R)-N-methyl-1-(2-bromophenyl)ethylamino |
| CF₃ | Me | —NH— | X¹ | G-1 | (1R)-N-methyl-1-(2-cyanophenyl)ethylamino |
| CF₃ | Me | —NH— | X¹ | G-1 | (1R)-N-methyl-1-(2-trifluoromethylphenyl)ethylamino |
| CF₃ | Me | —NH— | X¹ | G-1 | (1R)-N-methyl-1-(2-methoxyphenyl)ethylamino |
| CF₃ | Me | —NH— | X¹ | G-1 | (1R)-N-methyl-1-(2,6-dimethylphenyl)ethylamino |
| CF₃ | Me | —NH— | X¹ | G-1 | (1R)-N-methyl-1-(2,6-dimethoxyphenyl)ethylamino |
| CF₃ | Me | —NH— | X¹ | G-1 | (1R)-N-methyl-1-(2,6-difluorophenyl)ethylamino |
| CF₃ | Me | —NH— | X¹ | G-1 | (1R)-N-methyl-1-(2,6-dichlorophenyl)ethylamino |
| CF₃ | Me | —NH— | X¹ | G-1 | (1R)-N-methyl-1-(2,6-difluorophenyl)propylamino |
| CF₃ | H | —O— | X¹ | G-1 | (1R)-N-methyl-1-phenylethylamino |
| CF₃ | Me | —NH— | X¹ | G-1 | (1R)-N-methyl-1-(2,6-difluorophenyl)butylamino |
| CF₃ | H | —N(CH₃)— | X¹ | G-1 | (1R)-N-methyl-1-phenylethylamino |
| CF₃ | H | —N(CH₃)— | X¹ | G-1 | (1R)-N-methyl-1-phenylpropylamino |
| CF₃ | H | —N(CH₃)— | X¹ | G-1 | (1R)-N-methyl-1,2,3,4-tetrahydro-1-naphthalenylamino |
| CF₃ | H | —N(CH₃)— | X¹ | G-1 | N-methyl-4-hydroxy-1,2,3,4-tetrahydro-1-naphthalenylamino |
| CF₃ | H | —N(CH₃)— | X¹ | G-1 | N,2-dimethyl-1,2,3,4-tetrahydro-1-naphthalenylamino |
| CF₃ | H | —N(CH₃)— | X¹ | G-1 | N,2,2-trimethyl-1,2,3,4-tetrahydro-1-naphthalenylamino |
| CF₃ | H | —N(CH₃)— | X¹ | G-1 | N-methyl-4-oxo-1,2,3,4-tetrahydro-1-naphthalenylamino |
| CF₃ | H | —N(CH₃)— | X¹ | G-1 | (1R)-N-methyl-1-indanylamino |
| CF₃ | H | —N(CH₃)— | X¹ | G-1 | N,2-dimethyl-1-indanylamino |
| CF₃ | H | —N(CH₃)— | X¹ | G-1 | N,2,2-trimethyl-1-indanylamino |
| CF₃ | H | —N(CH₃)— | X¹ | G-1 | N-methyl-3-hydroxy-1-indanylamino |
| CF₃ | H | —N(CH₃)— | X¹ | G-1 | N-methyl-3-oxo-1-indanylamino |
| CF₃ | H | —N(CH₃)— | X¹ | G-1 | (1R)-N-ethyl-1-phenylethylamino |
| CF₃ | H | —N(CH₃)— | X¹ | G-1 | (1R)-N-propyl-1-phenylethylamino |
| CF₃ | H | —N(CH₃)— | X¹ | G-1 | (1R)-NH-1-phenylethylamino |
| CF₃ | H | —N(CH₃)— | X¹ | G-1 | (1R)-N-methyl-1-(2-methylphenyl)ethylamino |
| CF₃ | H | —N(CH₃)— | X¹ | G-1 | (1R)-N-methyl-1-(2-fluorophenyl)ethylamino |
| CF₃ | H | —N(CH₃)— | X¹ | G-1 | (1R)-N-methyl-1-(2-chlorophenyl)ethylamino |
| CF₃ | H | —N(CH₃)— | X¹ | G-1 | (1R)-N-methyl-1-(2-bromophenyl)ethylamino |
| CF₃ | H | —N(CH₃)— | X¹ | G-1 | (1R)-N-methyl-1-(2-cyanophenyl)ethylamino |
| CF₃ | H | —N(CH₃)— | X¹ | G-1 | (1R)-N-methyl-1-(2-trifluoromethylphenyl)ethylamino |
| CF₃ | H | —N(CH₃)— | X¹ | G-1 | (1R)-N-methyl-1-(2-methoxyphenyl)ethylamino |
| CF₃ | H | —N(CH₃)— | X¹ | G-1 | (1R)-N-methyl-1-(2,6-dimethylphenyl)ethylamino |
| CF₃ | H | —N(CH₃)— | X¹ | G-1 | (1R)-N-methyl-1-(2,6-dimethoxyphenyl)ethylamino |
| CF₃ | H | —N(CH₃)— | X¹ | G-1 | (1R)-N-methyl-1-(2,6-difluorophenyl)ethylamino |
| CF₃ | H | —N(CH₃)— | X¹ | G-1 | (1R)-N-methyl-1-(2,6-dichlorophenyl)ethylamino |
| CF₃ | H | —N(CH₃)— | X¹ | G-1 | (1R)-N-methyl-1-(2,6-difluorophenyl)propylamino |
| CF₃ | H | —N(CH₃)— | X¹ | G-1 | (1R)-N-methyl-1-(2,6-difluorophenyl)butylamino |
| CF₃ | Me | —N(CH₃)— | X¹ | G-1 | (1R)-N-methyl-1-phenylethylamino |
| CF₃ | Me | —N(CH₃)— | X¹ | G-1 | (1R)-N-methyl-1-phenylpropylamino |
| CF₃ | Me | —N(CH₃)— | X¹ | G-1 | (1R)-N-methyl-1,2,3,4-tetrahydro-1-naphthalenylamino |
| CF₃ | Me | —N(CH₃)— | X¹ | G-1 | N-methyl-4-hydroxy-1,2,3,4-tetrahydro-1-naphthalenylamino |
| CF₃ | Me | —N(CH₃)— | X¹ | G-1 | N,2-dimethyl-1,2,3,4-tetrahydro-1-naphthalenylamino |
| CF₃ | Me | —N(CH₃)— | X¹ | G-1 | N,2,2-trimethyl-1,2,3,4-tetrahydro-1-naphthalenylamino |
| CF₃ | H | —O— | X¹ | G-1 | (1R)-N-methyl-1-phenylethylamino |
| CF₃ | Me | —N(CH₃)— | X¹ | G-1 | N-methyl-4-oxo-1,2,3,4-tetrahydro-1-naphthalenylamino |
| CF₃ | Me | —N(CH₃)— | X¹ | G-1 | (1R)-N-methyl-1-indanylamino |
| CF₃ | Me | —N(CH₃)— | X¹ | G-1 | N,2-dimethyl-1-indanylamino |
| CF₃ | Me | —N(CH₃)— | X¹ | G-1 | N,2,2-trimethyl-1-indanylamino |
| CF₃ | Me | —N(CH₃)— | X¹ | G-1 | N-methyl-3-hydroxy-1-indanylamino |
| CF₃ | Me | —N(CH₃)— | X¹ | G-1 | N-methyl-3-oxo-1-indanylamino |
| CF₃ | Me | —N(CH₃)— | X¹ | G-1 | (1R)-N-ethyl-1-phenylethylamino |
| CF₃ | Me | —N(CH₃)— | X¹ | G-1 | (1R)-N-propyl-1-phenylethylamino |
| CF₃ | Me | —N(CH₃)— | X¹ | G-1 | (1R)-NH-1-phenylethylamino |
| CF₃ | Me | —N(CH₃)— | X¹ | G-1 | (1R)-N-methyl-1-(2-methylphenyl)ethylamino |
| CF₃ | Me | —N(CH₃)— | X¹ | G-1 | (1R)-N-methyl-1-(2-fluorophenyl)ethylamino |
| CF₃ | Me | —N(CH₃)— | X¹ | G-1 | (1R)-N-methyl-1-(2-chlorophenyl)ethylamino |
| CF₃ | Me | —N(CH₃)— | X¹ | G-1 | (1R)-N-methyl-1-(2-bromophenyl)ethylamino |
| CF₃ | Me | —N(CH₃)— | X¹ | G-1 | (1R)-N-methyl-1-(2-cyanophenyl)ethylamino |
| CF₃ | Me | —N(CH₃)— | X¹ | G-1 | (1R)-N-methyl-1-(2-trifluoromethylphenyl)ethylamino |
| CF₃ | Me | —N(CH₃)— | X¹ | G-1 | (1R)-N-methyl-1-(2-methoxyphenyl)ethylamino |
| CF₃ | Me | —N(CH₃)— | X¹ | G-1 | (1R)-N-methyl-1-(2,6-dimethylphenyl)ethylamino |
| CF₃ | Me | —N(CH₃)— | X¹ | G-1 | (1R)-N-methyl-1-(2,6-dimethoxyphenyl)ethylamino |
| CF₃ | Me | —N(CH₃)— | X¹ | G-1 | (1R)-N-methyl-1-(2,6-difluorophenyl)ethylamino |
| CF₃ | Me | —N(CH₃)— | X¹ | G-1 | (1R)-N-methyl-1-(2,6-dichlorophenyl)ethylamino |
| CF₃ | Me | —N(CH₃)— | X¹ | G-1 | (1R)-N-methyl-1-(2,6-difluorophenyl)propylamino |
| CF₃ | Me | —N(CH₃)— | X¹ | G-1 | (1R)-N-methyl-1-(2,6-difluorophenyl)butylamino |
| CF₃ | H | —O— | X¹ | G-2 | (1R)-N-methyl-1,2,3,4-tetrahydro-1-naphthalenylamino |
| CF₃ | H | —NH— | X¹ | G-2 | (1R)-N-methyl-1,2,3,4-tetrahydro-1-naphthalenylamino |
| CF₃ | H | —N(CH₃)— | X¹ | G-2 | (1R)-N-methyl-1,2,3,4-tetrahydro-1-naphthalenylamino |

-continued

| $R^1$ | $R^2$ | A | X | G | $NT^AT^B$ |
|---|---|---|---|---|---|
| $CF_3$ | H | —O— | $X^2$ | G-1 | (1R)-N-methyl-1,2,3,4-tetrahydro-1-naphthalenylamino |
| $CF_3$ | H | —NH— | $X^2$ | G-1 | (1R)-N-methyl-1,2,3,4-tetrahydro-1-naphthalenylamino |
| $CF_3$ | H | —N(CH$_3$)— | $X^2$ | G-1 | (1R)-N-methyl-1,2,3,4-tetrahydro-1-naphthalenylamino |
| $CF_3$ | H | —O— | $X^2$ | G-2 | (1R)-N-methyl-1,2,3,4-tetrahydro-1-naphthalenylamino |
| $CF_3$ | H | —NH— | $X^2$ | G-2 | (1R)-N-methyl-1,2,3,4-tetrahydro-1-naphthalenylamino |
| $CF_3$ | H | —N(CH$_3$)— | $X^2$ | G-2 | (1R)-N-methyl-1,2,3,4-tetrahydro-1-naphthalenylamino |
| $CF_3$ | Me | —O— | $X^2$ | G-2 | (1R)-N-methyl-1,2,3,4-tetrahydro-1-naphthalenylamino |
| $CF_3$ | Me | —NH— | $X^2$ | G-2 | (1R)-N-methyl-1,2,3,4-tetrahydro-1-naphthalenylamino |
| $CF_3$ | Me | —N(CH$_3$)— | $X^2$ | G-2 | (1R)-N-methyl-1,2,3,4-tetrahydro-1-naphthalenylamino |
| $CF_3$ | Me | O— | $X^2$ | G-1 | (1R)-N-methyl-1,2,3,4-tetrahydro-1-naphthalenylamino |
| $CF_3$ | H | —O— | $X^1$ | G-1 | (1R)-N-methyl-1-phenylethylamino |
| $CF_3$ | Me | —NH— | $X^2$ | G-1 | (1R)-N-methyl-1,2,3,4-tetrahydro-1-naphthalenylamino |
| $CF_3$ | Me | —N(CH$_3$)— | $X^2$ | G-1 | (1R)-N-methyl-1,2,3,4-tetrahydro-1-naphthalenylamino |
| $CF_3$ | Me | —O— | $X^2$ | G-2 | (1R)-N-methyl-1,2,3,4-tetrahydro-1-naphthalenylamino |
| $CF_3$ | Me | —NH— | $X^2$ | G-2 | (1R)-N-methyl-1,2,3,4-tetrahydro-1-naphthalenylamino |
| $CF_3$ | Me | —N(CH$_3$)— | $X^2$ | G-2 | (1R)-N-methyl-1,2,3,4-tetrahydro-1-naphthalenylamino |

TABLE 19

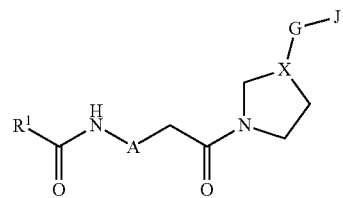

In Table 19 the structure of G-1 and G-2 is shown in Exhibit 2 in the above Embodiments wherein the bond projecting to the left is connected to X and the bond projecting to the right is connected to J in the above structure. The substituent $R^{26a}$ attached to G shown in Exhibit 2 is H.

J is C(=$W^2$)$NT^AT^B$ and $W^2$ is O.

| $R^1$ | A | X | G | $NT^AT^B$ |
|---|---|---|---|---|
| $CF_3$ | —O— | $X^1$ | G-1 | (1R)-N-methyl-1-phenylethylamino |
| $CF_3$ | —O— | $X^1$ | G-1 | (1R)-N-methyl-1-phenylpropylamino |
| $CF_3$ | —O— | $X^1$ | G-1 | (1R)-N-methyl-1,2,3,4-tetrahydro-1-naphthalenylamino |
| $CF_3$ | —O— | $X^1$ | G-1 | N-methyl-4-hydroxy-1,2,3,4-tetrahydro-1-naphthalenylamino |
| $CF_3$ | —O— | $X^1$ | G-1 | N,2-dimethyl-1,2,3,4-tetrahydro-1-naphthalenylamino |
| $CF_3$ | —O— | $X^1$ | G-1 | N,2,2-trimethyl-1,2,3,4-tetrahydro-1-naphthalenylamino |
| $CF_3$ | —O— | $X^1$ | G-1 | N-methyl-4-oxo-1,2,3,4-tetrahydro-1-naphthalenylamino |
| H | —O— | $X^1$ | G-1 | (1R)-N-methyl-1-indanylamino |
| $CF_3$ | —O— | $X^1$ | G-1 | N,2-dimethyl-1-indanylamino |
| $CF_3$ | —O— | $X^1$ | G-1 | N,2,2-trimethyl-1-indanylamino |
| $CF_3$ | —O— | $X^1$ | G-1 | N-methyl-3-hydroxy-1-indanylamino |
| $CF_3$ | —O— | $X^1$ | G-1 | N-methyl-3-oxo-1-indanylamino |
| $CF_3$ | —O— | $X^1$ | G-1 | (1R)-N-ethyl-1-phenylethylamino |
| $CF_3$ | —O— | $X^1$ | G-1 | (1R)-N-propyl-1-phenylethylamino |
| $CF_3$ | —O— | $X^1$ | G-1 | (1R)-NH-1-phenylethylamino |
| $CF_3$ | —O— | $X^1$ | G-1 | (1R)-N-methyl-1-(2-methylphenyl)ethylamino |
| $CF_3$ | —O— | $X^1$ | G-1 | (1R)-N-methyl-1-(2-fluorophenyl)ethylamino |
| $CF_3$ | —O— | $X^1$ | G-1 | (1R)-N-methyl-1-(2-chlorophenyl)ethylamino |
| $CF_3$ | —O— | $X^1$ | G-1 | (1R)-N-methyl-1-(2-bromophenyl)ethylamino |
| $CF_3$ | —O— | $X^1$ | G-1 | (1R)-N-methyl-1-(2-cyanophenyl)ethylamino |
| $CF_3$ | —O— | $X^1$ | G-1 | (1R)-N-methyl-1-(2-trifluoromethylphenyl)ethylamino |
| $CF_3$ | —O— | $X^1$ | G-1 | (1R)-N-methyl-1-(2-methoxyphenyl)ethylamino |
| $CF_3$ | —O— | $X^1$ | G-1 | (1R)-N-methyl-1-(2,6-dimethylphenyl)ethylamino |
| $CF_3$ | —O— | $X^1$ | G-1 | (1R)-N-methyl-1-(2,6-dimethoxyphenyl)ethylamino |
| $CF_3$ | —O— | $X^1$ | G-1 | (1R)-N-methyl-1-(2,6-difluorophenyl)ethylamino |
| $CF_3$ | —O— | $X^1$ | G-1 | (1R)-N-methyl-1-(2,6-dichlorophenyl)ethylamino |
| $CF_3$ | —O— | $X^1$ | G-1 | (1R)-N-methyl-1-(2,6-difluorophenyl)propylamino |
| $CF_3$ | —O— | $X^1$ | G-1 | (1R)-N-methyl-1-(2,6-difluorophenyl)butylamino |
| $CF_3$ | —NH— | $X^1$ | G-1 | (1R)-N-methyl-1-phenylethylamino |
| $CF_3$ | —NH— | $X^1$ | G-1 | (1R)-N-methyl-1-phenylpropylamino |

-continued

| R¹ | A | X | G | NT$^A$T$^B$ |
|---|---|---|---|---|
| CF₃ | —NH— | X¹ | G-1 | (1R)-N-methyl-1,2,3,4-tetrahydro-1-naphthalenylamino |
| CF₃ | —NH— | X¹ | G-1 | N-methyl-4-hydroxy-1,2,3,4-tetrahydro-1-naphthalenylamino |
| CF₃ | —NH— | X¹ | G-1 | N,2-dimethyl-1,2,3,4-tetrahydro-1-naphthalenylamino |
| CF₃ | —NH— | X¹ | G-1 | N,2,2-trimethyl-1,2,3,4-tetrahydro-1-naphthalenylamino |
| CF₃ | —NH— | X¹ | G-1 | N-methyl-4-oxo-1,2,3,4-tetrahydro-1-naphthalenylamino |
| CF₃ | —NH— | X¹ | G-1 | (1R)-N-methyl-1-indanylamino |
| CF₃ | —NH— | X¹ | G-1 | N,2-dimethyl-1-indanylamino |
| CF₃ | —NH— | X¹ | G-1 | N,2,2-trimethyl-1-indanylamino |
| CF₃ | —NH— | X¹ | G-1 | N-methyl-3-hydroxy-1-indanylamino |
| CF₃ | —NH— | X¹ | G-1 | N-methyl-3-oxo-1-indanylamino |
| CF₃ | —NH— | X¹ | G-1 | (1R)-N-ethyl-1-phenylethylamino |
| CF₃ | —NH— | X¹ | G-1 | (1R)-N-propyl-1-phenylethylamino |
| CF₃ | —NH— | X¹ | G-1 | (1R)-NH-1-phenylethylamino |
| CF₃ | —NH— | X¹ | G-1 | (1R)-N-methyl-1-(2-methylphenyl)ethylamino |
| CF₃ | —NH— | X¹ | G-1 | (1R)-N-methyl-1-(2-fluorophenyl)ethylamino |
| CF₃ | —NH— | X¹ | G-1 | (1R)-N-methyl-1-(2-chlorophenyl)ethylamino |
| CF₃ | —NH— | X¹ | G-1 | (1R)-N-methyl-1-(2-bromophenyl)ethylamino |
| CF₃ | —NH— | X¹ | G-1 | (1R)-N-methyl-1-(2-cyanophenyl)ethylamino |
| CF₃ | —NH— | X¹ | G-1 | (1R)-N-methyl-1-(2-trifluoromethylphenyl)ethylamino |
| CF₃ | —NH— | X¹ | G-1 | (1R)-N-methyl-1-(2-methoxyphenyl)ethylamino |
| CF₃ | —NH— | X¹ | G-1 | (1R)-N-methyl-1-(2,6-dimethylphenyl)ethylamino |
| CF₃ | —NH— | X¹ | G-1 | (1R)-N-methyl-1-(2,6-dimethoxyphenyl)ethylamino |
| CF₃ | —NH— | X¹ | G-1 | (1R)-N-methyl-1-(2,6-difluorophenyl)ethylamino |
| CF₃ | —NH— | X¹ | G-1 | (1R)-N-methyl-1-(2, 6-dichlorophenyl)ethylamino |
| CF₃ | —NH— | X¹ | G-1 | (1R)-N-methyl-1-(2,6-difluorophenyl)propylamino |
| CF₃ | —NH— | X¹ | G-1 | (1R)-N-methyl-1-(2,6-difluorophenyl)butylamino |
| CF₃ | —N(CH₃)— | X¹ | G-1 | (1R)-N-methyl-1-phenylethylamino |
| CF₃ | —N(CH₃)— | X¹ | G-1 | (1R)-N-methyl-1-phenylpropylamino |
| CF₃ | —N(CH₃)— | X¹ | G-1 | (1R)-N-methyl-1,2,3,4-tetrahydro-1-naphthalenylamino |
| CF₃ | —N(CH₃)— | X¹ | G-1 | N-methyl-4-hydroxy-1,2,3,4-tetrahydro-1-naphthalenylamino |
| CF₃ | —N(CH₃)— | X¹ | G-1 | N,2-dimethyl-1,2,3,4-tetrahydro-1-naphthalenylamino |
| CF₃ | —N(CH₃)— | X¹ | G-1 | N,2,2-trimethyl-1,2,3,4-tetrahydro-1-naphthalenylamino |
| CF₃ | —N(CH₃)— | X¹ | G-1 | N-methyl-4-oxo-1,2,3,4-tetrahydro-1-naphthalenylamino |
| CF₃ | —N(CH₃)— | X¹ | G-1 | (1R)-N-methyl-1-indanylamino |
| CF₃ | —N(CH₃)— | X¹ | G-1 | N,2-dimethyl-1-indanylamino |
| CF₃ | —N(CH₃)— | X¹ | G-1 | N,2,2-trimethyl-1-indanylamino |
| CF₃ | —N(CH₃)— | X¹ | G-1 | N-methyl-3-hydroxy-1-indanylamino |
| CF₃ | —N(CH₃)— | X¹ | G-1 | N-methyl-3-oxo-1-indanylamino |
| CF₃ | —N(CH₃)— | X¹ | G-1 | (1R)-N-ethyl-1-phenylethylamino |
| CF₃ | —N(CH₃)— | X¹ | G-1 | (1R)-N-propyl-1-phenylethylamino |
| CF₃ | —N(CH₃)— | X¹ | G-1 | (1R)-NH-1-phenylethylamino |
| CF₃ | —N(CH₃)— | X¹ | G-1 | (1R)-N-methyl-1-(2-methylphenyl)ethylamino |
| CF₃ | —N(CH₃)— | X¹ | G-1 | (1R)-N-methyl-1-(2-fluorophenyl)ethylamino |
| CF₃ | —N(CH₃)— | X¹ | G-1 | (1R)-N-methyl-1-(2-chlorophenyl)ethylamino |
| CF₃ | —N(CH₃)— | X¹ | G-1 | (1R)-N-methyl-1-(2-bromophenyl)ethylamino |
| CF₃ | —N(CH₃)— | X¹ | G-1 | (1R)-N-methyl-1-(2-cyanophenyl)ethylamino |
| CF₃ | —N(CH₃)— | X¹ | G-1 | (1R)-N-methyl-1-(2-trifluoromethylphenyl)ethylamino |
| CF₃ | —N(CH₃)— | X¹ | G-1 | (1R)-N-methyl-1-(2-methoxyphenyl)ethylamino |
| CF₃ | —N(CH₃)— | X¹ | G-1 | (1R)-N-methyl-1-(2,6-dimethylphenyl)ethylamino |
| CF₃ | —N(CH₃)— | X¹ | G-1 | (1R)-N-methyl-1-(2,6-dimethoxyphenyl)ethylamino |
| CF₃ | —N(CH₃)— | X¹ | G-1 | (1R)-N-methyl-1-(2,6-difluorophenyl)ethylamino |
| CF₃ | —N(CH₃)— | X¹ | G-1 | (1R)-N-methyl-1-(2,6-dichlorophenyl)ethylamino |
| CF₃ | —N(CH₃)— | X¹ | G-1 | (1R)-N-methyl-1-(2,6-difluorophenyl)propylamino |
| CF₃ | —N(CH₃)— | X¹ | G-1 | (1R)-N-methyl-1-(2,6-difluorophenyl)butylamino |
| Me | —O— | X¹ | G-1 | (1R)-N-methyl-1-phenylethylamino |
| Me | —O— | X¹ | G-1 | (1R)-N-methyl-1-phenylpropylamino |
| Me | —O— | X¹ | G-1 | (1R)-N-methyl-1,2,3,4-tetrahydro-1-naphthalenylamino |
| Me | —O— | X¹ | G-1 | N-methyl-4-hydroxy-1,2,3,4-tetrahydro-1-naphthalenylamino |
| Me | —O— | X¹ | G-1 | N,2-dimethyl-1,2,3,4-tetrahydro-1-naphthalenylamino |
| Me | —O— | X¹ | G-1 | N,2,2-trimethyl-1,2,3,4-tetrahydro-1-naphthalenylamino |
| Me | —O— | X¹ | G-1 | N-methyl-4-oxo-1,2,3,4-tetrahydro-1-naphthalenylamino |
| Me | —O— | X¹ | G-1 | (1R)-N-methyl-1-indanylamino |
| Me | —O— | X¹ | G-1 | N,2-dimethyl-1-indanylamino |
| Me | —O— | X¹ | G-1 | N,2,2-trimethyl-1-indanylamino |
| Me | —O— | X¹ | G-1 | N-methyl-3-hydroxy-1-indanylamino |
| Me | —O— | X¹ | G-1 | N-methyl-3-oxo-1-indanylamino |
| Me | —O— | X¹ | G-1 | (1R)-N-ethyl-1-phenylethylamino |
| Me | —O— | X¹ | G-1 | (1R)-N-propyl-1-phenylethylamino |
| Me | —O— | X¹ | G-1 | (1R)-NH-1-phenylethylamino |
| Me | —O— | X¹ | G-1 | (1R)-N-methyl-1-(2-methylphenyl)ethylamino |
| Me | —O— | X¹ | G-1 | (1R)-N-methyl-1-(2-fluorophenyl)ethylamino |
| Me | —O— | X¹ | G-1 | (1R)-N-methyl-1-(2-chlorophenyl)ethylamino |
| Me | —O— | X¹ | G-1 | (1R)-N-methyl-1-(2-bromophenyl)ethylamino |
| Me | —O— | X¹ | G-1 | (1R)-N-methyl-1-(2-cyanophenyl)ethylamino |
| Me | —O— | X¹ | G-1 | (1R)-N-methyl-1-(2-trifluoromethylphenyl)ethylamino |
| Me | —O— | X¹ | G-1 | (1R)-N-methyl-1-(2-methoxyphenyl)ethylamino |
| Me | —O— | X¹ | G-1 | (1R)-N-methyl-1-(2,6-dimethylphenyl)ethylamino |
| Me | —O— | X¹ | G-1 | (1R)-N-methyl-1-(2,6-dimethoxyphenyl)ethylamino |

-continued

| R¹ | A | X | G | NT⁴T^B |
|---|---|---|---|---|
| Me | —O— | X¹ | G-1 | (1R)-N-methyl-1-(2,6-difluorophenyl)ethylamino |
| Me | —O— | X¹ | G-1 | (1R)-N-methyl-1-(2,6-dichlorophenyl)ethylamino |
| Me | —O— | X¹ | G-1 | (1R)-N-methyl-1-(2,6-difluorophenyl)propylamino |
| Me | —O— | X¹ | G-1 | (1R)-N-methyl-1-(2,6-difluorophenyl)butylamino |
| Me | —NH— | X¹ | G-1 | (1R)-N-methyl-1,2,3,4-tetrahydro-1-naphthalenylamino |
| Me | —N(CH₃)— | X¹ | G-1 | (1R)-N-methyl-1,2,3,4-tetrahydro-1-naphthalenylamino |
| CF₃ | —O— | X² | G-2 | (1R)-N-methyl-1,2,3,4-tetrahydro-1-naphthalenylamino |
| CF₃ | —NH— | X² | G-2 | (1R)-N-methyl-1,2,3,4-tetrahydro-1-naphthalenylamino |
| CF₃ | —N(CH₃)— | X² | G-2 | (1R)-N-methyl-1,2,3,4-tetrahydro-1-naphthalenylamino |
| CF₃ | —O— | X¹ | G-2 | (1R)-N-methyl-1,2,3,4-tetrahydro-1-naphthalenylamino |
| CF₃ | —NH— | X¹ | G-2 | (1R)-N-methyl-1,2,3,4-tetrahydro-1-naphthalenylamino |
| CF₃ | —N(CH₃)— | X¹ | G-2 | (1R)-N-methyl-1,2,3,4-tetrahydro-1-naphthalenylamino |
| CF₃ | —O— | X² | G-1 | (1R)-N-methyl-1,2,3,4-tetrahydro-1-naphthalenylamino |
| CF₃ | —NH— | X² | G-1 | (1R)-N-methyl-1,2,3,4-tetrahydro-1-naphthalenylamino |
| CF₃ | —N(CH₃)— | X² | G-1 | (1R)-N-methyl-1,2,3,4-tetrahydro-1-naphthalenylamino |

TABLE 20

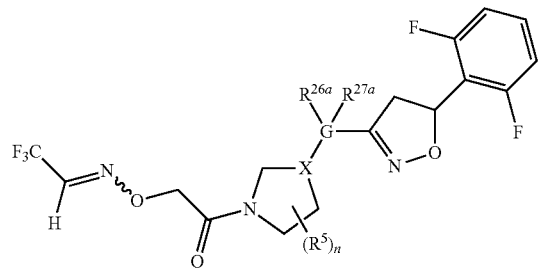

In Table 20 the structure of G (e.g., G-1) is shown in Exhibit 2 in the above Embodiments wherein the bond projecting to the left is connected to X and the bond projecting to the right is connected to the isoxazole ring of the above structure. A dash "-" in the $(R^5)_n$ column below indicates no $R^5$ substituent is present. Locant numbers in the $(R^5)_n$ column below indicate the position of the $R^5$ substituent(s) on the ring containing X relative to the nitrogen atom in said ring. A dash ("-") in the $R^{27a}$ column below indicates $R^{27a}$ is present the G ring depicted in Exhibit 2.

| X | $(R^5)_n$ | G | $R^{26a}$ | $R^{27a}$ |
|---|---|---|---|---|
| X¹ | — | G-1 | H | — |
| X¹ | — | G-2 | H | — |
| X¹ | — | G-3 | H | H |
| X¹ | — | G-4 | H | — |
| X¹ | — | G-5 | H | — |
| X¹ | — | G-6 | H | H |
| X¹ | — | G-7 | H | — |
| X¹ | — | G-8 | H | — |
| X¹ | — | G-9 | H | H |
| X¹ | — | G-10 | H | — |
| X¹ | — | G-11 | H | — |
| X¹ | — | G-12 | H | H |
| X¹ | — | G-13 | H | H |
| X¹ | — | G-14 | H | — |
| X¹ | — | G-15 | H | — |
| X¹ | — | G-16 | H | H |
| X¹ | — | G-17 | H | — |
| X¹ | — | G-18 | H | — |
| X¹ | — | G-19 | H | H |
| X¹ | — | G-20 | H | — |
| X¹ | — | G-21 | H | — |
| X¹ | — | G-22 | H | H |
| X¹ | — | G-23 | H | — |
| X¹ | — | G-24 | H | — |
| X¹ | — | G-25 | H | — |
| X¹ | — | G-26 | H | — |
| X¹ | — | G-27 | H | — |
| X¹ | — | G-28 | H | — |
| X¹ | — | G-29 | H | — |
| X¹ | — | G-30 | H | — |
| X¹ | — | G-31 | H | — |
| X¹ | — | G-32 | H | — |
| X¹ | — | G-33 | H | — |
| X¹ | — | G-34 | H | — |
| X¹ | — | G-35 | H | — |
| X¹ | — | G-36 | H | — |
| X¹ | — | G-37 | H | — |
| X¹ | — | G-38 | H | — |
| X¹ | — | G-39 | H | H |
| X¹ | — | G-40 | H | — |
| X¹ | — | G-41 | H | — |
| X¹ | — | G-42 | H | H |
| X¹ | — | G-43 | H | H |
| X¹ | — | G-44 | H | — |
| X¹ | — | G-45 | H | — |
| X¹ | — | G-46 | H | — |
| X¹ | — | G-47 | H | — |
| X¹ | — | G-48 | H | H |
| X¹ | — | G-49 | H | — |
| X¹ | — | G-50 | H | — |
| X¹ | — | G-51 | H | H |
| X¹ | — | G-52 | H | — |
| X¹ | — | G-53 | H | — |
| X¹ | — | G-54 | H | H |
| X¹ | — | G-55 | H | — |
| X¹ | — | G-56 | H | — |
| X¹ | — | G-57 | H | — |
| X¹ | — | G-58 | H | H |
| X¹ | — | G-59 | H | H |
| X¹ | — | G-2 | Me | — |
| X¹ | — | G-2 | Cl | — |
| X¹ | — | G-2 | F | — |
| X¹ | — | G-2 | CF₃ | — |
| X¹ | — | G-14 | n-Pr | — |
| X¹ | — | G-3 | H | Me |
| X¹ | — | G-3 | H | n-Pr |
| X¹ | — | G-26 | 5-Me | — |
| X¹ | 2-Me | G-1 | H | — |
| X¹ | 3-Me | G-1 | H | — |
| X¹ | 2,6-di-Me | G-1 | H | — |
| X¹ | 3,5-di-Me | G-1 | H | — |
| X¹ | 3-n-Bu | G-1 | H | — |
| X¹ | 4-MeO | G-1 | H | — |
| X¹ | 4-OH | G-1 | H | — |
| X¹ | 4-Cl | G-1 | H | — |
| X¹ | 4-Br | G-1 | H | — |
| X¹ | 4-CN | G-1 | H | — |
| X² | — | G-1 | H | — |
| X² | — | G-2 | H | — |
| X² | — | G-3 | H | H |

-continued

| X | $(R^5)_n$ | G | $R^{26a}$ | $R^{27a}$ |
|---|---|---|---|---|
| $X^2$ | — | G-4 | H | — |
| $X^2$ | — | G-5 | H | — |
| $X^2$ | — | G-6 | H | H |
| $X^2$ | — | G-7 | H | — |
| $X^2$ | — | G-8 | H | — |
| $X^2$ | — | G-9 | H | H |
| $X^2$ | — | G-10 | H | — |
| $X^2$ | — | G-11 | H | — |
| $X^2$ | — | G-12 | H | H |
| $X^2$ | — | G-13 | H | H |
| $X^2$ | — | G-14 | H | — |
| $X^2$ | — | G-15 | H | — |
| $X^2$ | — | G-16 | H | H |
| $X^2$ | — | G-17 | H | — |
| $X^2$ | — | G-18 | H | — |
| $X^2$ | — | G-19 | H | H |
| $X^2$ | — | G-20 | H | — |
| $X^2$ | — | G-21 | H | — |
| $X^2$ | — | G-22 | H | H |
| $X^2$ | — | G-23 | H | — |
| $X^2$ | — | G-24 | H | — |
| $X^2$ | — | G-31 | H | — |
| $X^2$ | — | G-32 | H | — |
| $X^2$ | — | G-33 | H | — |
| $X^2$ | — | G-34 | H | — |
| $X^2$ | — | G-35 | H | — |
| $X^2$ | — | G-37 | H | — |
| $X^2$ | — | G-38 | H | — |
| $X^2$ | — | G-39 | H | H |
| $X^2$ | — | G-40 | H | — |
| $X^2$ | — | G-41 | H | — |
| $X^2$ | — | G-42 | H | H |
| $X^2$ | — | G-43 | H | H |
| $X^2$ | — | G-44 | H | — |
| $X^2$ | — | G-45 | H | — |
| $X^2$ | — | G-46 | H | — |
| $X^2$ | — | G-47 | H | — |
| $X^2$ | — | G-48 | H | H |
| $X^2$ | — | G-49 | H | — |
| $X^2$ | — | G-50 | H | — |
| $X^2$ | — | G-51 | H | H |
| $X^2$ | — | G-52 | H | — |
| $X^2$ | — | G-53 | H | — |
| $X^2$ | — | G-54 | H | H |
| $X^2$ | — | G-2 | Me | — |
| $X^2$ | — | G-2 | Cl | — |
| $X^2$ | — | G-2 | F | — |
| $X^2$ | — | G-2 | $CF_3$ | — |
| $X^2$ | — | G-14 | n-Pr | — |
| $X^2$ | — | G-3 | H | Me |
| $X^2$ | — | G-3 | H | n-Pr |
| $X^2$ | 2-Me | G-1 | H | — |
| $X^2$ | 3-Me | G-1 | H | — |
| $X^2$ | 2,6-di-Me | G-1 | H | — |
| $X^2$ | 3,5-di-Me | G-1 | H | — |
| $X^2$ | 3-n-Bu | G-1 | H | — |
| $X^3$ | — | G-1 | H | — |
| $X^3$ | — | G-2 | H | — |
| $X^3$ | — | G-3 | H | H |
| $X^3$ | — | G-4 | H | — |
| $X^3$ | — | G-5 | H | — |
| $X^3$ | — | G-6 | H | H |
| $X^3$ | — | G-7 | H | — |
| $X^3$ | — | G-8 | H | — |
| $X^3$ | — | G-9 | H | H |
| $X^3$ | — | G-10 | H | — |
| $X^3$ | — | G-11 | H | — |
| $X^3$ | — | G-12 | H | H |
| $X^3$ | — | G-13 | H | H |
| $X^3$ | — | G-14 | H | — |
| $X^3$ | — | G-15 | H | — |
| $X^3$ | — | G-16 | H | H |
| $X^3$ | — | G-17 | H | — |
| $X^3$ | — | G-18 | H | — |
| $X^3$ | — | G-19 | H | H |
| $X^3$ | — | G-20 | H | — |
| $X^3$ | — | G-21 | H | — |
| $X^3$ | — | G-22 | H | H |
| $X^3$ | — | G-23 | H | — |
| $X^3$ | — | G-24 | H | — |
| $X^3$ | — | G-31 | H | — |
| $X^3$ | — | G-32 | H | — |
| $X^3$ | — | G-33 | H | — |
| $X^3$ | — | G-34 | H | — |
| $X^3$ | — | G-35 | H | — |
| $X^3$ | — | G-37 | H | — |
| $X^3$ | — | G-38 | H | — |
| $X^3$ | — | G-39 | H | H |
| $X^3$ | — | G-40 | H | — |
| $X^3$ | — | G-41 | H | — |
| $X^3$ | — | G-42 | H | H |
| $X^3$ | — | G-43 | H | H |
| $X^3$ | — | G-44 | H | — |
| $X^3$ | — | G-45 | H | — |
| $X^3$ | — | G-46 | H | — |
| $X^3$ | — | G-47 | H | — |
| $X^3$ | — | G-48 | H | H |
| $X^3$ | — | G-49 | H | — |
| $X^3$ | — | G-50 | H | — |
| $X^3$ | — | G-51 | H | H |
| $X^3$ | — | G-52 | H | — |
| $X^3$ | — | G-53 | H | — |
| $X^3$ | — | G-54 | H | H |
| $X^3$ | — | G-2 | Me | — |
| $X^3$ | — | G-2 | Cl | — |
| $X^3$ | — | G-2 | F | — |
| $X^3$ | — | G-2 | $CF_3$ | — |
| $X^3$ | — | G-14 | n-Pr | — |
| $X^3$ | — | G-3 | H | Me |
| $X^3$ | — | G-3 | H | n-Pr |
| $X^3$ | 2-Me | G-1 | H | — |
| $X^3$ | 3-Me | G-1 | H | — |
| $X^3$ | 2,6-di-Me | G-1 | H | — |
| $X^3$ | 3,5-di-Me | G-1 | H | — |
| $X^3$ | 3-n-Bu | G-1 | H | — |
| $X^3$ | 5-Me | G-1 | H | — |
| $X^3$ | 6-Me | G-1 | H | — |
| $X^4$ | — | G-1 | H | — |
| $X^5$ | — | G-1 | H | — |
| $X^6$ | — | G-1 | H | — |
| $X^7$ | — | G-1 | H | — |
| $X^8$ | — | G-1 | H | — |
| $X^9$ | — | G-1 | H | — |

TABLE 21

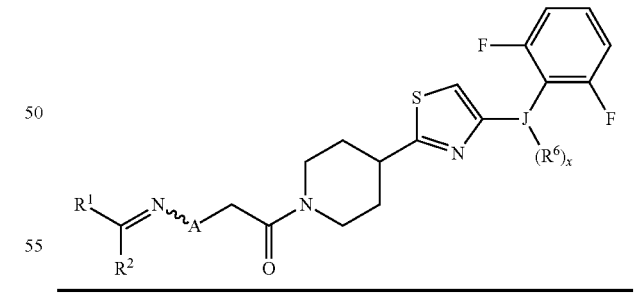

In Table 21 the structure of J (e.g., J-1) is shown in Exhibit 3 in the above Embodiments. The numbers in parentheses following J refer to the attachment points of J to the thiazole ring and 2,6-difluorophenyl ring in the above structure. The first number is the ring position on J where the thiazole ring is attached and the second number is the ring position on J where the 2,6-difluorophenyl ring is attached. The $(R^6)_x$ column below identities $R^6$ substituents other than the 2,6-difluorophenyl substituent depicted in the above structure.

| R¹ | R² | A | J | (R⁶)ₓ |
|---|---|---|---|---|
| CF₃ | H | —O— | J-1 (2/4) | H |
| CF₃ | Me | —O— | J-1 (2/4) | H |
| CF₃ | H | —NH— | J-1 (2/4) | H |
| CF₃ | Me | —NH— | J-1 (2/4) | H |
| CF₃ | H | —N(CH₃)— | J-1 (2/4) | H |
| CF₃ | Me | —N(CH₃)— | J-1 (2/4) | H |
| CF₃ | H | —N(CH₂CH₃)— | J-1 (2/4) | H |
| CF₃ | Me | —N(CH₂CH₃)— | J-1 (2/4) | H |
| Me | Me | —O— | J-1 (2/4) | H |
| Me | Me | —NH— | J-1 (2/4) | H |
| Me | Me | —N(CH₃)— | J-1 (2/4) | H |
| Me | Me | —N(CH₂CH₃)— | J-1 (2/4) | H |
| CF₃ | H | —O— | J-2 (2/4) | H |
| CF₃ | Me | —O— | J-2 (2/4) | H |
| CF₃ | H | —NH— | J-2 (2/4) | H |
| CF₃ | Me | —NH— | J-2 (2/4) | H |
| CF₃ | H | —N(CH₃)— | J-2 (2/4) | H |
| CF₃ | Me | —N(CH₃)— | J-2 (2/4) | H |
| CF₃ | H | —N(CH₂CH₃)— | J-2 (2/4) | H |
| CF₃ | Me | —N(CH₂CH₃)— | J-2 (2/4) | H |
| Me | Me | —O— | J-2 (2/4) | H |
| Me | Me | —NH— | J-2 (2/4) | H |
| Me | Me | —N(CH₃)— | J-2 (2/4) | H |
| Me | Me | —N(CH₂CH₃)— | J-2 (2/4) | H |
| CF₃ | H | —O— | J-3 (2/4) | 1-Me |
| CF₃ | Me | —O— | J-3 (2/4) | 1-Me |
| CF₃ | H | —NH— | J-3 (2/4) | 1-Me |
| CF₃ | Me | —NH— | J-3 (2/4) | 1-Me |
| CF₃ | H | —N(CH₃)— | J-3 (2/4) | 1-Me |
| CF₃ | Me | —N(CH₃)— | J-3 (2/4) | 1-Me |
| CF₃ | H | —N(CH₂CH₃)— | J-3 (2/4) | 1-Me |
| CF₃ | Me | —N(CH₂CH₃)— | J-3 (2/4) | 1-Me |
| Me | Me | —O— | J-3 (2/4) | 1-Me |
| Me | Me | —NH— | J-3 (2/4) | 1-Me |
| Me | Me | —N(CH₃)— | J-3 (2/4) | 1-Me |
| Me | Me | —N(CH₂CH₃)— | J-3 (2/4) | 1-Me |
| CF₃ | H | —O— | J-4 (2/5) | H |
| CF₃ | Me | —O— | J-4 (2/5) | H |
| CF₃ | H | —NH— | J-4 (2/5) | H |
| CF₃ | Me | —NH— | J-4 (2/5) | H |
| CF₃ | H | —N(CH₃)— | J-4 (2/5) | H |
| CF₃ | Me | —N(CH₃)— | J-4 (2/5) | H |
| CF₃ | H | —N(CH₂CH₃)— | J-4 (2/5) | H |
| CF₃ | Me | —N(CH₂CH₃)— | J-4 (2/5) | H |
| Me | Me | —O— | J-4 (2/5) | H |
| Me | Me | —NH— | J-4 (2/5) | H |
| Me | Me | —N(CH₃)— | J-4 (2/5) | H |
| Me | Me | —N(CH₂CH₃)— | J-4 (2/5) | H |
| CF₃ | H | —O— | J-8 (5/3) | H |
| CF₃ | Me | —O— | J-8 (5/3) | H |
| CF₃ | H | —NH— | J-8 (5/3) | H |
| CF₃ | Me | —NH— | J-8 (5/3) | H |
| CF₃ | H | —N(CH₃)— | J-8 (5/3) | H |
| CF₃ | Me | —N(CH₃)— | J-8 (5/3) | H |
| CF₃ | H | —N(CH₂CH₃)— | J-8 (5/3) | H |
| CF₃ | Me | —N(CH₂CH₃)— | J-8 (5/3) | H |
| Me | Me | —O— | J-8 (5/3) | H |
| Me | Me | —NH— | J-8 (5/3) | H |
| Me | Me | —N(CH₃)— | J-8 (5/3) | H |
| Me | Me | —N(CH₂CH₃)— | J-8 (5/3) | H |
| CF₃ | H | —O— | J-9 (5/3) | H |
| CF₃ | Me | —O— | J-9 (5/3) | H |
| CF₃ | H | —NH— | J-9 (5/3) | H |
| CF₃ | Me | —NH— | J-9 (5/3) | H |
| CF₃ | H | —N(CH₃)— | J-9 (5/3) | H |
| CF₃ | Me | —N(CH₃)— | J-9 (5/3) | H |
| CF₃ | H | —N(CH₂CH₃)— | J-9 (5/3) | H |
| CF₃ | Me | —N(CH₂CH₃)— | J-9 (5/3) | H |
| Me | Me | —O— | J-9 (5/3) | H |
| Me | Me | —NH— | J-9 (5/3) | H |
| Me | Me | —N(CH₃)— | J-9 (5/3) | H |
| Me | Me | —N(CH₂CH₃)— | J-9 (5/3) | H |
| CF₃ | H | —O— | J-11 (3/5) | H |
| CF₃ | Me | —O— | J-11 (3/5) | H |
| CF₃ | H | —NH— | J-11 (3/5) | H |
| CF₃ | Me | —NH— | J-11 (3/5) | H |
| CF₃ | H | —N(CH₃)— | J-11 (3/5) | H |
| CF₃ | Me | —N(CH₃)— | J-11 (3/5) | H |
| CF₃ | H | —N(CH₂CH₃)— | J-11 (3/5) | H |
| CF₃ | Me | —N(CH₂CH₃)— | J-11 (3/5) | H |
| Me | Me | —O— | J-11 (3/5) | H |
| Me | Me | —NH— | J-11 (3/5) | H |
| Me | Me | —N(CH₃)— | J-11 (3/5) | H |
| Me | Me | —N(CH₂CH₃)— | J-11 (3/5) | H |
| CF₃ | H | —O— | J-12 (3/5) | H |
| CF₃ | Me | —O— | J-12 (3/5) | H |
| CF₃ | H | —NH— | J-12 (3/5) | H |
| CF₃ | Me | —NH— | J-12 (3/5) | H |
| CF₃ | H | —N(CH₃)— | J-12 (3/5) | H |
| CF₃ | Me | —N(CH₃)— | J-12 (3/5) | H |
| CF₃ | H | —N(CH₂CH₃)— | J-12 (3/5) | H |
| CF₃ | Me | —N(CH₂CH₃)— | J-12 (3/5) | H |
| Me | Me | —O— | J-12 (3/5) | H |
| Me | Me | —NH— | J-12 (3/5) | H |
| Me | Me | —N(CH₃)— | J-12 (3/5) | H |
| Me | Me | —N(CH₂CH₃)— | J-12 (3/5) | H |
| CF₃ | H | —O— | J-12 (3/5) | 1-Me |
| CF₃ | Me | —O— | J-12 (3/5) | 1-Me |
| CF₃ | H | —NH— | J-12 (3/5) | 1-Me |
| CF₃ | Me | —NH— | J-12 (3/5) | 1-Me |
| CF₃ | H | —N(CH₃)— | J-12 (3/5) | 1-Me |
| CF₃ | Me | —N(CH₃)— | J-12 (3/5) | 1-Me |
| CF₃ | H | —N(CH₂CH₃)— | J-12 (3/5) | 1-Me |
| CF₃ | Me | —N(CH₂CH₃)— | J-12 (3/5) | 1-Me |
| Me | Me | —O— | J-12 (3/5) | 1-Me |
| Me | Me | —NH— | J-12 (3/5) | 1-Me |
| Me | Me | —N(CH₃)— | J-12 (3/5) | 1-Me |
| Me | Me | —N(CH₂CH₃)— | J-12 (3/5) | 1-Me |
| CF₃ | H | —O— | J-14 (3/5) | H |
| CF₃ | Me | —O— | J-14 (3/5) | H |
| CF₃ | H | —NH— | J-14 (3/5) | H |
| CF₃ | Me | —NH— | J-14 (3/5) | H |
| CF₃ | H | —N(CH₃)— | J-14 (3/5) | H |
| CF₃ | Me | —N(CH₃)— | J-14 (3/5) | H |
| CF₃ | H | —N(CH₂CH₃)— | J-14 (3/5) | H |
| CF₃ | Me | —N(CH₂CH₃)— | J-14 (3/5) | H |
| Me | Me | —O— | J-14 (3/5) | H |
| Me | Me | —NH— | J-14 (3/5) | H |
| Me | Me | —N(CH₃)— | J-14 (3/5) | H |
| Me | Me | —N(CH₂CH₃)— | J-14 (3/5) | H |
| CF₃ | H | —O— | J-15 (2/5) | H |
| CF₃ | Me | —O— | J-15 (2/5) | H |
| CF₃ | H | —NH— | J-15 (2/5) | H |
| CF₃ | Me | —NH— | J-15 (2/5) | H |
| CF₃ | H | —N(CH₃)— | J-15 (2/5) | H |
| CF₃ | Me | —N(CH₃)— | J-15 (2/5) | H |
| CF₃ | H | —N(CH₂CH₃)— | J-15 (2/5) | H |
| CF₃ | Me | —N(CH₂CH₃)— | J-15 (2/5) | H |
| Me | Me | —O— | J-15 (2/5) | H |
| Me | Me | —NH— | J-15 (2/5) | H |
| Me | Me | —N(CH₃)— | J-15 (2/5) | H |
| Me | Me | —N(CH₂CH₃)— | J-15 (2/5) | H |
| CF₃ | H | —O— | J-16 (2/5) | H |
| CF₃ | Me | —O— | J-16 (2/5) | H |
| CF₃ | H | —NH— | J-16 (2/5) | H |
| CF₃ | Me | —NH— | J-16 (2/5) | H |
| CF₃ | H | —N(CH₃)— | J-16 (2/5) | H |
| CF₃ | Me | —N(CH₃)— | J-16 (2/5) | H |
| CF₃ | H | —N(CH₂CH₃)— | J-16 (2/5) | H |
| CF₃ | Me | —N(CH₂CH₃)— | J-16 (2/5) | H |
| Me | Me | —O— | J-16 (2/5) | H |
| Me | Me | —NH— | J-16 (2/5) | H |
| Me | Me | —N(CH₃)— | J-16 (2/5) | H |
| Me | Me | —N(CH₂CH₃)— | J-16 (2/5) | H |
| CF₃ | H | —O— | J-22 (2/4) | H |
| CF₃ | Me | —O— | J-22 (2/4) | H |
| CF₃ | H | —NH— | J-22 (2/4) | H |
| CF₃ | Me | —NH— | J-22 (2/4) | H |
| CF₃ | H | —N(CH₃)— | J-22 (2/4) | H |
| CF₃ | Me | —N(CH₃)— | J-22 (2/4) | H |
| CF₃ | H | —N(CH₂CH₃)— | J-22 (2/4) | H |
| CF₃ | Me | —N(CH₂CH₃)— | J-22 (2/4) | H |
| Me | Me | —O— | J-22 (2/4) | H |
| Me | Me | —NH— | J-22 (2/4) | H |
| Me | Me | —N(CH₃)— | J-22 (2/4) | H |
| Me | Me | —N(CH₂CH₃)— | J-22 (2/4) | H |

| R¹ | R² | A | J | (R⁶)ₓ |
|---|---|---|---|---|
| CF₃ | H | —O— | J-24 (2/4) | H |
| CF₃ | Me | —O— | J-24 (2/4) | H |
| CF₃ | H | —NH— | J-24 (2/4) | H |
| CF₃ | Me | —NH— | J-24 (2/4) | H |
| CF₃ | H | —N(CH₃)— | J-24 (2/4) | H |
| CF₃ | Me | —N(CH₃)— | J-24 (2/4) | H |
| CF₃ | H | —N(CH₂CH₃)— | J-24 (2/4) | H |
| CF₃ | Me | —N(CH₂CH₃)— | J-24 (2/4) | H |
| Me | Me | —O— | J-24 (2/4) | H |
| Me | Me | —NH— | J-24 (2/4) | H |
| Me | Me | —N(CH₃)— | J-24 (2/4) | H |
| Me | Me | —N(CH₂CH₃)— | J-24 (2/4) | H |
| CF₃ | H | —O— | J-25 (2/4) | H |
| CF₃ | Me | —O— | J-25 (2/4) | H |
| CF₃ | H | —NH— | J-25 (2/4) | H |
| CF₃ | Me | —NH— | J-25 (2/4) | H |
| CF₃ | H | —N(CH₃)— | J-25 (2/4) | H |
| CF₃ | Me | —N(CH₃)— | J-25 (2/4) | H |
| CF₃ | H | —N(CH₂CH₃)— | J-25 (2/4) | H |
| CF₃ | Me | —N(CH₂CH₃)— | J-25 (2/4) | H |
| Me | Me | —O— | J-25 (2/4) | H |
| Me | Me | —NH— | J-25 (2/4) | H |
| Me | Me | —N(CH₃)— | J-25 (2/4) | H |
| Me | Me | —N(CH₂CH₃)— | J-25 (2/4) | H |
| CF₃ | H | —O— | J-26 (2/4) | H |
| CF₃ | Me | —O— | J-26 (2/4) | H |
| CF₃ | H | —NH— | J-26 (2/4) | H |
| CF₃ | Me | —NH— | J-26 (2/4) | H |
| CF₃ | H | —N(CH₃)— | J-26 (2/4) | H |
| CF₃ | Me | —N(CH₃)— | J-26 (2/4) | H |
| CF₃ | H | —N(CH₂CH₃)— | J-26 (2/4) | H |
| CF₃ | Me | —N(CH₂CH₃)— | J-26 (2/4) | H |
| Me | Me | —O— | J-26 (2/4) | H |
| Me | Me | —NH— | J-26 (2/4) | H |
| Me | Me | —N(CH₃)— | J-26 (2/4) | H |
| Me | Me | —N(CH₂CH₃)— | J-26 (2/4) | H |
| CF₃ | H | —O— | J-26 (2/4) | 1-Me |
| CF₃ | Me | —O— | J-26 (2/4) | 1-Me |
| CF₃ | H | —NH— | J-26 (2/4) | 1-Me |
| CF₃ | Me | —NH— | J-26 (2/4) | 1-Me |
| CF₃ | H | —N(CH₃)— | J-26 (2/4) | 1-Me |
| CF₃ | Me | —N(CH₃)— | J-26 (2/4) | 1-Me |
| CF₃ | H | —N(CH₂CH₃)— | J-26 (2/4) | 1-Me |
| CF₃ | Me | —N(CH₂CH₃)— | J-26 (2/4) | 1-Me |
| Me | Me | —O— | J-26 (2/4) | 1-Me |
| Me | Me | —NH— | J-26 (2/4) | 1-Me |
| Me | Me | —N(CH₃)— | J-26 (2/4) | 1-Me |
| Me | Me | —N(CH₂CH₃)— | J-26 (2/4) | 1-Me |
| CF₃ | H | —O— | J-26 (2/5) | 1-Me |
| CF₃ | Me | —O— | J-26 (2/5) | 1-Me |
| CF₃ | H | —NH— | J-26 (2/5) | 1-Me |
| CF₃ | Me | —NH— | J-26 (2/5) | 1-Me |
| CF₃ | H | —N(CH₃)— | J-26 (2/5) | 1-Me |
| CF₃ | Me | —N(CH₃)— | J-26 (2/5) | 1-Me |
| CF₃ | H | —N(CH₂CH₃)— | J-26 (2/5) | 1-Me |
| CF₃ | Me | —N(CH₂CH₃)— | J-26 (2/5) | 1-Me |
| Me | Me | —O— | J-26 (2/5) | 1-Me |
| Me | Me | —NH— | J-26 (2/5) | 1-Me |
| Me | Me | —N(CH₃)— | J-26 (2/5) | 1-Me |
| Me | Me | —N(CH₂CH₃)— | J-26 (2/5) | 1-Me |
| CF₃ | H | —O— | J-28 (3/5) | H |
| CF₃ | Me | —O— | J-28 (3/5) | H |
| CF₃ | H | —NH— | J-28 (3/5) | H |
| CF₃ | Me | —NH— | J-28 (3/5) | H |
| CF₃ | H | —N(CH₃)— | J-28 (3/5) | H |
| CF₃ | Me | —N(CH₃)— | J-28 (3/5) | H |
| CF₃ | H | —N(CH₂CH₃)— | J-28 (3/5) | H |
| CF₃ | Me | —N(CH₂CH₃)— | J-28 (3/5) | H |
| Me | Me | —O— | J-28 (3/5) | H |
| Me | Me | —NH— | J-28 (3/5) | H |
| Me | Me | —N(CH₃)— | J-28 (3/5) | H |
| Me | Me | —N(CH₂CH₃)— | J-28 (3/5) | H |
| CF₃ | H | —O— | J-30 (3/5) | H |
| CF₃ | Me | —O— | J-30 (3/5) | H |
| CF₃ | H | —NH— | J-30 (3/5) | H |
| CF₃ | Me | —NH— | J-30 (3/5) | H |
| CF₃ | H | —N(CH₃)— | J-30 (3/5) | H |
| CF₃ | Me | —N(CH₃)— | J-30 (3/5) | H |
| CF₃ | H | —N(CH₂CH₃)— | J-30 (3/5) | H |
| CF₃ | Me | —N(CH₂CH₃)— | J-30 (3/5) | H |
| Me | Me | —O— | J-30 (3/5) | H |
| Me | Me | —NH— | J-30 (3/5) | H |
| Me | Me | —N(CH₃)— | J-30 (3/5) | H |
| Me | Me | —N(CH₂CH₃)— | J-30 (3/5) | H |
| CF₃ | H | —O— | J-30 (3/5) | 1-Me |
| CF₃ | Me | —O— | J-30 (3/5) | 1-Me |
| CF₃ | H | —NH— | J-30 (3/5) | 1-Me |
| CF₃ | Me | —NH— | J-30 (3/5) | 1-Me |
| CF₃ | H | —N(CH₃)— | J-30 (3/5) | 1-Me |
| CF₃ | Me | —N(CH₃)— | J-30 (3/5) | 1-Me |
| CF₃ | H | —N(CH₂CH₃)— | J-30 (3/5) | 1-Me |
| CF₃ | Me | —N(CH₂CH₃)— | J-30 (3/5) | 1-Me |
| Me | Me | —O— | J-30 (3/5) | 1-Me |
| Me | Me | —NH— | J-30 (3/5) | 1-Me |
| Me | Me | —N(CH₃)— | J-30 (3/5) | 1-Me |
| Me | Me | —N(CH₂CH₃)— | J-30 (3/5) | 1-Me |
| CF₃ | H | —O— | J-36 (3/5) | 1-Me |
| CF₃ | Me | —O— | J-36 (3/5) | 1-Me |
| CF₃ | H | —NH— | J-36 (3/5) | 1-Me |
| CF₃ | Me | —NH— | J-36 (3/5) | 1-Me |
| CF₃ | H | —N(CH₃)— | J-36 (3/5) | 1-Me |
| CF₃ | Me | —N(CH₃)— | J-36 (3/5) | 1-Me |
| CF₃ | H | —N(CH₂CH₃)— | J-36 (3/5) | 1-Me |
| CF₃ | Me | —N(CH₂CH₃)— | J-36 (3/5) | 1-Me |
| Me | Me | —O— | J-36 (3/5) | 1-Me |
| Me | Me | —NH— | J-36 (3/5) | 1-Me |
| Me | Me | —N(CH₃)— | J-36 (3/5) | 1-Me |
| Me | Me | —N(CH₂CH₃)— | J-36 (3/5) | 1-Me |
| CF₃ | H | —O— | J-37 (2/5) | H |
| CF₃ | Me | —O— | J-37 (2/5) | H |
| CF₃ | H | —NH— | J-37 (2/5) | H |
| CF₃ | Me | —NH— | J-37 (2/5) | H |
| CF₃ | H | —N(CH₃)— | J-37 (2/5) | H |
| CF₃ | Me | —N(CH₃)— | J-37 (2/5) | H |
| CF₃ | H | —N(CH₂CH₃)— | J-37 (2/5) | H |
| CF₃ | Me | —N(CH₂CH₃)— | J-37 (2/5) | H |
| Me | Me | —O— | J-37 (2/5) | H |
| Me | Me | —NH— | J-37 (2/5) | H |
| Me | Me | —N(CH₃)— | J-37 (2/5) | H |
| Me | Me | —N(CH₂CH₃)— | J-37 (2/5) | H |
| CF₃ | H | —O— | J-38 (2/5) | H |
| CF₃ | Me | —O— | J-38 (2/5) | H |
| CF₃ | H | —NH— | J-38 (2/5) | H |
| CF₃ | Me | —NH— | J-38 (2/5) | H |
| CF₃ | H | —N(CH₃)— | J-38 (2/5) | H |
| CF₃ | Me | —N(CH₃)— | J-38 (2/5) | H |
| CF₃ | H | —N(CH₂CH₃)— | J-38 (2/5) | H |
| CF₃ | Me | —N(CH₂CH₃)— | J-38 (2/5) | H |
| Me | Me | —O— | J-38 (2/5) | H |
| Me | Me | —NH— | J-38 (2/5) | H |
| Me | Me | —N(CH₃)— | J-38 (2/5) | H |
| Me | Me | —N(CH₂CH₃)— | J-38 (2/5) | H |
| CF₃ | H | —O— | J-39 (3/5) | H |
| CF₃ | Me | —O— | J-39 (3/5) | H |
| CF₃ | H | —NH— | J-39 (3/5) | H |
| CF₃ | Me | —NH— | J-39 (3/5) | H |
| CF₃ | H | —N(CH₃)— | J-39 (3/5) | H |
| CF₃ | Me | —N(CH₃)— | J-39 (3/5) | H |
| CF₃ | H | —N(CH₂CH₃)— | J-39 (3/5) | H |
| CF₃ | Me | —N(CH₂CH₃)— | J-39 (3/5) | H |
| Me | Me | —O— | J-39 (3/5) | H |
| Me | Me | —NH— | J-39 (3/5) | H |
| Me | Me | —N(CH₃)— | J-39 (3/5) | H |
| Me | Me | —N(CH₂CH₃)— | J-39 (3/5) | H |
| CF₃ | H | —O— | J-40 (3/5) | H |
| CF₃ | Me | —O— | J-40 (3/5) | H |
| CF₃ | H | —NH— | J-40 (3/5) | H |
| CF₃ | Me | —NH— | J-40 (3/5) | H |
| CF₃ | H | —N(CH₃)— | J-40 (3/5) | H |
| CF₃ | Me | —N(CH₃)— | J-40 (3/5) | H |
| CF₃ | H | —N(CH₂CH₃)— | J-40 (3/5) | H |
| CF₃ | Me | —N(CH₂CH₃)— | J-40 (3/5) | H |
| Me | Me | —O— | J-40 (3/5) | H |
| Me | Me | —NH— | J-40 (3/5) | H |
| Me | Me | —N(CH₃)— | J-40 (3/5) | H |
| Me | Me | —N(CH₂CH₃)— | J-40 (3/5) | H |

-continued

| R¹ | R² | A | J | (R⁶)ₓ |
|---|---|---|---|---|
| CF₃ | H | —O— | J-69 (1/3) | H |
| CF₃ | Me | —O— | J-69 (1/3) | H |
| CF₃ | H | —NH— | J-69 (1/3) | H |
| CF₃ | Me | —NH— | J-69 (1/3) | H |
| CF₃ | H | —N(CH₃)— | J-69 (1/3) | H |
| CF₃ | Me | —N(CH₃)— | J-69 (1/3) | H |
| CF₃ | H | —N(CH₂CH₃)— | J-69 (1/3) | H |
| CF₃ | Me | —N(CH₂CH₃)— | J-69 (1/3) | H |
| Me | Me | —O— | J-69 (1/3) | H |
| Me | Me | —NH— | J-69 (1/3) | H |
| Me | Me | —N(CH₃)— | J-69 (1/3) | H |
| Me | Me | —N(CH₂CH₃)— | J-69 (1/3) | H |
| CF₃ | H | —O— | J-69 (1/4) | H |
| CF₃ | Me | —O— | J-69 (1/4) | H |
| CF₃ | H | —NH— | J-69 (1/4) | H |
| CF₃ | Me | —NH— | J-69 (1/4) | H |
| CF₃ | H | —N(CH₃)— | J-69 (1/4) | H |
| CF₃ | Me | —N(CH₃)— | J-69 (1/4) | H |
| CF₃ | H | —N(CH₂CH₃)— | J-69 (1/4) | H |
| CF₃ | Me | —N(CH₂CH₃)— | J-69 (1/4) | H |
| Me | Me | —O— | J-69 (1/4) | H |
| Me | Me | —NH— | J-69 (1/4) | H |
| Me | Me | —N(CH₃)— | J-69 (1/4) | H |
| Me | Me | —N(CH₂CH₃)— | J-69 (1/4) | H |
| CF₃ | H | —O— | J-29 (3/5) | 5-Me |
| CF₃ | Me | —O— | J-29 (3/5) | 5-Me |
| CF₃ | H | —NH— | J-29 (3/5) | 5-Me |
| CF₃ | Me | —NH— | J-29 (3/5) | 5-Me |
| CF₃ | H | —N(CH₃)— | J-29 (3/5) | 5-Me |
| CF₃ | Me | —N(CH₃)— | J-29 (3/5) | 5-Me |
| CF₃ | H | —N(CH₂CH₃)— | J-29 (3/5) | 5-Me |
| CF₃ | Me | —N(CH₂CH₃)— | J-29 (3/5) | 5-Me |
| Me | Me | —O— | J-29 (3/5) | 5-Me |
| Me | Me | —NH— | J-29 (3/5) | 5-Me |
| Me | Me | —N(CH₃)— | J-29 (3/5) | 5-Me |
| Me | Me | —N(CH₂CH₃)— | J-29 (3/5) | 5-Me |
| CF₃ | H | —O— | J-29 (3/5) | 4-Me |
| CF₃ | Me | —O— | J-29 (3/5) | 4-Me |
| CF₃ | H | —NH— | J-29 (3/5) | 4-Me |
| CF₃ | Me | —NH— | J-29 (3/5) | 4-Me |
| CF₃ | H | —N(CH₃)— | J-29 (3/5) | 4-Me |
| CF₃ | Me | —N(CH₃)— | J-29 (3/5) | 4-Me |
| CF₃ | H | —N(CH₂CH₃)— | J-29 (3/5) | 4-Me |
| CF₃ | Me | —N(CH₂CH₃)— | J-29 (3/5) | 4-Me |
| Me | Me | —O— | J-29 (3/5) | 4-Me |
| Me | Me | —NH— | J-29 (3/5) | 4-Me |
| Me | Me | —N(CH₃)— | J-29 (3/5) | 4-Me |
| Me | Me | —N(CH₂CH₃)— | J-29 (3/5) | 4-Me |
| CF₃ | H | —O— | J-29 (3/5) | 4,4-di-Me |
| CF₃ | Me | —O— | J-29 (3/5) | 4,4-di-Me |
| CF₃ | H | —NH— | J-29 (3/5) | 4,4-di-Me |
| CF₃ | Me | —NH— | J-29 (3/5) | 4,4-di-Me |
| CF₃ | H | —N(CH₃)— | J-29 (3/5) | 4,4-di-Me |
| CF₃ | Me | —N(CH₃)— | J-29 (3/5) | 4,4-di-Me |
| CF₃ | H | —N(CH₂CH₃)— | J-29 (3/5) | 4,4-di-Me |
| CF₃ | Me | —N(CH₂CH₃)— | J-29 (3/5) | 4,4-di-Me |
| Me | Me | —O— | J-29 (3/5) | 4,4-di-Me |
| Me | Me | —NH— | J-29 (3/5) | 4,4-di-Me |
| Me | Me | —N(CH₃)— | J-29 (3/5) | 4,4-di-Me |
| Me | Me | —N(CH₂CH₃)— | J-29 (3/5) | 4,4-di-Me |

Formulation/Utility

A compound of Formula 1 of this invention will generally be used as a fungicidal active ingredient in a composition, i.e. formulation, with at least one additional component selected from the group consisting of surfactants, solid diluents and liquid diluents, which serve as a carrier. Compounds within the scope of exclusion of proviso (a) of Formula 1 can also be used. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil® 416)), sedimentation of active ingredients (suspending agents), viscosity (thixotropic thickeners), in-container microbial growth (antimicrobials), product freezing (antifreezes), color (dyes/pigment dispersions (e.g., Pro-lzed® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume* 2: *Functional Materials,* annual International and North American editions published by McCutcheon's Division, The Manufacturing Confectioner Publishing Co.; and PCT Publication WO 03/024222.

Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and, usually, grinding as in a hammer mill or fluid-energy mill. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

| High Strength Concentrate | |
|---|---|
| Compound 1 | 98.5% |
| silica aerogel | 0.5% |
| synthetic amorphous fine silica | 1.0% |

EXAMPLE B

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

| Granule | |
|---|---|
| Compound 3 | 10.0% |
| attapulgite granules (low volatile matter, 0.71/0.30 mm; U.S.S. No. 25-50 sieves) | 90.0% |

EXAMPLE D

| Aqueous Suspension | |
|---|---|
| Compound 4 | 25.0% |
| hydrated attapulgite | 3.0% |
| crude calcium ligninsulfonate | 10.0% |
| sodium dihydrogen phosphate | 0.5% |
| water | 61.5% |

EXAMPLE E

| Extruded Pellet | |
|---|---|
| Compound 8 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE F

| Microemulsion | |
|---|---|
| Compound 16 | 5.0% |
| polyvinylpyrrolidone-vinyl acetate copolymer | 30.0% |
| $C_8$-$C_{10}$ alkylpolyglycoside | 30.0% |
| glyceryl monooleate | 15.0% |
| Water | 20.0% |

EXAMPLE G

| Emulsifiable Concentrate | |
|---|---|
| Compound 20 | 10.0% |
| polyoxyethylene sorbitol hexoleate | 20.0% |
| $C_6$-$C_{10}$ fatty acid methyl ester | 70.0% |

Formulations such as those in the Formulation Table are typically diluted with water to form aqueous compositions before application. Aqueous compositions for direct applications to the plant or portion thereof (e.g., spray tank compositions) typically comprise at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. This aspect of the present invention can also be described as a method for protecting a plant or plant seed from diseases caused by fungal pathogens comprising applying a fungicidally effective amount of a compound of the invention (e.g., as a composition described herein) to the plant (or portion thereof) or plant seed (directly or through the environment (e.g., growing medium) of the plant or plant seed). The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici repentis*, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite*, *Puccinia striiformis*, *Puccinia hordei*, *Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; and other genera and species closely related to these pathogens. In addition to their fungicidal activity, the compositions or combinations also have activity against bacteria such as *Erwinia amylovora*, *Xanthomonas campestris*, *Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Of note is a composition which in addition to the compound of Formula 1 include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-) pyrimidine fungicides; (9) anilinopyrimidine fungicides; (10) N-phenyl carbamate fungicides; (11) quinone outside inhibitor (QoI) fungicides; (12) phenylpyrrole fungicides; (13)

quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, N-[2-(1S,2R)-[1,1'-bicyclopropyl]-2-ylphenyl]-3-(difluoromethyl)-1-methyl-1H-pyrazole-4-carboxamide and penflufen (N-[2-(1,3-dimethylbutyl)phenyl]-5-fluoro-1,3-dimethyl-1H-pyrazole-4-carboxamide). The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly.

Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071), picoxystrobin and pyraoxystrobin (SYP-3343). The methoxycarbamates include pyraclostrobin and pyrametostrobin (SYP-4155). The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy] imino]-methyl]benzeneacetamide and 2-[[[3-(2,6-dichlorophenyl)-1-methyl-2-propen-1-ylidene]-amino]oxy] methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen and tebufloquin are examples of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb, valifenalate and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides (b42)" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolylfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7), (46.4) "benzophenone fungicides" (Fungicide Resistance Action Committee (FRAC) code U8) and (46.5) "triazolopyrimidine fungicides". The thiazole carboxamides include ethaboxam. The phenyl-acetamides include cyflufenamid and N—[[(cyclopropylmethoxy)-amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone. The triazolopyrimidines include ametoctradin. The (b46) class also includes bethoxazin, neo-asozin (ferric methanearsonate), pyrrolnitrin, quinomethionate, N-[2-[4-

[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]-acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3-difluorophenyl]methylene]benzeneacetamide, N-[4-[4-chloro-3-(trifluoromethyl)phenoxy]-2,5-dimethylphenyl]-N-ethyl-N-methylmethanimidamide, 1-[(2-propenylthio)carbonyl]-2-(1-methylethyl)-4-(2-methylphenyl)-5-amino-1H-pyrazol-3-one and 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone.

Therefore of note is a mixture (i.e. composition) comprising a compound of Formula 1 and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, milbemycin oxime, monocrotophos, methoxyfenozide, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Pyrimidinone fungicides (group (4)) include compounds of Formula A1

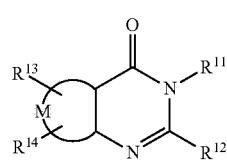

wherein M forms a fused phenyl, thiophene or pyridine ring; $R^{11}$ is $C_1$-$C_6$ alkyl; $R^{12}$ is $C_1$-$C_6$ alkyl or $C_1$-$C_6$ alkoxy; $R^{13}$ is halogen; and $R^{14}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propyl-thieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propyl-thieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of further note are combinations of compounds of Formula 1 with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

Preferred for better control of plant diseases caused by fungal plant pathogens (e.g., lower use rate or broader spectrum of plant pathogens controlled) or resistance management are mixtures of a compound of this invention with a fungicide selected from the group: azoxystrobin, kresoxim-methyl, trifloxystrobin, pyraclostrobin, picoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, tebuconazole, triticonazole, famoxadone and penthiopyrad. Specifically preferred mixtures (compound numbers refer to compounds in Index Tables A-B) are selected from the group:

Compound 1, Compound 2, Compound 3, Compound 4, Compound 8, Compound 16, Compound 18, Compound 20, Compound 29, Compound 35, Compound 42, Compound 43 or Compound 44 with ametoctradin, combinations of Compound 1, Compound 2, Compound 3, Compound 4, Compound 8, Compound 16, Compound 18, Compound 20, Compound 29, Compound 35, Compound 42, Compound 43 or Compound 44 with azoxystrobin, combinations of Compound 1, Compound 2, Compound 3, Compound 4, Compound 8, Compound 16, Compound 18, Compound 20, Compound 29, Compound 35, Compound 42, Compound 43 or Compound 44 with bixafen, combinations of Compound 1, Compound 2, Compound 3, Compound 4, Compound 8, Compound 16, Compound 18, Compound 20, Compound 29, Compound 35, Compound 42, Compound 43 or Compound 44 with boscalid, combinations of Compound 1, Compound 2, Compound 3, Compound 4, Compound 8, Compound 16, Compound 18, Compound 20, Compound 29, Compound 35, Compound 42, Compound 43 or Compound 44 with cyflufenamid, combinations of Compound 1, Compound 2, Compound 3, Compound 4, Compound 8, Compound 16, Compound 18, Compound 20, Compound 29, Compound 35, Compound 42, Compound 43 or Compound 44 with cyproconazole, combinations of Compound 1, Compound 2, Compound 3, Compound 4, Compound 8, Compound 16, Compound 18, Compound 20, Compound 29, Compound 35, Compound 42, Compound 43 or Compound 44 with dimoxystrobin, combinations of Compound 1, Compound 2, Compound 3, Compound 4, Compound 8, Compound 16, Compound 18, Compound 20, Compound 29, Compound 35, Compound 42, Compound 43 or Compound 44 with epoxiconazole, combinations of Compound 1, Compound 2, Compound 3, Compound 4, Compound 8, Compound 16, Compound 18, Compound 20, Compound 29, Compound 35, Compound 42, Compound 43 or Compound 44 with famoxadone, combinations of Compound 1, Compound 2, Compound 3, Compound 4, Compound 8, Compound 16, Compound 18, Compound 20, Compound 29, Compound 35, Compound 42, Compound 43 or Compound 44 with fenpropidine, combinations of Compound 1, Compound 2, Compound 3, Compound 4, Compound 8, Compound 16, Compound 18, Compound 20, Compound 29, Compound 35, Compound 42, Compound 43 or Compound 44 with fenpropimorph, combinations of Compound 1, Compound 2, Compound 3, Compound 4, Compound 8, Compound 16, Compound 18, Compound 20, Compound 29, Compound 35, Compound 42, Compound 43 or Compound 44 with fluopyram, combinations of Compound 1, Compound 2, Compound 3, Compound 4, Compound 8, Compound 16, Compound 18, Compound 20, Compound 29, Compound 35, Compound 42, Compound 43 or Compound 44 with flusilazole, combinations of Compound 1, Compound 2, Compound 3, Compound 4, Compound 8, Compound 16, Compound 18, Compound 20, Compound 29, Compound 35, Compound 42, Compound 43 or Compound 44 with flutianil, combinations of Compound 1, Compound 2, Compound 3, Compound 4, Compound 8, Compound 16, Compound 18, Compound 20, Compound 29, Compound 35, Compound 42, Compound 43 or Compound 44 with isopyrazam, combinations of Compound 1, Compound 2, Compound 3, Compound 4, Compound 8, Compound 16, Compound 18, Compound 20, Compound 29, Compound 35, Compound 42, Compound 43 or Compound 44 with isotianil, combinations of Compound 1, Compound 2, Compound 3, Compound 4, Compound 8, Compound 16, Compound 18, Compound 20, Compound 29, Compound 35, Compound 42, Compound 43 or Compound 44 with kresoxim-methyl, combinations of Compound 1, Compound 2, Compound 3, Compound 4, Compound 8, Compound 16, Compound 18, Compound 20, Compound 29, Compound 35, Compound 42, Compound 43 or Compound 44 with mandipropamid, combinations of Compound 1, Compound 2, Compound 3, Compound 4, Compound 8, Compound 16, Compound 18, Compound 20, Compound 29, Compound 35, Compound 42, Compound 43 or Compound 44 with meptyldinocap, combinations of Compound 1, Compound 2, Compound 3, Compound 4, Compound 8, Compound 16, Compound 18, Compound 20, Compound 29, Compound 35, Compound 42, Compound 43 or Compound 44 with metconazole, combinations of Compound 1, Compound 2, Compound 3, Compound 4, Compound 8, Compound 16, Compound 18, Compound 20, Compound 29, Compound 35, Compound 42, Compound 43 or Compound 44 with metominostrobin/fenominostrobin, combinations of Compound 1, Compound 2, Compound 3, Compound 4, Compound 8, Compound 16, Compound 18, Compound 20, Compound 29, Compound 35, Compound 42, Compound 43 or Compound 44 with metrafenone, combinations of Compound 1, Compound 2, Compound 3, Compound 4, Compound 8, Compound 16, Compound 18, Compound 20, Compound 29, Compound 35, Compound 42, Compound 43 or Compound 44 with penflufen, combinations of Compound 1, Compound 2, Compound 3, Compound 4, Compound 8, Compound 16, Compound 18, Compound 20, Compound 29, Compound 35, Compound 42, Compound 43 or Compound 44 with penthiopyrad, combinations of Compound 1, Compound 2, Compound 3, Compound 4, Compound 8, Compound 16, Compound 18, Compound 20, Compound 29, Compound 35, Compound 42, Compound 43 or Compound 44 with picoxystrobin, combinations of Compound 1, Compound 2, Compound 3, Compound 4, Compound 8, Compound 16, Compound 18, Compound 20, Compound 29, Compound 35, Compound 42, Compound 43 or Compound 44 with propiconazole, combinations of Compound 1, Compound 2, Compound 3, Compound 4, Compound 8, Compound 16, Compound 18, Compound 20, Compound 29, Compound 35, Compound 42, Compound 43 or Compound 44 with proquinazid, combinations of Compound 1, Compound 2, Compound 3, Compound 4, Compound 8, Compound 16, Compound 18, Compound 20, Compound 29, Compound 35, Compound 42, Compound 43 or Compound 44 with prothioconazole, combinations of Compound 1, Compound 2, Compound 3, Compound 4, Compound 8, Compound 16, Compound 18, Compound 20, Compound 29, Compound 35, Compound 42, Compound 43 or Compound 44 with pyraclostrobin, combinations of Compound 1, Compound 2, Compound 3, Compound 4, Compound 8, Compound 16, Compound 18, Compound 20, Compound 29, Compound 35, Compound 42, Compound 43 or Compound 44 with pyrametostrobin, combinations of Compound 1, Compound 2, Compound 3, Compound 4, Compound 8, Compound 16, Compound 18, Compound 20, Compound 29, Compound 35, Compound 42, Compound 43 or Compound 44 with pyraoxystrobin, combinations of Compound 1, Compound 2, Compound 3, Compound 4, Compound 8, Compound 16, Compound 18, Compound 20, Compound 29, Compound 35, Compound 42, Compound 43 or Compound 44 with pyribencarb, combinations of Compound 1, Compound 2, Compound 3, Compound 4, Compound 8, Compound 16, Compound 18, Compound 20, Compound 29, Compound 35, Compound 42, Compound 43 or Compound 44 with quinoxyfen, combinations of Compound 1, Compound 2, Compound 3, Compound 4, Compound 8, Compound 16, Compound 18, Compound 20, Compound 29, Compound 35, Compound 42, Compound 43 or Compound 44 with tebuconazole, combinations of Compound 1, Compound 2, Compound 3, Compound 4, Compound 8, Compound 16, Compound 18, Compound 20, Compound 29, Compound 35, Compound 42, Compound 43 or Compound 44 with tebufloquin, combinations of Compound 1, Compound 2, Compound 3, Compound 4, Compound 8, Compound 16, Compound 18, Compound 20, Compound 29, Compound 35, Compound 42, Compound 43 or Compound 44 with trifloxystrobin, combinations of Compound 1, Compound 2, Compound 3, Compound 4, Compound 8, Compound 16, Compound 18, Compound 20, Compound 29, Compound 35, Compound 42, Compound 43 or Compound 44 with triticonazole and combinations of Compound 1, Compound 2, Compound 3, Compound 4, Compound 8, Compound 16, Compound 18, Compound 20, Compound 29, Compound 35, Compound 42, Compound 43 or Compound 44 with valifenalate.

For embodiments where one or more of the various other biologically active compounds or agents (i.e. mixing partner) are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone. Furthermore, certain combinations of fungicides can demonstrate a greater-than-additive (i.e. synergistic) effect to provide commercially important levels of plant disease control.

Illustrative of the mixtures, compositions and methods of the present invention is Table A1 which discloses mixtures of a compound of Formula 1 and another biologically active compound. Specifically, a mixture of Compound 4 (see Index Table A for compound description) with the compound listed under the column heading "Mixing Partner" is disclosed, along with two specific weight ratios listed under the column heading "Illustrative Ratios". For example, the first row discloses a mixture of Compound 4 and acibenzolar-S-methyl in weight ratios of 1:3 or 3:1 of Compound 4 to acibenzolar-S-methyl.

TABLE A1

| Compound | Mixing Partner | Illustrative Ratios (*) | |
|---|---|---|---|
| 4 | acibenzolar-S-methyl | 1:3 | 3:1 |
| 4 | aldimorph | 1:50 | 1:7 |
| 4 | amisulbrom | 1:10 | 1:2 |
| 4 | anilazine | 1:150 | 1:23 |
| 4 | azaconazole | 1:15 | 1:2 |
| 4 | azoxystrobin | 1:20 | 1:3 |
| 4 | benalaxyl | 1:10 | 1:2 |
| 4 | benalaxyl-M | 1:7 | 2:1 |
| 4 | benodanil | 1:30 | 1:4 |
| 4 | benomyl | 1:75 | 1:9 |
| 4 | benthiavalicarb | 1:3 | 2:1 |
| 4 | benthiavalicarb-isopropyl | 1:3 | 2:1 |
| 4 | bethoxazin | 1:100 | 1:12 |
| 4 | binapacryl | 1:100 | 1:12 |
| 4 | biphenyl | 1:100 | 1:12 |
| 4 | bitertanol | 1:25 | 1:5 |
| 4 | bixafen | 1:15 | 1:3 |
| 4 | blasticidin-S | 1:1 | 5:1 |
| 4 | Bordeaux mixture (tribasic copper sulfate) | 1:300 | 1:34 |
| 4 | boscalid | 1:30 | 1:4 |
| 4 | bromuconazole | 1:20 | 1:3 |
| 4 | bupirimate | 1:2 | 5:1 |

TABLE A1-continued

| Compound | Mixing Partner | Illustrative Ratios (*) | |
|---|---|---|---|
| 4 | captafol | 1:100 | 1:12 |
| 4 | captan | 1:100 | 1:12 |
| 4 | carbendazim | 1:75 | 1:9 |
| 4 | carboxin | 1:30 | 1:4 |
| 4 | carpropamid | 1:20 | 1:3 |
| 4 | chloroneb | 1:700 | 1:89 |
| 4 | chlorothalonil | 1:100 | 1:12 |
| 4 | chlozolinate | 1:75 | 1:12 |
| 4 | clotrimazole | 1:20 | 1:3 |
| 4 | copper oxychloride | 1:400 | 1:45 |
| 4 | copper salts such as copper sulfate and copper hydroxide | 1:50 | 1:6 |
| 4 | cyazofamid | 1:7 | 1:2 |
| 4 | cyflufenamid | 1:2 | 4:1 |
| 4 | cymoxanil | 1:12 | 1:2 |
| 4 | cyproconazole | 1:8 | 1:2 |
| 4 | cyprodinil | 1:30 | 1:4 |
| 4 | dichlofluanid | 1:100 | 1:12 |
| 4 | diclocymet | 1:100 | 1:12 |
| 4 | diclomezine | 1:25 | 1:3 |
| 4 | dicloran | 1:100 | 1:12 |
| 4 | diethofencarb | 1:50 | 1:6 |
| 4 | difenoconazole | 1:5 | 2:1 |
| 4 | diflumetorim | 1:100 | 1:12 |
| 4 | dimethirimol | 1:2 | 5:1 |
| 4 | dimethomorph | 1:20 | 1:4 |
| 4 | dimoxystrobin | 1:15 | 1:2 |
| 4 | diniconazole | 1:6 | 2:1 |
| 4 | diniconazole M | 1:5 | 2:1 |
| 4 | dinocap | 1:15 | 1:3 |
| 4 | dithianon | 1:33 | 1:6 |
| 4 | dodemorph | 1:50 | 1:7 |
| 4 | dodine | 1:70 | 1:12 |
| 4 | edifenphos | 1:25 | 1:3 |
| 4 | enestroburin | 1:15 | 1:2 |
| 4 | epoxiconazole | 1:8 | 1:1 |
| 4 | ethaboxam | 1:15 | 1:3 |
| 4 | etridiazole | 1:50 | 1:6 |
| 4 | famoxadone | 1:15 | 1:2 |
| 4 | fenamidone | 1:13 | 1:2 |
| 4 | fenarimol | 1:2 | 4:1 |
| 4 | fenbuconazole | 1:5 | 2:1 |
| 4 | fenfuram | 1:30 | 1:4 |
| 4 | fenhexamid | 1:66 | 1:12 |
| 4 | fenoxanil | 1:100 | 1:12 |
| 4 | fenpiclonil | 1:100 | 1:12 |
| 4 | fenpropidin | 1:50 | 1:7 |
| 4 | fenpropimorph | 1:50 | 1:7 |
| 4 | fentin acetate | 1:20 | 1:3 |
| 4 | fentin chloride | 1:20 | 1:3 |
| 4 | fentin hydroxide | 1:20 | 1:3 |
| 4 | ferbam | 1:200 | 1:23 |
| 4 | ferimzone | 1:50 | 1:6 |
| 4 | fluazinam | 1:25 | 1:5 |
| 4 | fludioxonil | 1:15 | 1:2 |
| 4 | flumetover | 1:20 | 1:4 |
| 4 | flumorph | 1:20 | 1:3 |
| 4 | fluopicolide | 1:7 | 1:2 |
| 4 | fluopyram | 1:20 | 1:3 |
| 4 | fluoromide | 1:250 | 1:28 |
| 4 | fluoxastrobin | 1:10 | 1:2 |
| 4 | fluquinconazole | 1:10 | 1:2 |
| 4 | flusilazole | 1:20 | 1:3 |
| 4 | flusulfamide | 1:100 | 1:12 |
| 4 | flutianil | 1:10 | 11:2 |
| 4 | flutolanil | 1:30 | 1:4 |
| 4 | flutriafol | 1:10 | 1:2 |
| 4 | folpet | 1:100 | 1:12 |
| 4 | fosetyl-aluminum | 1:200 | 1:34 |
| 4 | fuberidazole | 1:75 | 1:9 |
| 4 | furalaxyl | 1:10 | 1:2 |
| 4 | furametpyr | 1:100 | 1:12 |
| 4 | guazatine | 1:100 | 1:12 |
| 4 | hexaconazole | 1:12 | 1:2 |
| 4 | hymexazol | 1:500 | 1:56 |
| 4 | imazalil | 1:12 | 1:2 |
| 4 | imibenconazole | 1:12 | 1:2 |

TABLE A1-continued

| Compound | Mixing Partner | Illustrative Ratios (*) | |
|---|---|---|---|
| 4 | iodocarb | 1:100 | 1:12 |
| 4 | ipconazole | 1:12 | 1:2 |
| 4 | iprobenfos | 1:100 | 1:12 |
| 4 | iprodione | 1:100 | 1:12 |
| 4 | iprovalicarb | 1:15 | 1:3 |
| 4 | isoprothiolane | 1:300 | 1:34 |
| 4 | isopyrazam | 1:15 | 1:3 |
| 4 | isotianil | 1:15 | 1:3 |
| 4 | kasugamycin | 1:2 | 4:1 |
| 4 | kresoxim-methyl | 1:15 | 1:2 |
| 4 | mancozeb | 1:150 | 1:17 |
| 4 | mandipropamid | 1:13 | 1:2 |
| 4 | maneb | 1:150 | 1:17 |
| 4 | mepanipyrim | 1:40 | 1:7 |
| 4 | mepronil | 1:10 | 1:2 |
| 4 | meptyldinocap | 1:15 | 1:3 |
| 4 | metalaxyl | 1:10 | 1:2 |
| 4 | metalaxyl-M | 1:10 | 1:2 |
| 4 | metconazole | 1:6 | 1:2 |
| 4 | methasulfocarb | 1:100 | 1:12 |
| 4 | metiram | 1:100 | 1:12 |
| 4 | metominostrobin | 1:20 | 1:3 |
| 4 | metrafenone | 1:13 | 1:2 |
| 4 | myclobutanil | 1:7 | 2:1 |
| 4 | naftifine | 1:100 | 1:12 |
| 4 | neo-asozin (ferric methanearsonate) | 1:100 | 1:12 |
| 4 | nuarimol | 1:20 | 1:3 |
| 4 | octhilinone | 1:100 | 1:12 |
| 4 | ofurace | 1:10 | 1:2 |
| 4 | orysastrobin | 1:20 | 1:3 |
| 4 | oxadixyl | 1:10 | 1:2 |
| 4 | oxolinic acid | 1:50 | 1:6 |
| 4 | oxpoconazole | 1:12 | 1:2 |
| 4 | oxycarboxin | 1:30 | 1:4 |
| 4 | oxytetracycline | 1:25 | 1:3 |
| 4 | pefurazoate | 1:100 | 1:12 |
| 4 | penconazole | 1:2 | 3:1 |
| 4 | pencycuron | 1:75 | 1:12 |
| 4 | penthiopyrad | 1:15 | 1:3 |
| 4 | phosphorous acid and salts | 1:100 | 1:12 |
| 4 | phthalide | 1:100 | 1:12 |
| 4 | picoxystrobin | 1:12 | 1:2 |
| 4 | piperalin | 1:20 | 1:3 |
| 4 | polyoxin | 1:25 | 1:3 |
| 4 | probenazole | 1:20 | 1:3 |
| 4 | prochloraz | 1:50 | 1:6 |
| 4 | procymidone | 1:75 | 1:9 |
| 4 | propamocarb | 1:66 | 1:12 |
| 4 | propamocarb-hydrochloride | 1:66 | 1:12 |
| 4 | propiconazole | 1:10 | 1:2 |
| 4 | propineb | 1:75 | 1:12 |
| 4 | proquinazid | 1:5 | 2:1 |
| 4 | prothioconazole | 1:12 | 1:2 |
| 4 | pyraclostrobin | 1:15 | 1:2 |
| 4 | pyrazophos | 1:100 | 1:12 |
| 4 | pyribencarb | 1:30 | 1:4 |
| 4 | pyrifenox | 1:20 | 1:3 |
| 4 | pyrimethanil | 1:25 | 1:4 |
| 4 | pyroquilon | 1:20 | 1:3 |
| 4 | pyrrolnitrin | 1:100 | 1:12 |
| 4 | quinmethionate | 1:100 | 1:12 |
| 4 | quinoxyfen | 1:7 | 1:2 |
| 4 | quintozene | 1:100 | 1:12 |
| 4 | silthiofam | 1:15 | 1:2 |
| 4 | simeconazole | 1:12 | 1:2 |
| 4 | spiroxamine | 1:37 | 1:6 |
| 4 | streptomycin | 1:25 | 1:3 |
| 4 | sulfur | 1:500 | 1:56 |
| 4 | tebuconazole | 1:12 | 1:2 |
| 4 | tecloftalam | 1:100 | 1:12 |
| 4 | tecnazene | 1:100 | 1:12 |
| 4 | terbinafine | 1:100 | 1:12 |
| 4 | tetraconazole | 1:12 | 1:2 |
| 4 | thiabendazole | 1:75 | 1:9 |
| 4 | thifluzamide | 1:20 | 1:3 |
| 4 | thiophanate | 1:75 | 1:9 |
| 4 | thiophanate-methyl | 1:75 | 1:9 |
| 4 | thiram | 1:250 | 1:28 |
| 4 | tiadinil | 1:15 | 1:3 |
| 4 | tolclofos-methyl | 1:250 | 1:28 |
| 4 | tolyfluanid | 1:100 | 1:12 |
| 4 | triadimefon | 1:12 | 1:2 |
| 4 | triadimenol | 1:12 | 1:2 |
| 4 | triazoxide | 1:100 | 1:12 |
| 4 | tricyclazole | 1:20 | 1:3 |
| 4 | tridemorph | 1:50 | 1:7 |
| 4 | trifloxystrobin | 1:13 | 1:2 |
| 4 | triflumizole | 1:20 | 1:3 |
| 4 | triforine | 1:20 | 1:3 |
| 4 | trimorphamide | 1:50 | 1:6 |
| 4 | triticonazole | 1:12 | 1:2 |
| 4 | uniconazole | 1:12 | 1:2 |
| 4 | validamycin | 1:20 | 1:3 |
| 4 | valiphenal | 1:13 | 1:2 |
| 4 | vinclozolin | 1:100 | 1:12 |
| 4 | zineb | 1:250 | 1:28 |
| 4 | ziram | 1:250 | 1:28 |
| 4 | zoxamide | 1:13 | 1:2 |
| 4 | 3-[5-(4-chlorophenyl)-2,3-dimethyl-3-isoxazolidinyl]pyridine | 1:20 | 1:3 |
| 4 | 4-fluorophenyl N-[1-[[[1-(4-cyanophenyl)ethyl]sulfonyl]methyl]-propyl]carbamate | 1:13 | 1:2 |
| 4 | 5-chloro-6-(2,4,6-trifluorophenyl)-7-(4-methylpiperidin-1-yl)[1,2,4]triazolo[1,5-a]pyrimidine | 1:10 | 1:2 |
| 4 | α-[methoxyimino]-N-methyl-2-[[[1-[3-(trifluoromethyl)phenyl]-ethoxy]imino]methyl]-benzeneacetamide | 1:20 | 1:3 |
| 4 | N-(4-chloro-2-nitrophenyl)-N-ethyl-4-methylbenzenesulfonamide | 1:20 | 1:3 |
| 4 | N-[[(cyclopropylmethoxy)amino][6-(difluoromethoxy)-2,3-difluorophenyl]methylene]benzene-acetamide | 1:2 | 4:1 |
| 4 | N-[2-(1,3-dimethylbutyl)phenyl]-5-fluoro-1,3-dimethyl-1H-pyrazol-4-carboxamide | 1:15 | 1:3 |
| 4 | N-[2-[4-[[3-(4-chlorophenyl)-2-propyn-1-yl]oxy]-3-methoxyphenyl]ethyl]-3-methyl-2-[(ethylsulfonyl)amino]butanamide | 1:13 | 1:2 |
| 4 | N-[2-[4-[[3-(4-chlorophenyl)-2-propyn-1-yl]oxy]-3-methoxyphenyl]ethyl]-3-methyl-2-[(methylsulfonyl)amino]butanamide | 1:13 | 1:2 |
| 4 | N'-[4-[4-chloro-3-(trifluoromethyl)phenoxy]-2,5-dimethylphenyl]-N-ethyl-N-methyl-methanimidamide | 1:20 | 1:3 |

(*) Ratios of Compound 4 to Mixing Partner relative by weight.

The present disclosure also includes Tables A2 through A7, each of which is constructed the same as Table A1 above except that the entries under the column heading "Compound" are replaced with the respective compound numbers shown below (see Index Tables A-B for compound descriptions). Therefore, Table A2 is identical to Table A1 except each entry of "4" under the column heading "Compound" is replaced with "2". Tables A3 through A7 are constructed similarly to Table A2.

| Table Number | Compound |
|---|---|
| A2 | 2 |
| A3 | 18 |
| A4 | 20 |

-continued

| Table Number | Compound |
|---|---|
| A5 | 42 |
| A6 | 43 |
| A7 | 44 |

The following TESTS demonstrate the control efficacy of compounds of this invention on specific pathogens. The pathogen control protection afforded by the compounds is not limited, however, to these species. See Index Tables A-B for compound descriptions. See Index Table C for $^1$H NMR data. In the Index Tables A-B the abbreviation "Cmpd." stands for "Compound", and the abbreviation "Ex." stands for "Example" and is followed by a number indicating in which example the compound is prepared. The numerical value reported in the column "AP$^+$(M+1)", is the molecular weight of the observed molecular ion formed by addition of H$^+$ (molecular weight of 1) to the molecule having the greatest isotopic abundance (i.e. M). The presence of molecular ions containing one or more higher atomic weight isotopes of lower abundance (e.g., $^{37}$C, $^{81}$C) is not reported. The reported M+1 peaks were observed by mass spectrometry using atmospheric pressure chemical ionization (AP$^+$). The substituent L shown in Markus structures at the top of Index Tables A-B represents the moiety (R$^1$)(R$^2$)=N~AC(R$^3$)(R$^4$)C(=W)— shown in Formula 1 in the Summary of the Invention. In Index Tables A-B under the column heading "L" is an entry selected from L-1 through L-30. For example, L for Compound number 1 is L-1, L for Compound number 7 is L-2 and L for Compound number 12 is L-8. The structures of L-1 through L-30 are shown below.

The bond projecting to the right is connected to the nitrogen atom of the piperidine ring in the Markush structures shown at the top of Index Tables A and B.

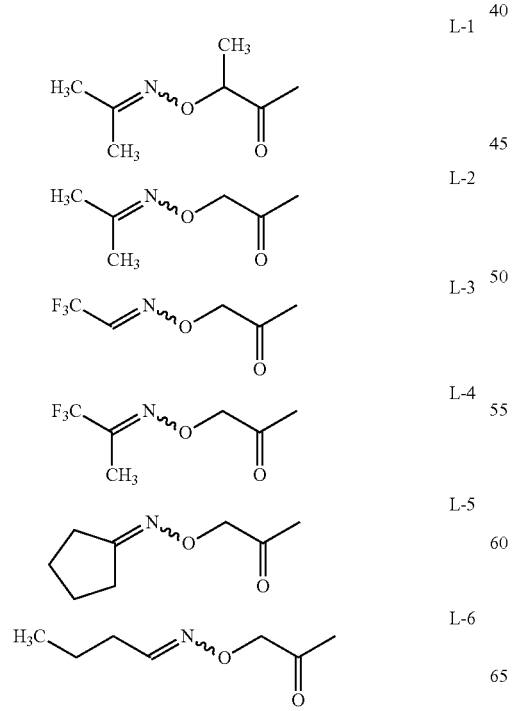

-continued

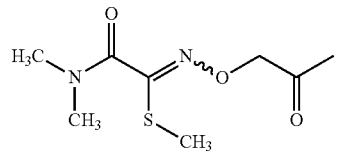
L-7

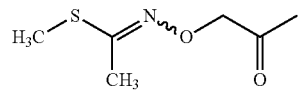
L-8

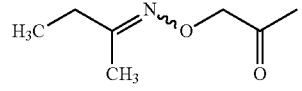
L-9

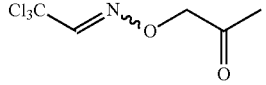
L-10

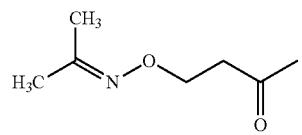
L-11

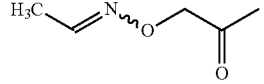
L-12

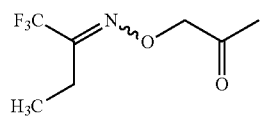
L-13

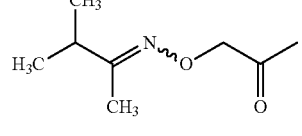
L-14

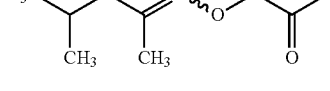
L-15

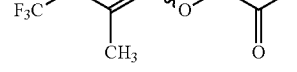
L-16

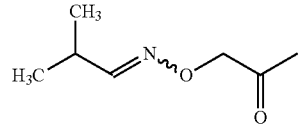
L-17

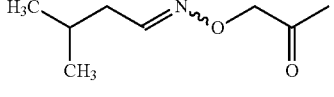
L-18

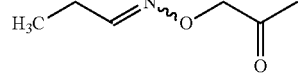
L-19

-continued

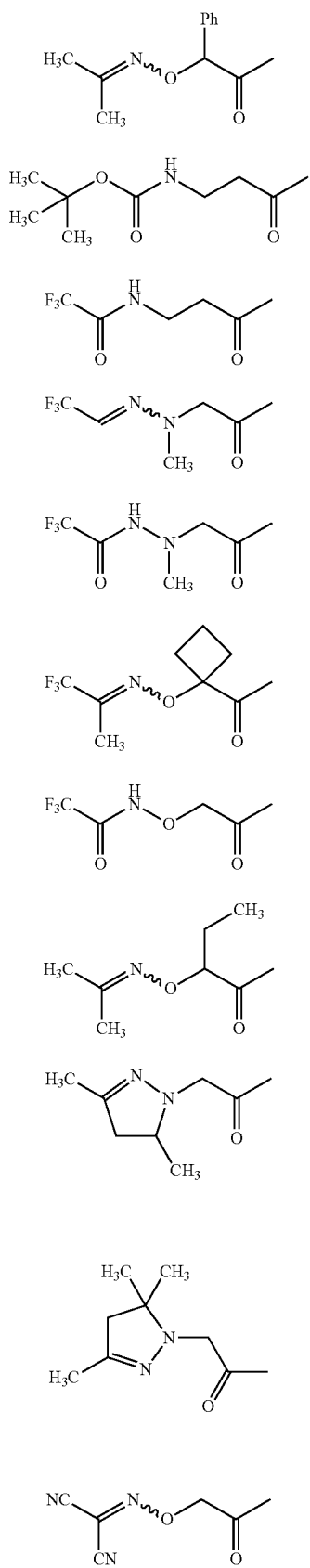

INDEX TABLE A

L-20

[Structure: thiazole-isoxazoline with piperidine-L and Q substituents]

L-21

| Cmpd. | L | Q | AP+ (M + 1) |
|---|---|---|---|
| 1 | L-1 | 2,6-difluorophenyl | 447 |
| 2 | L-2 | 2,6-difluorophenyl | 463 |
| 3 | L-3 | 2,6-difluorophenyl | 503 |
| 4 | L-4 | 2,6-difluorophenyl | 517 |
| 5 | L-5 | 2,6-difluorophenyl | 489 |
| 6 | L-2 | phenyl | 427 |
| 7 | L-2 | 2-fluorophenyl | 445 |
| 8 | L-2 | 3-methylbenzoxazol-2(3H)-one-yl | 484 |
| 9 | L-1 | 3-methylbenzoxazol-2(3H)-one-yl | 498 |
| 10 | L-6 | 2,6-difluorophenyl | 477 |
| 11 | L-7 | 2,6-difluorophenyl | 552 |
| 12 | L-8 | 2,6-difluorophenyl | 495 |
| 14 | L-2 | 2-methylphenyl | 441 |
| 16 | L-9 | 2,6-difluorophenyl | 477 |
| 17 | L-10 | 2,6-difluorophenyl | 551 |
| 18 | L-3 | 3-methylbenzoxazol-2(3H)-one-yl | 524 |
| 19 | L-3 | 2-methylisoindoline-1,3-dione-yl | 536 |
| 20 | L-3 | 2-cyanophenyl | 492 |
| 21 | L-11 | 2,6-difluorophenyl | 477 |
| 22 | L-12 | 2,6-difluorophenyl | 449 |
| 23 | L-13 | 2,6-difluorophenyl | 532 |
| 24 | L-14 | 2,6-difluorophenyl | 492 |
| 25 | L-15 | 2,6-difluorophenyl | 506 |
| 26 | L-16 | 2,6-difluorophenyl | 531 |
| 27 | L-17 | 2,6-difluorophenyl | 478 |
| 28 | L-18 | 2,6-difluorophenyl | 491 |
| 30 | L-19 | 2,6-difluorophenyl | 463 |
| 32 | L-20 | 2,6-difluorophenyl | * |
| 33 | L-21 | 2,6-difluorophenyl | 521 |
| 34 | L-22 | 2,6-difluorophenyl | 517 |
| 35 | L-23 | 2,6-difluorophenyl | 516 |
| 36 | L-24 | 2,6-difluorophenyl | 532 |
| 37 | L-25 | 2,6-difluorophenyl | 503 |
| 38 | L-26 | 2,6-difluorophenyl | 519 |
| 39 | L-27 | 2,6-difluorophenyl | 491 |
| 40 | L-28 | 2,6-difluorophenyl | 488 |
| 41 | L-2 | 2-cyanophenyl | 452 |
| 42 | L-4 | 2-cyanophenyl | 506 |

INDEX TABLE A-continued
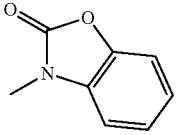
| Cmpd. | L | Q | AP+ (M + 1) |
|---|---|---|---|
| 43 | L-4 | 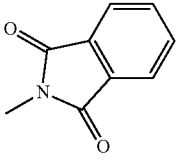 | 538 |
| 44 | L-4 | 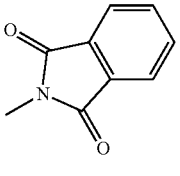 | 550 |
| 45 | L-2 | 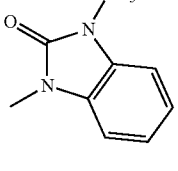 | 496 |
| 46 | L-29 | 2,6-difluorophenyl | 502 |
| 48 | L-3 | 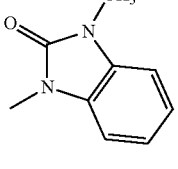 | 537 |
| 49 | L-4 | 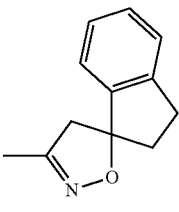 | 551 |
| 51 | L-30 | 2,6-difluorophenyl | 485 |
*See Index Table C for ¹H NMR data.
INDEX TABLE B
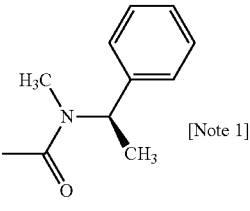
J is connected to the thiazole ring of the above structure through the bond projecting to the left.
| Cmpd. | L | J | AP+ (M + 1) |
|---|---|---|---|
| 13 | L-2 | 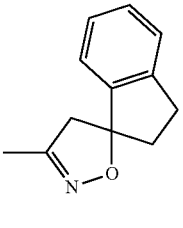 | 453 |
| 15 | L-2 | 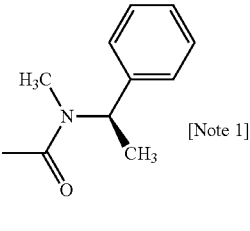 [Note 1] | 443 |
| 29 | L-3 | 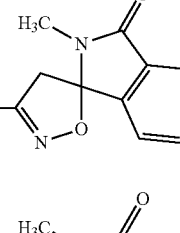 | 493 |
| 31 | L-3 | 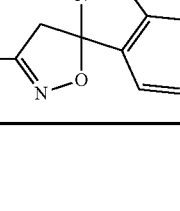 [Note 1] | 483 |
| 47 | L-3 |  | 522 |
| 50 | L-4 |  | 536 |
[Note 1]:
R-isomer.

INDEX TABLE C

| Compd. No. | ¹H NMR Data (CDCl₃ solution unless indicated otherwise)[a] |
|---|---|
| 32 | δ 7.60 (d, 1H), 7.43 (d, 2H), 7.36-7.27 (m, 4H), 6.89 (t, 2H), 6.04 (t, 1H), 5.90 (d, 1H), 4.65 (t, 1H), 4.07-4.02 (m, 2H), 3.75 (t, 1H), 3.61-3.54 (m, 1H), 3.19 (br s, 1H), 3.02 (q, 1H), 2.81 (q, 1H), 2.12 (d, 1H), 1.96 (s, 3H), 1.88 (s, 3H), 1.80-1.52 (m, 2H). |

[a]¹H NMR data are in ppm downfield from tetramethylsilane. Couplings are designated by (s)-singlet, (d)-doublet, (t)-triplet, (m)-multiplet, (q)-quartet and (br s)-broad singlet.

BIOLOGICAL EXAMPLES OF THE INVENTION

General protocol for preparing test suspensions for Tests A-B2: The test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-B2. Spraying a 200 ppm test suspension to the point of run-off on the test plants was the equivalent of a rate of 800 g/ha.

Test A

Grape seedlings were inoculated with a spore suspension of *Plasmopara viticola* (the causal agent of grape downy mildew) and incubated in a saturated atmosphere at 20° C. for 24 h. After a short drying period, the grape seedlings were sprayed with the test suspension to the point of run-off, then moved to a growth chamber at 20° C. for 5 days, and then back into a saturated atmosphere at 20° C. for 24 h. Upon removal, visual disease ratings were made.

Test B1

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test B2

Tomato seedlings were inoculated with a spore suspension of *Phytophthora infestans* (the causal agent of tomato late blight) and incubated in a saturated atmosphere at 20° C. for 17 h. After a short drying period, the tomato seedlings were sprayed with test suspension to the point of run-off, and then moved to a growth chamber at 20° C. for 4 days, after which time visual disease ratings were made.

Results for Tests A-B2 are given in Table A. In the Table, a rating of 100 indicates 100% disease control and a rating of 0 indicates no disease control (relative to the controls). All results are for 10 ppm except where followed by an "*" which indicates 40 ppm and "**" which indicates 200 ppm.

TABLE A

| Cmpd. No. | Test A | Test B1 | Test B2 |
|---|---|---|---|
| 1 | 100 | 100 | 99 |
| 2 | 100 | 100 | 100 |
| 3 | 100 | 100 | 99 |
| 4 | 100 | 100 | 99 |
| 5 | 95 | 95 | 98 |
| 6 | 98 | 90 | 90 |
| 7 | 100 | 100 | 98 |
| 8 | 100 | 99 | 99 |
| 9 | 100 | 100 | 97 |
| 10 | 98 | 95 | 88 |
| 11 | 0 | 26 | 0 |
| 12 | 17 | 47 | 0 |
| 13 | 99 | 99 | 99 |
| 14 | 100 | 98 | 88 |
| 15 | 99* | 39* | 91* |
| 16 | 100 | 100 | 99 |
| 17 | 66 | 97 | 47 |
| 18 | 100 | 100 | 98 |
| 19 | 99 | 100 | 94 |
| 20 | 100 | 100 | 99 |
| 21 | 100* | 100* | 98* |
| 22 | 100 | 100 | 99 |
| 23 | 98 | 99 | 83 |
| 24 | 95* | 100* | 96* |
| 25 | 93* | 100* | 58* |
| 26 | 100 | 100 | 99 |
| 27 | 98* | 100* | 99* |
| 28 | 98* | 95* | 68* |
| 29 | 100 | 100 | 99 |
| 30 | 100* | 100* | 99* |
| 31 | 100* | 100* | 99* |
| 32 | 94* | 100* | 92* |
| 33 | 0** | 68** | 0** |
| 34 | 33** | 97** | 40** |
| 35 | 100* | 100* | 99* |
| 36 | 60** | 100** | 93** |
| 37 | 75* | 84* | 0* |
| 38 | 99* | 100* | 99* |
| 39 | 100* | 100* | 99* |
| 40 | 97* | 100* | 99* |
| 41 | 100 | 100 | 99 |
| 42 | 100 | 100 | 99 |
| 43 | 100 | 100 | 99 |
| 44 | 100 | 100 | 99 |
| 45 | 96 | 95 | 99 |
| 46 | 9* | 90* | 81* |
| 47 | 100 | 100 | 99 |
| 48 | 100 | 100 | 99 |
| 49 | 100 | 100 | 99 |
| 50 | 100 | 100 | 99 |
| 51 | 99 | 100 | 99 |

What is claimed is:

1. A compound selected from Formula 1, tautomers, N-oxides, and salts thereof,

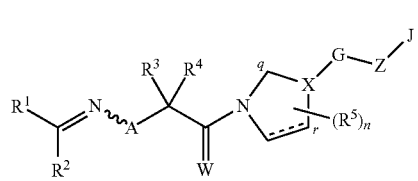

wherein

A is —O—, wherein the bond projecting to the left is connected to the nitrogen atom of Formula 1, and the bond projecting to the right is connected to the carbon atom of Formula 1;

W is O;

G is

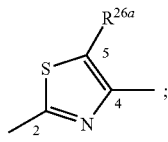 G-1

Z is a direct bond;
J is

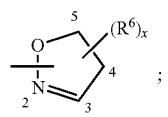 J-29

X is a radical selected from

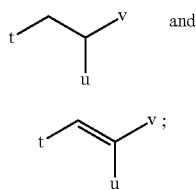

wherein the bond of $X^1$ or $X^3$ which is identified with "t" is connected to the carbon atom identified with "q" of Formula 1, the bond which is identified with "u" is connected to the carbon atom identified with "r" of Formula 1, and the bond which is identified with "v" is connected to G of Formula 1;

$R^1$ is methyl, trifluoromethyl or $CF_3CH_2$;
$R^2$ is H, methyl, or trifluoromethyl;
$R^3$ is H;
$R^4$ is H;
each $R^5$ is independently cyano, methyl or methoxy;
$R^6$ is $-Z^2Q$;
$Z^2$ is a direct bond;
Q is selected from

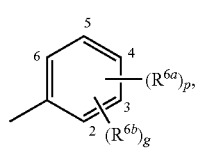 Q-45

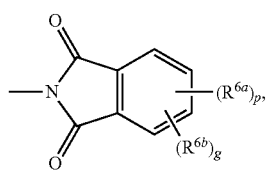 Q-63

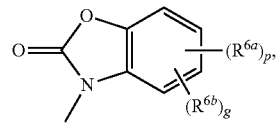 Q-70

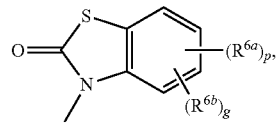 Q-71

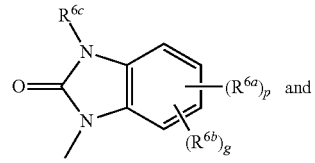 Q-72

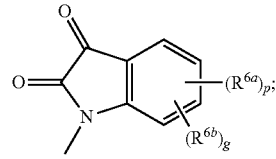 Q-84 each $R^{6a}$ is independently F, Cl, Br, hydroxy, cyano, methyl or methoxy;

each $R^{6b}$ is independently phenyl optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy; or a 5- to 6-membered heteroaromatic ring containing ring members selected from carbon atoms and up to 4 heteroatoms independently selected from up to 2 O, up to 2 S and up to 4 N atoms, the ring optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members; or a 3- to 7-membered nonaromatic ring containing ring members selected from carbon atoms and up to 4 heteroatoms independently selected from up to 2 O, up to 2 S and up to 4 N atoms, wherein up to 3 carbon atom ring members are independently selected from C(=O) and C(=S), the ring optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^{26}$ is hydrogen, halogen, $C_1$-$C_3$ alkyl or $C_1$-$C_3$ haloalkyl;
p is an integer from 0 to 5;
g is an integer from 0 to 1;
each m is independently 0, 1 or 2;
n is 0 or 1; and
x is 1.

2. The compound of claim 1 wherein:
Q is Q-45;
p is 1 or 2; and
each $R^{6a}$ is F.

3. The compound of claim 1 wherein:
Q is Q-45;
p is 1; and
$R^{6a}$ is cyano or methyl.

4. A compound of claim 1 selected from the group consisting of:
- 2-[4,5-dihydro-3-[2-[1-[2-[[(2,2,2-trifluoroethylidene)amino]oxy]acetyl]-4-piperidinyl]-4-thiazolyl]-5-isoxazolyl]benzonitrile;
- 2,2,2-trifluoroacetaldehyde, O-[2-[4-[4-[5-(2,6-difluorophenyl)-4,5-dihydro-3-isoxazolyl]-2-thiazolyl]-1-piperidinyl]-2-oxoethyl]oxime;
- 2,2,2-trifluoroacetaldehyde, O-[2-[4-[4-[4,5-dihydro-5-(2-oxo-3(2H)-benzoxazolyl)-3-isoxazolyl]-2-thiazolyl]-1-piperidinyl]-2-oxoethyl]oxime;
- 1,1,1-trifluoro-2-propanone, O-[2-[4-[4-[5-(2,6-difluorophenyl)-4,5-dihydro-3-isoxazolyl]-2-thiazolyl]-1-piperidinyl]-2-oxoethyl]oxime;
- 2-propanone, O-[2-[4-[4-[5-(2,6-difluorophenyl)-4,5-dihydro-3-isoxazolyl]-2-thiazolyl]-1-piperidinyl]-2-oxoethyl]oxime;
- 2-[4,5-dihydro-3-[2-[1-[2-[[(2,2,2,-trifluoro-1-methylethylidene)amino]oxy]acetyl]-4-piperidinyl]-4-thiazolyl]-5-isoxazolyl]benzonitrile;
- 1,1,1-trifluoro-2-propanone, O-[2-[4-[4-[4,5-dihydro-5-(2-oxo-3-(2H)-benzoxazolylidene)-3-isoxazolyl]-2-thiazolyl]-1-piperidinyl]-2-oxoethyl]oxime; and
- 2-propanone, O-[2-[4-[4-[5-(1,3-dihydro-1,3-dioxo-2H-isoindol-2-yl)-4,5-dihydro-3-isoxazoly]-2-thiazolyl]-1-piperidinyl]-2-oxoethyl]oxime.

5. A fungicidal composition comprising (a) a compound of claim 1; and (b) at least one additional component selected from the group consisting of surfactants, solid diluents and liquid diluents.

6. A method for controlling plant diseases caused by Oomycete fungal plant pathogens comprising applying to the plant or portion thereof, or to the plant seed, a fungicidally effective amount of a compound of claim 1.

* * * * *